United States Patent [19]
Sawai et al.

[11] Patent Number: 5,663,440
[45] Date of Patent: Sep. 2, 1997

[54] DIAMINO COMPOUNDS AND METHODS FOR PREPARING THEM

[75] Inventors: Toshiya Sawai; Seiji Oikawa; Masaaki Yazawa; Shizuo Murata; Masaharu Hayakawa; Etsuo Nakagawa; Shinichi Sawada, all of Chibaken, Japan

[73] Assignee: Chisso Corporation, Osaka, Japan

[21] Appl. No.: 537,479

[22] Filed: Oct. 2, 1995

[30] Foreign Application Priority Data

Oct. 20, 1994 [JP] Japan ................................. 6-281256
May 25, 1995 [JP] Japan ................................. 7-150889

[51] Int. Cl.$^6$ ........................... C07C 211/00; C09K 19/56
[52] U.S. Cl. ..................... 564/384; 252/299.4; 564/433; 564/376
[58] Field of Search .................. 252/299.01, 299.6, 252/299.4; 564/374, 376, 433

[56] References Cited

FOREIGN PATENT DOCUMENTS

| | | |
|---|---|---|
| 0 575 083 | 12/1993 | European Pat. Off. . |
| 0 601 813 | 6/1994 | European Pat. Off. . |
| 195 14 348 | 4/1994 | Germany . |
| 51-65960 | 6/1976 | Japan . |
| 5-281551 | 10/1993 | Japan . |
| 5-281550 | 10/1993 | Japan . |

OTHER PUBLICATIONS

Chem. Abs. 94:175723; Chem. Str. and glass transition temperature of polyarimide. 1981.
Abstract of bulletin of EP 575083–A1, Jun. 1992.

*Primary Examiner*—C. H. Kelly
*Attorney, Agent, or Firm*—Lowe, Price, LeBlanc & Becker

[57] ABSTRACT

An object of the invention is to propose diamino compounds expressed by the following general formula (1) which are suitable to obtain a raw material, a polyimide resin, for a liquid crystal aligning film without any image sticking and with a high voltage holding ratio at from a low temperature to a high temperature as well as the preparation thereof:

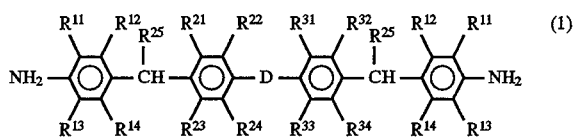

18 Claims, 15 Drawing Sheets

DIAMINO COMPOUNDS AND METHODS FOR PREPARING THEM

BACKGROUND OF THE INVENTION

1. Field of the Invention

This invention relates to novel diamino compounds and methods for preparing them.

2. Description of the Related Art

For liquid crystal display elements used in watches and electronic computers, there is mainly adopted a twist nematic (hereinafter referred to TN) mode in which aligning directions of nematic liquid crystal molecules being twisted by 90 degrees between one pair of upper and lower two electrode substrates. Also, there has been developed a super twisted nematic (hereinafter referred to STN) mode in which a twist angle being increased to 180–300 degrees and thus liquid crystal display elements with good display quality can be obtained even for a large image plane.

Furthermore, since matrix displays and color displays etc. have been recently realized, there have been actively developed MIM (metal-insulator-metal) elements and TFT (field-effect mode thin film transistor) elements adopting a number of selective electrodes and an active type twist nematic mode by which their ON-OFF actions can be carried out.

As a problem common to all these modes, a phenomenon called an image sticking is caused, that is, after displaying the same image for a long term, the previous image is left as an after-image at the time of changing to the next image. Particularly, in order to obtain liquid crystal display elements with high quality, it becomes a very important problem to improve the said image sticking.

The cause of the image sticking is considered to be an electric potential difference produced between the upper and lower substrates by a deviation of electric charge and kept stably, and the said deviation is caused by production of electric double layers due to ion components of impurities contained in the liquid crystal at an aligning film surface by a DC component applied On a liquid crystal element. Particularly, in TFT element, since a DC component cannot be eliminated owing to characteristics of the element, the image sticking is more eminent and serious than in TN and STN elements.

Also in a TFT mode, in order to prevent any flicker in an image plane owing to an after-image, there is required an aligning film having a high voltage holding ratio even at 60° C. to 90° C., at which temperatures a decrease in the voltage holding ratio is hitherto particularly eminent.

Furthermore, Vth (threshold voltage) around a liquid crystal panel tends to rise partly under an atmosphere of a high temperature and a high humidity (called Vth unevenness). Although the cause thereof is not certain, it is considerable that water and impurities in a sealing material are diffused and permeated in the liquid crystal aligning film to cause the phenomenon.

As aligning films used in the said liquid crystal display elements, organic films such as polyimide and polyamide types are mainly used, and a liquid crystal display element with a liquid crystal aligning film is disclosed in Japan Open-laid Patent Application Sho 51-65960, in which polyimide resin having a repeating unit represented by

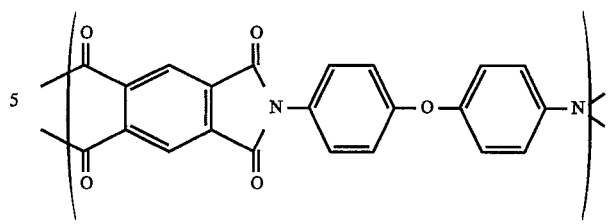

is used. However, in the said element using the polyimide aligning film, the image sticking and the Vth unevenness are easily produced.

Problems to be solved by the Invention

An object of the invention is to solve the above-mentioned problem as well as to propose diamino compounds which is suitable to obtain a raw material, a polyimide resin, for a liquid crystal aligning film with a less image sticking, with a high voltage holding ratio from a low temperature to a high temperature and without any Vth unevenness around the liquid crystal panel even under an atmosphere of a high temperature and a high humidity.

Means to solve the Problem

We inventors have gone on with studies and developments in earnest, and thus found that the image sticking, the voltage holding ratio, Vth unevenness are correlated to a polarity of an aligning film surface and that an aligning film with a less image sticking, with a high voltage holding ratio from at a lower temperature to a high temperature, and without any Vth unevenness around the liquid crystal panel even under an atmosphere of a high temperature and a high humidity can be obtained by using as the polyimide raw material for the aligning film a diamino compound with a specified structure which is able to decrease the polarity, to complete this invention.

Since the said diamino compound has not a polar group such as —O— or —$SO_2$— and also has a large molecular weight, the proportion of the imide group with a large polarity can be decreased relatively in the case that the compound is used as the polyimide raw material.

SUMMARY OF THE INVENTION

This invention is constituted by the following items (1) to (18).

(1) Diamino compounds expressed by the following general formula (1):

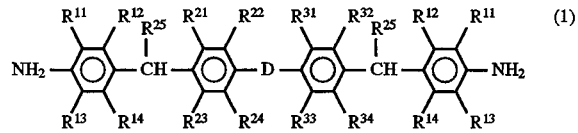

wherein, (a) when $R^{25}$ being a hydrogen atom and D being

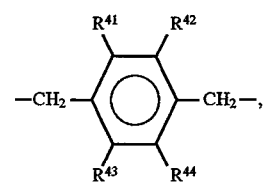

all of $R^{11}$, $R^{12}$, $R^{13}$ and $R^{14}$ denote a hydrogen atom, and $R^{21}$, $R^{22}$, $R^{23}$, $R^{24}$, $R^{31}$, $R^{32}$, $R^{33}$, $R^{34}$, $R^{41}$, $R^{42}$, $R^{43}$ and $R^{44}$ denote independently each other a hydrogen atom or an alkyl group with 1 to 8 carbon atoms, (b) when $R^{25}$ being a hydrogen atom and D being

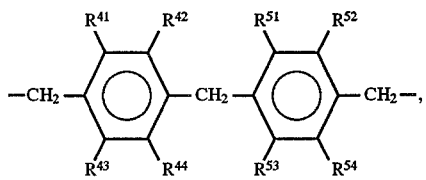

all of $R^{11}$, $R^{12}$, $R^{13}$ and $R^{14}$ denote a hydrogen atom, and $R^{21}$ and $R^{32}$, $R^{22}$ and $R^{31}$, $R^{23}$ and $R^{34}$, as well as $R^{24}$ and $R^{33}$ are respectively the same atoms or groups and denote independently each other hydrogen atoms or straight-chain or branched alkyl groups with 1 to 8 carbon atoms, and $R^{41}$, $R^{42}$, $R^{43}$, $R^{44}$, $R^{51}$, $R^{52}$, $R^{53}$ and $R^{54}$ denote independently each other a hydrogen atom or an alkyl group with 1 to 8 carbon atoms, (c) when $R^{25}$ being a hydrogen atom and D being a divalent straight-chain or branched hydrocarbon group with 2 to 30 carbon atoms, $R^{11}$, $R^{12}$, $R^{13}$ and $R^{14}$ denote independently a hydrogen atom or a straight-chain or branched alkyl group with 1 to 8 carbon atoms, and $R^{21}$ and $R^{32}$, $R^{22}$ and $R^{31}$, $R^{23}$ and $R^{34}$ as well as $R^{24}$ and $R^{33}$ are respectively the same atoms or groups and denote independently each other hydrogen atoms or straight-chain or branched alkyl groups with 1 to 8 carbon atoms, (d) when $R^{25}$ being a straight-chain or branched alkyl group with 1 to 12 carbon atoms, D denotes a direct bond, an aliphatic group with 1 to 30 carbon atoms, an aromatic group with 6 to 30 carbon atoms, or a hydrocarbon group with 7 to 30 carbon atoms having both an aliphatic group and an aromatic group, $R^{11}$, $R^{12}$, $R^{13}$ and $R^{14}$ denote independently a hydrogen atom or a straight-chain or branched alkyl group with 1 to 8 carbon atoms, and $R^{21}$ and $R^{32}$, $R^{22}$ and $R^{31}$, $R^{23}$ and $R^{34}$ as well as $R^{24}$ and $R^{33}$ are respectively the same atoms or groups and denote independently each other hydrogen atoms or straight-chain or branched alkyl groups with 1 to 8 carbon atoms.

(2) The diamino compounds according to item (1), in which all of $R^{11}$, $R^{12}$, $R^{13}$, $R^{14}$, $R^{21}$, $R^{22}$, $R^{23}$, $R^{24}$, $R^{25}$, $R^{31}$, $R^{32}$, $R^{33}$ and $R^{34}$ denote a hydrogen atom and D denotes

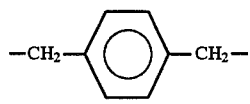

in the general formula (1).

(3) The diamino compounds according to item (1), in which all of $R^{11}$, $R^{12}$, $R^{13}$, $R^{14}$, $R^{21}$, $R^{22}$, $R^{23}$, $R^{24}$, $R^{25}$, $R^{31}$, $R^{32}$, $R^{33}$ and $R^{34}$ denote a hydrogen atom and D denotes

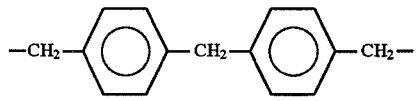

in the general formula (1).

(4) The diamino compounds according to item (1), in which $R^{25}$ denotes a hydrogen atom, D denotes a group expressed by the following formula (2), $R^{11}$, $R^{12}$, $R^{13}$ and $R^{14}$ denote independently a hydrogen atom or a straight-chain or branched alkyl group with 1 to 8 carbon atoms, $R^{21}$ and $R^{32}$, $R^{22}$ and $R^{31}$, $R^{23}$ and $R^{34}$, as well as $R^{24}$ and $R^{33}$ are respectively the same atoms or groups and denote independently each other hydrogen atoms or straight-chain or branched alkyl groups with 1 to 8 carbon atoms in the general formula (1):

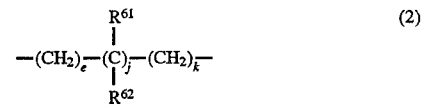

wherein, $R^{61}$ denotes a hydrogen atom or a straight-chain or branched alkyl group with 1 to 12 carbon atoms, $R^{62}$ denotes a straight-chain or branched alkyl group with 1 to 12 carbon atoms, e and k denote independently each other 0 to 10, j denotes 0 to 20, and when J being 0, the sum of e and k is 2 or more than 2, and when j being 1 or more than 1, the sum of e and k is 0 or more than 0 in the general formula (2).

(5) Diamino compounds according to item (1), in which $R^{25}$ denotes a straight-chain or branched alkyl group with 1 to 12 carbon atoms, D denotes any group expressed by the following formulae, $R^{11}$, $R^{12}$, $R^{13}$ and $R^{14}$ denote independently a hydrogen atom or a straight-chain or branched alkyl group with 1 to 8 carbon atoms, $R^{21}$ and $R^{32}$, $R^{22}$ and $R^{31}$, $R^{23}$ and $R^{34}$, as well as $R^{24}$ and $R^{33}$ are respectively the same atoms or groups and denote independently each other hydrogen atoms or straight-chain or branched alkyl groups with 1 to 8 carbon atoms in the general formula (1):

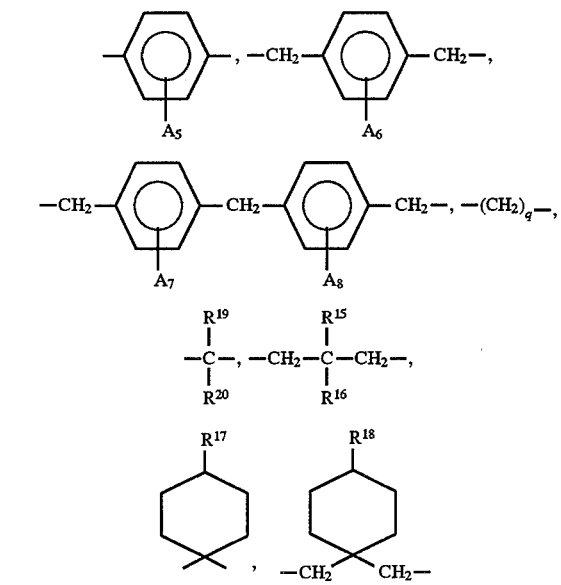

wherein, $A_5$, $A_6$, $A_7$ and $A_8$ denote independently each other a hydrogen atom or a straight-chain or branched alkyl group with 1 to 8 carbon atoms, q denotes an integer of 0 or more than 0, $R^{15}$, $R^{16}$, $R^{19}$ and $R^{20}$ denote independently each other a straight-chain or branched alkyl group with 1 to 20 carbon atoms, and $R^{17}$ and $R^{18}$ denote independently each other a hydrogen atom or a straight-chain or branched alkyl group with 1 to 8 carbon atoms.

(6) The diamino compounds according to item (1), in which all of $R^{11}$, $R^{12}$, $R^{13}$, $R^{14}$, $R^{21}$, $R^{22}$, $R^{23}$, $R^{24}$, $R^{25}$, $R^{31}$, $R^{32}$, $R^{33}$ and $R^{34}$ denote a hydrogen atom and D denotes a group expressed by the general formula (2) in the general formula (1). (7) The diamino compounds according to item (1), in which all of $R^{11}$, $R^{12}$, $R^{13}$, $R^{14}$, $R^{21}$, $R^{22}$, $R^{23}$, $R^{24}$, $R^{25}$, $R^{31}$, $R^{32}$, $R^{33}$ and $R^{34}$ denote a hydrogen atom and D denotes a group expressed by the general formula (2) in the general formula (1), as well as j is 0 and the sum of e and k is from 2 to 10 in the general formula (2).

(8) The diamino compounds according to item (1), in which all of $R^{11}, R^{12}, R^{13}, R^{14}, R^{21}, R^{22}, R^{23}, R^{24}, R^{25}, R^{31}, R^{32}, R^{33}$ and $R^{34}$ denote a hydrogen atom and D denotes a group expressed by the general formula (2) in the general formula (1), as well as $R^{61}$ denotes a hydrogen atom, $R^{62}$ denotes a straight-chain alkyl group with 1 to 10 carbon atoms, and all of e, j and k are 1 in the general formula (2).

(9) The diamino compounds according to item (1), in which all of $R^{11}, R^{12}, R^{13}, R^{14}, R^{21}, R^{22}, R^{23}, R^{24}, R^{25}, R^{31}, R^{32}, R^{33}$ and $R^{34}$ denote a hydrogen atom and D denotes a group expressed by the general formula (2) in the general formula (1), as well as $R^{61}$ denotes a hydrogen atom, $R^{62}$ denotes a straight-chain alkyl group with 1 to 9 carbon atoms, and e and k are both 0 in the general formula (2).

(10) The diamino compounds according to item (5), in which all of $R^{11}, R^{12}, R^{13}, R^{14}, R^{21}, R^{22}, R^{23}, R^{24}, R^{31}, R^{32}, R^{33}$ and $R^{34}$ denote a hydrogen atom in the general formula (1).

(11) Bis-(4-(1-(4-aminophenyl)alkyl)phenyl)methanes of the general formula (1), in which $R^{25}$ denotes a straight-chain alkyl group with 1 to 6 carbon atoms.

(12) Bis-(4-(1-(4-aminophenyl)alkyl)phenyl) cyclohexanes of the general formula (1), in which $R^{25}$ denotes a straight-chain alkyl group with 1 to 6 carbon atoms.

(13) Bis-(4-(1-(4-aminophenyl)alkyl)phenyl)4-butylcyclohexanes of the general formula (1), in which $R^{25}$ denotes a straight-chain alkyl group with 1 to 6 carbon atoms.

(14) A method for preparing a diamino compound expressed by the following general formula (1), characterized in that an aromatic compound expressed by the following formula (3) is reacted with a paranitrobenzoyl halide derivative expressed by the following general formula (4) and thereafter carbonyl groups are reduced or alkylated and nitro groups are reduced:

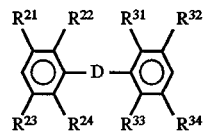   (3)

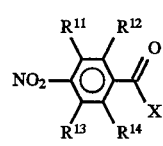   (4)

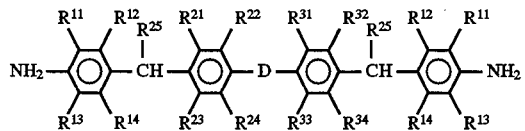   (1)

wherein, (a) when $R^{25}$ being a hydrogen atom and D being

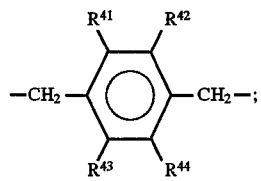

all of $R^{11}$, $R^{12}$, $R^{13}$ and $R^{14}$ denote a hydrogen atom, and $R^{21}$, $R^{22}$, $R^{23}$, $R^{24}$, $R^{31}$, $R^{32}$, $R^{33}$, $R^{34}$, $R^{41}$, $R^{42}$, $R^{43}$ and $R^{44}$ denote independently each other a hydrogen atom or an alkyl group with 1 to 8 carbon atoms, (b) when $R^{25}$ being a hydrogen atom and D being

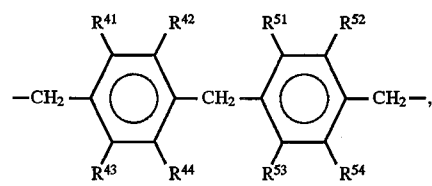

all of $R^{11}$, $R^{12}$, $R^{13}$ and $R^{14}$ denote a hydrogen atom, and $R^{21}$ and $R^{32}$, $R^{22}$ and $R^{31}$, $R^{23}$ and $R^{34}$, as well as $R^{24}$ and $R^{33}$ are respectively the same atoms or groups and denote independently each other hydrogen atoms or straight-chain or branched alkyl groups with 1 to 8 carbon atoms and $R^{41}$, $R^{42}$, $R^{43}$, $R^{44}$, $R^{51}$, $R^{52}$, $R^{53}$ and $R^{54}$ denote independently each other a hydrogen atom or an alkyl group with 1 to 8 carbon atoms, (c) when $R^{25}$ being a hydrogen atom and D being a divalent straight-chain or branched hydrocarbon group with 2 to 30 carbon atoms, $R^{11}, R^{12}, R^{13}$ and $R^{14}$ denote independently a hydrogen atom or a straight-chain or branched alkyl group with 1 to 8 carbon atoms, and $R^{21}$ and $R^{32}$, $R^{22}$ and $R^{31}$, $R^{23}$ and $R^{34}$ as well as $R^{24}$ and $R^{33}$ are respectively the same atoms or groups and denote independently each other hydrogen atoms or straight-chain or branched alkyl groups with 1 to 8 carbon atoms, (d) when $R^{25}$ being a straight-chain or branched alkyl group with 1 to 12 carbon atoms, D denotes a direct bond, an aliphatic group with 1 to 30 carbon atoms, an aromatic group with 6 to 30 carbon atoms, or a hydrocarbon group with 7 to 30 carbon atoms having both an aliphatic group and an aromatic group, $R^{11}, R^{12}, R^{13}$ and $R^{14}$ denote independently a hydrogen atom or a straight-chain or branched alkyl group with 1 to 8 carbon atoms, and $R^{21}$ and $R^{32}$, $R^{22}$ and $R^{31}$, $R^{23}$ and $R^{34}$ as well as $R^{24}$ and $R^{33}$ are respectively the same atoms or groups and denote independently each other hydrogen atoms or straight-chain or branched alkyl groups with 1 to 8 carbon atoms, and X denotes a chlorine or a bromine atom in the general formulae (1), (3) and (4).

(15) A method for preparing a diamino compound according to item (14), characterized in that a diphenyl methane derivative expressed by the following formula (5) is reacted with a benzoyl halide derivative expressed by the following general formula (6) and thereafter a carbonyl group is reduced to synthesize an aromatic compound expressed by the formula (3), which is subsequently reacted with paranitrobenzoyl halide expressed by the general formula (4) and thereafter carbonyl groups and nitro groups are reduced:

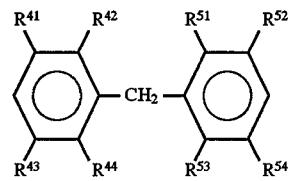   (5)

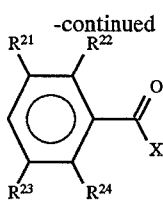

wherein,

D denotes

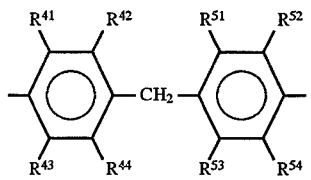

in the general formula (3), and all of $R^{11}$, $R^{12}$, $R^{13}$ and $R^{14}$ denote a hydrogen atom, and $R^{21}$, $R^{22}$, $R^{23}$, $R^{24}$, $R^{31}$, $R^{32}$, $R^{33}$, $R^{34}$, $R^{41}$, $R^{42}$, $R^{43}$, $R^{44}$, $R^{51}$, $R^{52}$, $R^{53}$ and $R^{54}$ denote independently each other a hydrogen atom or an alkyl group with 1 to 8 carbon atoms, X denotes a chlorine atom or a bromine atom in the general formulae (4), (5) and (6).

(16) A method for preparing a diamino compound according to item (14), characterized in that a dibenzyl benzene derivative expressed by the following formula (7) is reacted with paranitrobenzoyl halide expressed by the following general formula (4) and thereafter carbonyl groups and nitro groups are reduced:

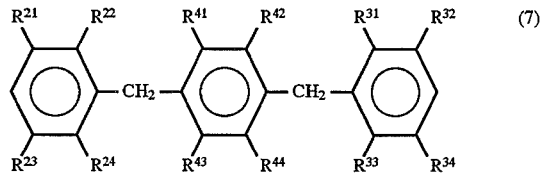

wherein, $R^{21}$, $R^{22}$, $R^{23}$, $R^{24}$, $R^{31}$, $R^{32}$, $R^{33}$, $R^{34}$, $R^{41}$, $R^{42}$, $R^{43}$ and $R^{44}$ denote independently each other a hydrogen atom or an alkyl group with 1 to 8 carbon atoms in the general formula (7).

(17) A method for preparing a diamino compound according to item (14), characterized in that a diphenyl alkane derivative expressed by the following formula (8) is reacted with a paranitrobenzoyl halide derivative expressed by the following general formula (4) and thereafter carbonyl groups and nitro groups are reduced:

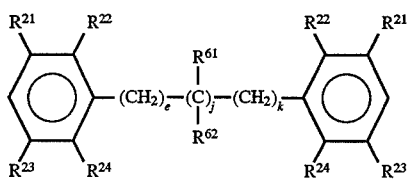

wherein, $R^{61}$ denotes a hydrogen atom or a straight-chain or branched alkyl group with 1 to 12 carbon atoms, $R^{62}$ denotes a straight-chain or branched alkyl group with 1 to 12 carbon atoms, e and k denote independently each other 0 to 10, j denotes 0 to 20, and when j being 0, the sum of e and k is 2 or more than 2, and when j being 1 or more than 1, the sum of e and k is 0 or more than 0, as well as $R^{21}$, $R^{22}$, $R^{23}$ and $R^{24}$ denote independently each other a hydrogen atom or an alkyl group with 1 to 8 carbon atoms in the general formula (8).

(18) A method for preparing a diamino compound expressed by the general formula (10), characterized in that a compound expressed by the following formula (9) is reacted with a paranitrobenzoyl halide derivative expressed by the general formula (4) and thereafter carbonyl groups are alkylated and nitro groups are reduced:

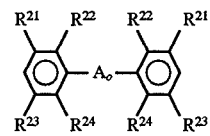

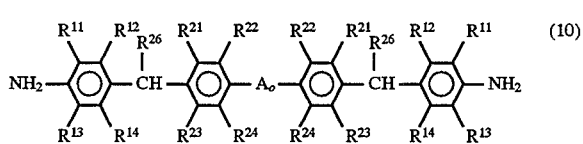

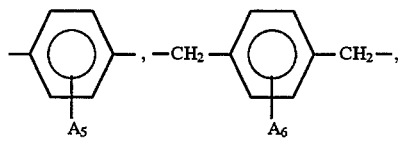

wherein, $A_0$ denotes any of the following groups in the general formulae (9) and (10):

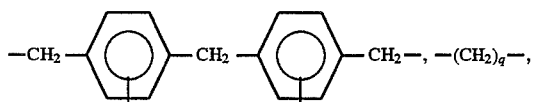

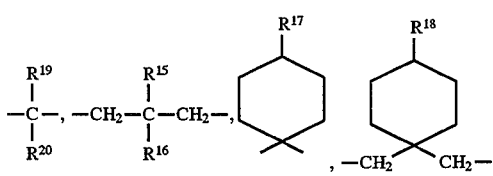

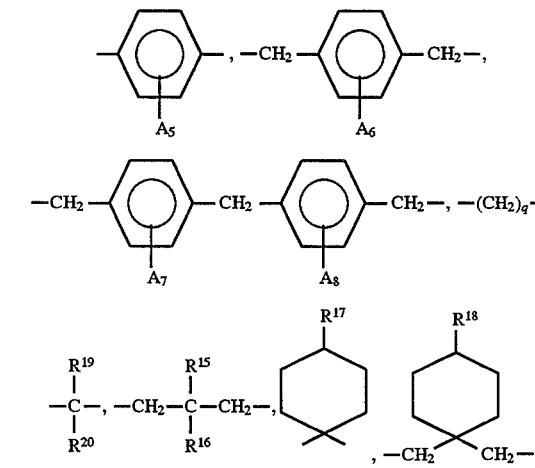

wherein, $A_5$, $A_6$, $A_7$ and $A_8$ denote independently each other a hydrogen atom or a straight-chain or branched alkyl group with 1 to 8 carbon atoms, q denotes an integer of 0 or more than 0, $R^{15}$, $R^{16}$, $R^{19}$ and $R^{20}$ denote independently each other a hydrogen atom or a straight-chain or branched alkyl group with 1 to 20 carbon atoms, $R^{11}$, $R^{12}$, $R^{13}$, $R^{14}$, $R^{17}$, $R^{18}$, $R^{21}$, $R^{22}$, $R^{23}$, and $R^{24}$ denote independently each other a hydrogen atom or an alkyl group with 1 to 8 carbon atoms, and $R^{26}$ denotes a straight-chain or branched alkyl group with 1 to 12 carbon atoms.

BRIEF DESCRIPTION OF THE ACCOMPANYING DRAWING

Figure 2:
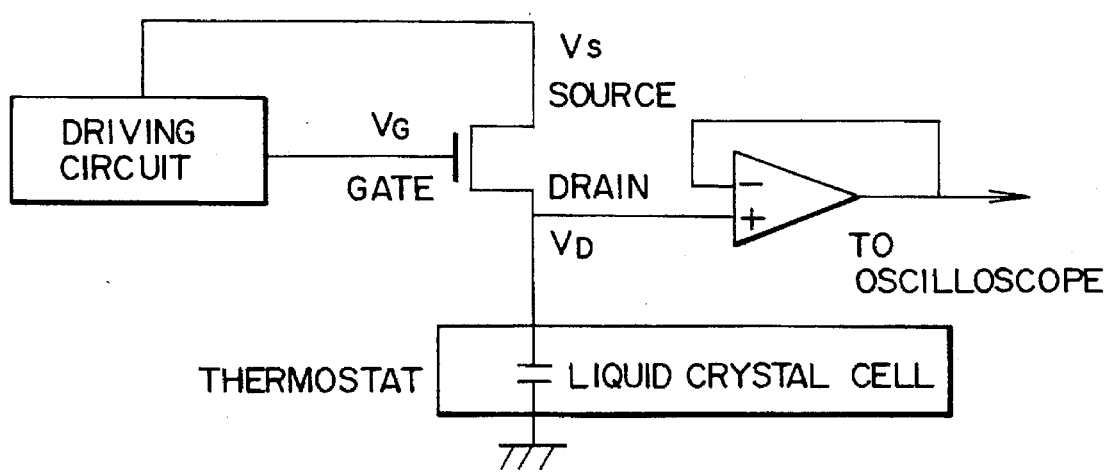
FIG. 2 is a circuit drawing used for determination of voltage holding ratios.
Figure 3:
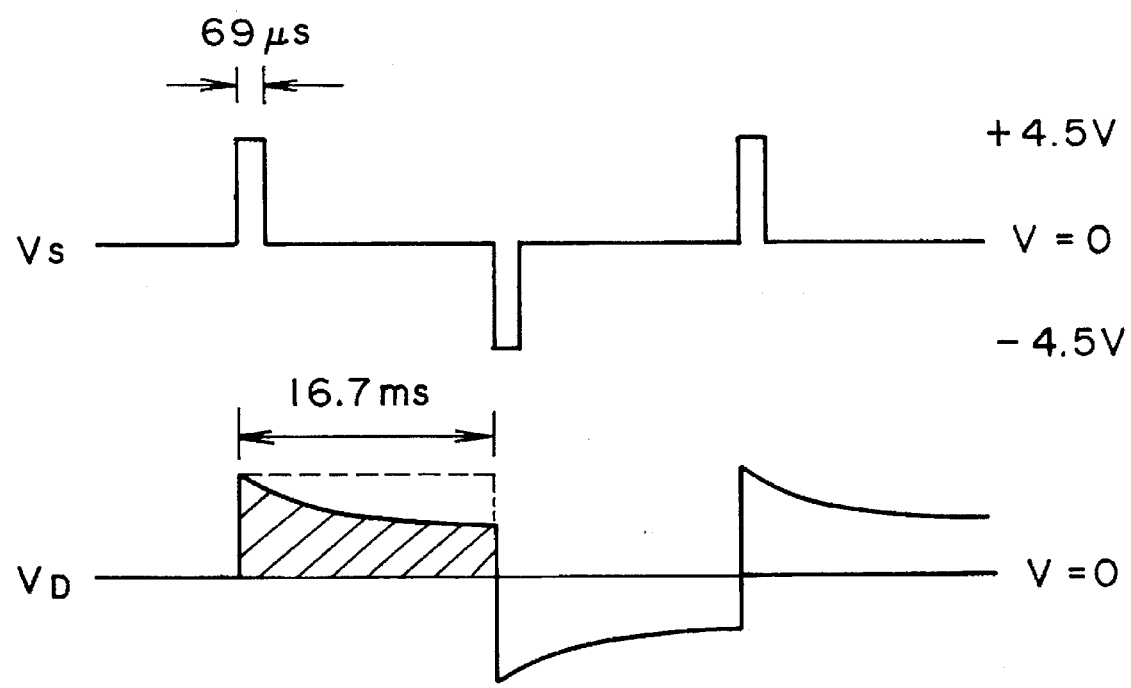

In FIG. 3, Vs is a rectangular wave with a gate pulse width of 69 μs, a frequency of 30 Hz and a wave height of ±4.5 V, and Vd is a wave form read from an oscilloscope after applying Vs on a source of the circuit shown in FIG. 2.

Figure 4:
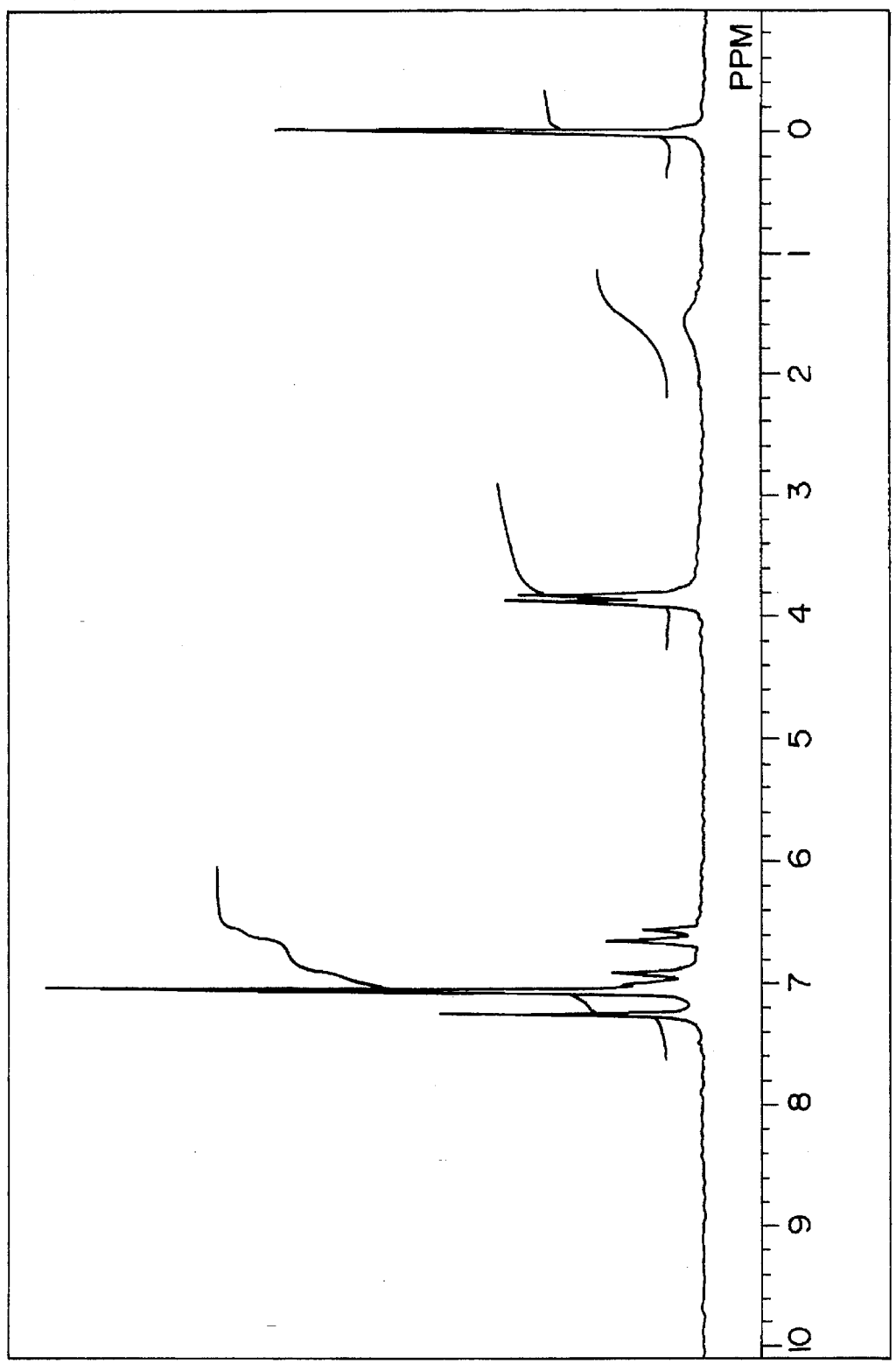

FIG. 4 is a 1H-NMR spectrum diagram of the diamino compound obtained in Example 1.

Figure 5:
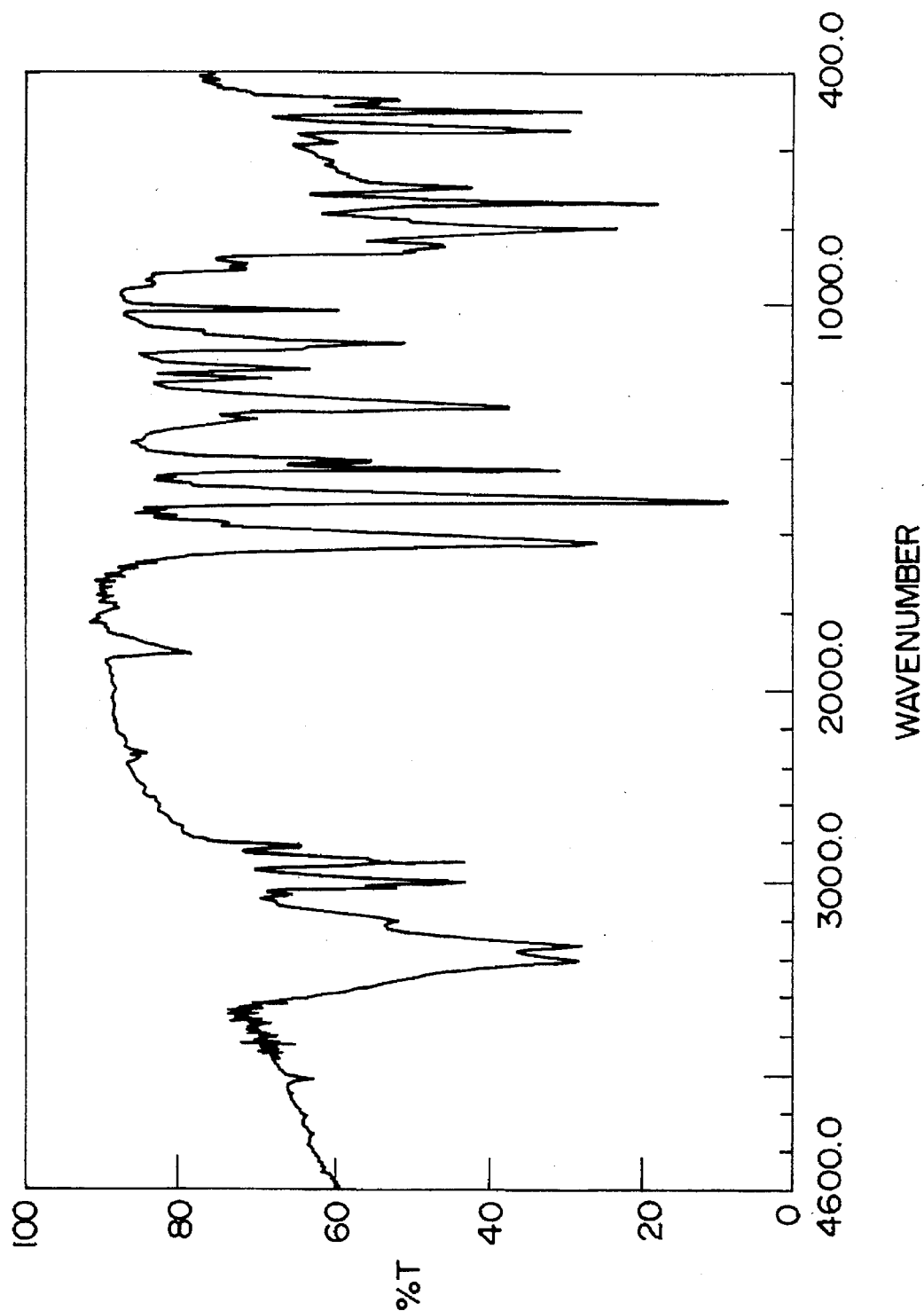

FIG. 5 is an infrared absorption spectrum diagram of the diamino compound obtained in Example 1. In the diagram, an unit of wavenumber is cm-1, which being identically referred to hereinafter.

Figure 6:
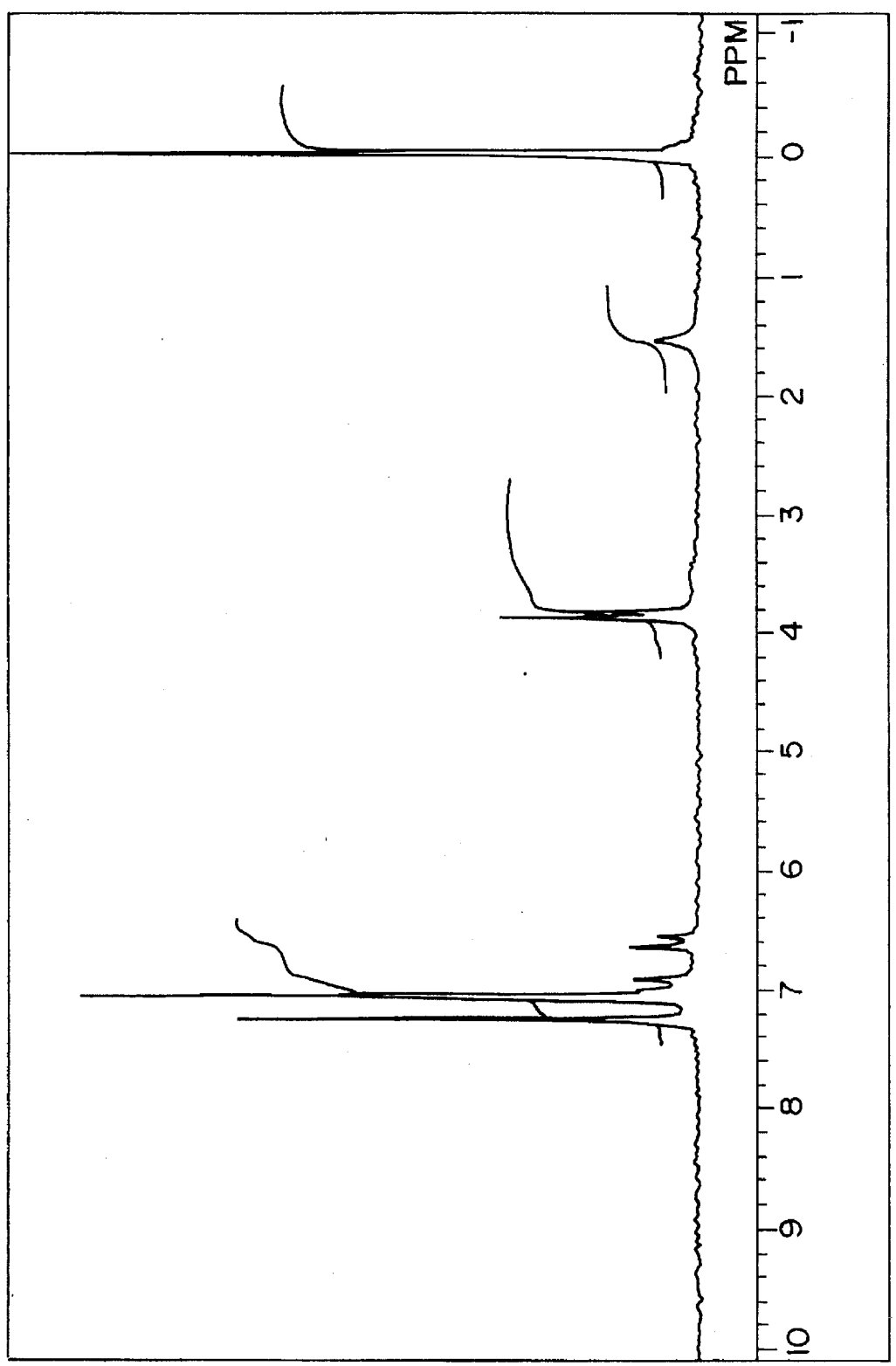

FIG. 6 is a 1H-NMR spectrum diagram of the diamino compound obtained in Example 2.

Figure 7:
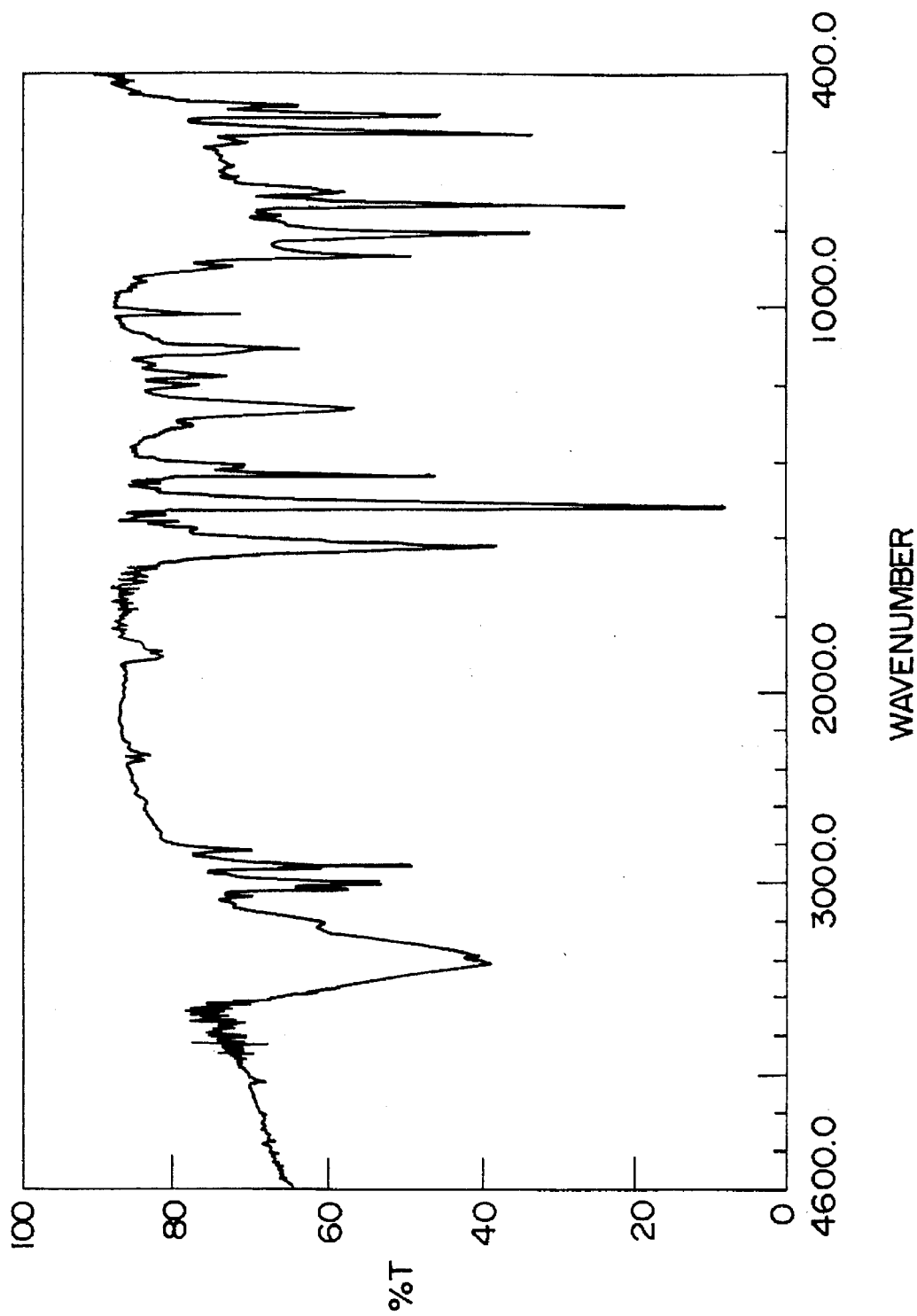

FIG. 7 is an infrared absorption spectrum diagram of the diamino compound obtained in Example 2.

Figure 8:
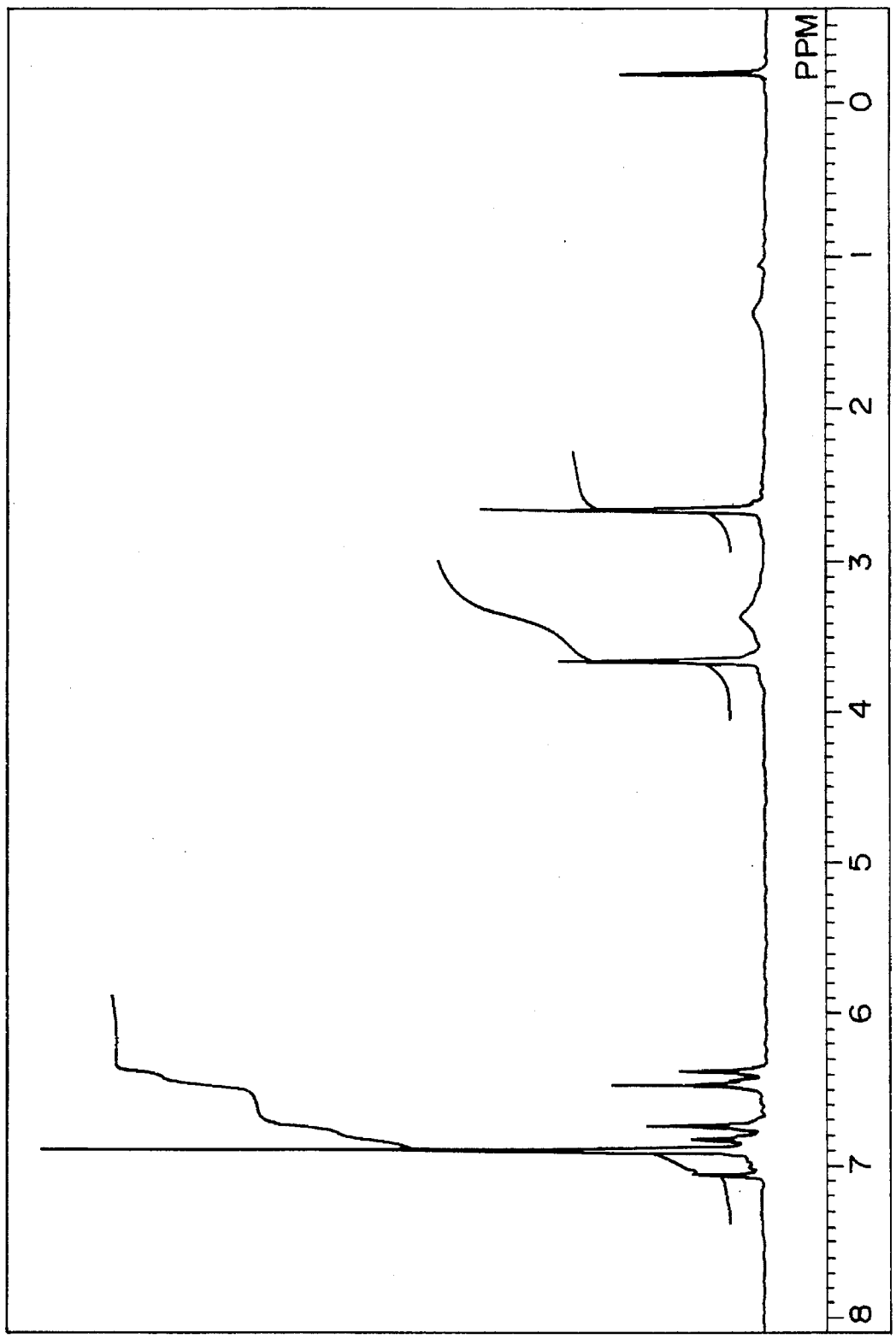

FIG. 8 is a 1H-NMR spectrum diagram of the diamino compound obtained in Example 8.

Figure 9:
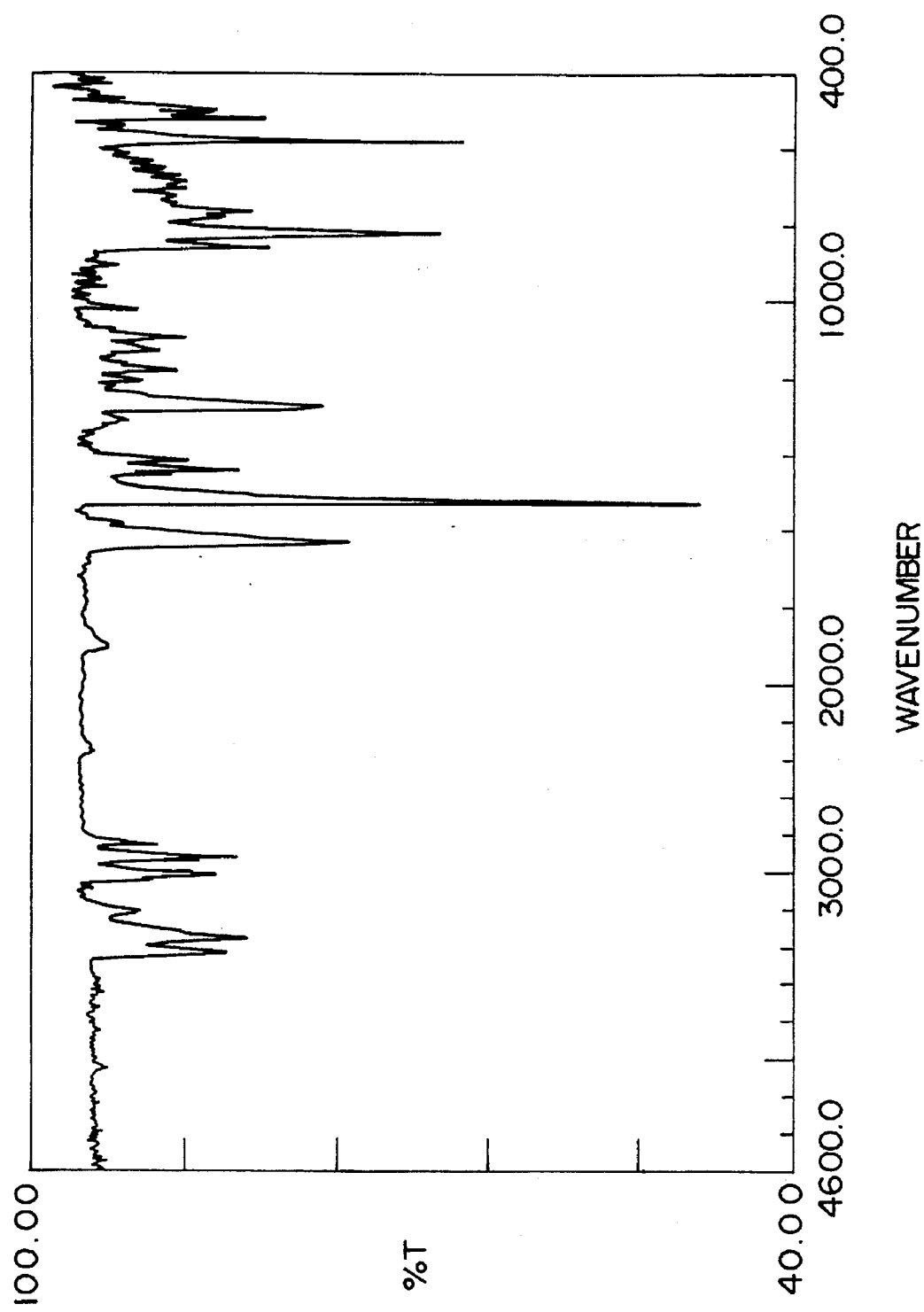

FIG. 9 is an infrared absorption spectrum diagram of the diamino compound obtained in Example 8.

Figure 10:
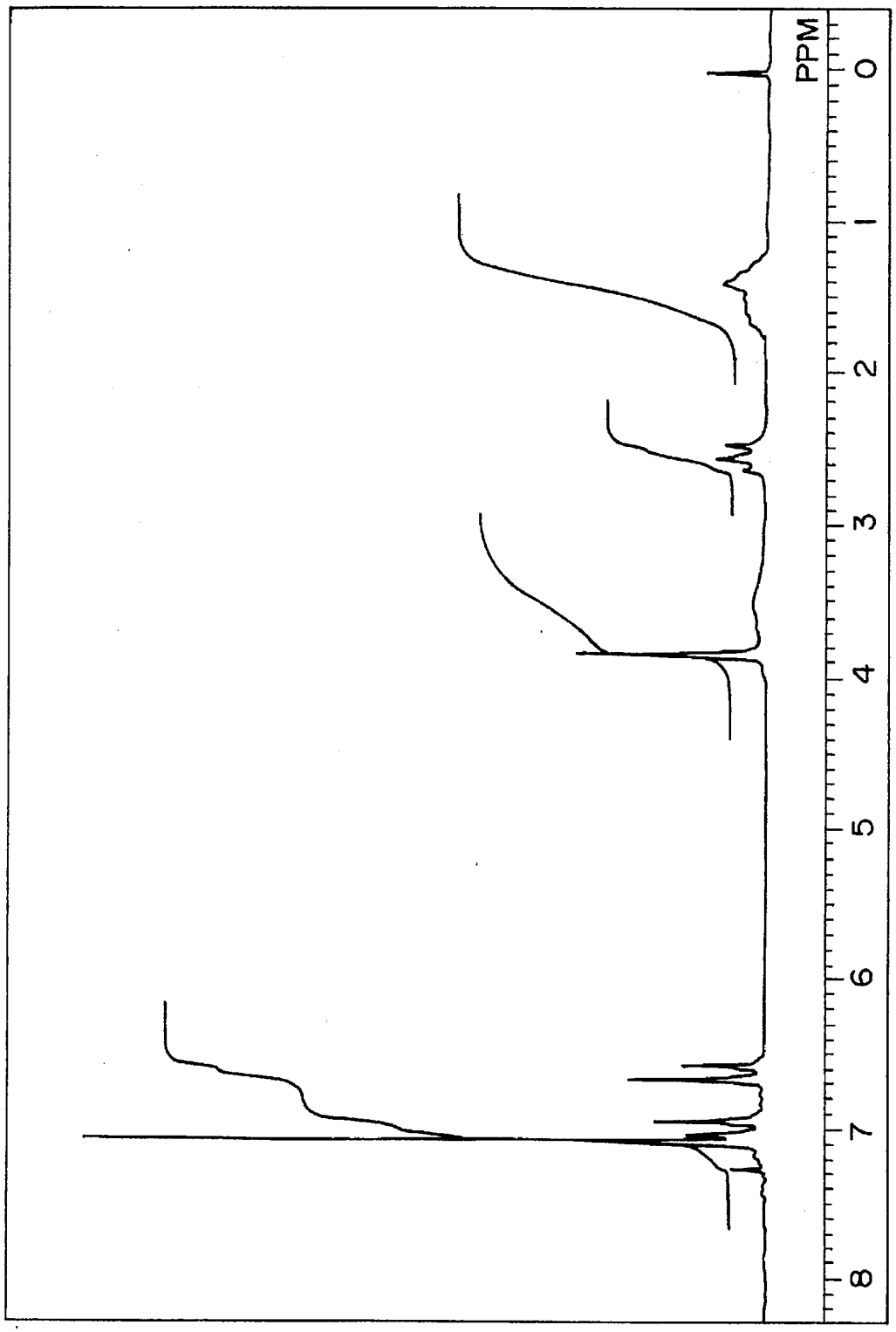

FIG. 10 is a 1H-NMR spectrum diagram of the diamino compound obtained in Example 9.

Figure 11:
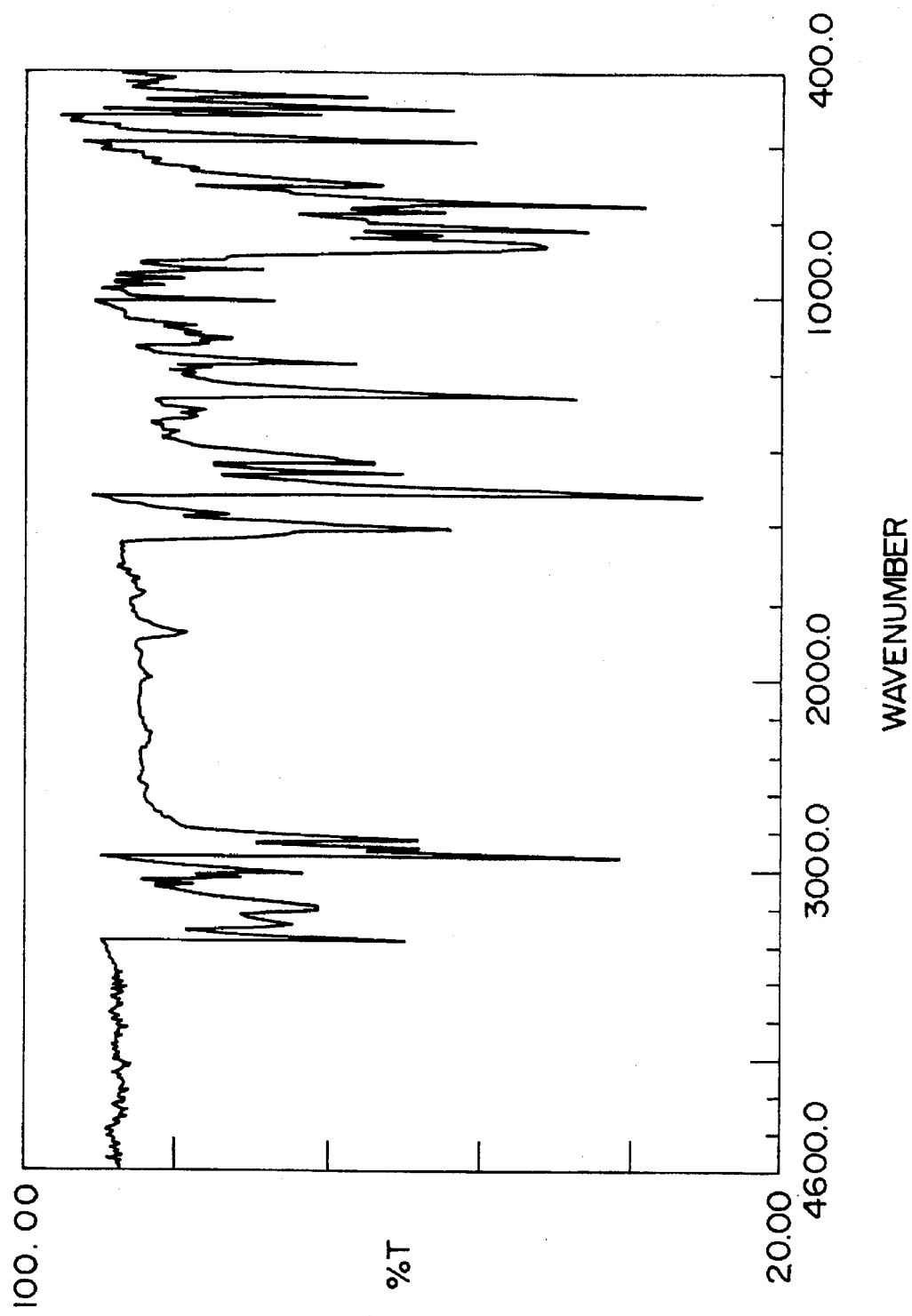

FIG. 11 is an infrared absorption spectrum diagram of the diamino compound obtained in Example 9.

Figure 12:
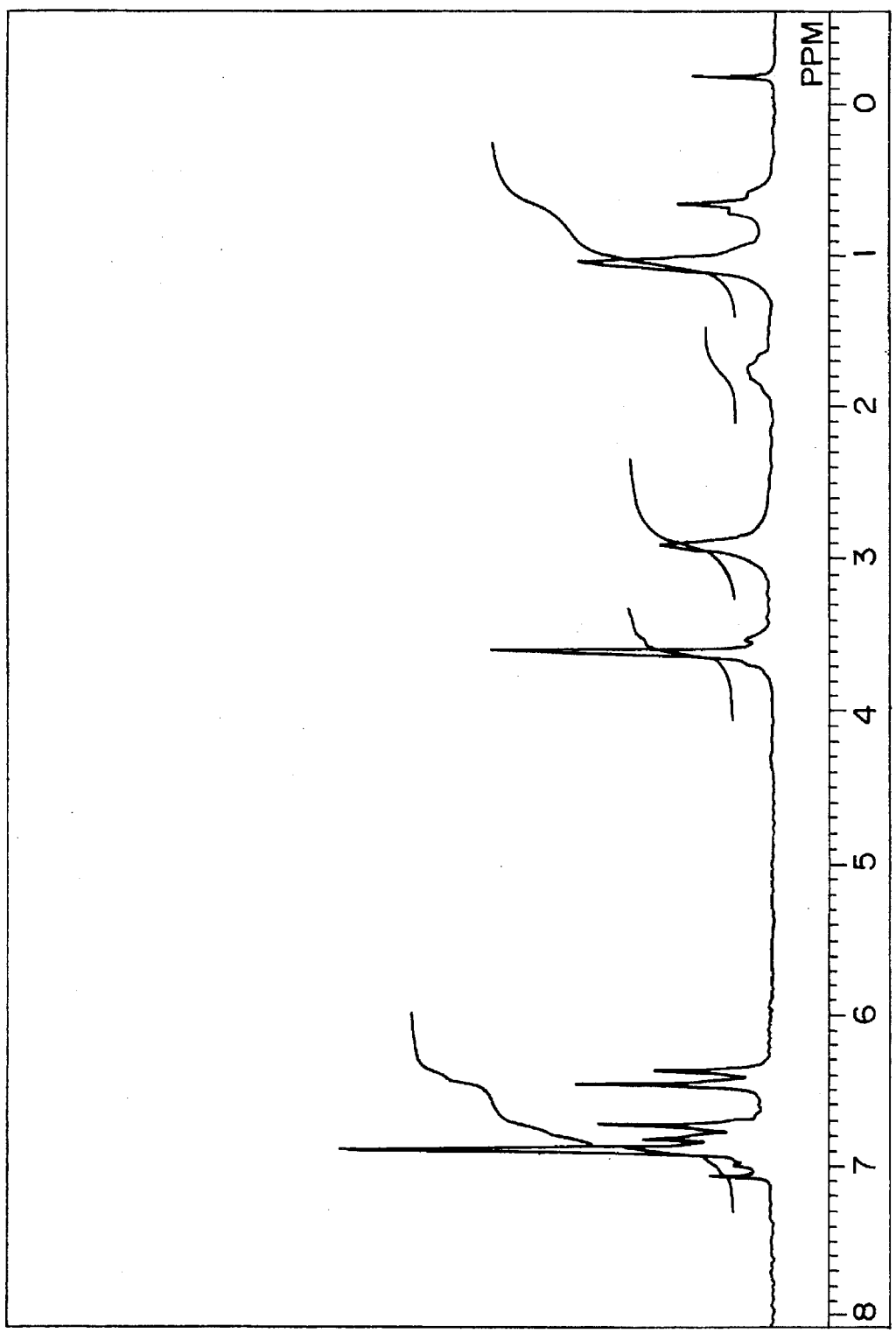

FIG. 12 is a 1H-NMR spectrum diagram of the diamino compound obtained in Example 10.

Figure 13:
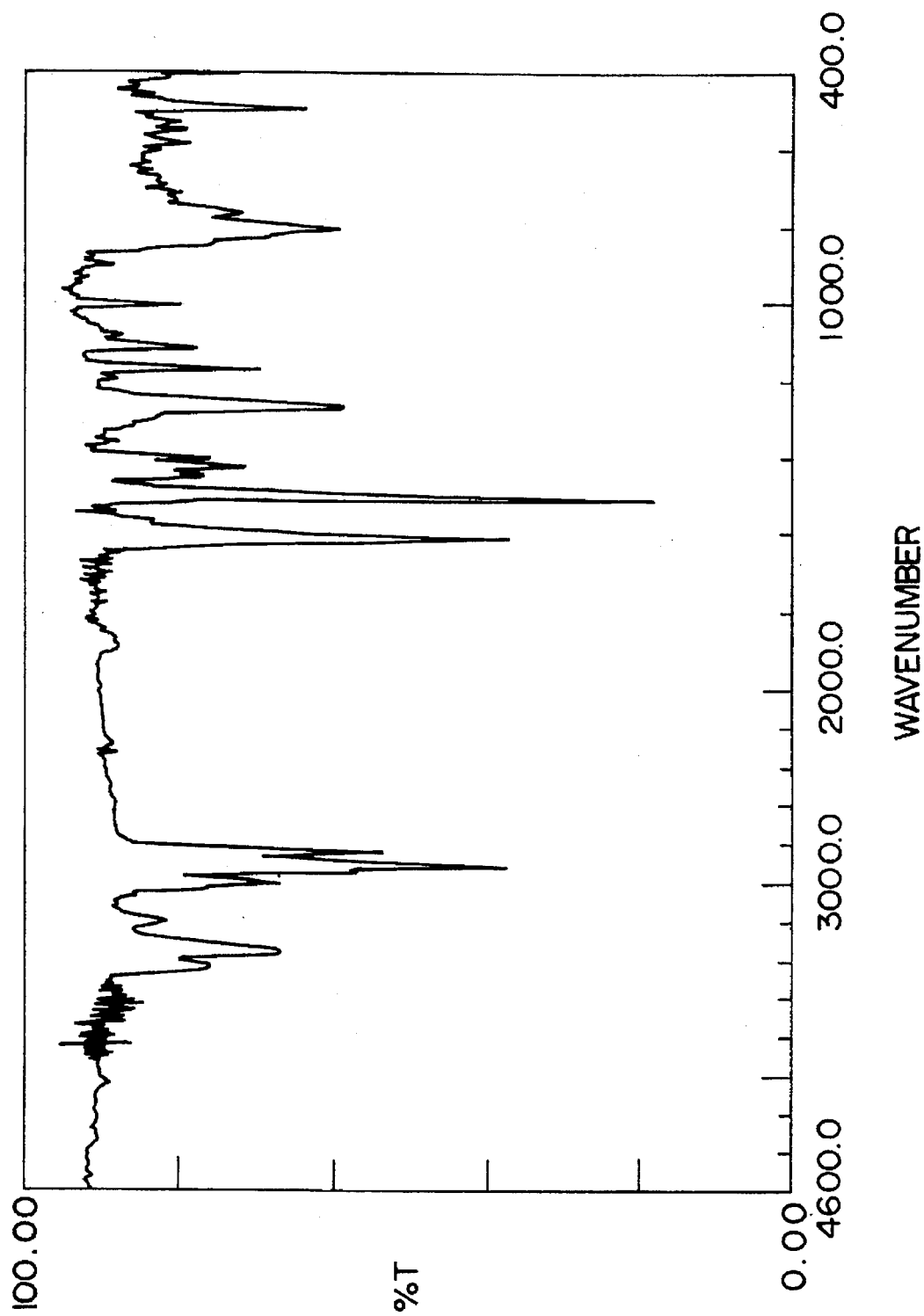

FIG. 13 is an infrared absorption spectrum diagram of the diamino compound obtained in Example 10.

Figure 14:
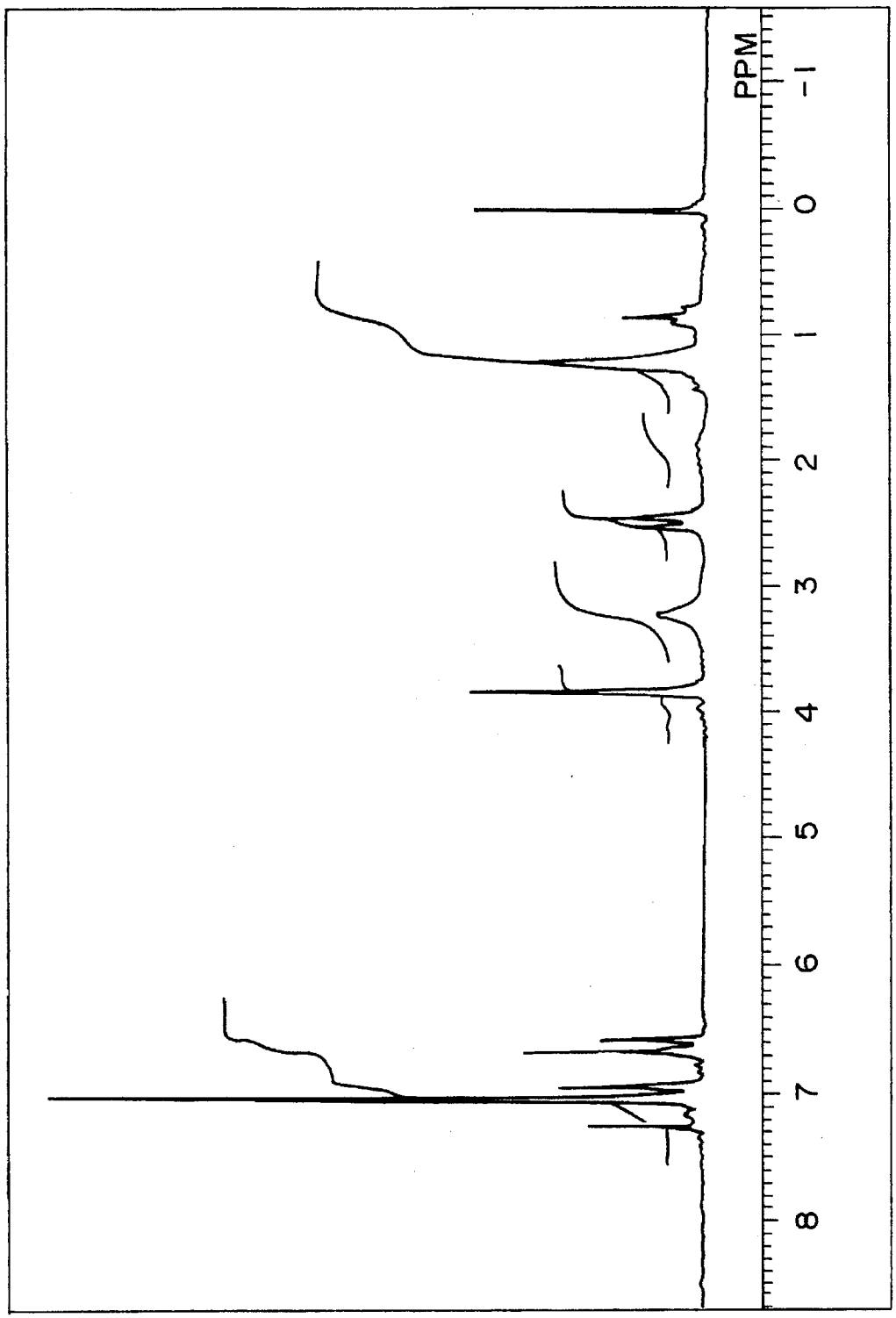

FIG. 14 is a 1H-NMR spectrum diagram of the diamino compound obtained in Example 11.

Figure 15:
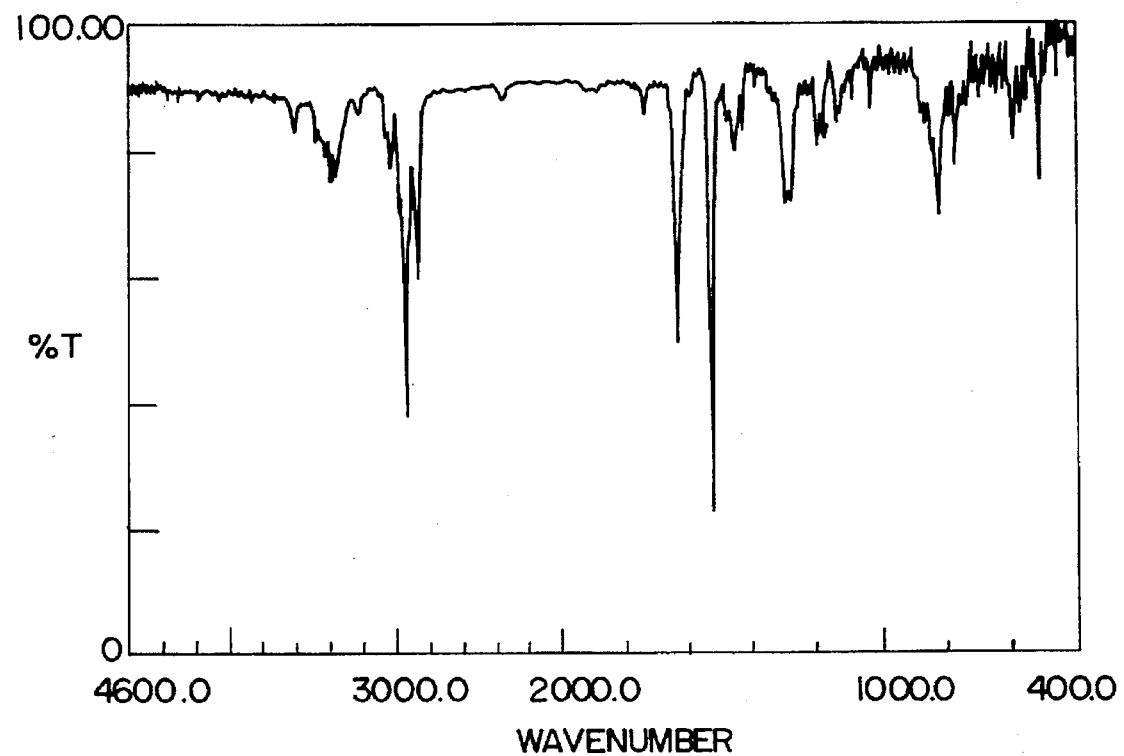

FIG. 15 is an infrared absorption spectrum diagram of the diamino compound obtained in Example 11.

Figure 16:
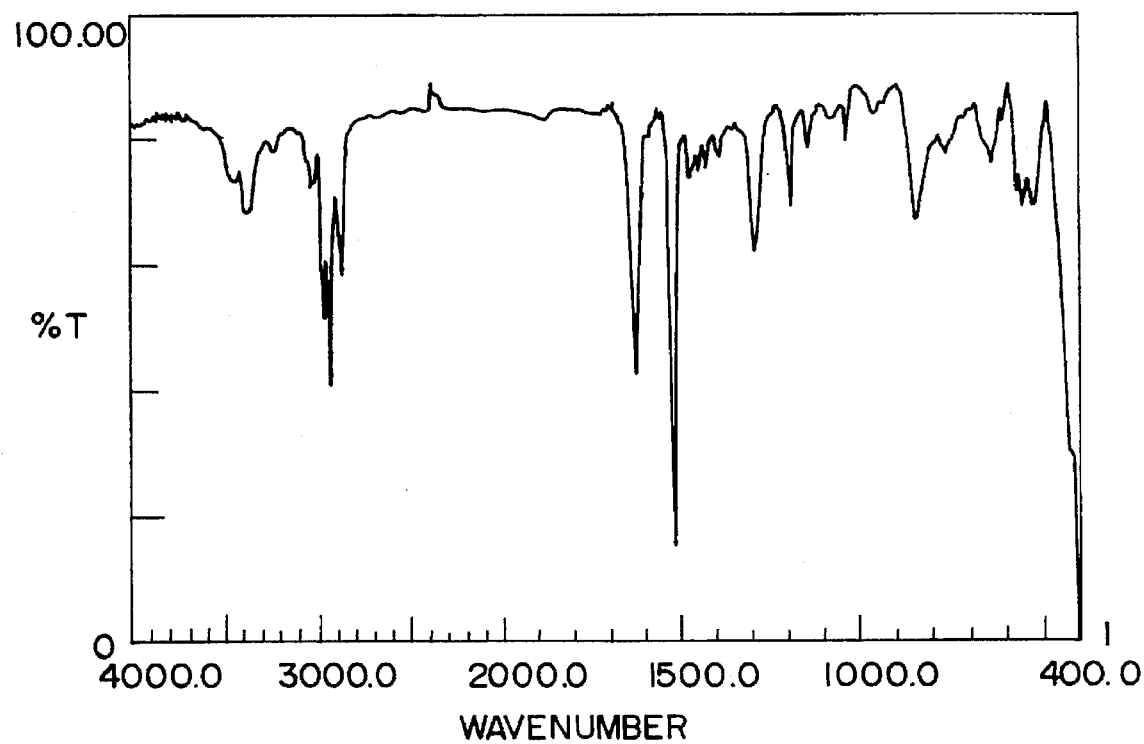

FIG. 16 is an infrared absorption spectrum diagram of the diamino compound obtained in Example 12.

Figure 17:
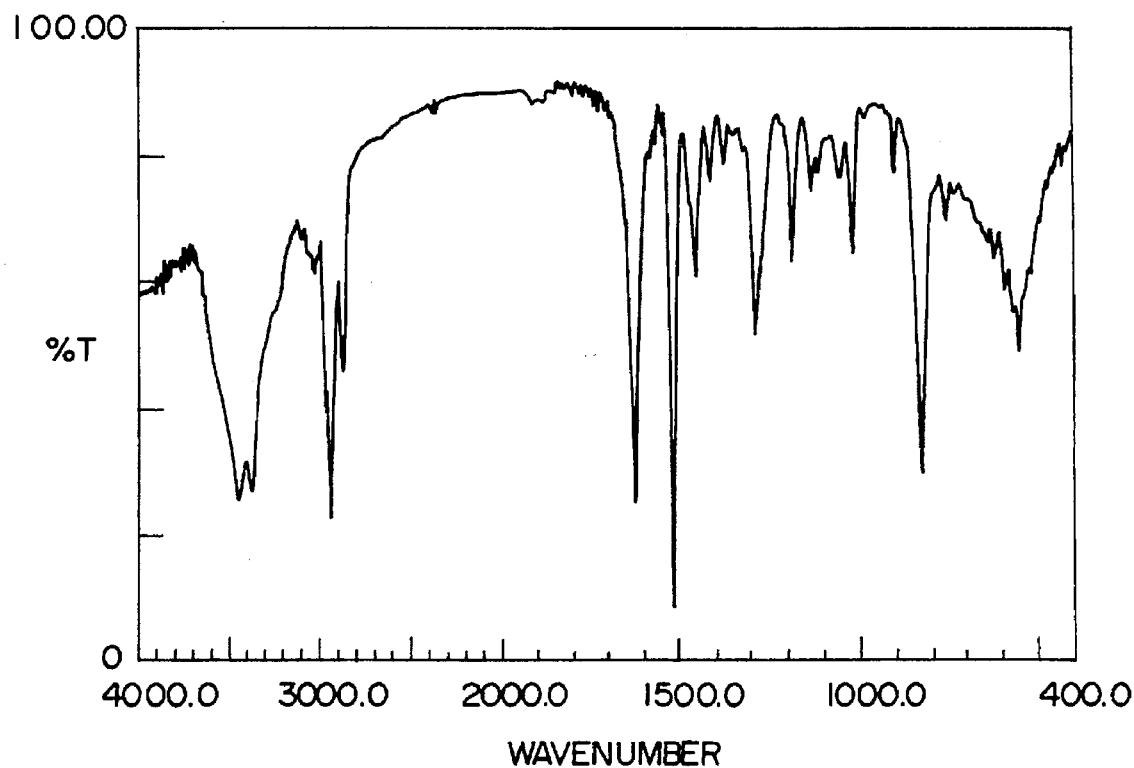

FIG. 17 is an infrared absorption spectrum diagram of the diamino compound obtained in Example 13.

Figure 18:
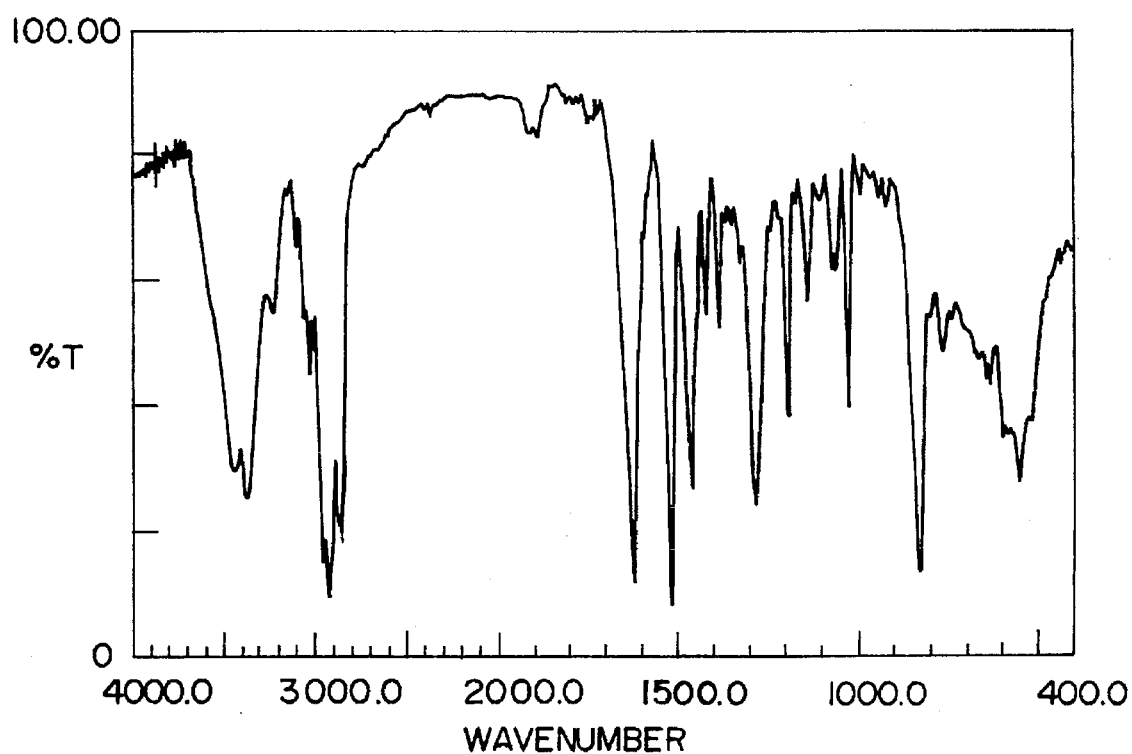

FIG. 18 is an infrared absorption spectrum diagram of the diamino compound obtained in Example 13.

DETAILED DESCRIPTION OF PREFERRED EMBODIMENTS

Diamino compounds according to the invention are expressed by the general formula (I), and specific examples thereof are mentioned as follows:
1,4-bis(4-(4-aminophenylmethyl)phenylmethyl)benzene,
1,4-bis(2-methyl-4-(4-aminophenylmethyl)phenylmethyl)benzene,
1,4-bis(2-ethyl-4-(4-aminophenylmethyl)phenylmethyl)benzene,
1,4-bis(2-propyl-4-(4-aminophenylmethyl)phenylmethyl)benzene,
1,4-bis(2-butyl-4-(4-aminophenylmethyl)phenylmethyl)benzene,
1,4-bis(2-pentyl-4-(4-aminophenylmethyl)phenylmethyl)benzene,
1,4-bis(2-hexyl-4-(4-aminophenylmethyl)phenylmethyl)benzene,
1,4-bis(2-heptyl-4-(4-aminophenylmethyl)phenylmethyl)benzene,
1,4-bis(2-octyl-4-(4-aminophenylmethyl)phenylmethyl)benzene,
1,4-bis(3-methyl-4-(4-aminophenylmethyl)phenylmethyl)benzene,
1,4-bis(3-ethyl-4-(4-aminophenylmethyl)phenylmethyl)benzene,
1,4-bis(3-propyl-4-(4-aminophenylmethyl)phenylmethyl)benzene,
1,4-bis(3-butyl-4-(4-aminophenylmethyl)phenylmethyl)benzene,
1,4-bis(3-pentyl-4-(4-aminophenylmethyl)phenylmethyl)benzene,
1,4-bis(3-hexyl-4-(4-aminophenylmethyl)phenylmethyl)benzene,
1,4-bis(3-heptyl-4-(4-aminophenylmethyl)phenylmethyl)benzene,
1,4-bis(3-octyl-4-(4-aminophenylmethyl)phenylmethyl)benzene,
1,4-bis(4-(4-aminophenylmethyl)phenylmethyl)-2-methylbenzene,
1,4-bis(4-(4-aminophenylmethyl)phenylmethyl)-2-ethylbenzene,
1,4-bis(4-(4-aminophenylmethyl)phenylmethyl)-2-propylbenzene,
1,4-bis(4-(4-aminophenylmethyl)phenylmethyl)-2-butylbenzene,
1,4-bis(4-(4-aminophenylmethyl)phenylmethyl)-2-pentylbenzene,
1,4-bis(4-(4-aminophenylmethyl)phenylmethyl)-2-hexylbenzene,
1,4-bis(4-(4-aminophenylmethyl)phenylmethyl)-2-heptylbenzene,
1,4-bis(4-(4-aminophenylmethyl)phenylmethyl)-2-octylbenzene,
1-(4-(4-aminophenylmethyl)phenylmethyl)-4-(2-methyl-4-(4-aminophenylmethyl)phenylmethyl)benzene,
1-(4-(4-aminophenylmethyl)phenylmethyl)-4-(2-ethyl-4-(4-aminophenylmethyl)phenylmethyl)benzene,
1-(4-(4-aminophenylmethyl)phenylmethyl)-4-(2-propyl-4-(4-aminophenylmethyl)phenylmethyl)benzene,
1-(4-(4-aminophenylmethyl)phenylmethyl)-4-(2-butyl-4-(4-aminophenylmethyl)phenylmethyl)benzene,
1-(4-(4-aminophenylmethyl)phenylmethyl)-4-(2-pentyl-4-(4-aminophenylmethyl)phenylmethyl)benzene,
1-(4-(4-aminophenylmethyl)phenylmethyl)-4-(2-hexyl-4-(4-aminophenylmethyl)phenylmethyl)benzene,
1-(4-(4-aminophenylmethyl)phenylmethyl)-4-(2-heptyl-4-(4-aminophenylmethyl)phenylmethyl)benzene,
1-(4-(4-aminophenylmethyl)phenylmethyl)-4-(2-octyl-4-(4-aminophenylmethyl)phenylmethyl)benzene,
1-(4-(4-aminophenylmethyl)phenylmethyl)-4-(3-methyl-4-(4-aminophenylmethyl)phenylmethyl)benzene,
1-(4-(4-aminophenylmethyl)phenylmethyl)-4-(3-ethyl-4-(4-aminophenylmethyl)phenylmethyl)benzene,
1-(4-(4-aminophenylmethyl)phenylmethyl)-4-(3-propyl-4-(4-aminophenylmethyl)phenylmethyl)benzene,
1-(4-(4-aminophenylmethyl)phenylmethyl)-4-(3-butyl-4-(4-aminophenylmethyl)phenylmethyl)benzene,
1-(4-(4-aminophenylmethyl)phenylmethyl)-4-(3-pentyl-4-(4-aminophenylmethyl)phenylmethyl)benzene,
1-(4-(4-aminophenylmethyl)phenylmethyl)-4-(3-hexyl-4-(4-aminophenylmethyl)phenylmethyl)benzene,
1-(4-(4-aminophenylmethyl)phenylmethyl)-4-(3-heptyl-4-(4-aminophenylmethyl)phenylmethyl)benzene,
1-(4-(4-aminophenylmethyl)phenylmethyl)-4-(3-octyl-4-(4-aminophenylmethyl)phenylmethyl)benzene,
1-(4-(4-aminophenylmethyl)phenylmethyl)-4-(2-methyl-4-(4-aminophenylmethyl)phenylmethyl)-2-methylbenzene,
1-(4-(4-aminophenylmethyl)phenylmethyl)-4-(2-ethyl-4-(4-aminophenylmethyl)phenylmethyl)-2-ethylbenzene,
1-(4-(4-aminophenylmethyl)phenylmethyl)-4-(2-propyl-4-(4-aminophenylmethyl)phenylmethyl)-2-propylbenzene,
1-(4-(4-aminophenylmethyl)phenylmethyl)-4-(2-butyl-4-(4-aminophenylmethyl)phenylmethyl)-2-butylbenzene,
1-(4-(4-aminophenylmethyl)phenylmethyl)-4-(2-pentyl-4-(4-aminophenylmethyl)phenylmethyl)-2-pentylbenzene,
1-(4-(4-aminophenylmethyl)phenylmethyl)-4-(2-hexyl-4-(4-aminophenylmethyl)phenylmethyl)-2-hexylbenzene,
1-(4-(4-aminophenylmethyl)phenylmethyl)-4-(2-heptyl-4-(4-aminophenylmethyl)phenylmethyl)-2-heptylbenzene,
1-(4-(4-aminophenylmethyl)phenylmethyl)-4-(2-octyl-4-(4-aminophenylmethyl)phenylmethyl)-2-octylbenzene,
1-(4-(4-aminophenylmethyl)phenylmethyl)-4-(3-methyl-4-(4-aminophenylmethyl)phenylmethyl)-2-methylbenzene, 1-(4-(4-aminophenylmethyl)phenylmethyl)-4-(3-ethyl-4-(4-aminophenylmethyl)phenylmethyl)-2-ethylbenzene,
1-(4-(4-aminophenylmethyl)phenylmethyl)-4-(3-propyl-4-(4-aminophenylmethyl)phenylmethyl)-2-propylbenzene,
1-(4-(4-aminophenylmethyl)phenylmethyl)-4-(3-butyl-4-(4-aminophenylmethyl)phenylmethyl)-2-butylbenzene,
1-(4-(4-aminophenylmethyl)phenylmethyl)-4-(3-pentyl-4-(4-aminophenylmethyl)phenylmethyl)-2-pentylbenzene,
1-(4-(4-aminophenylmethyl)phenylmethyl)-4-(3-hexyl-4-(4-aminophenylmethyl)phenylmethyl)-2-hexylbenzene,
1-(4-(4-aminophenylmethyl)phenylmethyl)-4-(3-heptyl-4-(4-aminophenylmethyl)phenylmethyl)-2-heptylbenzene,
1-(4-(4-aminophenylmethyl)phenylmethyl)-4-(3-octyl-4-(4-aminophenylmethyl)phenylmethyl)-2-octylbenzene,
1-(4-(4-aminophenylmethyl)phenylmethyl)-4-(2-ethyl-4-(4-aminophenylmethyl)phenylmethyl)-2-methylbenzene,
1-(4-(4-aminophenylmethyl)phenylmethyl)-4-(2-propyl-4-(4-aminophenylmethyl)phenylmethyl)-2-methylbenzene,
1-(4-(4-aminophenylmethyl)phenylmethyl)-4-(2-butyl-4-(4-aminophenylmethyl)phenylmethyl)-2-methylbenzene,
1-(4-(4-aminophenylmethyl)phenylmethyl)-4-(2-pentyl-4-(4-aminophenylmethyl)phenylmethyl)-2-methylbenzene,
1-(4-(4-aminophenylmethyl)phenylmethyl)-4-(2-hexyl-4-(4-aminophenylmethyl)phenylmethyl)-2-methylbenzene,
1-(4-(4-aminophenylmethyl)phenylmethyl)-4-(2-heptyl-4-(4-aminophenylmethyl)phenylmethyl)-2-methylbenzene,
1-(4-(4-aminophenylmethyl)phenylmethyl)-4-(2-octyl-4-(4-aminophenylmethyl)phenylmethyl)-2-methylbenzene,
1-(4-(4-aminophenylmethyl)phenylmethyl)-4-(3-ethyl-4-(4-aminophenylmethyl)phenylmethyl)-2-methylbenzene,
1-(4-(4-aminophenylmethyl)phenylmethyl)-4-(3-propyl-4-(4-aminophenylmethyl)phenylmethyl)-2-methylbenzene,
1-(4-(4-aminophenylmethyl)phenylmethyl)-4-(3-butyl-4-(4-aminophenylmethyl)phenylmethyl)-2-methylbenzene,
1-(4-(4-aminophenylmethyl)phenylmethyl)-4-(3-pentyl-4-(4-aminophenylmethyl)phenylmethyl)-2-methylbenzene,
1-(4-(4-aminophenylmethyl)phenylmethyl)-4-(3-hexyl-4-(4-aminophenylmethyl)phenylmethyl)-2-methylbenzene,
1-(4-(4-aminophenylmethyl)phenylmethyl)-4-(3-heptyl-4-(4-aminophenylmethyl)phenylmethyl)-2-methylbenzene,
1-(4-(4-aminophenylmethyl)phenylmethyl)-4-(3-octyl-4-(4-aminophenylmethyl)phenylmethyl)-2-methylbenzene,
1,1-bis(4-(4-(4-aminophenylmethyl)phenylmethyl)phenyl)methane,
1,1-bis(4-(2-methyl-4-(4-aminophenylmethyl)phenylmethyl)phenyl)methane,
1,1-bis(4-(2-ethyl-4-(4-aminophenylmethyl)phenylmethyl)phenyl)methane,
1,1-bis(4-(2-propyl-4-(4-aminophenylmethyl)phenylmethyl)phenyl)methane,
1,1-bis(4-(2-butyl-4-(4-aminophenylmethyl)phenylmethyl)phenyl)methane,
1,1-bis(4-(2-pentyl-4-(4-aminophenylmethyl)phenylmethyl)phenyl)methane,
1,1-bis(4-(2-hexyl-4-(4-aminophenylmethyl)phenylmethyl)phenyl)methane,
1,1-bis(4-(2-heptyl-4-(4-aminophenylmethyl)phenylmethyl)phenyl)methane,
1,1-bis(4-(2-octyl-4-(4-aminophenylmethyl)phenylmethyl)phenyl)methane,
1,1-bis(4-(3-methyl-4-(4-aminophenylmethyl)phenylmethyl)phenyl)methane,
1,1-bis(4-(3-ethyl-4-(4-aminophenylmethyl)phenylmethyl)phenyl)methane,
1,1-bis(4-(3-propyl-4-(4-aminophenylmethyl)phenylmethyl)phenyl)methane,
1,1-bis(4-(3-butyl-4-(4-aminophenylmethyl)phenylmethyl)phenyl)methane,
1,1-bis(4-(3-pentyl-4-(4-aminophenylmethyl)phenylmethyl)phenyl)methane,
1,1-bis(4-(3-hexyl-4-(4-aminophenylmethyl)phenylmethyl)phenyl)methane,
1,1-bis(4-(3-heptyl-4-(4-aminophenylmethyl)phenylmethyl)phenyl)methane,
1,1-bis(4-(3-octyl-4-(4-aminophenylmethyl)phenylmethyl)phenyl)methane,
1,1-bis(2-methyl-4-(4-(4-aminophenylmethyl)phenylmethyl)phenyl)methane,
1,1-bis(2-ethyl-4-(4-(4-aminophenylmethyl)phenylmethyl)phenyl)methane,
1,1-bis(2-propyl-4-(4-(4-aminophenylmethyl)phenylmethyl)phenyl)methane,
1,1-bis(2-butyl-4-(4-(4-aminophenylmethyl)phenylmethyl)phenyl)methane,
1,1-bis(2-pentyl-4-(4-(4-aminophenylmethyl)phenylmethyl)phenyl)methane,
1,1-bis(2-hexyl-4-(4-(4-aminophenylmethyl)phenylmethyl)phenyl)methane,
1,1-bis(2-heptyl-4-(4-(4-aminophenylmethyl)phenylmethyl)phenyl)methane,
1,1-bis(2-octyl-4-(4-(4-aminophenylmethyl)phenylmethyl)phenyl)methane,
1,1-bis(3-methyl-4-(4-(4-aminophenylmethyl)phenylmethyl)phenyl)methane,
1,1-bis(3-ethyl-4-(4-(4-aminophenylmethyl)phenylmethyl)phenyl)methane,
1,1-bis(3-propyl-4-(4-(4-aminophenylmethyl)phenylmethyl)phenyl)methane,
1,1-bis(3-butyl-4-(4-(4-aminophenylmethyl)phenylmethyl)phenyl)methane,
1,1-bis(3-pentyl-4-(4-(4-aminophenylmethyl)phenylmethyl)phenyl)methane,
1,1-bis(3-hexyl-4-(4-(4-aminophenylmethyl)phenylmethyl)phenyl)methane,
1,1-bis(3-heptyl-4-(4-(4-aminophenylmethyl)phenylmethyl)phenyl)methane,
1,1-bis(3-octyl-4-(4-(4-aminophenylmethyl)phenylmethyl)phenyl)methane,
1-(4-(4-(4-aminophenylmethyl)phenylmethyl)phenyl)-1-(2-methyl-4-(4-(4-aminophenylmethyl)phenylmethyl)phenyl)methane,
1-(4-(4-(4-aminophenylmethyl)phenylmethyl)phenyl)-1-(2-ethyl-4-(4-(4-aminophenylmethyl)phenylmethyl)phenyl)methane,
1-(4-(4-(4-aminophenylmethyl)phenylmethyl)phenyl)-1-(2-propyl-4-(4-(4-aminophenylmethyl)phenylmethyl)phenyl)methane,
1-(4-(4-(4-aminophenylmethyl)phenylmethyl)phenyl)-1-(2-butyl-4-(4-(4-aminophenylmethyl)phenylmethyl)phenyl)methane,
1-(4-(4-(4-aminophenylmethyl)phenylmethyl)phenyl)-1-(2-pentyl-4-(4-(4-aminophenylmethyl)phenylmethyl)phenyl)methane,
1-(4-(4-(4-aminophenylmethyl)phenylmethyl)phenyl)-1-(2-hexyl-4-(4-(4-aminophenylmethyl)phenylmethyl)phenyl)methane,
1-(4-(4-(4-aminophenylmethyl)phenylmethyl)phenyl)-1-(2-heptyl-4-(4-(4-aminophenylmethyl)phenylmethyl)phenyl)methane,
1-(4-(4-(4-aminophenylmethyl)phenylmethyl)phenyl)-1-(2-octyl-4-(4-(4-aminophenylmethyl)phenylmethyl)phenyl)methane,
1-(4-(4-(4-aminophenylmethyl)phenylmethyl)phenyl)-1-(3-methyl-4-(4-(4-aminophenylmethyl)phenylmethyl)phenyl)methane, 1-(4-(4-(4-aminophenylmethyl)phenylmethyl)phenyl)-1-(3-
ethyl-4-(4-(4-aminophenylmethyl)phenylmethyl)phenyl)
methane,
1-(4-(4-(4-aminophenylmethyl)phenylmethyl)phenyl)-1-(3-
propyl-4-(4-(4-aminophenylmethyl)phenylmethyl)
phenyl)methane,
1-(4-(4-(4-aminophenylmethyl)phenylmethyl)phenyl)-1-(3-
butyl-4-(4-(4-aminophenylmethyl)phenylmethyl)phenyl)
methane,
1-(4-(4-(4-aminophenylmethyl)phenylmethyl)phenyl)-1-(3-
pentyl-4-(4-(4-aminophenylmethyl)phenylmethyl)
phenyl)methane,
1-(4-(4-(4-aminophenylmethyl)phenylmethyl)phenyl)-1-(3-
hexyl-4-(4-(4-aminophenylmethyl)phenylmethyl)phenyl)
methane,
1-(4-(4-(4-aminophenylmethyl)phenylmethyl)phenyl)-1-(3-
heptyl-4-(4-(4-aminophenylmethyl)phenylmethyl)
phenyl)methane,
1-(4-(4-(4-aminophenylmethyl)phenylmethyl)phenyl)-1-(3-
octyl-4-(4-(4-aminophenylmethyl)phenylmethyl)phenyl)
methane,
1-(4-(4-(4-aminophenylmethyl)phenylmethyl)phenyl)-1-(4-
(2-methyl-4-(4-aminophenylmethyl)phenylmethyl)
phenyl)methane,
1-(4-(4-(4-aminophenylmethyl)phenylmethyl)phenyl)-1-(4-
(2-ethyl-4-(4-aminophenylmethyl)phenylmethyl)phenyl)
methane,
1-(4-(4-(4-aminophenylmethyl)phenylmethyl)phenyl)-1-(4-
(2-propyl-4-(4-aminophenylmethyl)phenylmethyl)
phenyl)methane,
1-(4-(4-(4-aminophenylmethyl)phenylmethyl)phenyl)-1-(4-
(2-butyl-4-(4-aminophenylmethyl)phenylmethyl)phenyl)
methane,
1-(4-(4-(4-aminophenylmethyl)phenylmethyl)phenyl)-1-(4-
(2-pentyl-4-(4-aminophenylmethyl)phenylmethyl)
phenyl)methane,
1-(4-(4-(4-aminophenylmethyl)phenylmethyl)phenyl)-1-(4-
(2-hexyl-4-(4-aminophenylmethyl)phenylmethyl)phenyl)
methane,
1-(4-(4-(4-aminophenylmethyl)phenylmethyl)phenyl)-1-(4-
(2-heptyl-4-(4-aminophenylmethyl)phenylmethyl)
phenyl)methane,
1-(4-(4-(4-aminophenylmethyl)phenylmethyl)phenyl)-1-(4-
(2-octyl-4-(4-aminophenylmethyl)phenylmethyl)phenyl)
methane,
1-(4-(4-(4-aminophenylmethyl)phenylmethyl)phenyl)-1-(4-
(3-methyl-4-(4-aminophenylmethyl)phenylmethyl)
phenyl)methane,
1-(4-(4-(4-aminophenylmethyl)phenylmethyl)phenyl)-1-(4-
(3-ethyl-4-(4-aminophenylmethyl)phenylmethyl)phenyl)
methane,
1-(4-(4-(4-aminophenylmethyl)phenylmethyl)phenyl)-1-(4-
(3-propyl-4-(4-aminophenylmethyl)phenylmethyl)
phenyl)methane,
1-(4-(4-(4-aminophenylmethyl)phenylmethyl)phenyl)-1-(4-
(3-butyl-4-(4-aminophenylmethyl)phenylmethyl)phenyl)
methane,
1-(4-(4-(4-aminophenylmethyl)phenylmethyl)phenyl)-1-(4-
(3-pentyl-4-(4-aminophenylmethyl)phenylmethyl)
phenyl)methane,
1-(4-(4-(4-aminophenylmethyl)phenylmethyl)phenyl)-1-(4-
(3-hexyl-4-(4-aminophenylmethyl)phenylmethyl)phenyl)
methane,
1-(4-(4-(4-aminophenylmethyl)phenylmethyl)phenyl)-1-(4-
(3-heptyl-4-(4-aminophenylmethyl)phenylmethyl)
phenyl)methane,
1-(4-(4-(4-aminophenylmethyl)phenylmethyl)phenyl)-1-(4-
(3-octyl-4-(4-aminophenylmethyl)phenylmethyl)phenyl)
methane,
1,2-bis(4-(4-aminobenzyl)phenyl)ethane,
1,3-bis(4-(4-aminobenzyl)phenyl)propane,
1,4-bis(4-(4-aminobenzyl)phenyl)butane,
1,5-bis(4-(4-aminobenzyl)phenyl)pentane,
1,6-bis(4-(4-aminobenzyl)phenyl)hexane,
1,7-bis(4-(4-aminobenzyl)phenyl)heptane,
1,8-bis(4-(4-aminobenzyl)phenyl)octane,
1,9-bis(4-(4-aminobenzyl)phenyl)nonane,
1,10-bis(4-(4-aminobenzyl)phenyl)decane,
1,11-bis(4-(4-aminobenzyl)phenyl)undecane,
1,12-bis(4-(4-aminobenzyl)phenyl)dodecane,
1,13-bis(4-(4-aminobenzyl)phenyl)tridecane,
1,14-bis(4-(4-aminobenzyl)phenyl)tetradecane,
1,15-bis(4-(4-aminobenzyl)phenyl)pentadecane,
1,16-bis(4-(4-aminobenzyl)phenyl)hexadecane,
1,17-bis(4-(4-aminobenzyl)phenyl)heptadecane,
1,18-bis(4-(4-aminobenzyl)phenyl)octadecane,
1,19-bis(4-(4-aminobenzyl)phenyl)nonadecane,
1,20-bis(4-(4-aminobenzyl)phenyl)icosane,
1,2-bis(2-methyl-4-(4-aminobenzyl)phenyl)ethane,
1,3-bis(2-methyl-4-(4-aminobenzyl)phenyl)propane,
1,4-bis(2-methyl-4-(4-aminobenzyl)phenyl)butane,
1,5-bis(2-methyl-4-(4-aminobenzyl)phenyl)pentane,
1,6-bis(2-methyl-4-(4-aminobenzyl)phenyl)hexane,
1,7-bis(2-methyl-4-(4-aminobenzyl)phenyl)heptane,
1,8-bis(2-methyl-4-(4-aminobenzyl)phenyl)octane,
1,9-bis(2-methyl-4-(4-aminobenzyl)phenyl)nonane,
1,10-bis(2-methyl-4-(4-aminobenzyl)phenyl)decane,
1,11-bis(2-methyl-4-(4-aminobenzyl)phenyl)undecane,
1,12-bis(2-methyl-4-(4-aminobenzyl)phenyl)dodecane,
1,13-bis(2-methyl-4-(4-aminobenzyl)phenyl)tridecane,
1,14-bis(2-methyl-4-(4-aminobenzyl)phenyl)tetradecane,
1,15-bis(2-methyl-4-(4-aminobenzyl)phenyl)pentadecane,
1,16-bis(2-methyl-4-(4-aminobenzyl)phenyl)hexadecane,
1,17-bis(2-methyl-4-(4-aminobenzyl)phenyl)heptadecane,
1,18-bis(2-methyl-4-(4-aminobenzyl)phenyl)octadecane,
1,19-bis(2-methyl-4-(4-aminobenzyl)phenyl)nonadecane,
1,20-bis(2-methyl-4-(4-aminobenzyl)phenyl)icosane,
1,2-bis(2-ethyl-4-(4-aminobenzyl)phenyl)ethane,
1,3-bis(2-ethyl-4-(4-aminobenzyl)phenyl)propane,
1,4-bis(2-ethyl-4-(4-aminobenzyl)phenyl)butane,
1,5-bis(2-ethyl-4-(4-aminobenzyl)phenyl)pentane,
1,6-bis(2-ethyl-4-(4-aminobenzyl)phenyl)hexane,
1,7-bis(2-ethyl-4-(4-aminobenzyl)phenyl)heptane,
1,8-bis(2-ethyl-4-(4-aminobenzyl)phenyl)octane,
1,9-bis(2-ethyl-4-(4-aminobenzyl)phenyl)nonane,
1,10-bis(2-ethyl-4-(4-aminobenzyl)phenyl)decane,
1,11-bis(2-ethyl-4-(4-aminobenzyl)phenyl)undecane,
1,12-bis(2-ethyl-4-(4-aminobenzyl)phenyl)dodecane,
1,13-bis(2-ethyl-4-(4-aminobenzyl)phenyl)tridecane,
1,14-bis(2-ethyl-4-(4-aminobenzyl)phenyl)tetradecane,
1,15-bis(2-ethyl-4-(4-aminobenzyl)phenyl)pentadecane,
1,16-bis(2-ethyl-4-(4-aminobenzyl)phenyl)hexadecane,
1,17(2-ethyl-4-(4-aminobenzyl)phenyl)heptadecane,
1,18-bis(2-ethyl-4-(4-aminobenzyl)phenyl)octadecane,
1,19-bis(2-ethyl-4-(4-aminobenzyl)phenyl)nonadecane,
1,20-bis(2-ethyl-4-(4-aminobenzyl)phenyl)icosane,
1,2-bis(2-propyl-4-(4-aminobenzyl)phenyl)ethane,
1,3-bis(2-propyl-4-(4-aminobenzyl)phenyl)propane,
1,4-bis(2-propyl-4-(4-aminobenzyl)phenyl)butane,
1,5-bis(2-propyl-4-(4-aminobenzyl)phenyl)pentane,
1,6-bis(2-propyl-4-(4-aminobenzyl)phenyl)hexane,
1,7-bis(2-propyl-4-(4-aminobenzyl)phenyl)heptane,
1,8-bis(2-propyl-4-(4-aminobenzyl)phenyl)octane,
1,9-bis(2-propyl-4-(4-aminobenzyl)phenyl)nonane,
1,10-bis(2-propyl-4-(4-aminobenzyl)phenyl)decane,
1,11-bis(2-propyl-4-(4-aminobenzyl)phenyl)undecane, 1,12-bis(2-propyl-4-(4-aminobenzyl)phenyl)dodecane,
1,13-bis(2-propyl-4-(4-aminobenzyl)phenyl)tridecane,
1,14-bis(2-propyl-4-(4-aminobenzyl)phenyl)tetradecane,
1,15-bis(2-propyl-4-(4-aminobenzyl)phenyl)pentadecane,
1,16-bis(2-propyl-4-(4-aminobenzyl)phenyl)hexadecane,
1,17-bis(2-propyl-4-(4-aminobenzyl)phenyl)heptadecane,
1,18-bis(2-propyl-4-(4-aminobenzyl)phenyl)octadecane,
1,19-bis(2-propyl-4-(4-aminobenzyl)phenyl)nonadecane,
1,20-bis(2-propyl-4-(4-aminobenzyl)phenyl)icosane,
1,2-bis(2-butyl-4-(4-aminobenzyl)phenyl)ethane,
1,3-bis(2-butyl-4-(4-aminobenzyl)phenyl)propane,
1,4-bis(2-butyl-4-(4-aminobenzyl)phenyl)butane,
1,5-bis(2-butyl-4-(4-aminobenzyl)phenyl)pentane,
1,6-bis(2-butyl-4-(4-aminobenzyl)phenyl)hexane,
1,7-bis(2-butyl-4-(4-aminobenzyl)phenyl)heptane,
1,8-bis(2-butyl-4-(4-aminobenzyl)phenyl)octane,
1,9-bis(2-butyl-4-(4-aminobenzyl)phenyl)nonane,
1,10-bis(2-butyl-4-(4-aminobenzyl)phenyl)decane,
1,11-bis(2-butyl-4-(4-aminobenzyl)phenyl)undecane,
1,12-bis(2-butyl-4-(4-aminobenzyl)phenyl)dodecane,
1,13-bis(2-butyl-4-(4-aminobenzyl)phenyl)tridecane,
1,14-bis(2-butyl-4-(4-aminobenzyl)phenyl)tetradecane,
1,15-bis(2-butyl-4-(4-aminobenzyl)phenyl)pentadecane,
1,16-bis(2-butyl-4-(4-aminobenzyl)phenyl)hexadecane,
1,17-bis(2-butyl-4-(4-aminobenzyl)phenyl)heptadecane,
1,18-bis(2-butyl-4-(4-aminobenzyl)phenyl)octadecane,
1,19-bis(2-butyl-4-(4-aminobenzyl)phenyl)nonadecane,
1,20-bis(2-butyl-4-(4-aminobenzyl)phenyl)icosane,
1,2-bis(2-pentyl-4-(4-aminobenzyl)phenyl)ethane,
1,3-bis(2-pentyl-4-(4-aminobenzyl)phenyl)propane,
1,4-bis(2-pentyl-4-(41aminobenzyl)phenyl)butane,
1,5-bis(2-pentyl-4-(4-aminobenzyl)phenyl)pentane,
1,6-bis(2-pentyl-4-(4-aminobenzyl)phenyl)hexane,
1,7-bis(2-pentyl-4-(4-aminobenzyl)phenyl)heptane,
1,8-bis(2-pentyl-4-(4-aminobenzyl)phenyl)octane,
1,9-bis(2-pentyl-4-(4-aminobenzyl)phenyl)nonane,
1,10-bis(2-pentyl-4-(4-aminobenzyl)phenyl)decane,
1,11-bis(2-pentyl-4-(4-aminobenzyl)phenyl)undecane,
1,12-bis(2-pentyl-4-(4-aminobenzyl)phenyl)dodecane,
1,13-bis(2-pentyl-4-(4-aminobenzyl)phenyl)tridecane,
1,14-bis(2-pentyl-4-(4-aminobenzyl)phenyl)tetradecane,
1,15-bis(2-pentyl-4-(4-aminobenzyl)phenyl)pentadecane,
1,16-bis(2-pentyl-4-(4-aminobenzyl)phenyl)hexadecane,
1,17-bis(2-pentyl-4-(4-aminobenzyl)phenyl)heptadecane,
1,18-bis(2-pentyl-4-(4-aminobenzyl)phenyl)octadecane,
1,19-bis(2-pentyl-4-(4-aminobenzyl)phenyl)nonadecane,
1,20-bis(2-pentyl-4-(4-aminobenzyl)phenyl)icosane,
1,2-bis(2-hexyl-4-(4-aminobenzyl)phenyl)ethane,
1,3-bis(2-hexyl-4-(4-aminobenzyl)phenyl)propane,
1,4-bis(2-hexyl-4-(4-aminobenzyl)phenyl)butane,
1,5-bis(2-hexyl-4-(4-aminobenzyl)phenyl)pentane,
1,6-bis(2-hexyl-4-(4-aminobenzyl)phenyl)hexane,
1,7-bis(2-hexyl-4-(4-aminobenzyl)phenyl)heptane,
1,8-bis(2-hexyl-4-(4-aminobenzyl)phenyl)octane,
1,9-bis(2-hexyl-4-(4-aminobenzyl)phenyl)nonane,
1,10-bis(2-hexyl-4-(4-aminobenzyl)phenyl)decane,
1,11-bis(2-hexyl-4-(4-aminobenzyl)phenyl)undecane,
1,12-bis(2-hexyl-4-(4-aminobenzyl)phenyl)dodecane,
1,13-bis(2-hexyl-4-(4-aminobenzyl)phenyl)tridecane,
1,14-bis(2-hexyl-4-(4-aminobenzyl)phenyl)tetradecane,
1,15-bis(2-hexyl-4-(4-aminobenzyl)phenyl)pentadecane,
1,16-bis(2-hexyl-4-(4-aminobenzyl)phenyl)hexadecane,
1,17-bis(2-hexyl-4-(4-aminobenzyl)phenyl)heptadecane,
1,18-bis(2-hexyl-4-(4-aminobenzyl)phenyl)octadecane,
1,19-bis(2-hexyl-4-(4-aminobenzyl)phenyl)nonadecane,
1,20-bis(2-hexyl-4-(4-aminobenzyl)phenyl)icosane,
1,2-bis(2-heptyl-4-(4-aminobenzyl)phenyl)ethane,
1,3-bis(2-heptyl-4-(4-aminobenzyl)phenyl)propane,
1,4-bis(2-heptyl-4-(4-aminobenzyl)phenyl)butane,
1,5-bis(2-heptyl-4-(4-aminobenzyl)phenyl)pentane,
1,6-bis(2-heptyl-4-(4-aminobenzyl)phenyl)hexane,
1,7-bis(2-heptyl-4-(4-aminobenzyl)phenyl)heptane,
1,8-bis(2-heptyl-4-(4-aminobenzyl)phenyl)octane,
1,9-bis(2-heptyl-4-(4-aminobenzyl)phenyl)nonane,
1,10-bis(2-heptyl-4-(4-aminobenzyl)phenyl)decane,
1,11-bis(2-heptyl-4-(4-aminobenzyl)phenyl)undecane,
1,12-bis(2-heptyl-4-(4-aminobenzyl)phenyl)dodecane,
1,13-bis(2-heptyl-4-(4-aminobenzyl)phenyl)tridecane,
1,14-bis(2-heptyl-4-(4-aminobenzyl)phenyl)tetradecane,
1,15-bis(2-heptyl-4-(4-aminobenzyl)phenyl)pentadecane,
1,16-bis(2-heptyl-4-(4-aminobenzyl)phenyl)hexadecane,
1,17-bis(2-heptyl-4-(4-aminobenzyl)phenyl)heptadecane,
1,18-bis(2-heptyl-4-(4-aminobenzyl)phenyl)octadecane,
1,19-bis(2-heptyl-4-(4-aminobenzyl)phenyl)nonadecane,
1,20-bis(2-heptyl-4-(4-aminobenzyl)phenyl)icosane,
1,2-bis(2-octyl-4-(4-aminobenzyl)phenyl)ethane,
1,3-bis(2-octyl-4-(4-aminobenzyl)phenyl)propane,
1,4-bis(2-octyl-4-(4-aminobenzyl)phenyl)butane,
1,5-bis(2-octyl-4-(4-aminobenzyl)phenyl)pentane,
1,6-bis(2-octyl-4-(4-aminobenzyl)phenyl)hexane,
1,7-bis(2-octyl-4-(4-aminobenzyl)phenyl)heptane,
1,8-bis(2-octyl-4-(4-aminobenzyl)phenyl)octane,
1,9-bis(2-octyl-4-(4-aminobenzyl)phenyl)nonane,
1,10-bis(2-octyl-4-(4-aminobenzyl)phenyl)decane,
1,11-bis(2-octyl-4-(4-aminobenzyl)phenyl)undecane,
1,12-bis(2-octyl-4-(4-aminobenzyl)phenyl)dodecane,
1,13-bis(2-octyl-4-(4-aminobenzyl)phenyl)tridecane,
1,14-bis(2-octyl-4-(4-aminobenzyl)phenyl)tetradecane,
1,15-bis(2-octyl-4-(4-aminobenzyl)phenyl)pentadecane,
1,16-bis(2-octyl-4-(4-aminobenzyl)phenyl)hexadecane,
1,17-bis(2-octyl-4-(4-aminobenzyl)phenyl)heptadecane,
1,18-bis(2-octyl-4-(4-aminobenzyl)phenyl)octadecane,
1,19-bis(2-octyl-4-(4-aminobenzyl)phenyl)nonadecane,
1,20-bis(2-octyl-4-(4-aminobenzyl)phenyl)icosane,
1,2-bis(3-methyl-4-(4-aminobenzyl)phenyl)ethane,
1,3-bis(3-methyl-4-(4-aminobenzyl)phenyl)propane,
1,4-bis(3-methyl-4-(4-aminobenzyl)phenyl)butane,
1,5-bis(3-methyl-4-(4-aminobenzyl)phenyl)pentane,
1,6-bis(3-methyl-4-(4-aminobenzyl)phenyl)hexane,
1,7-bis(3-methyl-4-(4-aminobenzyl)phenyl)heptane,
1,8-bis(3-methyl-4-(4-aminobenzyl)phenyl)octane,
1,9-bis(3-methyl-4-(4-aminobenzyl)phenyl)nonane,
1,10-bis(3-methyl-4-(4-aminobenzyl)phenyl)decane,
1,11-bis(3-methyl-4-(4-aminobenzyl)phenyl)undecane,
1,12-bis(3-methyl-4-(4-aminobenzyl)phenyl)dodecane,
1,13-bis(3-methyl-4-(4-aminobenzyl)phenyl)tridecane,
1,14-bis(3-methyl-4-(4-aminobenzyl)phenyl)tetradecane,
1,15-bis(3-methyl-4-(4-aminobenzyl)phenyl)pentadecane,
1,16-bis(3-methyl-4-(4-aminobenzyl)phenyl)hexadecane,
1,17-bis(3-methyl-4-(4-aminobenzyl)phenyl)heptadecane,
1,18-bis(3-methyl-4-(4-aminobenzyl)phenyl)octadecane,
1,19-bis(3-methyl-4-(4-aminobenzyl)phenyl)nonadecane,
1,20-bis(3-methyl-4-(4-aminobenzyl)phenyl)icosane,
1,2-bis(3-ethyl-4-(4-aminobenzyl)phenyl)ethane,
1,3-bis(3-ethyl-4-(4-aminobenzyl)phenyl)propane,
1,4-bis(3-ethyl-4-(4-aminobenzyl)phenyl)butane,
1,5-bis(3-ethyl-4-(4-aminobenzyl)phenyl)pentane,
1,6-bis(3-ethyl-4-(4-aminobenzyl)phenyl)hexane,
1,7-bis(3-ethyl-4-(4-aminobenzyl)phenyl)heptane,
1,8-bis(3-ethyl-4-(4-aminobenzyl)phenyl)octane,
1,9-bis(3-ethyl-4-(4-aminobenzyl)phenyl)nonane,
1,10-bis(3-ethyl-4-(4-aminobenzyl)phenyl)decane,
1,11-bis(3-ethyl-4-(4-aminobenzyl)phenyl)undecane,
1,12-bis(3-ethyl-4-(4-aminobenzyl)phenyl)dodecane, 1,13-bis(3-ethyl-4-(4-aminobenzyl)phenyl)tridecane,
1,14-bis(3-ethyl-4-(4-aminobenzyl)phenyl)tetradecane,
1,15-bis(3-ethyl-4-(4-aminobenzyl)phenyl)pentadecane,
1,16-bis(3-ethyl-4-(4-aminobenzyl)phenyl)hexadecane,
1,17-bis(3-ethyl-4-(4-aminobenzyl)phenyl)heptadecane,
1,18-bis(3-ethyl-4-(4-aminobenzyl)phenyl)octadecane,
1,19-bis(3-ethyl-4-(4-aminobenzyl)phenyl)nonadecane,
1,20-bis(3-ethyl-4-(4-aminobenzyl)phenyl)icosane,
1,2-bis(3-propyl-4-(4-aminobenzyl)phenyl)ethane,
1,3-bis(3-propyl-4-(4-aminobenzyl)phenyl)propane,
1,4-bis(3-propyl-4-(4-aminobenzyl)phenyl)butane,
1,5-bis(3-propyl-4-(4-aminobenzyl)phenyl)pentane,
1,6-bis(3-propyl-4-(4-aminobenzyl)phenyl)hexane,
1,7-bis(3-propyl-4-(4-aminobenzyl)phenyl)heptane,
1,8-bis(3-propyl-4-(4-aminobenzyl)phenyl)octane,
1,9-bis(3-propyl-4-(4-aminobenzyl)phenyl)nonane,
1,10-bis(3-propyl-4-(4-aminobenzyl)phenyl)decane,
1,11-bis(3-propyl-4-(4-aminobenzyl)phenyl)undecane,
1,12-bis(3-propyl-4-(4-aminobenzyl)phenyl)dodecane,
1,13-bis(3-propyl-4-(4-aminobenzyl)phenyl)tridecane,
1,14-bis(3-propyl-4-(4-aminobenzyl)phenyl)tetradecane,
1,15-bis(3-propyl-4-(4-aminobenzyl)phenyl)pentadecane,
1,16-bis(3-propyl-4-(4-aminobenzyl)phenyl)hexadecane,
1,17-bis(3-propyl-4-(4-aminobenzyl)phenyl)heptadecane,
1,18-bis(3-propyl-4-(4-aminobenzyl)phenyl)octadecane,
1,19-bis(3-propyl-4-(4-aminobenzyl)phenyl)nonadecane,
1,20-bis(3-propyl-4-(4-aminobenzyl)phenyl)icosane,
1,2-bis(3-butyl-4-(4-aminobenzyl)phenyl)ethane,
1,3-bis(3-butyl-4-(4-aminobenzyl)phenyl)propane,
1,4-bis(3-butyl-4-(4-aminobenzyl)phenyl)butane,
1,5-bis(3-butyl-4-(4-aminobenzyl)phenyl)pentane,
1,6-bis(3-butyl-4-(4-aminobenzyl)phenyl)hexane, 1,7-bis(3-butyl-4-(4-aminobenzyl)phenyl)heptane,
1,8-bis(3-butyl-4-(4-aminobenzyl)phenyl)octane,
1,9-bis(3-butyl-4-(4-aminobenzyl)phenyl)nonane,
1,10-bis(3-butyl-4-(4-aminobenzyl)phenyl)decane,
1,11-bis(3-butyl-4-(4-aminobenzyl)phenyl)undecane,
1,12-bis(3-butyl-4-(4-aminobenzyl)phenyl)dodecane,
1,13-bis(3-butyl-4-(4-aminobenzyl)phenyl)tridecane,
1,14-bis(3-butyl-4-(4-aminobenzyl)phenyl)tetradecane,
1,15-bis(3-butyl-4-(4-aminobenzyl)phenyl)pentadecane,
1,16-bis(3-butyl-4-(4-aminobenzyl)phenyl)hexadecane,
1,17-bis(3-butyl-4-(4-aminobenzyl)phenyl)heptadecane,
1,18-bis(3-butyl-4-(4-aminobenzyl)phenyl)octadecane,
1,19-bis(3-butyl-4-(4-aminobenzyl)phenyl)nonadecane,
1,20-bis(3-butyl-4-(4-aminobenzyl)phenyl)icosane,
1,2-bis(3-pentyl-4-(4-aminobenzyl)phenyl)ethane,
1,3-bis(3-pentyl-4-(4-aminobenzyl)phenyl)propane,
1,4-bis(3-pentyl-4-(4-aminobenzyl)phenyl)butane,
1,5-bis(3-pentyl-4-(4-aminobenzyl)phenyl)pentane,
1,6-bis(3-pentyl-4-(4-aminobenzyl)phenyl)hexane,
1,7-bis(3-pentyl-4-(4-aminobenzyl)phenyl)heptane,
1,8-bis(3-pentyl-4-(4-aminobenzyl)phenyl)octane,
1,9-bis(3-pentyl-4-(4-aminobenzyl)phenyl)nonane,
1,10-bis(3-pentyl-4-(4-aminobenzyl)phenyl)decane,
1,11-bis(3-pentyl-4-(4-aminobenzyl)phenyl)undecane,
1,12-bis(3-pentyl-4-(4-aminobenzyl)phenyl)dodecane,
1,13-bis(3-pentyl-4-(4-aminobenzyl)phenyl)tridecane,
1,14-bis(3-pentyl-4-(4-aminobenzyl)phenyl)tetradecane,
1,15-bis(3-pentyl-4-(4-aminobenzyl)phenyl)pentadecane,
1,16-bis(3-pentyl-4-(4-aminobenzyl)phenyl)hexadecane,
1,17-bis(3-pentyl-4-(4-aminobenzyl)phenyl)heptadecane,
1,18-bis(3-pentyl-4-(4-aminobenzyl)phenyl)octadecane,
1,19-bis(3-pentyl-4-(4-aminobenzyl)phenyl)nonadecane,
1,20-bis(3-pentyl-4-(4-aminobenzyl)phenyl)icosane,
1,2-bis(3-hexyl-4-(4-aminobenzyl)phenyl)ethane,
1,3-bis(3-hexyl-4-(4-aminobenzyl)phenyl)propane,
1,4-bis(3-hexyl-4-(4-aminobenzyl)phenyl)butane,
1,5-bis(3-hexyl-4-(4-aminobenzyl)phenyl)pentane,
1,6-bis(3-hexyl-4-(4-aminobenzyl)phenyl)hexane,
1,7-bis(3-hexyl-4-(4-aminobenzyl)phenyl)heptane,
1,8-bis(3-hexyl-4-(4-aminobenzyl)phenyl)octane,
1,9-bis(3-hexyl-4-(4-aminobenzyl)phenyl)nonane,
1,10-bis(3-hexyl-4-(4-aminobenzyl)phenyl)decane,
1,11-bis(3-hexyl-4-(4-aminobenzyl)phenyl)undecane,
1,12-bis(3-hexyl-4-(4-aminobenzyl)phenyl)dodecane,
1,13-bis(3-hexyl-4-(4-aminobenzyl)phenyl)tridecane,
1,14-bis(3-hexyl-4-(4-aminobenzyl)phenyl)tetradecane,
1,15-bis(3-hexyl-4-(4-aminobenzyl)phenyl)pentadecane,
1,16-bis(3-hexyl-4-(4-aminobenzyl)phenyl)hexadecane,
1,17-bis(3-hexyl-4-(4-aminobenzyl)phenyl)heptadecane,
1,18-bis(3-hexyl-4-(4-aminobenzyl)phenyl)octadecane,
1,19-bis(3-hexyl-4-(4-aminobenzyl)phenyl)nonadecane,
1,20-bis(3-hexyl-4-(4-aminobenzyl)phenyl)icosane,
1,2-bis(3-heptyl-4-(4-aminobenzyl)phenyl)ethane,
1,3-bis(3-heptyl-4-(4-aminobenzyl)phenyl)propane,
1,4-bis(3-heptyl-4-(4-aminobenzyl)phenyl)butane,
1,5-bis(3-heptyl-4-(4-aminobenzyl)phenyl)pentane,
1,6-bis(3-heptyl-4-(4-aminobenzyl)phenyl)hexane,
1,7-bis(3-heptyl-4-(4-aminobenzyl)phenyl)heptane,
1,8-bis(3-heptyl-4-(4-aminobenzyl)phenyl)octane,
1,9-bis(3-heptyl-4-(4-aminobenzyl)phenyl)nonane,
1,10-bis(3-heptyl-4-(4-aminobenzyl)phenyl)decane,
1,11-bis(3-heptyl-4-(4-aminobenzyl)phenyl)undecane,
1,12-bis(3-heptyl-4-(4-aminobenzyl)phenyl)dodecane,
1,13-bis(3-heptyl-4-(4-aminobenzyl)phenyl)tridecane,
1,14-bis(3-heptyl-4-(4-aminobenzyl)phenyl)tetradecane,
1,15-bis(3-heptyl-4-(4-aminobenzyl)phenyl)pentadecane,
1,16-bis(3-heptyl-4-(4-aminobenzyl)phenyl)hexadecane,
1,17-bis(3-heptyl-4-(4-aminobenzyl)phenyl)heptadecane,
1,18-bis(3-heptyl-4-(4-aminobenzyl)phenyl)octadecane,
1,19-bis(3-heptyl-4-(4-aminobenzyl)phenyl)nonadecane,
1,20-bis(3-heptyl-4-(4-aminobenzyl)phenyl)icosane,
1,2-bis(3-octyl-4-(4-aminobenzyl)phenyl)ethane,
1,3-bis(3-octyl-4-(4-aminobenzyl)phenyl)propane,
1,4-bis(3-octyl-4-(4-aminobenzyl)phenyl)butane,
1,5-bis(3-octyl-4-(4-aminobenzyl)phenyl)pentane,
1,6-bis(3-octyl-4-(4-aminobenzyl)phenyl)hexane,
1,7-bis(3-octyl-4-(4-aminobenzyl)phenyl)heptane,
1,8-bis(3-octyl-4-(4-aminobenzyl)phenyl)octane,
1,9-bis(3-octyl-4-(4-aminobenzyl)phenyl)nonane,
1,10-bis(3-octyl-4-(4-aminobenzyl)phenyl)decane,
1,11-bis(3-octyl-4-(4-aminobenzyl)phenyl)undecane,
1,12-bis(3-octyl-4-(4-aminobenzyl)phenyl)dodecane,
1,13-bis(3-octyl-4-(4-aminobenzyl)phenyl)tridecane,
1,14-bis(3-octyl-4-(4-aminobenzyl)phenyl)tetradecane,
1,15-bis(3-octyl-4-(4-aminobenzyl)phenyl)pentadecane,
1,16-bis(3-octyl-4-(4-aminobenzyl)phenyl)hexadecane,
1,17-bis(3-octyl-4-(4-aminobenzyl)phenyl)heptadecane,
1,18-bis(3-octyl-4-(4-aminobenzyl)phenyl)octadecane,
1,19-bis(3-octyl-4-(4-aminobenzyl)phenyl)nonadecane,
1,20-bis(3-octyl-4-(4-aminobenzyl)phenyl)icosane,
1,2-bis(4-(2-methyl-4-aminobenzyl)phenyl)ethane,
1,3-bis(4-(2-methyl-4-aminobenzyl)phenyl)propane,
1,4-bis(4-(2-methyl-4-aminobenzyl)phenyl)butane,
1,5-bis(4-(2-methyl-4-aminobenzyl)phenyl)pentane,
1,6-bis(4-(2-methyl-4-aminobenzyl)phenyl)hexane,
1,7-bis(4-(2-methyl-4-aminobenzyl)phenyl)heptane,
1,8-bis(4-(2-methyl-4-aminobenzyl)phenyl)octane,
1,9-bis(4-(2-methyl-4-aminobenzyl)phenyl)nonane,
1,10-bis(4-(2-methyl-4-aminobenzyl)phenyl)decane,
1,11-bis(4-(2-methyl-4-aminobenzyl)phenyl)undecane,
1,12-bis(4-(2-methyl-4-aminobenzyl)phenyl)dodecane,
1,13-bis(4-(2-methyl-4-aminobenzyl)phenyl)tridecane, 1,14-bis(4-(2-methyl-4-aminobenzyl)phenyl)tetradecane,
1,15-bis(4-(2-methyl-4-aminobenzyl)phenyl)pentadecane,
1,16-bis(4-(2-methyl-4-aminobenzyl)phenyl)hexadecane,
1,17-bis(4-(2-methyl-4-aminobenzyl)phenyl)heptadecane,
1,18-bis(4-(2-methyl-4-aminobenzyl)phenyl)octadecane,
1,19-bis(4-(2-methyl-4-aminobenzyl)phenyl)nonadecane,
1,20-bis(4-(2-methyl-4-aminobenzyl)phenyl)icosane,
1,2-bis(4-(2-ethyl-4-aminobenzyl)phenyl)ethane,
1,3-bis(4-(2-ethyl-4-aminobenzyl)phenyl)propane,
1,4-bis(4-(2-ethyl-4-aminobenzyl)phenyl)butane,
1,5-bis(4-(2-ethyl-4-aminobenzyl)phenyl)pentane,
1,6-bis(4-(2-ethyl-4-aminobenzyl)phenyl)hexane,
1,7-bis(4-(2-ethyl-4-aminobenzyl)phenyl)heptane,
1,8-bis(4-(2-ethyl-4-aminobenzyl)phenyl)octane,
1,9-bis(4-(2-ethyl-4-aminobenzyl)phenyl)nonane,
1,10-bis(4-(2-ethyl-4-aminobenzyl)phenyl)decane,
1,11-bis(4-(2-ethyl-4-aminobenzyl)phenyl)undecane,
1,12-bis(4-(2-ethyl-4-aminobenzyl)phenyl)dodecane,
1,13-bis(4-(2-ethyl-4-aminobenzyl)phenyl)tridecane,
1,14-bis(4-(2-ethyl-4-aminobenzyl)phenyl)tetradecane,
1,15-bis(4-(2-ethyl-4-aminobenzyl)phenyl)pentadecane,
1,16-bis(4-(2-ethyl-4-aminobenzyl)phenyl)hexadecane,
1,17-bis(4-(2-ethyl-4-aminobenzyl)phenyl)heptadecane,
1,18-bis(4-(2-ethyl-4-aminobenzyl)phenyl)octadecane,
1,19-bis(4-(2-ethyl-4-aminobenzyl)phenyl)nonadecane,
1,20-bis(4-(2-ethyl-4-aminobenzyl)phenyl)icosane,
1,2-bis(4-(2-propyl-4-aminobenzyl)phenyl)ethane,
1,3-bis(4-(2-propyl-4-aminobenzyl)phenyl)propane,
1,4-bis(4-(2-propyl-4-aminobenzyl)phenyl)butane,
1,5-bis(4-(2-propyl-4-aminobenzyl)phenyl)pentane,
1,6-bis(4-(2-propyl-4-aminobenzyl)phenyl)hexane,
1,7-bis(4-(2-propyl-4-aminobenzyl)phenyl)heptane,
1,8-bis(4-(2-propyl-4-aminobenzyl)phenyl)octane,
1,9-bis(4-(2-propyl-4-aminobenzyl)phenyl)nonane,
1,10-bis(4-(2-propyl-4-aminobenzyl)phenyl)decane,
1,11-bis(4-(2-propyl-4-aminobenzyl)phenyl)undecane,
1,12-bis(4-(2-propyl-4-aminobenzyl)phenyl)dodecane,
1,13-bis(4-(2-propyl-4-aminobenzyl)phenyl)tridecane,
1,14-bis(4-(2-propyl-4-aminobenzyl)phenyl)tetradecane,
1,15-bis(4-(2-propyl-4-aminobenzyl)phenyl)pentadecane,
1,16-bis(4-(2-propyl-4-aminobenzyl)phenyl)hexadecane,
1,17-bis(4-(2-propyl-4-aminobenzyl)phenyl)heptadecane,
1,18-bis(4-(2-propyl-4-aminobenzyl)phenyl)octadecane,
1,19-bis(4-(2-propyl-4-aminobenzyl)phenyl)nonadecane,
1,20-bis(4-(2-propyl-4-aminobenzyl)phenyl)icosane,
1,2-bis(4-(2-butyl-4-aminobenzyl)phenyl)ethane,
1,3-bis(4-(2-butyl-4-aminobenzyl)phenyl)propane,
1,4-bis(4-(2-butyl-4-aminobenzyl)phenyl)butane,
1,5-bis(4-(2-butyl-4-aminobenzyl)phenyl)pentane,
1,6-bis(4-(2-butyl-4-aminobenzyl)phenyl)hexane,
1,7-bis(4-(2-butyl-4-aminobenzyl)phenyl)heptane,
1,8-bis(4-(2-butyl-4-aminobenzyl)phenyl)octane,
1,9-bis(4-(2-butyl-4-aminobenzyl)phenyl)nonane,
1,10-bis(4-(2-butyl-4-aminobenzyl)phenyl)decane,
1,11-bis(4-(2-butyl-4-aminobenzyl)phenyl)undecane,
1,12-bis(4-(2-butyl-4-aminobenzyl)phenyl)dodecane,
1,13-bis(4-(2-butyl-4-aminobenzyl)phenyl)tridecane,
1,14-bis(4-(2-butyl-4-aminobenzyl)phenyl)tetradecane,
1,15-bis(4-(2-butyl-4-aminobenzyl)phenyl)pentadecane,
1,16-bis(4-(2-butyl-4-aminobenzyl)phenyl)hexadecane,
1,17-bis(4-(2-butyl-4-aminobenzyl)phenyl)heptadecane,
1,18-bis(4-(2-butyl-4-aminobenzyl)phenyl)octadecane,
1,19-bis(4-(2-butyl-4-aminobenzyl)phenyl)nonadecane,
1,20-bis(4-(2-butyl-4-aminobenzyl)phenyl)icosane,
1,2-bis(4-(2-pentyl-4-aminobenzyl)phenyl)ethane,
1,3-bis(4-(2-pentyl-4-aminobenzyl)phenyl)propane,
1,4-bis(4-(2-pentyl-4-aminobenzyl)phenyl)butane,
1,5-bis(4-(2-pentyl-4-aminobenzyl)phenyl)pentane,
1,6-bis(4-(2-pentyl-4-aminobenzyl)phenyl)hexane,
1,7-bis(4-(2-pentyl-4-aminobenzyl)phenyl)heptane,
1,8-bis(4-(2-pentyl-4-aminobenzyl)phenyl)octane,
1,9-bis(4-(2-pentyl-4-aminobenzyl)phenyl)nonane,
1,10-bis(4-(2-pentyl-4-aminobenzyl)phenyl)decane,
1,11-bis(4-(2-pentyl-4-aminobenzyl)phenyl)undecane,
1,12-bis(4-(2-pentyl-4-aminobenzyl)phenyl)dodecane,
1,13-bis(4-(2-pentyl-4-aminobenzyl)phenyl)tridecane,
1,14-bis(4-(2-pentyl-4-aminobenzyl)phenyl)tetradecane,
1,15-bis(4-(2-pentyl-4-aminobenzyl)phenyl)pentadecane,
1,16-bis(4-(2-pentyl-4-aminobenzyl)phenyl)hexadecane,
1,17-bis(4-(2-pentyl-4-aminobenzyl)phenyl)heptadecane,
1,18-bis(4-(2-pentyl-4-aminobenzyl)phenyl)octadecane,
1,19-bis(4-(2-pentyl-4-aminobenzyl)phenyl)nonadecane,
1,20-bis(4-(2-pentyl-4-aminobenzyl)phenyl)icosane,
1,2-bis(4-(2-hexyl-4-aminobenzyl)phenyl)ethane,
1,3-bis(4-(2-hexyl-4-aminobenzyl)phenyl)propane,
1,4-bis(4-(2-hexyl-4-aminobenzyl)phenyl)butane,
1,5-bis(4-(2-hexyl-4-aminobenzyl)phenyl)pentane,
1,6-bis(4-(2-hexyl-4-aminobenzyl)phenyl)hexane,
1,7-bis(4-(2-hexyl-4-aminobenzyl)phenyl)heptane,
1,8-bis(4-(2-hexyl-4-aminobenzyl)phenyl)octane,
1,9-bis(4-(2-hexyl-4-aminobenzyl)phenyl)nonane,
1,10-bis(4-(2-hexyl-4-aminobenzyl)phenyl)decane,
1,11-bis(4-(2-hexyl-4-aminobenzyl)phenyl)undecane,
1,12-bis(4-(2-hexyl-4-aminobenzyl)phenyl)dodecane,
1,13-bis(4-(2-hexyl-4-aminobenzyl)phenyl)tridecane,
1,14-bis(4-(2-hexyl-4-aminobenzyl)phenyl)tetradecane,
1,15-bis(4-(2-hexyl-4-aminobenzyl)phenyl)pentadecane,
1,16-bis(4-(2-hexyl-4-aminobenzyl)phenyl)hexadecane,
1,17-bis(4-(2-hexyl-4-aminobenzyl)phenyl)heptadecane,
1,18-bis(4-(2-hexyl-4-aminobenzyl)phenyl)octadecane,
1,19-bis(4-(2-hexyl-4-aminobenzyl)phenyl)nonadecane,
1,20-bis(4-(2-hexyl-4-aminobenzyl)phenyl)icosane,
1,2-bis(4-(2-heptyl-4-aminobenzyl)phenyl)ethane,
1,3-bis(4-(2heptyl-4-aminobenzyl)phenyl)propane,
1,4-bis(4-(2-heptyl-4-aminobenzyl)phenyl)butane,
1,5-bis(4-(2-heptyl-4-aminobenzyl)phenyl)pentane,
1,6-bis(4-(2-heptyl-4-aminobenzyl)phenyl)hexane,
1,7-bis(4-(2-heptyl-4-aminobenzyl)phenyl)heptane,
1,8-bis(4-(2-heptyl-4-aminobenzyl)phenyl)octane,
1,9-bis(4-(2-heptyl-4-aminobenzyl)phenyl)nonane,
1,10-bis(4-(2-heptyl-4-aminobenzyl)phenyl)decane,
1,11-bis(4-(2-heptyl-4-aminobenzyl)phenyl)undecane,
1,12-bis(4-(2-heptyl-4-aminobenzyl)phenyl)dodecane,
1,13-bis(4-(2-heptyl-4-aminobenzyl)phenyl)tridecane,
1,14-bis(4-(2-heptyl-4-aminobenzyl)phenyl)tetradecane,
1,15-bis(4-(2-heptyl-4-aminobenzyl)phenyl)pentadecane,
1,16-bis(4-(2-heptyl-4-aminobenzyl)phenyl)hexadecane,
1,17-bis(4-(2-heptyl-4-aminobenzyl)phenyl)heptadecane,
1,18-bis(4-(2-heptyl-4-aminobenzyl)phenyl)octadecane,
1,19-bis(4-(2-heptyl-4-aminobenzyl)phenyl)nonadecane,
1,20-bis(4-(2-heptyl-4-aminobenzyl)phenyl)icosane,
1,2-bis(4-(2-octyl-4-aminobenzyl)phenyl)ethane,
1,3-bis(4-(2-octyl-4-aminobenzyl)phenyl)propane,
1,4-bis(4-(2-octyl-4-aminobenzyl)phenyl)butane,
1,5-bis(4-(2-octyl-4-aminobenzyl)phenyl)pentane,
1,6-bis(4-(2-octyl-4-aminobenzyl)phenyl)hexane,
1,7-bis(4-(2-octyl-4-aminobenzyl)phenyl)heptane,
1,8-bis(4-(2-octyl-4-aminobenzyl)phenyl)octane,
1,9-bis(4-(2-octyl-4-aminobenzyl)phenyl)nonane,
1,10-bis(4-(2-octyl-4-aminobenzyl)phenyl)decane,
1,11-bis(4-(2-octyl-4-aminobenzyl)phenyl)undecane,
1,12-bis(4-(2-octyl-4-aminobenzyl)phenyl)dodecane,
1,13-bis(4-(2-octyl-4-aminobenzyl)phenyl)tridecane,
1,14-bis(4-(2-octyl-4-aminobenzyl)phenyl)tetradecane, 1,15-bis(4-(2-octyl-4-aminobenzyl)phenyl)pentadecane,
1,16-bis(4-(2-octyl-4-aminobenzyl)phenyl)hexadecane,
1,17-bis(4-(2-octyl-4-aminobenzyl)phenyl)heptadecane,
1,18-bis(4-(2-octyl-4-aminobenzyl)phenyl)octadecane,
1,19-bis(4-(2-octyl-4-aminobenzyl)phenyl)nonadecane,
1,20-bis(4-(2-octyl-4-aminobenzyl)phenyl)icosane,
1,2-bis(4-(3-methyl-4-aminobenzyl)phenyl)ethane,
1,3-bis(4-(3-methyl-4-aminobenzyl)phenyl)propane,
1,4-bis(4-(3-methyl-4-aminobenzyl)phenyl)butane,
1,5-bis(4-(3-methyl-4-aminobenzyl)phenyl)pentane,
1,6-bis(4-(3-methyl-4-aminobenzyl)phenyl)hexane,
1,7-bis(4-(3-methyl-4-aminobenzyl)phenyl)heptane,
1,8-bis(4-(3-methyl-4-aminobenzyl)phenyl)octane,
1,9-bis(4-(3-methyl-4-aminobenzyl)phenyl)nonane,
1,10-bis(4-(3-methyl-4-aminobenzyl)phenyl)decane,
1,11-bis(4-(3-methyl-4-aminobenzyl)phenyl)undecane,
1,12-bis(4-(3-methyl-4-aminobenzyl)phenyl)dodecane,
1,13-bis(4-(3-methyl-4-aminobenzyl)phenyl)tridecane,
1,14-bis(4-(3-methyl-4-aminobenzyl)phenyl)tetradecane,
1,15-bis(4-(3-methyl-4-aminobenzyl)phenyl)pentadecane,
1,16-bis(4-(3-methyl-4-aminobenzyl)phenyl)hexadecane,
1,17-bis(4-(3-methyl-4-aminobenzyl)phenyl)heptadecane,
1,18-bis(4-(3-methyl-4-aminobenzyl)phenyl)octadecane,
1,19-bis(4-(3-methyl-4-aminobenzyl)phenyl)nonadecane,
1,20-bis(4-(3-methyl-4-aminobenzyl)phenyl)icosane,
1,2-bis(4-(3-ethyl-4-aminobenzyl)phenyl)ethane,
1,3-bis(4-(3-ethyl-4-aminobenzyl)phenyl)propane,
1,4-bis(4-(3-ethyl-4-aminobenzyl)phenyl)butane,
1,5-bis(4-(3-ethyl-4-aminobenzyl)phenyl)pentane,
1,6-bis(4-(3-ethyl-4-aminobenzyl)phenyl)hexane,
1,7-bis(4-(3-ethyl-4-aminobenzyl)phenyl)heptane,
1,8-bis(4-(3-ethyl-4-aminobenzyl)phenyl)octane,
1,9-bis(4-(3-ethyl-4-aminobenzyl)phenyl)nonane,
1,10-bis(4-(3-ethyl-4-aminobenzyl)phenyl)decane,
1,11-bis(4-(3-ethyl-4-aminobenzyl)phenyl)undecane,
1,12-bis(4-(3-ethyl-4-aminobenzyl)phenyl)dodecane,
1,13-bis(4-(3-ethyl-4-aminobenzyl)phenyl)tridecane,
1,14-bis(4-(3-ethyl-4-aminobenzyl)phenyl)tetradecane,
1,15-bis(4-(3-ethyl-4-aminobenzyl)phenyl)pentadecane,
1,16-bis(4-(3-ethyl-4-aminobenzyl)phenyl)hexadecane,
1,17-bis(4-(3-ethyl-4-aminobenzyl)phenyl)heptadecane,
1,18-bis(4-(3-ethyl-4-aminobenzyl)phenyl)octadecane,
1,19-bis(4-(3-ethyl-4-aminobenzyl)phenyl)nonadecane,
1,20-bis(4-(3-ethyl-4-aminobenzyl)phenyl)icosane,
1,2-bis(4-(3-propyl-4-aminobenzyl)phenyl)ethane,
1,3-bis(4-(3-propyl-4-aminobenzyl)phenyl)propane,
1,4-bis(4-(3-propyl-4-aminobenzyl)phenyl)butane,
1,5-bis(4-(3-propyl-4-aminobenzyl)phenyl)pentane,
1,6-bis(4-(3-propyl-4-aminobenzyl)phenyl)hexane,
1,7-bis(4-(3-propyl-4-aminobenzyl)phenyl)heptane,
1,8-bis(4-(3-propyl-4-aminobenzyl)phenyl)octane,
1,9-bis(4-(3-propyl-4-aminobenzyl)phenyl)nonane,
1,10-bis(4-(3-propyl-4-aminobenzyl)phenyl)decane,
1,11-bis(4-(3-propyl-4-aminobenzyl)phenyl)undecane,
1,12-bis(4-(3-propyl-4-aminobenzyl)phenyl)dodecane,
1,13-bis(4-(3-propyl-4-aminobenzyl)phenyl)tridecane,
1,14-bis(4-(3-propyl-4-aminobenzyl)phenyl)tetradecane,
1,15-bis(4-(3-propyl-4-aminobenzyl)phenyl)pentadecane,
1,16-bis(4-(3-propyl-4-aminobenzyl)phenyl)hexadecane,
1,17-bis(4-(3-propyl-4-aminobenzyl)phenyl)heptadecane,
1,18-bis(4-(3-propyl-4-aminobenzyl)phenyl)octadecane,
1,19-bis(4-(3-propyl-4-aminobenzyl)phenyl)nonadecane,
1,20-bis(4-(3-propyl-4-aminobenzyl)phenyl)icosane,
1,2-bis(4-(3-butyl-4-aminobenzyl)phenyl)ethane,
1,3-bis(4-(3-butyl-4-aminobenzyl)phenyl)propane,
1,4-bis(4-(3-butyl-4-aminobenzyl)phenyl)butane,
1,5-bis(4-(3-butyl-4-aminobenzyl)phenyl)pentane,
1,6-bis(4-(3-butyl-4-aminobenzyl)phenyl)hexane,
1,7-bis(4-(3-butyl-4-aminobenzyl)phenyl)heptane,
1,8-bis(4-(3-butyl-4-aminobenzyl)phenyl)octane,
1,9-bis(4-(3-butyl-4-aminobenzyl)phenyl)nonane,
1,10-bis(4-(3-butyl-4-aminobenzyl)phenyl)decane,
1,11-bis(4-(3-butyl-4-aminobenzyl)phenyl)undecane,
1,12-bis(4-(3-butyl-4-aminobenzyl)phenyl)dodecane,
1,13-bis(4-(3-butyl-4-aminobenzyl)phenyl)tridecane,
1,14-bis(4-(3-butyl-4-aminobenzyl)phenyl)tetradecane,
1,15-bis(4-(3-butyl-4-aminobenzyl)phenyl)pentadecane,
1,16-bis(4-(3-butyl-4-aminobenzyl)phenyl)hexadecane,
1,17-bis(4-(3-butyl-4-aminobenzyl)phenyl)heptadecane,
1,18-bis(4-(3-butyl-4-aminobenzyl)phenyl)octadecane,
1,19-bis(4-(3-butyl-4-aminobenzyl)phenyl)nonadecane,
1,20-bis(4-(3-butyl-4-aminobenzyl)phenyl)icosane,
1,2-bis(4-(3-pentyl-4-aminobenzyl)phenyl)ethane,
1,3-bis(4-(3-pentyl-4-aminobenzyl)phenyl)propane,
1,4-bis(4-(3-pentyl-4-aminobenzyl)phenyl)butane,
1,5-bis(4-(3-pentyl-4-aminobenzyl)phenyl)pentane,
1,6-bis(4-(3-pentyl-4-aminobenzyl)phenyl)hexane,
1,7-bis(4-(3-pentyl-4-aminobenzyl)phenyl)heptane,
1,8-bis(4-(3-pentyl-4-aminobenzyl)phenyl)octane,
1,9-bis(4-(3-pentyl-4-aminobenzyl)phenyl)nonane,
1,10-bis(4-(3-pentyl-4-aminobenzyl)phenyl)decane,
1,11-bis(4-(3-pentyl-4-aminobenzyl)phenyl)undecane,
1,12-bis(4-(3-pentyl-4-aminobenzyl)phenyl)dodecane,
1,13-bis(4-(3-pentyl-4-aminobenzyl)phenyl)tridecane,
1,14-bis(4-(3-pentyl-4-aminobenzyl)phenyl)tetradecane,
1,15-bis(4-(3-pentyl-4-aminobenzyl)phenyl)pentadecane,
1,16-bis(4-(3-pentyl-4-aminobenzyl)phenyl)hexadecane,
1,17-bis(4-(3-pentyl-4-aminobenzyl)phenyl)heptadecane,
1,18-bis(4-(3-pentyl-4-aminobenzyl)phenyl)octadecane,
1,19-bis(4-(3-pentyl-4-aminobenzyl)phenyl)nonadecane,
1,20-bis(4-(3-pentyl-4-aminobenzyl)phenyl)icosane,
1,2-bis(4-(3-hexyl-4-aminobenzyl)phenyl)ethane,
1,3-bis(4-(3-hexyl-4-aminobenzyl)phenyl)propane,
1,4-bis(4-(3-hexyl-4-aminobenzyl)phenyl)butane,
1,5-bis(4-(3-hexyl-4-aminobenzyl)phenyl)pentane,
1,6-bis(4-(3-hexyl-4-aminobenzyl)phenyl)hexane,
1,7-bis(4-(3-hexyl-4-aminobenzyl)phenyl)heptane,
1,8-bis(4-(3-hexyl-4-aminobenzyl)phenyl)octane,
1,9-bis(4-(3-hexyl-4-aminobenzyl)phenyl)nonane,
1,10-bis(4-(3-hexyl-4-aminobenzyl)phenyl)decane,
1,11-bis(4-(3-hexyl-4-aminobenzyl)phenyl)undecane,
1,12-bis(4-(3-hexyl-4-aminobenzyl)phenyl)dodecane,
1,13-bis(4-(3-hexyl-4-aminobenzyl)phenyl)tridecane,
1,14-bis(4-(3-hexyl-4-aminobenzyl)phenyl)tetradecane,
1,15-bis(4-(3-hexyl-4-aminobenzyl)phenyl)pentadecane,
1,16-bis(4-(3-hexyl-4-aminobenzyl)phenyl)hexadecane,
1,17-bis(4-(3-hexyl-4-aminobenzyl)phenyl)heptadecane,
1,18-bis(4-(3-hexyl-4-aminobenzyl)phenyl)octadecane,
1,19-bis(4-(3-hexyl-4-aminobenzyl)phenyl)nonadecane,
1,20-bis(4-(3-hexyl-4-aminobenzyl)phenyl)icosane,
1,2-bis(4-(3-heptyl-4-aminobenzyl)phenyl)ethane,
1,3-bis(4-(3-heptyl-4-aminobenzyl)phenyl)propane,
1,4-bis(4-(3-heptyl-4-aminobenzyl)phenyl)butane,
1,5-bis(4-(3-heptyl-4-aminobenzyl)phenyl)pentane,
1,6-bis(4-(3-heptyl-4-aminobenzyl)phenyl)hexane,
1,7-bis(4-(3-heptyl-4-aminobenzyl)phenyl)heptane,
1,8-bis(4-(3-heptyl-4-aminobenzyl)phenyl)octane,
1,9-bis(4-(3-heptyl-4-aminobenzyl)phenyl)nonane,
1,10-bis(4-(3-heptyl-4-aminobenzyl)phenyl)decane,
1,11-bis(4-(3-heptyl-4-aminobenzyl)phenyl)undecane,
1,12-bis(4-(3-heptyl-4-aminobenzyl)phenyl)dodecane,
1,13-bis(4-(3-heptyl-4-aminobenzyl)phenyl)tridecane,
1,14-bis(4-(3-heptyl-4-aminobenzyl)phenyl)tetradecane,
1,15-bis(4-(3-heptyl-4-aminobenzyl)phenyl)pentadecane, 1,16-bis(4-(3-heptyl-4-aminobenzyl)phenyl)hexadecane,
1,17-bis(4-(3-heptyl-4-aminobenzyl)phenyl)heptadecane,
1,18-bis(4-(3-heptyl-4-aminobenzyl)phenyl)octadecane,
1,19-bis(4-(3-heptyl-4-aminobenzyl)phenyl)nonadecane,
1,20-bis(4-(3-heptyl-4-aminobenzyl)phenyl)icosane,
1,2-bis(4-(3-octyl-4-aminobenzyl)phenyl)ethane,
1,3-bis(4-(3-octyl-4-aminobenzyl)phenyl)propane,
1,4-bis(4-(3-octyl-4-aminobenzyl)phenyl)butane,
1,5-bis(4-(3-octyl-4-aminobenzyl)phenyl)pentane,
1,6-bis(4-(3-octyl-4-aminobenzyl)phenyl)hexane,
1,7-bis(4-(3-octyl-4-aminobenzyl)phenyl)heptane,
1,8-bis(4-(3-octyl-4-aminobenzyl)phenyl)octane,
1,9-bis(4-(3-octyl-4-aminobenzyl)phenyl)nonane,
1,10-bis(4-(3-octyl-4-aminobenzyl)phenyl)decane,
1,11-bis(4-(3-octyl-4-aminobenzyl)phenyl)undecane,
1,12-bis(4-(3-octyl-4-aminobenzyl)phenyl)dodecane,
1,13-bis(4-(3-octyl-4-aminobenzyl)phenyl)tridecane,
1,14-bis(4-(3-octyl-4-aminobenzyl)phenyl)tetradecane,
1,15-bis(4-(3-octyl-4-aminobenzyl)phenyl)pentadecane,
1,16-bis(4-(3-octyl-4-aminobenzyl)phenyl)hexadecane,
1,17-bis(4-(3-octyl-4-aminobenzyl)phenyl)heptadecane,
1,18-bis(4-(3-octyl-4-aminobenzyl)phenyl)octadecane,
1,19-bis(4-(3-octyl-4-aminobenzyl)phenyl)nonadecane,
1,20-bis(4-(3-octyl-4-aminobenzyl)phenyl)icosane,
1,2-bis(2,6-dimethyl-4-(4-aminobenzyl)phenyl)ethane,
1,3-bis(2,6-dimethyl-4-(4-aminobenzyl)phenyl)propane,
1,4-bis(2,6-dimethyl-4-(4-aminobenzyl)phenyl)butane,
1,5-bis(2,6-dimethyl-4-(4-aminobenzyl)phenyl)pentane,
1,6-bis(2,6-dimethyl-4-(4-aminobenzyl)phenyl)hexane,
1,7-bis(2,6-dimethyl-4-(4-aminobenzyl)phenyl)heptane,
1,8-bis(2,6-dimethyl-4-(4-aminobenzyl)phenyl)octane,
1,9-bis(2,6-dimethyl-4-(4-aminobenzyl)phenyl)nonane,
1,10-bis(2,6-dimethyl-4-(4-aminobenzyl)phenyl)decane,
1,11-bis(2,6-dimethyl-4-(4-aminobenzyl)phenyl)undecane,
1,12-bis(2,6-dimethyl-4-(4-aminobenzyl)phenyl)dodecane,
1,13-bis(2,6-dimethyl-4-(4-aminobenzyl)phenyl)tridecane,
1,14-bis(2,6-dimethyl-4-(4-aminobenzyl)phenyl)tetradecane,
1,15-bis(2,6-dimethyl-4-(4-aminobenzyl)phenyl)pentadecane,
1,16-bis(2,6-dimethyl-4-(4-aminobenzyl)phenyl)hexadecane,
1,17-bis(2,6-dimethyl-4-(4-aminobenzyl)phenyl)heptadecane,
1,18-bis(2,6-dimethyl-4-(4-aminobenzyl)phenyl)octadecane,
1,19-bis(2,6-dimethyl-4-(4-aminobenzyl)phenyl)nonadecane,
1,20-bis(2,6-dimethyl-4-(4-aminobenzyl)phenyl)icosane,
1,2-bis(3,5-dimethyl-4-(4-aminobenzyl)phenyl)ethane,
1,3-bis(3,5-dimethyl-4-(4-aminobenzyl)phenyl)propane,
1,4-bis(3,5-dimethyl-4-(4-aminobenzyl)phenyl)butane,
1,5-bis(3,5-dimethyl-4-(4-aminobenzyl)phenyl)pentane,
1,6-bis(3,5-dimethyl-4-(4-aminobenzyl)phenyl)hexane,
1,7-bis(3,5-dimethyl-4-(4-aminobenzyl)phenyl)heptane,
1,8-bis(3,5-dimethyl-4-(4-aminobenzyl)phenyl)octane,
1,9-bis(3,5-dimethyl-4-(4-aminobenzyl)phenyl)nonane,
1,10-bis(3,5-dimethyl-4-(4-aminobenzyl)phenyl)decane,
1,11-bis(3,5-dimethyl-4-(4-aminobenzyl)phenyl)undecane,
1,12-bis(3,5-dimethyl-4-(4-aminobenzyl)phenyl)dodecane,
1,13-bis(3,5-dimethyl-4-(4-aminobenzyl)phenyl)tridecane,
1,14-bis(3,5-dimethyl-4-(4-aminobenzyl)phenyl)tetradecane,
1,15-bis(3,5-dimethyl-4-(4-aminobenzyl)phenyl)pentadecane,
1,16-bis(3,5-dimethyl-4-(4-aminobenzyl)phenyl)hexadecane,
1,17-bis(3,5-dimethyl-4-(4-aminobenzyl)phenyl)heptadecane,
1,18-bis(3,5-dimethyl-4-(4-aminobenzyl)phenyl)octadecane,
1,19-bis(3,5-dimethyl-4-(4-aminobenzyl)phenyl)nonadecane,
1,20-bis(3,5-dimethyl-4-(4-aminobenzyl)phenyl)icosane,
1,2-bis(2,3,5,6-tetramethyl-4-(4-aminobenzyl)phenyl)ethane,
1,3-bis(2,3,5,6-tetramethyl-4-(4-aminobenzyl)phenyl)propane,
1,4-bis(2,3,5,6-tetramethyl-4-(4-aminobenzyl)phenyl)butane,
1,5-bis(2,3,5,6-tetramethyl-4-(4-aminobenzyl)phenyl)pentane,
1,6-bis(2,3,5,6-tetramethyl-4-(4-aminobenzyl)phenyl)hexane,
1,7-bis(2,3,5,6-tetramethyl-4-(4-aminobenzyl)phenyl)heptane,
1,8-bis(2,3,5,6-tetramethyl-4-(4-aminobenzyl)phenyl)octane,
1,9-bis(2,3,5,6-tetramethyl-4-(4-aminobenzyl)phenyl)nonane,
1,10-bis(2,3,5,6-tetramethyl-4-(4-aminobenzyl)phenyl)decane,
1,11-bis(2,3,5,6-tetramethyl-4-(4-aminobenzyl)phenyl)undecane,
1,12-bis(2,3,5,6-tetramethyl-4-(4-aminobenzyl)phenyl)dodecane,
1,13-bis(2,3,5,6-tetramethyl-4-(4-aminobenzyl)phenyl)tridecane,
1,14-bis(2,3,5,6-tetramethyl-4-(4-aminobenzyl)phenyl)tetradecane,
1,15-bis(2,3,5,6-tetramethyl-4-(4-aminobenzyl)phenyl)pentadecane,
1,16-bis(2,3,5,6-tetramethyl-4-(4-aminobenzyl)phenyl)hexadecane,
1,17-bis(2,3,5,6-tetramethyl-4-(4-aminobenzyl)phenyl)heptadecane,
1,18-bis(2,3,5,6-tetramethyl-4-(4-aminobenzyl)phenyl)octadecane,
1,19-bis(2,3,5,6-tetramethyl-4-(4-aminobenzyl)phenyl)nonadecane,
1,20-bis(2,3,5,6-tetramethyl-4-(4-aminobenzyl)phenyl)icosane,
1,2-bis(4-(2,6-dimethyl-4-aminobenzyl)phenyl)ethane,
1,3-bis(4-(2,6-dimethyl-4-aminobenzyl)phenyl)propane,
1,4-bis(4-(2,6-dimethyl-4-aminobenzyl)phenyl)butane,
1,5-bis(4-(2,6-dimethyl-4-aminobenzyl)phenyl)pentane,
1,6-bis(4-(2,6-dimethyl-4-aminobenzyl)phenyl)hexane,
1,7-bis(4-(2,6-dimethyl-4-aminobenzyl)phenyl)heptane,
1,8-bis(4-(2,6-dimethyl-4-aminobenzyl)phenyl)octane,
1,9-bis(4-(2,6-dimethyl-4-aminobenzyl)phenyl)nonane,
1,10-bis(4-(2,6-dimethyl-4-aminobenzyl)phenyl)decane,
1,11-bis(4-(2,6-dimethyl-4-aminobenzyl)phenyl)undecane,
1,12-bis(4-(2,6-dimethyl-4-aminobenzyl)phenyl)dodecane,
1,13-bis(4-(2,6-dimethyl-4-aminobenzyl)phenyl)tridecane,
1,14-bis(4-(2,6-dimethyl-4-aminobenzyl)phenyl)tetradecane,
1,15-bis(4-(2,6-dimethyl-4-aminobenzyl)phenyl)pentadecane,
1,16-bis(4-(2,6-dimethyl-4-aminobenzyl)phenyl)hexadecane,
1,17-bis(4-(2,6-dimethyl-4-aminobenzyl)phenyl)heptadecane,
1,18-bis(4-(2,6-dimethyl-4-aminobenzyl)phenyl)octadecane, 1,19-bis(4-(2,6-dimethyl-4-aminobenzyl)phenyl)
nonadecane,
1,20-bis(4-(2,6-dimethyl-4-aminobenzyl)phenyl)icosane,
1,2-bis(4-(3,5-dimethyl-4-aminobenzyl)phenyl)ethane,
1,3-bis(4-(3,5-dimethyl-4-aminobenzyl)phenyl)propane,
1,4-bis(4-(3,5-dimethyl-4-aminobenzyl)phenyl)butane,
1,5-bis(4-(3,5-dimethyl-4-aminobenzyl)phenyl)pentane,
1,6-bis(4-(3,5-dimethyl-4-aminobenzyl)phenyl)hexane,
1,7-bis(4-(3,5-dimethyl-4-aminobenzyl)phenyl)heptane,
1,8-bis(4-(3,5-dimethyl-4-aminobenzyl)phenyl)octane,
1,9-bis(4-(3,5-dimethyl-4-aminobenzyl)phenyl)nonane,
1,10-bis(4-(3,5-dimethyl-4-aminobenzyl)phenyl)decane,
1,11-bis(4-(3,5-dimethyl-4-aminobenzyl)phenyl)undecane,
1,12-bis(4-(3,5-dimethyl-4-aminobenzyl)phenyl)dodecane,
1,13-bis(4-(3,5-dimethyl-4-aminobenzyl)phenyl)tridecane,
1,14-bis(4-(3,5-dimethyl-4-aminobenzyl)phenyl)tetradecane,
1,15-bis(4-(3,5-dimethyl-4-aminobenzyl)phenyl)pentadecane,
1,16-bis(4-(3,5-dimethyl-4-aminobenzyl)phenyl)hexadecane,
1,17-bis(4-(3,5-dimethyl-4-aminobenzyl)phenyl)heptadecane,
1,18-bis(4-(3,5-dimethyl-4-aminobenzyl)phenyl)octadecane,
1,19-bis(4-(3,5-dimethyl-4-aminobenzyl)phenyl)nonadecane,
1,20-bis(4-(3,5-dimethyl-4-aminobenzyl)phenyl)icosane,
1,1-bis(4-(4-aminobenzyl)phenyl)ethane,
1,1-bis(4-(4-aminobenzyl)phenyl)propane,
1,1-bis(4-(4-aminobenzyl)phenyl)butane,
1,1-bis(4-(4-aminobenzyl)phenyl)pentane,
1,1-bis(4-(4-aminobenzyl)phenyl)hexane,
1,1-bis(4-(4-aminobenzyl)phenyl)heptane,
1,1-bis(4-(4-aminobenzyl)phenyl)octane,
1,1-bis(4-(4-aminobenzyl)phenyl)nonane,
1,1-bis(4-(4-aminobenzyl)phenyl)decane,
1,1-bis(4-(4-aminobenzyl)phenyl)undecane,
1,1-bis(4-(4-aminobenzyl)phenyl)dodecane,
1,1-bis(4-(2-methyl-4-aminobenzyl)phenyl)ethane,
1,1-bis(4-(2-methyl-4-aminobenzyl)phenyl)propane,
1,1-bis(4-(2-methyl-4-aminobenzyl)phenyl)butane,
1,1-bis(4-(2-methyl-4-aminobenzyl)phenyl)pentane,
1,1-bis(4-(2-methyl-4-aminobenzyl)phenyl)hexane,
1,1-bis(4-(2-methyl-4-aminobenzyl)phenyl)heptane,
1,1-bis(4-(2-methyl-4-aminobenzyl)phenyl)octane,
1,1-bis(4-(2-methyl-4-aminobenzyl)phenyl)nonane,
1,1-bis(4-(2-methyl-4-aminobenzyl)phenyl)decane,
1,1-bis(4-(2-methyl-4-aminobenzyl)phenyl)undecane,
1,1-bis(4-(2-methyl-4-aminobenzyl)phenyl)dodecane,
1,3-bis(4-(4-aminobenzyl)phenyl)-2-methylpropane,
1,3-bis(4-(4-aminobenzyl)phenyl)-2-ethylpropane,
1,3-bis(4-(4-aminobenzyl)phenyl)-2-propylpropane,
1,3-bis(4-(4-aminobenzyl)phenyl)-2-butylpropane,
1,3-bis(4-(4-aminobenzyl)phenyl)-2-pentylpropane,
1,3-bis(4-(4-aminobenzyl)phenyl)-2-hexylpropane,
1,3-bis(4-(4-aminobenzyl)phenyl)-2-heptylpropane,
1,3-bis(4-(4-aminobenzyl)phenyl)-2-octylpropane,
1,3-bis(4-(4-aminobenzyl)phenyl)-2-nonylpropane,
1,3-bis(4-(4-aminobenzyl)phenyl)-2-decylpropane,
1,3-bis(4-(4-aminobenzyl)phenyl)-2-undecylpropane,
1,3-bis(4-(4-aminobenzyl)phenyl)-2-dodecylpropane,
1,3-bis(4-(2-methyl-4-aminobenzyl)phenyl)-2-methylpropane,
1,3-bis(4-(2-methyl-4-aminobenzyl)phenyl)-2-ethylpropane,
1,3-bis(4-(2-methyl-4-aminobenzyl)phenyl)-2-propylpropane,
1,3-bis(4-(2-methyl-4-aminobenzyl)phenyl)-2-butylpropane,
1,3-bis(4-(2-methyl-4-aminobenzyl)phenyl)-2-pentylpropane,
1,3-bis(4-(2-methyl-4-aminobenzyl)phenyl)-2-hexylpropane,
1,3-bis(4-(2-methyl-4-aminobenzyl)phenyl)-2-heptylpropane,
1,3-bis(4-(2-methyl-4-aminobenzyl)phenyl)-2-octylpropane,
1,3-bis(4-(2-methyl-4-aminobenzyl)phenyl)-2-nonylpropane,
1,3-bis(4-(2-methyl-4-aminobenzyl)phenyl)-2-decylpropane,
1,3-bis(4-(2-methyl-4-aminobenzyl)phenyl)-2-undecylpropane,
1,3-bis(4-(2-methyl-4-aminobenzyl)phenyl)-2-dodecylpropane,
1,5-bis(4-(4-aminobenzyl)phenyl)-3-methylpentane,
1,5-bis(4-(4-aminobenzyl)phenyl)-3-ethylpentane,
1,5-bis(4-(4-aminobenzyl)phenyl)-3-propylpentane,
1,5-bis(4-(4-aminobenzyl)phenyl)-3-butylpentane,
1,5-bis(4-(4-aminobenzyl)phenyl)-3-pentylpentane,
1,5-bis(4-(4-aminobenzyl)phenyl)-3-hexylpentane,
1,5-bis(4-(4-aminobenzyl)phenyl)-3-heptylpentane,
1,5-bis(4-(4-aminobenzyl)phenyl)-3-octylpentane,
1,5-bis(4-(4-aminobenzyl)phenyl)-3-nonylpentane,
1,5-bis(4-(4-aminobenzyl)phenyl)-3-decylpentane,
1,5-bis(4-(4-aminobenzyl)phenyl)-3-undecylpentane,
1,5-bis(4-(4-aminobenzyl)phenyl)-3-dodecylpentane,
1,5-bis(4-(2-methyl-4-aminobenzyl)phenyl)-3-methylpentane,
1,5-bis(4-(2-methyl-4-aminobenzyl)phenyl)-3-ethylpentane,
1,5-bis(4-(2-methyl-4-aminobenzyl)phenyl)-3-propylpentane,
1,5-bis(4-(2-methyl-4-aminobenzyl)phenyl)-3-butylpentane,
1,5-bis(4-(2-methyl-4-aminobenzyl)phenyl)-3-pentylpentane,
1,5-bis(4-(2-methyl-4-aminobenzyl)phenyl)-3-hexylpentane,
1,5-bis(4-(2-methyl-4-aminobenzyl)phenyl)-3-heptylpentane,
1,5-bis(4-(2-methyl-4-aminobenzyl)phenyl)-3-octylpentane,
1,5-bis(4-(2-methyl-4-aminobenzyl)phenyl)-3-nonylpentane,
1,5-bis(4-(2-methyl-4-aminobenzyl)phenyl)-3-decylpentane,
1,5-bis(4-(2-methyl-4-aminobenzyl)phenyl)-3-undecylpentane,
1,5-bis(4-(2-methyl-4-aminobenzyl)phenyl)-3-dodecylpentane,
2,2-bis(4-(4-aminobenzyl)phenyl)propane,
2,2-bis(4-(4-aminobenzyl)phenyl)butane,
2,2-bis(4-(4-aminobenzyl)phenyl)pentane,
2,2-bis(4-(4-aminobenzyl)phenyl)hexane,
2,2-bis(4-(4-aminobenzyl)phenyl)heptane,
2,2-bis(4-(4-aminobenzyl)phenyl)octane,
2,2-bis(4-(4-aminobenzyl)phenyl)nonane,
2,2-bis(4-(4-aminobenzyl)phenyl)decane,
2,2-bis(4-(4-aminobenzyl)phenyl)undecane,
2,2-bis(4-(4-aminobenzyl)phenyl)dodecane,
2,2-bis(4-(4-aminobenzyl)phenyl)tridecane,
2,2-bis(4-(4-aminobenzyl)phenyl)tetradecane,
2,2-bis(4-(2-methyl-4-aminobenzyl)phenyl)propane, 2,2-bis(4-(2-methyl-4-aminobenzyl)phenyl)butane,
2,2-bis(4-(2-methyl-4-aminobenzyl)phenyl)pentane,
2,2-bis(4-(2-methyl-4-aminobenzyl)phenyl)hexane,
2,2-bis(4-(2-methyl-4-aminobenzyl)phenyl)heptane,
2,2-bis(4-(2-methyl-4-aminobenzyl)phenyl)octane,
2,2-bis(4-(2-methyl-4-aminobenzyl)phenyl)nonane,
2,2-bis(4-(2-methyl-4-aminobenzyl)phenyl)decane,
2,2-bis(4-(2-methyl-4-aminobenzyl)phenyl)undecane,
2,2-bis(4-(2-methyl-4-aminobenzyl)phenyl)dodecane,
2,2-bis(4-(2-methyl-4-aminobenzyl)phenyl)tridecane,
2,2-bis(4-(2-methyl-4-aminobenzyl)phenyl)tetradecane,
bis(4-(1-(4-aminophenyl)ethyl)phenyl)methane,
bis(4-(1-(4-aminophenyl)propyl)phenyl)methane,
bis(4-(1-(4-aminophenyl)butyl)phenyl)methane,
bis(4-(1-(4-aminophenyl)pentyl)phenyl)methane,
bis(4-(1-(4-aminophenyl)hexyl)phenyl)methane,
bis(4-(1-(4-aminophenyl)heptyl)phenyl)methane,
bis(4-(1-(4-aminophenyl)nonyl)phenyl)methane,
bis(4-(1-(4-aminophenyl)decyl)phenyl)methane,
bis(4-(1-(4-aminophenyl)undecyl)phenyl)methane,
bis(4-(1-(4-aminophenyl)dodecyl)phenyl)methane,
bis(4-(1-(4-aminophenyl)tridecyl)phenyl)methane,
1,2-bis(4-(1-(4-aminophenyl)ethyl)phenyl)ethane,
1,2-bis(4-(1-(4-aminophenyl)propyl)phenyl)ethane,
1,2-bis(4-(1-(4-aminophenyl)butyl)phenyl)ethane,
1,2-bis(4-(1-(4-aminophenyl)pentyl)phenyl)ethane,
1,2-bis(4-(1-(4-aminophenyl)hexyl)phenyl)ethane,
1,2-bis(4-(1-(4-aminophenyl)heptyl)phenyl)ethane,
1,2-bis(4-(1-(4-aminophenyl)nonyl)phenyl)ethane,
1,2-bis(4-(1-(4-aminophenyl)decyl)phenyl)ethane,
1,2-bis(4-(1-(4-aminophenyl)undecyl)phenyl)ethane,
1,2-bis(4-(1-(4-aminophenyl)dodecyl)phenyl)ethane,
1,2-bis(4-(1-(4-aminophenyl)tridecyl)phenyl)ethane,
1,3-bis(4-(1-(4-aminophenyl)ethyl)phenyl)propane,
1,3-bis(4-(1-(4-aminophenyl)propyl)phenyl)propane,
1,3-bis(4-(1-(4-aminophenyl)butyl)phenyl)propane,
1,3-bis(4-(1-(4-aminophenyl)pentyl)phenyl)propane,
1,3-bis(4-(1-(4-aminophenyl)hexyl)phenyl)propane,
1,3-bis(4-(1-(4-aminophenyl)heptyl)phenyl)propane,
1,3-bis(4-(1-(4-aminophenyl)nonyl)phenyl)propane,
1,3-bis(4-(1-(4-aminophenyl)decyl)phenyl)propane,
1,3-bis(4-(1-(4-aminophenyl)undecyl)phenyl)propane,
1,3-bis(4-(1-(4-aminophenyl)dodecyl)phenyl)propane,
1,3-bis(4-(1-(4-aminophenyl)tridecyl)phenyl)propane,
1,4-bis(4-(1-(4-aminophenyl)ethyl)phenyl)butane,
1,4-bis(4-(1-(4-aminophenyl)propyl)phenyl)butane,
1,4-bis(4-(1-(4-aminophenyl)butyl)phenyl)butane,
1,4-bis(4-(1-(4-aminophenyl)pentyl)phenyl)butane,
1,4-bis(4-(1-(4-aminophenyl)hexyl)phenyl)butane,
1,4-bis(4-(1-(4-aminophenyl)heptyl)phenyl)butane,
1,4-bis(4-(1-(4-aminophenyl)nonyl)phenyl)butane,
1,4-bis(4-(1-(4-aminophenyl)decyl)phenyl)butane,
1,4-bis(4-(1-(4-aminophenyl)undecyl)phenyl)butane,
1,4-bis(4-(1-(4-aminophenyl)dodecyl)phenyl)butane,
1,4-bis(4-(1-(4-aminophenyl)tridecyl)phenyl)butane,
1,5-bis(4-(1-(4-aminophenyl)ethyl)phenyl)pentane,
1,5-bis(4-(1-(4-aminophenyl)propyl)phenyl)pentane,
1,5-bis(4-(1-(4-aminophenyl)butyl)phenyl)pentane,
1,5-bis(4-(1-(4-aminophenyl)pentyl)phenyl)pentane,
1,5-bis(4-(1-(4-aminophenyl)hexyl)phenyl)pentane,
1,5-bis(4-(1-(4-aminophenyl)heptyl)phenyl)pentane,
1,5-bis(4-(1-(4-aminophenyl)nonyl)phenyl)pentane,
1,5-bis(4-(1-(4-aminophenyl)decyl)phenyl)pentane,
1,5-bis(4-(1-(4-aminophenyl)undecyl)phenyl)pentane,
1,5-bis(4-(1-(4-aminophenyl)dodecyl)phenyl)pentane,
1,5-bis(4-(1-(4-aminophenyl)tridecyl)phenyl)pentane,
1,6-bis(4-(1-(4-aminophenyl)ethyl)phenyl)hexane,
1,6-bis(4-(1-(4-aminophenyl)propyl)phenyl)hexane,
1,6-bis(4-(1-(4-aminophenyl)butyl)phenyl)hexane,
1,6-bis(4-(1-(4-aminophenyl)pentyl)phenyl)hexane,
1,6-bis(4-(1-(4-aminophenyl)hexyl)phenyl)hexane,
1,6-bis(4-(1-(4-aminophenyl)heptyl)phenyl)hexane,
1,6-bis(4-(1-(4-aminophenyl)nonyl)phenyl)hexane,
1,6-bis(4-(1-(4-aminophenyl)decyl)phenyl)hexane,
1,6-bis(4-(1-(4-aminophenyl)undecyl)phenyl)hexane,
1,6-bis(4-(1-(4-aminophenyl)dodecyl)phenyl)hexane,
1,6-bis(4-(1-(4-aminophenyl)tridecyl)phenyl)hexane,
1,7-bis(4-(1-(4-aminophenyl)ethyl)phenyl)heptane,
1,7-bis(4-(1-(4-aminophenyl)propyl)phenyl)heptane,
1,7-bis(4-(1-(4-aminophenyl)butyl)phenyl)heptane,
1,7-bis(4-(1-(4-aminophenyl)pentyl)phenyl)heptane,
1,7-bis(4-(1-(4-aminophenyl)hexyl)phenyl)heptane,
1,7-bis(4-(1-(4-aminophenyl)heptyl)phenyl)heptane,
1,7-bis(4-(1-(4-aminophenyl)nonyl)phenyl)heptane,
1,7-bis(4-(1-(4-aminophenyl)decyl)phenyl)heptane,
1,7-bis(4-(1-(4-aminophenyl)undecyl)phenyl)heptane,
1,7-bis(4-(1-(4-aminophenyl)dodecyl)phenyl)heptane,
1,7-bis(4-(1-(4-aminophenyl)tridecyl)phenyl)heptane,
1,8-bis(4-(1-(4-aminophenyl)ethyl)phenyl)octane,
1,8-bis(4-(1-(4-aminophenyl)propyl)phenyl)octane,
1,8-bis(4-(1-(4-aminophenyl)butyl)phenyl)octane,
1,8-bis(4-(1-(4-aminophenyl)pentyl)phenyl)octane,
1,8-bis(4-(1-(4-aminophenyl)hexyl)phenyl)octane,
1,8-bis(4-(1-(4-aminophenyl)heptyl)phenyl)octane,
1,8-bis(4-(1-(4-aminophenyl)nonyl)phenyl)octane,
1,8-bis(4-(1-(4-aminophenyl)decyl)phenyl)octane,
1,8-bis(4-(1-(4-aminophenyl)undecyl)phenyl)octane,
1,8-bis(4-(1-(4-aminophenyl)dodecyl)phenyl)octane,
1,8-bis(4-(1-(4-aminophenyl)tridecyl)phenyl)octane,
1,9-bis(4-(1-(4-aminophenyl)ethyl)phenyl)nonane,
1,9-bis(4-(1-(4-aminophenyl)propyl)phenyl)nonane,
1,9-bis(4-(1-(4-aminophenyl)butyl)phenyl)nonane,
1,9-bis(4-(1-(4-aminophenyl)pentyl)phenyl)nonane,
1,9-bis(4-(1-(4-aminophenyl)hexyl)phenyl)nonane,
1,9-bis(4-(1-(4-aminophenyl)heptyl)phenyl)nonane,
1,9-bis(4-(1-(4-aminophenyl)nonyl)phenyl)nonane,
1,9-bis(4-(1-(4-aminophenyl)decyl)phenyl)nonane,
1,9-bis(4-(1-(4-aminophenyl)undecyl)phenyl)nonane,
1,9-bis(4-(1-(4-aminophenyl)dodecyl)phenyl)nonane,
1,9-bis(4-(1-(4-aminophenyl)tridecyl)phenyl)nonane,
1,10-bis(4-(1-(4-aminophenyl)ethyl)phenyl)decane,
1,10-bis(4-(1-(4-aminophenyl)propyl)phenyl)decane,
1,10-bis(4-(1-(4-aminophenyl)butyl)phenyl)decane,
1,10-bis(4-(1-(4-aminophenyl)pentyl)phenyl)decane,
1,10-bis(4-(1-(4-aminophenyl)hexyl)phenyl)decane,
1,10-bis(4-(1-(4-aminophenyl)heptyl)phenyl)decane,
1,10-bis(4-(1-(4-aminophenyl)nonyl)phenyl)decane,
1,10-bis(4-(1-(4-aminophenyl)decyl)phenyl)decane,
1,10-bis(4-(1-(4-aminophenyl)undecyl)phenyl)decane,
1,10-bis(4-(1-(4-aminophenyl)dodecyl)phenyl)decane,
1,10-bis(4-(1-(4-aminophenyl)tridecyl)phenyl)decane,
1,11-bis(4-(1-(4-aminophenyl)ethyl)phenyl)undecane,
1,11-bis(4-(1-(4-aminophenyl)propyl)phenyl)undecane,
1,11-bis(4-(1-(4-aminophenyl)butyl)phenyl)undecane,
1,11-bis(4-(1-(4-aminophenyl)pentyl)phenyl)undecane,
1,11-bis(4-(1-(4-aminophenyl)hexyl)phenyl)undecane,
1,11-bis(4-(1-(4-aminophenyl)heptyl)phenyl)undecane,
1,11-bis(4-(1-(4-aminophenyl)nonyl)phenyl)undecane,
1,11-bis(4-(1-(4-aminophenyl)decyl)phenyl)undecane,
1,11-bis(4-(1-(4-aminophenyl)undecyl)phenyl)undecane,
1,11-bis(4-(1-(4-aminophenyl)dodecyl)phenyl)undecane,
1,11-bis(4-(1-(4-aminophenyl)tridecyl)phenyl)undecane,
1,12-bis(4-(1-(4-aminophenyl)ethyl)phenyl)dodecane,
1,12-bis(4-(1-(4-aminophenyl)propyl)phenyl)dodecane, 1,12-bis(4-(1-(4-aminophenyl)butyl)phenyl)dodecane,
1,12-bis(4-(1-(4-aminophenyl)pentyl)phenyl)dodecane,
1,12-bis(4-(1-(4-aminophenyl)hexyl)phenyl)dodecane,
1,12-bis(4-(1-(4-aminophenyl)heptyl)phenyl)dodecane,
1,12-bis(4-(1-(4-aminophenyl)nonyl)phenyl)dodecane,
1,12-bis(4-(1-(4-aminophenyl)decyl)phenyl)dodecane,
1,12-bis(4-(1-(4-aminophenyl)undecyl)phenyl)dodecane,
1,12-bis(4-(1-(4-aminophenyl)dodecyl)phenyl)dodecane,
1,12-bis(4-(1-(4-aminophenyl)tridecyl)phenyl)dodecane,
1,13-bis(4-(1-(4-aminophenyl)ethyl)phenyl)tridecane,
1,13-bis(4-(1-(4-aminophenyl)propyl)phenyl)tridecane,
1,13-bis(4-(1-(4-aminophenyl)butyl)phenyl)tridecane,
1,13-bis(4-(1-(4-aminophenyl)pentyl)phenyl)tridecane,
1,13-bis(4-(1-(4-aminophenyl)hexyl)phenyl)tridecane,
1,13-bis(4-(1-(4-aminophenyl)heptyl)phenyl)tridecane,
1,13-bis(4-(1-(4-aminophenyl)nonyl)phenyl)tridecane,
1,13-bis(4-(1-(4-aminophenyl)decyl)phenyl)tridecane,
1,13-bis(4-(1-(4-aminophenyl)undecyl)phenyl)tridecane,
1,13-bis(4-(1-(4-aminophenyl)dodecyl)phenyl)tridecane,
1,13-bis(4-(1-(4-aminophenyl)tridecyl)phenyl)tridecane,
1,14-bis(4-(1-(4-aminophenyl)ethyl)phenyl)tetradecane,
1,14-bis(4-(1-(4-aminophenyl)propyl)phenyl)tetradecane,
1,14-bis(4-(1-(4-aminophenyl)butyl)phenyl)tetradecane,
1,14-bis(4-(1-(4-aminophenyl)pentyl)phenyl)tetradecane,
1,14-bis(4-(1-(4-aminophenyl)hexyl)phenyl)tetradecane,
1,14-bis(4-(1-(4-aminophenyl)heptyl)phenyl)tetradecane,
1,14-bis(4-(1-(4-aminophenyl)nonyl)phenyl)tetradecane,
1,14-bis(4-(1-(4-aminophenyl)decyl)phenyl)tetradecane,
1,14-bis(4-(1-(4-aminophenyl)undecyl)phenyl)tetradecane,
1,14-bis(4-(1-(4-aminophenyl)dodecyl)phenyl)tetradecane,
1,14-bis(4-(1-(4-aminophenyl)tridecyl)phenyl)tetradecane,
1,15-bis(4-(1-(4-aminophenyl)ethyl)phenyl)pentadecane,
1,15-bis(4-(1-(4-aminophenyl)propyl)phenyl)pentadecane,
1,15-bis(4-(1-(4-aminophenyl)butyl)phenyl)pentadecane,
1,15-bis(4-(1-(4-aminophenyl)pentyl)phenyl)pentadecane,
1,15-bis(4-(1-(4-aminophenyl)hexyl)phenyl)pentadecane,
1,15-bis(4-(1-(4-aminophenyl)heptyl)phenyl)pentadecane,
1,15-bis(4-(1-(4-aminophenyl)nonyl)phenyl)pentadecane,
1,15-bis(4-(1-(4-aminophenyl)decyl)phenyl)pentadecane,
1,15-bis(4-(1-(4-aminophenyl)undecyl)phenyl)pentadecane,
1,15-bis(4-(1-(4-aminophenyl)dodecyl)phenyl)pentadecane,
1,15-bis(4-(1-(4-aminophenyl)tridecyl)phenyl)pentadecane,
1,16-bis(4-(1-(4-aminophenyl)ethyl)phenyl)hexadecane,
1,16-bis(4-(1-(4-aminophenyl)propyl)phenyl)hexadecane,
1,16-bis(4-(1-(4-aminophenyl)butyl)phenyl)hexadecane,
1,16-bis(4-(1-(4-aminophenyl)pentyl)phenyl)hexadecane,
1,16-bis(4-(1-(4-aminophenyl)hexyl)phenyl)hexadecane,
1,16-bis(4-(1-(4-aminophenyl)heptyl)phenyl)hexadecane,
1,16-bis(4-(1-(4-aminophenyl)nonyl)phenyl)hexadecane,
1,16-bis(4-(1-(4-aminophenyl)decyl)phenyl)hexadecane,
1,16-bis(4-(1-(4-aminophenyl)undecyl)phenyl)hexadecane,
1,16-bis(4-(1-(4-aminophenyl)dodecyl)phenyl)hexadecane,
1,16-bis(4-(1-(4-aminophenyl)tridecyl)phenyl)hexadecane,
1,17-bis(4-(1-(4-aminophenyl)ethyl)phenyl)heptadecane,
1,17-bis(4-(1-(4-aminophenyl)propyl)phenyl)heptadecane,
1,17-bis(4-(1-(4-aminophenyl)butyl)phenyl)heptadecane,
1,17-bis(4-(1-(4-aminophenyl)pentyl)phenyl)heptadecane,
1,17-bis(4-(1-(4-aminophenyl)hexyl)phenyl)heptadecane,
1,17-bis(4-(1-(4-aminophenyl)heptyl)phenyl)heptadecane,
1,17-bis(4-(1-(4-aminophenyl)nonyl)phenyl)heptadecane,
1,17-bis(4-(1-(4-aminophenyl)decyl)phenyl)heptadecane,
1,17-bis(4-(1-(4-aminophenyl)undecyl)phenyl)heptadecane,
1,17-bis(4-(1-(4-aminophenyl)dodecyl)phenyl)heptadecane,
1,17-bis(4-(1-(4-aminophenyl)tridecyl)phenyl)heptadecane,
1,18-bis(4-(1-(4-aminophenyl)ethyl)phenyl)octadecane,
1,18-bis(4-(1-(4-aminophenyl)propyl)phenyl)octadecane,
1,18-bis(4-(1-(4-aminophenyl)butyl)phenyl)octadecane,
1,18-bis(4-(1-(4-aminophenyl)pentyl)phenyl)octadecane,
1,18-bis(4-(1-(4-aminophenyl)hexyl)phenyl)octadecane,
1,18-bis(4-(1-(4-aminophenyl)heptyl)phenyl)octadecane,
1,18-bis(4-(1-(4-aminophenyl)nonyl)phenyl)octadecane,
1,18-bis(4-(1-(4-aminophenyl)decyl)phenyl)octadecane,
1,18-bis(4-(1-(4-aminophenyl)undecyl)phenyl)octadecane,
1,18-bis(4-(1-(4-aminophenyl)dodecyl)phenyl)octadecane,
1,18-bis(4-(1-(4-aminophenyl)tridecyl)phenyl)octadecane,
1,19-bis(4-(1-(4-aminophenyl)ethyl)phenyl)nonadecane,
1,19-bis(4-(1-(4-aminophenyl)propyl)phenyl)nonadecane,
1,19-bis(4-(1-(4-aminophenyl)butyl)phenyl)nonadecane,
1,19-bis(4-(1-(4-aminophenyl)pentyl)phenyl)nonadecane,
1,19-bis(4-(1-(4-aminophenyl)hexyl)phenyl)nonadecane,
1,19-bis(4-(1-(4-aminophenyl)heptyl)phenyl)nonadecane,
1,19-bis(4-(1-(4-aminophenyl)nonyl)phenyl)nonadecane,
1,19-bis(4-(1-(4-aminophenyl)decyl)phenyl)nonadecane,
1,19-bis(4-(1-(4-aminophenyl)undecyl)phenyl)nonadecane,
1,19-bis(4-(1-(4-aminophenyl)dodecyl)phenyl)nonadecane,
1,19-bis(4-(1-(4-aminophenyl)tridecyl)phenyl)nonadecane,
1,20-bis(4-(1-(4-aminophenyl)ethyl)phenyl)icosane,
1,20-bis(4-(1-(4-aminophenyl)propyl)phenyl)icosane,
1,20-bis(4-(1-(4-aminophenyl)butyl)phenyl)icosane,
1,20-bis(4-(1-(4-aminophenyl)pentyl)phenyl)icosane,
1,20-bis(4-(1-(4-aminophenyl)hexyl)phenyl)icosane,
1,20-bis(4-(1-(4-aminophenyl)heptyl)phenyl)icosane,
1,20-bis(4-(1-(4-aminophenyl)nonyl)phenyl)icosane,
1,20-bis(4-(1-(4-aminophenyl)decyl)phenyl)icosane,
1,20-bis(4-(1-(4-aminophenyl)undecyl)phenyl)icosane,
1,20-bis(4-(1-(4-aminophenyl)dodecyl)phenyl)icosane,
1,20-bis(4-(1-(4-aminophenyl)tridecyl)phenyl)icosane,
bis(4-(1-(2-methyl-4-aminophenyl)ethyl)phenyl)methane,
bis(4-(1-(2-methyl-4-aminophenyl)propyl)phenyl)methane,
bis(4-(1-(2-methyl-4-aminophenyl)butyl)phenyl)methane,
bis(4-(1-(2-methyl-4-aminophenyl)pentyl)phenyl)methane,
bis(4-(1-(2-methyl-4-aminophenyl)hexyl)phenyl)methane,
bis(4-(1-(2-methyl-4-aminophenyl)heptyl)phenyl)methane,
bis(4-(1-(2-methyl-4-aminophenyl)nonyl)phenyl)methane,
bis(4-(1-(2-methyl-4-aminophenyl)decyl)phenyl)methane,
bis(4-(1-(2-methyl-4-aminophenyl)undecyl)phenyl)methane,
bis(4-(1-(2-methyl-4-aminophenyl)dodecyl)phenyl)methane,
bis(4-(1-(2-methyl-4-aminophenyl)tridecyl)phenyl)methane,
1,2-bis(4-(1-(2-methyl-4-aminophenyl)ethyl)phenyl)ethane,
1,2-bis(4-(1-(2-methyl-4-aminophenyl)propyl)phenyl)ethane,
1,2-bis(4-(1-(2-methyl-4-aminophenyl)butyl)phenyl)ethane,
1,2-bis(4-(1-(2-methyl-4-aminophenyl)pentyl)phenyl)ethane,
1,2-bis(4-(1-(2-methyl-4-aminophenyl)hexyl)phenyl)ethane,
1,2-bis(4-(1-(2-methyl-4-aminophenyl)heptyl)phenyl)ethane,
1,2-bis(4-(1-(2-methyl-4-aminophenyl)nonyl)phenyl)ethane,
1,2-bis(4-(1-(2-methyl-4-aminophenyl)decyl)phenyl)ethane,
1,2-bis(4-(1-(2-methyl-4-aminophenyl)undecyl)phenyl)ethane,
1,2-bis(4-(1-(2-methyl-4-aminophenyl)dodecyl)phenyl)ethane, 1,2-bis(4-(1-(2-methyl-4-aminophenyl)tridecyl)phenyl)
ethane,
1,3-bis(4-(1-(2-methyl-4-aminophenyl)ethyl)phenyl)
propane,
1,3-bis(4-(1-(2-methyl-4-aminophenyl)propyl)phenyl)
propane,
1,3-bis(4-(1-(2-methyl-4-aminophenyl)butyl)phenyl)
propane,
1,3-bis(4-(1-(2-methyl-4-aminophenyl)pentyl)phenyl)
propane,
1,3-bis(4-(1-(2-methyl-4-aminophenyl)hexyl)phenyl)
propane,
1,3-bis(4-(1-(2-methyl-4-aminophenyl)heptyl)phenyl)
propane,
1,3-bis(4-(1-(2-methyl-4-aminophenyl)nonyl)phenyl)
propane,
1,3-bis(4-(1-(2-methyl-4-aminophenyl)decyl)phenyl)
propane,
1,3-bis(4-(1-(2-methyl-4-aminophenyl)undecyl)phenyl)
propane,
1,3-bis(4-(1-(2-methyl-4-aminophenyl)dodecyl)phenyl)
propane,
1,3-bis(4-(1-(2-methyl-4-aminophenyl)tridecyl)phenyl)
propane,
1,4-bis(4-(1-(2-methyl-4-aminophenyl)ethyl)phenyl)
butane,
1,4-bis(4-(1-(2-methyl-4-aminophenyl)propyl)phenyl)
butane,
1,4-bis(4-(1-(2-methyl-4-aminophenyl)butyl)phenyl)
butane,
1,4-bis(4-(1-(2-methyl-4-aminophenyl)pentyl)phenyl)
butane,
1,4-bis(4-(1-(2-methyl-4-aminophenyl)hexyl)phenyl)
butane,
1,4-bis(4-(1-(2-methyl-4-aminophenyl)heptyl)phenyl)
butane,
1,4-bis(4-(1-(2-methyl-4-aminophenyl)nonyl)phenyl)
butane,
1,4-bis(4-(1-(2-methyl-4-aminophenyl)decyl)phenyl)
butane,
1,4-bis(4-(1-(2-methyl-4-aminophenyl)undecyl)phenyl)
butane,
1,4-bis(4-(1-(2-methyl-4-aminophenyl)dodecyl)phenyl)
butane,
1,4-bis(4-(1-(2-methyl-4-aminophenyl)tridecyl)phenyl)
butane,
1,5-bis(4-(1-(2-methyl-4-aminophenyl)ethyl)phenyl)
pentane,
1,5-bis(4-(1-(2-methyl-4-aminophenyl)propyl)phenyl)
pentane,
1,5-bis(4-(1-(2-methyl-4-aminophenyl)butyl)phenyl)
pentane,
1,5-bis(4-(1-(2-methyl-4-aminophenyl)pentyl)phenyl)
pentane,
1,5-bis(4-(1-(2-methyl-4-aminophenyl)hexyl)phenyl)
pentane,
1,5-bis(4-(1-(2-methyl-4-aminophenyl)heptyl)phenyl)
pentane,
1,5-bis(4-(1-(2-methyl-4-aminophenyl)nonyl)phenyl)
pentane,
1,5-bis(4-(1-(2-methyl-4-aminophenyl)decyl)phenyl)
pentane,
1,5-bis(4-(1-(2-methyl-4-aminophenyl)undecyl)phenyl)
pentane,
1,5-bis(4-(1-(2-methyl-4-aminophenyl)dodecyl)phenyl)
pentane,
1,5-bis(4-(1-(2-methyl-4-aminophenyl)tridecyl)phenyl)
pentane,
1,6-bis(4-(1-(2-methyl-4-aminophenyl)ethyl)phenyl)
hexane,
1,6-bis(4-(1-(2-methyl-4-aminophenyl)propyl)phenyl)
hexane,
1,6-bis(4-(1-(2-methyl-4-aminophenyl)butyl)phenyl)
hexane,
1,6-bis(4-(1-(2-methyl-4-aminophenyl)pentyl)phenyl)
hexane,
1,6-bis(4-(1-(2-methyl-4-aminophenyl)hexyl)phenyl)
hexane,
1,6-bis(4-(1-(2-methyl-4-aminophenyl)heptyl)phenyl)
hexane,
1,6-bis(4-(1-(2-methyl-4-aminophenyl)nonyl)phenyl)
hexane,
1,6-bis(4-(1-(2-methyl-4-aminophenyl)decyl)phenyl)
hexane,
1,6-bis(4-(1-(2-methyl-4-aminophenyl)undecyl)phenyl)
hexane,
1,6-bis(4-(1-(2-methyl-4-aminophenyl)dodecyl)phenyl)
hexane,
1,6-bis(4-(1-(2-methyl-4-aminophenyl)tridecyl)phenyl)
hexane,
1,7-bis(4-(1-(2-methyl-4-aminophenyl)ethyl)phenyl)
heptane
1,7-bis(4-(1-(2-methyl-4-aminophenyl)propyl)phenyl)
heptane,
1,7-bis(4-(1-(2-methyl-4-aminophenyl)butyl)phenyl)
heptane,
1,7-bis(4-(1-(2-methyl-4-aminophenyl)pentyl)phenyl)
heptane,
1,7-bis(4-(1-(2-methyl-4-aminophenyl)hexyl)phenyl)
heptane,
1,7-bis(4-(1-(2-methyl-4-aminophenyl)heptyl)phenyl)
heptane,
1,7-bis(4-(1-(2-methyl-4-aminophenyl)nonyl)phenyl)
heptane,
1,7-bis(4-(1-(2-methyl-4-aminophenyl)decyl)phenyl)
heptane,
1,7-bis(4-(1-(2-methyl-4-aminophenyl)undecyl)phenyl)
heptane,
1,7-bis(4-(1-(2-methyl-4-aminophenyl)dodecyl)phenyl)
heptane,
1,7-bis(4-(1-(2-methyl-4-aminophenyl)tridecyl)phenyl)
heptane,
1,8-bis(4-(1-(2-methyl-4-aminophenyl)ethyl)phenyl)octane,
1,8-bis(4-(1-(2-methyl-4-aminophenyl)propyl)phenyl)
octane,
1,8-bis(4-(1-(2-methyl-4-aminophenyl)butyl)phenyl)
octane,
1,8-bis(4-(1-(2-methyl-4-aminophenyl)pentyl)phenyl)
octane,
1,8-bis(4-(1-(2-methyl-4-aminophenyl)hexyl)phenyl)
octane,
1,8-bis(4-(1-(2-methyl-4-aminophenyl)heptyl)phenyl)
octane,
1,8-bis(4-(1-(2-methyl-4-aminophenyl)nonyl)phenyl)
octane,
1,8-bis(4-(1-(2-methyl-4-aminophenyl)decyl)phenyl)
octane,
1,8-bis(4-(1-(2-methyl-4-aminophenyl)undecyl)phenyl)
octane,
1,8-bis(4-(1-(2-methyl-4-aminophenyl)dodecyl)phenyl)
octane,
1,8-bis(4-(1-(2-methyl-4-aminophenyl)tridecyl)phenyl)
octane,
1,9-bis(4-(1-(2-methyl-4-aminophenyl)ethyl)phenyl)
nonane, 1,9-bis(4-(1-(2-methyl-4-aminophenyl)propyl)phenyl) nonane,
1,9-bis(4-(1-(2-methyl-4-aminophenyl)butyl)phenyl) nonane,
1,9-bis(4-(1-(2-methyl-4-aminophenyl)pentyl)phenyl) nonane,
1,9-bis(4-(1-(2-methyl-4-aminophenyl)hexyl)phenyl) nonane,
1,9-bis(4-(1-(2-methyl-4-aminophenyl)heptyl)phenyl) nonane,
1,9-bis(4-(1-(2-methyl-4-aminophenyl)nonyl)phenyl) nonane,
1,9-bis(4-(1-(2-methyl-4-aminophenyl)decyl)phenyl) nonane,
1,9-bis(4-(1-(2-methyl-4-aminophenyl)undecyl)phenyl) nonane,
1,9-bis(4-(1-(2-methyl-4-aminophenyl)dodecyl)phenyl) nonane,
1,9-bis(4-(1-(2-methyl-4-aminophenyl)tridecyl)phenyl) nonane,
1,10-bis(4-(1-(2-methyl-4-aminophenyl)ethyl)phenyl) decane,
1,10-bis(4-(1-(2-methyl-4-aminophenyl)propyl)phenyl) decane,
1,10-bis(4-(1-(2-methyl-4-aminophenyl)butyl)phenyl) decane,
1,10-bis(4-(1-(2-methyl-4-aminophenyl)pentyl)phenyl) decane,
1,10-bis(4-(1-(2-methyl-4-aminophenyl)hexyl)phenyl) decane,
1,10-bis(4-(1-(2-methyl-4-aminophenyl)heptyl)phenyl) decane,
1,10-bis(4-(1-(2-methyl-4-aminophenyl)nonyl)phenyl) decane,
1,10-bis(4-(1-(2-methyl-4-aminophenyl)decyl)phenyl) decane,
1,10-bis(4-(1-(2-methyl-4-aminophenyl)undecyl)phenyl) decane,
1,10-bis(4-(1-(2-methyl-4-aminophenyl)dodecyl)phenyl) decane,
1,10-bis(4-(1-(2-methyl-4-aminophenyl)tridecyl)phenyl) decane,
1,11-bis(4-(1-(2-methyl-4-aminophenyl)ethyl)phenyl) undecane,
1,11-bis(4-(1-(2-methyl-4-aminophenyl)propyl)phenyl) undecane,
1,11-bis(4-(1-(2-methyl-4-aminophenyl)butyl)phenyl) undecane,
1,11-bis(4-(1-(2-methyl-4-aminophenyl)pentyl)phenyl) undecane,
1,11-bis(4-(1-(2-methyl-4-aminophenyl)hexyl)phenyl) undecane,
1,11-bis(4-(1-(2-methyl-4-aminophenyl)heptyl)phenyl) undecane,
1,11-bis(4-(1-(2-methyl-4-aminophenyl)nonyl)phenyl) undecane,
1,11-bis(4-(1-(2-methyl-4-aminophenyl)decyl)phenyl) undecane,
1,11-bis(4-(1-(2-methyl-4-aminophenyl)undecyl)phenyl) undecane,
1,11-bis(4-(1-(2-methyl-4-aminophenyl)dodecyl)phenyl) undecane,
1,11-bis(4-(1-(2-methyl-4-aminophenyl)tridecyl)phenyl) undecane,
1,12-bis(4-(1-(2-methyl-4-aminophenyl)ethyl)phenyl) dodecane,
1,12-bis(4-(1-(2-methyl-4-aminophenyl)propyl)phenyl) dodecane,
1,12-bis(4-(1-(2-methyl-4-aminophenyl)butyl)phenyl) dodecane,
1,12-bis(4-(1-(2-methyl-4-aminophenyl)pentyl)phenyl) dodecane,
1,12-bis(4-(1-(2-methyl-4-aminophenyl)hexyl)phenyl) dodecane,
1,12-bis(4-(1-(2-methyl-4-aminophenyl)heptyl)phenyl) dodecane,
1,12-bis(4-(1-(2-methyl-4-aminophenyl)nonyl)phenyl) dodecane,
1,12-bis(4-(1-(2-methyl-4-aminophenyl)decyl)phenyl) dodecane,
1,12-bis(4-(1-(2-methyl-4-aminophenyl)undecyl)phenyl) dodecane,
1,12-bis(4-(1-(2-methyl-4-aminophenyl)dodecyl)phenyl) dodecane,
1,12-bis(4-(1-(2-methyl-4-aminophenyl)tridecyl)phenyl) dodecane,
1,13-bis(4-(1-(2-methyl-4-aminophenyl)ethyl)phenyl) tridecane,
1,13-bis(4-(1-(2-methyl-4-aminophenyl)propyl)phenyl) tridecane,
1,13-bis(4-(1-(2-methyl-4-aminophenyl)butyl)phenyl) tridecane,
1,13-bis(4-(1-(2-methyl-4-aminophenyl)pentyl)phenyl) tridecane,
1,13-bis(4-(1-(2-methyl-4-aminophenyl)hexyl)phenyl) tridecane,
1,13-bis(4-(1-(2-methyl-4-aminophenyl)heptyl)phenyl) tridecane,
1,13-bis(4-(1-(2-methyl-4-aminophenyl)nonyl)phenyl) tridecane,
1,13-bis(4-(1-(2-methyl-4-aminophenyl)decyl)phenyl) tridecane,
1,13-bis(4-(1-(2-methyl-4-aminophenyl)undecyl)phenyl) tridecane,
1,13-bis(4-(1-(2-methyl-4-aminophenyl)dodecyl)phenyl) tridecane,
1,13-bis(4-(1-(2-methyl-4-aminophenyl)tridecyl)phenyl) tridecane,
1,14-bis(4-(1-(2-methyl-4-aminophenyl)ethyl)phenyl) tetradecane,
1,14-bis(4-(1-(2-methyl-4-aminophenyl)propyl)phenyl) tetradecane,
1,14-bis(4-(1-(2-methyl-4-aminophenyl)butyl)phenyl) tetradecane,
1,14-bis(4-(1-(2-methyl-4-aminophenyl)pentyl)phenyl) tetradecane,
1,14-bis(4-(1-(2-methyl-4-aminophenyl)hexyl)phenyl) tetradecane,
1,14-bis(4-(1-(2-methyl-4-aminophenyl)heptyl)phenyl) tetradecane,
1,14-bis(4-(1-(2-methyl-4-aminophenyl)nonyl)phenyl) tetradecane,
1,14-bis(4-(1-(2-methyl-4-aminophenyl)decyl)phenyl) tetradecane,
1,14-bis(4-(1-(2-methyl-4-aminophenyl)undecyl)phenyl) tetradecane,
1,14-bis(4-(1-(2-methyl-4-aminophenyl)dodecyl)phenyl) tetradecane,
1,14-bis(4-(1-(2-methyl-4-aminophenyl)tridecyl)phenyl) tetradecane,
1,15-bis(4-(1-(2-methyl-4-aminophenyl)ethyl)phenyl) pentadecane,
1,15-bis(4-(1-(2-methyl-4-aminophenyl)propyl)phenyl) pentadecane,
1,15-bis(4-(1-(2-methyl-4-aminophenyl)butyl)phenyl) pentadecane, 1,15-bis(4-(1-(2-methyl-4-aminophenyl)pentyl)phenyl) pentadecane,
1,15-bis(4-(1-(2-methyl-4-aminophenyl)hexyl)phenyl) pentadecane,
1,15-bis(4-(1-(2-methyl-4-aminophenyl)heptyl)phenyl) pentadecane,
1,15-bis(4-(1-(2-methyl-4-aminophenyl)nonyl)phenyl) pentadecane,
1,15-bis(4-(1-(2-methyl-4-aminophenyl)decyl)phenyl) pentadecane,
1,15-bis(4-(1-(2-methyl-4-aminophenyl)undecyl)phenyl) pentadecane,
1,15-bis(4-(1-(2-methyl-4-aminophenyl)dodecyl)phenyl) pentadecane,
1,15-bis(4-(1-(2-methyl-4-aminophenyl)tridecyl)phenyl) pentadecane,
1,16-bis(4-(1-(2-methyl-4-aminophenyl)ethyl)phenyl) hexadecane,
1,16-bis(4-(1-(2-methyl-4-aminophenyl)propyl)phenyl) hexadecane,
1,16-bis(4-(1-(2-methyl-4-aminophenyl)butyl)phenyl) hexadecane,
1,16-bis(4-(1-(2-methyl-4-aminophenyl)pentyl)phenyl) hexadecane,
1,16-bis(4-(1-(2-methyl-4-aminophenyl)hexyl)phenyl) hexadecane,
1,16-bis(4-(1-(2-methyl-4-aminophenyl)heptyl)phenyl) hexadecane,
1,16-bis(4-(1-(2-methyl-4-aminophenyl)nonyl)phenyl) hexadecane,
1,16-bis(4-(1-(2-methyl-4-aminophenyl)decyl)phenyl) hexadecane,
1,16-bis(4-(1-(2-methyl-4-aminophenyl)undecyl)phenyl) hexadecane,
1,16-bis(4-(1-(2-methyl-4-aminophenyl)dodecyl)phenyl) hexadecane,
1,16-bis(4-(1-(2-methyl-4-aminophenyl)tridecyl)phenyl) hexadecane,
1,17-bis(4-(1-(2-methyl-4-aminophenyl)ethyl)phenyl) heptadecane,
1,17-bis(4-(1-(2-methyl-4-aminophenyl)propyl)phenyl) heptadecane,
1,17-bis(4-(1-(2-methyl-4-aminophenyl)butyl)phenyl) heptadecane,
1,17-bis(4-(1-(2-methyl-4-aminophenyl)pentyl)phenyl) heptadecane,
1,17-bis(4-(1-(2-methyl-4-aminophenyl)hexyl)phenyl) heptadecane,
1,17-bis(4-(1-(2-methyl-4-aminophenyl)heptyl)phenyl) heptadecane,
1,17-bis(4-(1-(2-methyl-4-aminophenyl)nonyl)phenyl) heptadecane,
1,17-bis(4-(1-(2-methyl-4-aminophenyl)decyl)phenyl) heptadecane,
1,17-bis(4-(1-(2-methyl-4-aminophenyl)undecyl)phenyl) heptadecane,
1,17-bis(4-(1-(2-methyl-4-aminophenyl)dodecyl)phenyl) heptadecane,
1,17-bis(4-(1-(2-methyl-4-aminophenyl)tridecyl)phenyl) heptadecane,
1,18-bis(4-(1-(2-methyl-4-aminophenyl)ethyl)phenyl) octadecane,
1,18-bis(4-(1-(2-methyl-4-aminophenyl)propyl)phenyl) octadecane,
1,18-bis(4-(1-(2-methyl-4-aminophenyl)butyl)phenyl) octadecane,
1,18-bis(4-(1-(2-methyl-4-aminophenyl)pentyl)phenyl) octadecane,
1,18-bis(4-(1-(2-methyl-4-aminophenyl)hexyl)phenyl) octadecane,
1,18-bis(4-(1-(2-methyl-4-aminophenyl)heptyl)phenyl) octadecane,
1,18-bis(4-(1-(2-methyl-4-aminophenyl)nonyl)phenyl) octadecane,
1,18-bis(4-(1-(2-methyl-4-aminophenyl)decyl)phenyl) octadecane,
1,18-bis(4-(1-(2-methyl-4-aminophenyl)undecyl)phenyl) octadecane,
1,18-bis(4-(1-(2-methyl-4-aminophenyl)dodecyl)phenyl) octadecane,
1,18-bis(4-(1-(2-methyl-4-aminophenyl)tridecyl)phenyl) octadecane,
1,19-bis(4-(1-(2-methyl-4-aminophenyl)ethyl)phenyl) nonadecane,
1,19-bis(4-(1-(2-methyl-4-aminophenyl)propyl)phenyl) nonadecane,
1,19-bis(4-(1-(2-methyl-4-aminophenyl)butyl)phenyl) nonadecane,
1,19-bis(4-(1-(2-methyl-4-aminophenyl)pentyl)phenyl) nonadecane,
1,19-bis(4-(1-(2-methyl-4-aminophenyl)hexyl)phenyl) nonadecane,
1,19-bis(4-(1-(2-methyl-4-aminophenyl)heptyl)phenyl) nonadecane,
1,19-bis(4-(1-(2-methyl-4-aminophenyl)nonyl)phenyl) nonadecane,
1,19-bis(4-(1-(2-methyl-4-aminophenyl)decyl)phenyl) nonadecane,
1,19-bis(4-(1-(2-methyl-4-aminophenyl)undecyl)phenyl) nonadecane,
1,19-bis(4-(1-(2-methyl-4-aminophenyl)dodecyl)phenyl) nonadecane,
1,19-bis(4-(1-(2-methyl-4-aminophenyl)tridecyl)phenyl) nonadecane,
1,20-bis(4-(1-(2-methyl-4-aminophenyl)ethyl)phenyl) icosane,
1,20-bis(4-(1-(2-methyl-4-aminophenyl)propyl)phenyl) icosane,
1,20-bis(4-(1-(2-methyl-4-aminophenyl)butyl)phenyl) icosane,
1,20-bis(4-(1-(2-methyl-4-aminophenyl)pentyl)phenyl) icosane,
1,20-bis(4-(1-(2-methyl-4-aminophenyl)hexyl)phenyl) icosane,
1,20-bis(4-(1-(2-methyl-4-aminophenyl)heptyl)phenyl) icosane,
1,20-bis(4-(1-(2-methyl-4-aminophenyl)nonyl)phenyl) icosane,
1,20-bis(4-(1-(2-methyl-4-aminophenyl)decyl)phenyl) icosane,
1,20-bis(4-(1-(2-methyl-4-aminophenyl)undecyl)phenyl) icosane,
1,20-bis(4-(1-(2-methyl-4-aminophenyl)dodecyl)phenyl) icosane,
1,20-bis(4-(1-(2-methyl-4-aminophenyl)tridecyl)phenyl) icosane,
1,1-bis(4-(1-(4-aminophenyl)ethyl)phenyl)ethane,
1,1-bis(4-(1-(4-aminophenyl)propyl)phenyl)ethane,
1,1-bis(4-(1-(4-aminophenyl)butyl)phenyl)ethane,
1,1-bis(4-(1-(4-aminophenyl)pentyl)phenyl)ethane,
1,1-bis(4-(1-(4-aminophenyl)hexyl)phenyl)ethane,
1,1-bis(4-(1-(4-aminophenyl)heptyl)phenyl)ethane,
1,1-bis(4-(1-(4-aminophenyl)nonyl)phenyl)ethane,
1,1-bis(4-(1-(4-aminophenyl)decyl)phenyl)ethane,
1,1-bis(4-(1-(4-aminophenyl)undecyl)phenyl)ethane, 1,1-bis(4-(1-(4-aminophenyl)dodecyl)phenyl)ethane,
1,1-bis(4-(1-(4-aminophenyl)tridecyl)phenyl)ethane,
1,1-bis(4-(1-(4-aminophenyl)ethyl)phenyl)propane,
1,1-bis(4-(1-(4-aminophenyl)propyl)phenyl)propane,
1,1-bis(4-(1-(4-aminophenyl)butyl)phenyl)propane,
1,1-bis(4-(1-(4-aminophenyl)pentyl)phenyl)propane,
1,1-bis(4-(1-(4-aminophenyl)hexyl)phenyl)propane,
1,1-bis(4-(1-(4-aminophenyl)heptyl)phenyl)propane,
1,1-bis(4-(1-(4-aminophenyl)nonyl)phenyl)propane,
1,1-bis(4-(1-(4-aminophenyl)decyl)phenyl)propane,
1,1-bis(4-(1-(4-aminophenyl)undecyl)phenyl)propane,
1,1-bis(4-(1-(4-aminophenyl)dodecyl)phenyl)propane,
1,1-bis(4-(1-(4-aminophenyl)tridecyl)phenyl)propane,
1,1-bis(4-(1-(4-aminophenyl)ethyl)phenyl)butane,
1,1-bis(4-(1-(4-aminophenyl)propyl)phenyl)butane,
1,1-bis(4-(1-(4-aminophenyl)butyl)phenyl)butane,
1,1-bis(4-(1-(4-aminophenyl)pentyl)phenyl)butane,
1,1-bis(4-(1-(4-aminophenyl)hexyl)phenyl)butane,
1,1-bis(4-(1-(4-aminophenyl)heptyl)phenyl)butane,
1,1-bis(4-(1-(4-aminophenyl)nonyl)phenyl)butane,
1,1-bis(4-(1-(4-aminophenyl)decyl)phenyl)butane,
1,1-bis(4-(1-(4-aminophenyl)undecyl)phenyl)butane,
1,1-bis(4-(1-(4-aminophenyl)dodecyl)phenyl)butane,
1,1-bis(4-(1-(4-aminophenyl)tridecyl)phenyl)butane,
1,1-bis(4-(1-(4-aminophenyl)ethyl)phenyl)pentane,
1,1-bis(4-(1-(4-aminophenyl)propyl)phenyl)pentane,
1,1-bis(4-(1-(4-aminophenyl)butyl)phenyl)pentane,
1,1-bis(4-(1-(4-aminophenyl)pentyl)phenyl)pentane,
1,1-bis(4-(1-(4-aminophenyl)hexyl)phenyl)pentane,
1,1-bis(4-(1-(4-aminophenyl)heptyl)phenyl)pentane,
1,1-bis(4-(1-(4-aminophenyl)nonyl)phenyl)pentane,
1,1-bis(4-(1-(4-aminophenyl)decyl)phenyl)pentane,
1,1-bis(4-(1-(4-aminophenyl )undecyl)phenyl)pentane,
1,1-bis(4-(1-(4-aminophenyl)dodecyl)phenyl)pentane,
1,1-bis(4-(1-(4-aminophenyl)tridecyl)phenyl)pentane,
1,1-bis(4-(1-(4-aminophenyl)ethyl)phenyl)hexane,
1,1-bis(4-(1-(4-aminophenyl)propyl)phenyl)hexane,
1,1-bis(4-(1-(4-aminophenyl)butyl)phenyl)hexane,
1,1-bis(4-(1-(4-aminophenyl)pentyl)phenyl)hexane,
1,1-bis(4-(1-(4-aminophenyl)hexyl)phenyl)hexane,
1,1-bis(4-(1-(4-aminophenyl)heptyl)phenyl)hexane,
1,1-bis(4-(1-(4-aminophenyl)nonyl)phenyl)hexane,
1,1-bis(4-(1-(4-aminophenyl)decyl)phenyl)hexane,
1,1-bis(4-(1-(4-aminophenyl)undecyl)phenyl)hexane,
1,1-bis(4-(1-(4-aminophenyl)dodecyl)phenyl)hexane,
1,1-bis(4-(1-(4-aminophenyl)tridecyl)phenyl)hexane,
1,1-bis(4-(1-(4-aminophenyl)ethyl)phenyl)heptane,
1,1-bis(4-(1-(4-aminophenyl)propyl)phenyl)heptane,
1,1-bis(4-(1-(4-aminophenyl)butyl)phenyl)heptane,
1,1-bis(4-(1-(4-aminophenyl)pentyl)phenyl)heptane,
1,1-bis(4-(1-(4-aminophenyl)hexyl)phenyl)heptane,
1,1-bis(4-(1-(4-aminophenyl)heptyl)phenyl)heptane,
1,1-bis(4-(1-(4-aminophenyl)nonyl)phenyl)heptane,
1,1-bis(4-(1-(4-aminophenyl)decyl)phenyl)heptane,
1,1-bis(4-(1-(4-aminophenyl)undecyl)phenyl)heptane,
1,1-bis(4-(1-(4-aminophenyl)dodecyl)phenyl)heptane,
1,1-bis(4-(1-(4-aminophenyl)tridecyl)phenyl)heptane,
1,1-bis(4-(1-(4-aminophenyl)ethyl)phenyl)octane,
1,1-bis(4-(1-(4-aminophenyl)propyl)phenyl)octane,
1,1-bis(4-(1-(4-aminophenyl)butyl)phenyl)octane,
1,1-bis(4-(1-(4-aminophenyl)pentyl)phenyl)octane,
1,1-bis(4-(1-(4-aminophenyl)hexyl)phenyl)octane,
1,1-bis(4-(1-(4-aminophenyl)heptyl)phenyl)octane,
1,1-bis(4-(1-(4-aminophenyl)nonyl)phenyl)octane,
1,1-bis(4-(1-(4-aminophenyl)decyl)phenyl)octane,
1,1-bis(4-(1-(4-aminophenyl)undecyl)phenyl)octane,
1,1-bis(4-(1-(4-aminophenyl)dodecyl)phenyl)octane,
1,1-bis(4-(1-(4-aminophenyl)tridecyl)phenyl)octane,
1,1-bis(4-(1-(4-aminophenyl)ethyl)phenyl)nonane,
1,1-bis(4-(1-(4-aminophenyl)propyl)phenyl)nonane,
1,1-bis(4-(1-(4-aminophenyl)butyl)phenyl)nonane,
1,1-bis(4-(1-(4-aminophenyl)pentyl)phenyl)nonane,
1,1-bis(4-(1-(4-aminophenyl)hexyl)phenyl)nonane,
1,1-bis(4-(1-(4-aminophenyl)heptyl)phenyl)nonane,
1,1-bis(4-(1-(4-aminophenyl)nonyl)phenyl)nonane,
1,1-bis(4-(1-(4-aminophenyl)decyl)phenyl)nonane,
1,1-bis(4-(1-(4-aminophenyl)undecyl)phenyl)nonane,
1,1-bis(4-(1-(4-aminophenyl)dodecyl)phenyl)nonane,
1,1-bis(4-(1-(4-aminophenyl)tridecyl)phenyl)nonane,
1,1-bis(4-(1-(4-aminophenyl)ethyl)phenyl)decane,
1,1-bis(4-(1-(4-aminophenyl)propyl)phenyl)decane,
1,1-bis(4-(1-(4-aminophenyl)butyl)phenyl)decane,
1,1-bis(4-(1-(4-aminophenyl)pentyl)phenyl)decane,
1,1-bis(4-(1-(4-aminophenyl)hexyl)phenyl)decane,
1,1-bis(4-(1-(4-aminophenyl)heptyl)phenyl)decane,
1,1-bis(4-(1-(4-aminophenyl)nonyl)phenyl)decane,
1,1-bis(4-(1-(4-aminophenyl)decyl)phenyl)decane,
1,1-bis(4-(1-(4-aminophenyl)undecyl)phenyl)decane,
1,1-bis(4-(1-(4-aminophenyl)dodecyl)phenyl)decane,
1,1-bis(4-(1-(4-aminophenyl)tridecyl)phenyl)decane,
1,1-bis(4-(1-(4-aminophenyl)ethyl)phenyl)undecane,
1,1-bis(4-(1-(4-aminophenyl)propyl)phenyl)undecane,
1,1-bis(4-(1-(4-aminophenyl)butyl)phenyl)undecane,
1,1-bis(4-(1-(4-aminophenyl)pentyl)phenyl)undecane,
1,1-bis(4-(1-(4-aminophenyl)hexyl)phenyl)undecane,
1,1-bis(4-(1-(4-aminophenyl)heptyl)phenyl)undecane,
1,1-bis(4-(1-(4-aminophenyl)nonyl)phenyl)undecane,
1,1-bis(4-(1-(4-aminophenyl)decyl)phenyl)undecane,
1,1-bis(4-(1-(4-aminophenyl)undecyl)phenyl)undecane,
1,1-bis(4-(1-(4-aminophenyl)dodecyl)phenyl)undecane,
1,1-bis(4-(1-(4-aminophenyl)tridecyl)phenyl)undecane,
1,1-bis(4-(1-(4-aminophenyl)ethyl)phenyl)dodecane,
1,1-bis(4-(1-(4-aminophenyl)propyl)phenyl)dodecane,
1,1-bis(4-(1-(4-aminophenyl)butyl)phenyl)dodecane,
1,1-bis(4-(1-(4-aminophenyl)pentyl)phenyl)dodecane,
1,1-bis(4-(1-(4-aminophenyl)hexyl)phenyl)dodecane,
1,1-bis(4-(1-(4-aminophenyl)heptyl)phenyl)dodecane,
1,1-bis(4-(1-(4-aminophenyl)nonyl)phenyl)dodecane,
1,1-bis(4-(1-(4-aminophenyl)decyl)phenyl)dodecane,
1,1-bis(4-(1-(4-aminophenyl)undecyl)phenyl)dodecane,
1,1-bis(4-(1-(4-aminophenyl)dodecyl)phenyl)dodecane,
1,1-bis(4-(1-(4-aminophenyl)tridecyl)phenyl)dodecane,
1,1-bis(4-(1-(2-methyl-4-aminophenyl)ethyl)phenyl)ethane,
1,1-bis(4-(1-(2-methyl-4-aminophenyl)propyl)phenyl) ethane,
1,1-bis(4-(1-(2-methyl-4-aminophenyl)butyl)phenyl) ethane,
1,1-bis(4-(1-(2-methyl-4-aminophenyl)pentyl)phenyl) ethane,
1,1-bis(4-(1-(2-methyl-4-aminophenyl)hexyl)phenyl) ethane,
1,1-bis(4-(1-(2-methyl-4-aminophenyl)heptyl)phenyl) ethane,
1,1-bis(4-(1-(2-methyl-4-aminophenyl)nonyl)phenyl) ethane,
1,1-bis(4-(1-(2-methyl-4-aminophenyl)decyl)phenyl) ethane,
1,1-bis(4-(1-(2-methyl-4-aminophenyl)undecyl)phenyl) ethane,
1,1-bis(4-(1-(2-methyl-4-aminophenyl)dodecyl)phenyl) ethane,
1,1-bis(4-(1-(2-methyl-4-aminophenyl)tridecyl)phenyl) ethane,
1,1-bis(4-(1-(2-methyl-4-aminophenyl)ethyl)phenyl) propane, 1,1-bis(4-(1-(2-methyl-4-aminophenyl)propyl)phenyl) propane,
1,1-bis(4-(1-(2-methyl-4-aminophenyl)butyl)phenyl) propane,
1,1-bis(4-(1-(2-methyl-4-aminophenyl)pentyl)phenyl) propane,
1,1-bis(4-(1-(2-methyl-4-aminophenyl)hexyl)phenyl) propane,
1,1-bis(4-(1-(2-methyl-4-aminophenyl)heptyl)phenyl) propane,
1,1-bis(4-(1-(2-methyl-4-aminophenyl)nonyl)phenyl) propane,
1,1-bis(4-(1-(2-methyl-4-aminophenyl)decyl)phenyl) propane,
1,1-bis(4-(1-(2-methyl-4-aminophenyl)undecyl)phenyl) propane,
1,1-bis(4-(1-(2-methyl-4-aminophenyl)dodecyl)phenyl) propane,
1,1-bis(4-(1-(2-methyl-4-aminophenyl)tridecyl)phenyl) propane,
1,1-bis(4-(1-(2-methyl-4-aminophenyl)ethyl)phenyl) butane,
1,1-bis(4-(1-(2-methyl-4-aminophenyl)propyl)phenyl) butane,
1,1-bis(4-(1-(2-methyl-4-aminophenyl)butyl)phenyl) butane,
1,1-bis(4-(1-(2-methyl-4-aminophenyl)pentyl)phenyl) butane,
1,1-bis(4-(1-(2-methyl-4-aminophenyl)hexyl)phenyl) butane,
1,1-bis(4-(1-(2-methyl-4-aminophenyl)heptyl)phenyl) butane,
1,1-bis(4-(1-(2-methyl-4-aminophenyl)nonyl)phenyl) butane,
1,1-bis(4-(1-(2-methyl-4-aminophenyl)decyl)phenyl) butane,
1,1-bis(4-(1-(2-methyl-4-aminophenyl)undecyl)phenyl) butane,
1,1-bis(4-(1-(2-methyl-4-aminophenyl)dodecyl)phenyl) butane,
1,1-bis(4-(1-(2-methyl-4-aminophenyl)tridecyl)phenyl) butane,
1,1-bis(4-(1-(2-methyl-4-aminophenyl)ethyl)phenyl) pentane,
1,1-bis(4-(1-(2-methyl-4-aminophenyl)propyl)phenyl) pentane,
1,1-bis(4-(1-(2-methyl-4-aminophenyl)butyl)phenyl) pentane,
1,1-bis(4-(1-(2-methyl-4-aminophenyl)pentyl)phenyl) pentane,
1,1-bis(4-(1-(2-methyl-4-aminophenyl)hexyl)phenyl) pentane,
1,1-bis(4-(1-(2-methyl-4-aminophenyl)heptyl)phenyl) pentane,
1,1-bis(4-(1-(2-methyl-4-aminophenyl)nonyl)phenyl) pentane,
1,1-bis(4-(1-(2-methyl-4-aminophenyl)decyl)phenyl) pentane,
1,1-bis(4-(1-(2-methyl-4-aminophenyl)undecyl)phenyl) pentane,
1,1-bis(4-(1-(2-methyl-4-aminophenyl)dodecyl)phenyl) pentane,
1,1-bis(4-(1-(2-methyl-4-aminophenyl)tridecyl)phenyl) pentane,
1,1-bis(4-(1-(2-methyl-4-aminophenyl)ethyl)phenyl) hexane,
1,1-bis(4-(1-(2-methyl-4-aminophenyl)propyl)phenyl) hexane,
1,1-bis(4-(1-(2-methyl-4-aminophenyl)butyl)phenyl) hexane,
1,1-bis(4-(1-(2-methyl-4-aminophenyl)pentyl)phenyl) hexane,
1,1-bis(4-(1-(2-methyl-4-aminophenyl)hexyl)phenyl) hexane,
1,1-bis(4-(1-(2-methyl-4-aminophenyl)heptyl)phenyl) hexane,
1,1-bis(4-(1-(2-methyl-4-aminophenyl)nonyl)phenyl) hexane,
1,1-bis(4-(1-(2-methyl-4-aminophenyl)decyl)phenyl) hexane,
1,1-bis(4-(1-(2-methyl-4-aminophenyl)undecyl)phenyl) hexane,
1,1-bis(4-(1-(2-methyl-4-aminophenyl)dodecyl)phenyl) hexane,
1,1-bis(4-(1-(2-methyl-4-aminophenyl)tridecyl)phenyl) hexane,
1,1-bis(4-(1-(2-methyl-4-aminophenyl)ethyl)phenyl) heptane,
1,1-bis(4-(1-(2-methyl-4-aminophenyl)propyl)phenyl) heptane,
1,1-bis(4-(1-(2-methyl-4-aminophenyl)butyl)phenyl) heptane,
1,1-bis(4-(1-(2-methyl-4-aminophenyl)pentyl)phenyl) heptane,
1,1-bis(4-(1-(2-methyl-4-aminophenyl)hexyl)phenyl) heptane,
1,1-bis(4-(1-(2-methyl-4-aminophenyl)heptyl)phenyl) heptane,
1,1-bis(4-(1-(2-methyl-4-aminophenyl)nonyl)phenyl) heptane,
1,1-bis(4-(1-(2-methyl-4-aminophenyl)decyl)phenyl) heptane,
1,1-bis(4-(1-(2-methyl-4-aminophenyl)undecyl)phenyl) heptane,
1,1-bis(4-(1-(2-methyl-4-aminophenyl)dodecyl)phenyl) heptane,
1,1-bis(4-(1-(2-methyl-4-aminophenyl)tridecyl)phenyl) heptane,
1,1-bis(4-(1-(2-methyl-4-aminophenyl)ethyl)phenyl)octane,
1,1-bis(4-(1-(2-methyl-4-aminophenyl)propyl)phenyl) octane,
1,1-bis(4-(1-(2-methyl-4-aminophenyl)butyl)phenyl) octane,
1,1-bis(4-(1-(2-methyl-4-aminophenyl)pentyl)phenyl) octane,
1,1-bis(4-(1-(2-methyl-4-aminophenyl)hexyl)phenyl) octane,
1,1-bis(4-(1-(2-methyl-4-aminophenyl)heptyl)phenyl) octane,
1,1-bis(4-(1-(2-methyl-4-aminophenyl)nonyl)phenyl) octane,
1,1-bis(4-(1-(2-methyl-4-aminophenyl)decyl)phenyl) octane,
1,1-bis(4-(1-(2-methyl-4-aminophenyl)undecyl)phenyl) octane,
1,1-bis(4-(1-(2-methyl-4-aminophenyl)dodecyl)phenyl) octane,
1,1-bis(4-(1-(2-methyl-4-aminophenyl)tridecyl)phenyl) octane,
1,1-bis(4-(1-(2-methyl-4-aminophenyl)ethyl)phenyl) nonane,
1,1-bis(4-(1-(2-methyl-4-aminophenyl)propyl)phenyl) nonane,
1,1-bis(4-(1-(2-methyl-4-aminophenyl)butyl)phenyl) nonane, 1,1-bis(4-(1-(2-methyl-4-aminophenyl)pentyl)phenyl) nonane,
1,1-bis(4-(1-(2-methyl-4-aminophenyl)hexyl)phenyl) nonane,
1,1-bis(4-(1-(2-methyl-4-aminophenyl)heptyl)phenyl) nonane,
1,1-bis(4-(1-(2-methyl-4-aminophenyl)nonyl)phenyl) nonane,
1,1-bis(4-(1-(2-methyl-4-aminophenyl)decyl)phenyl) nonane,
1,1-bis(4-(1-(2-methyl-4-aminophenyl)undecyl)phenyl) nonane,
1,1-bis(4-(1-(2-methyl-4-aminophenyl)dodecyl)phenyl) nonane,
1,1-bis(4-(1-(2-methyl-4-aminophenyl)tridecyl)phenyl) nonane,
1,1-bis(4-(1-(2-methyl-4-aminophenyl)ethyl)phenyl) decane,
1,1-bis(4-(1-(2-methyl-4-aminophenyl)propyl)phenyl) decane,
1,1-bis(4-(1-(2-methyl-4-aminophenyl)butyl)phenyl) decane,
1,1-bis(4-(1-(2-methyl-4-aminophenyl)pentyl)phenyl) decane,
1,1-bis(4-(1-(2-methyl-4-aminophenyl)hexyl)phenyl) decane,
1,1-bis(4-(1-(2-methyl-4-aminophenyl)heptyl)phenyl) decane,
1,1-bis(1-(2-methyl-4-aminophenyl)nonyl)phenyl)decane,
1,1-bis(4-(1-(2-methyl-4-aminophenyl)decyl)phenyl) decane,
1,1-bis(4-(1-(2-methyl-4-aminophenyl)undecyl)phenyl) decane,
1,1-bis(4-(1-(2-methyl-4-aminophenyl)dodecyl)phenyl) decane,
1,1-bis(4-(1-(2-methyl-4-aminophenyl)tridecyl)phenyl) decane,
1,1-bis(4-(1-(2-methyl-4-aminophenyl)ethyl)phenyl) undecane,
1,1-bis(4-(1-(2-methyl-4-aminophenyl)propyl)phenyl) undecane,
1,1-bis(4-(1-(2-methyl-4-aminophenyl)butyl)phenyl) undecane,
1,1-bis(4-(1-(2-methyl-4-aminophenyl)pentyl)phenyl) undecane,
1,1-bis(4-(1-(2-methyl-4-aminophenyl)hexyl)phenyl) undecane,
1,1-bis(4-(1-(2-methyl-4-aminophenyl)heptyl)phenyl) undecane,
1,1-bis(4-(1-(2-methyl-4-aminophenyl)nonyl)phenyl) undecane,
1,1-bis(4-(1-(2-methyl-4-aminophenyl)decyl)phenyl) undecane,
1,1-bis(4-(1-(2-methyl-4-aminophenyl)undecyl)phenyl) undecane,
1,1-bis(4-(1-(2-methyl-4-aminophenyl)dodecyl)phenyl) undecane,
1,1-bis(4-(1-(2-methyl-4-aminophenyl)tridecyl)phenyl) undecane,
1,1-bis(4-(1-(2-methyl-4-aminophenyl)ethyl)phenyl) dodecane,
1,1-bis(4-(1-(2-methyl-4-aminophenyl)propyl)phenyl) dodecane,
1,1-bis(4-(1-(2-methyl-4-aminophenyl)butyl)phenyl) dodecane,
1,1-bis(4-(1-(2-methyl-4-aminophenyl)pentyl)phenyl) dodecane,
1,1-bis(4-(1-(2-methyl-4-aminophenyl)hexyl)phenyl) dodecane,
1,1-bis(4-(1-(2-methyl-4-aminophenyl)heptyl)phenyl) dodecane,
1,1-bis(4-(1-(2-methyl-4-aminophenyl)nonyl)phenyl) dodecane,
1,1-bis(4-(1-(2-methyl-4-aminophenyl)decyl)phenyl) dodecane,
1,1-bis(4-(1-(2-methyl-4-aminophenyl)undecyl)phenyl) dodecane,
1,1-bis(4-(1-(2-methyl-4-aminophenyl)dodecyl)phenyl) dodecane,
1,1-bis(4-(1-(2-methyl-4-aminophenyl)tridecyl)phenyl) dodecane,
1,2-bis(4-(1-(4-aminophenyl)ethyl)phenyl)propane,
1,2-bis(4-(1-(4-aminophenyl)propyl)phenyl)propane,
1,2-bis(4-(1-(4-aminophenyl)butyl)phenyl)propane,
1,2-bis(4-(1-(4-aminophenyl)pentyl)phenyl)propane,
1,2-bis(4-(1-(4-aminophenyl)hexyl)phenyl)propane,
1,2-bis(4-(1-(4-aminophenyl)heptyl)phenyl)propane,
1,2-bis(4-(1-(4-aminophenyl)nonyl)phenyl)propane,
1,2-bis(4-(1-(4-aminophenyl)decyl)phenyl)propane,
1,2-bis(4-(1-(4-aminophenyl)undecyl)phenyl)propane,
1,2-bis(4-(1-(4-aminophenyl)dodecyl)phenyl)propane,
1,2-bis(4-(1-(4-aminophenyl)tridecyl)phenyl)propane,
1,2-bis(4-(1-(4-aminophenyl)ethyl)phenyl)butane,
1,2-bis(4-(1-(4-aminophenyl)propyl)phenyl)butane,
1,2-bis(4-(1-(4-aminophenyl)butyl)phenyl)butane,
1,2-bis(4-(1-(4-aminophenyl)pentyl)phenyl)butane,
1,2-bis(4-(1-(4-aminophenyl)hexyl)phenyl)butane,
1,2-bis(4-(1-(4-aminophenyl)heptyl)phenyl)butane,
1,2-bis(4-(1-(4-aminophenyl)nonyl)phenyl)butane,
1,2-bis(4-(1-(4-aminophenyl)decyl)phenyl)butane,
1,2-bis(4-(1-(4-aminophenyl)undecyl)phenyl)butane,
1,2-bis(4-(1-(4-aminophenyl)dodecyl)phenyl)butane,
1,2-bis(4-(1-(4-aminophenyl)tridecyl)phenyl)butane,
1,2-bis(4-(1-(4-aminophenyl)ethyl)phenyl)pentane,
1,2-bis(4-(1-(4-aminophenyl)propyl)phenyl)pentane,
1,2-bis(4-(1-(4-aminophenyl)butyl)phenyl)pentane,
1,2-bis(4-(1-(4-aminophenyl)pentyl)phenyl)pentane,
1,2-bis(4-(1-(4-aminophenyl)hexyl)phenyl)pentane,
1,2-bis(4-(1-(4-aminophenyl)heptyl)phenyl)pentane,
1,2-bis(4-(1-(4-aminophenyl)nonyl)phenyl)pentane,
1,2-bis(4-(1-(4-aminophenyl)decyl)phenyl)pentane,
1,2-bis(4-(1-(4-aminophenyl)undecyl)phenyl)pentane,
1,2-bis(4-(1-(4-aminophenyl)dodecyl)phenyl)pentane,
1,2-bis(4-(1-(4-aminophenyl)tridecyl)phenyl)pentane,
1,2-bis(4-(1-(4-aminophenyl)ethyl)phenyl)hexane,
1,2-bis(4-(1-(4-aminophenyl)propyl)phenyl)hexane,
1,2-bis(4-(1-(4-aminophenyl)butyl)phenyl)hexane,
1,2-bis(4-(1-(4-aminophenyl)pentyl)phenyl)hexane,
1,2-bis(4-(1-(4-aminophenyl)hexyl)phenyl)hexane,
1,2-bis(4-(1-(4-aminophenyl)heptyl)phenyl)hexane,
1,2-bis(4-(1-(4-aminophenyl)nonyl)phenyl)hexane,
1,2-bis(4-(1-(4-aminophenyl)decyl)phenyl)hexane,
1,2-bis(4-(1-(4-aminophenyl)undecyl)phenyl)hexane,
1,2-bis(4-(1-(4-aminophenyl)dodecyl)phenyl)hexane,
1,2-bis(4-(1-(4-aminophenyl)tridecyl)phenyl)hexane,
1,2-bis(4-(1-(4-aminophenyl)ethyl)phenyl)heptane,
1,2-bis(4-(1-(4-aminophenyl)propyl)phenyl)heptane,
1,2-bis(4-(1-(4-aminophenyl)butyl)phenyl)heptane,
1,2-bis(4-(1-(4-aminophenyl)pentyl)phenyl)heptane,
1,2-bis(4-(1-(4-aminophenyl)hexyl)phenyl)heptane,
1,2-bis(4-(1-(4-aminophenyl)heptyl)phenyl)heptane,
1,2-bis(4-(1-(4-aminophenyl)nonyl)phenyl)heptane,
1,2-bis(4-(1-(4-aminophenyl)decyl)phenyl)heptane,
1,2-bis(4-(1-(4-aminophenyl)undecyl)phenyl)heptane, 1,2-bis(4-(1-(4-aminophenyl)dodecyl)phenyl)heptane,
1,2-bis(4-(1-(4-aminophenyl)tridecyl)phenyl)heptane,
1,2-bis(4-(1-(4-aminophenyl)ethyl)phenyl)octane,
1,2-bis(4-(1-(4-aminophenyl)propyl)phenyl)octane,
1,2-bis(4-(1-(4-aminophenyl)butyl)phenyl)octane,
1,2-bis(4-(1-(4-aminophenyl)pentyl)phenyl)octane,
1,2-bis(4-(1-(4-aminophenyl)hexyl)phenyl)octane,
1,2-bis(4-(1-(4-aminophenyl)heptyl)phenyl)octane,
1,2-bis(4-(1-(4-aminophenyl)nonyl)phenyl)octane,
1,2-bis(4-(1-(4-aminophenyl)decyl)phenyl)octane,
1,2-bis(4-(1-(4-aminophenyl)undecyl)phenyl)octane,
1,2-bis(4-(1-(4-aminophenyl)dodecyl)phenyl)octane,
1,2-bis(4-(1-(4-aminophenyl)tridecyl)phenyl)octane,
1,2-bis(4-(1-(4-aminophenyl)ethyl)phenyl)nonane,
1,2-bis(4-(1-(4-aminophenyl)propyl)phenyl)nonane,
1,2-bis(4-(1-(4-aminophenyl)butyl)phenyl)nonane,
1,2-bis(4-(1-(4-aminophenyl)pentyl)phenyl)nonane,
1,2-bis(4-(1-(4-aminophenyl)hexyl)phenyl)nonane,
1,2-bis(4-(1-(4-aminophenyl)heptyl)phenyl)nonane,
1,2-bis(4-(1-(4-aminophenyl)nonyl)phenyl)nonane,
1,2-bis(4-(1-(4-aminophenyl)decyl)phenyl)nonane,
1,2-bis(4-(1-(4-aminophenyl)undecyl)phenyl)nonane,
1,2-bis(4-(1-(4-aminophenyl)dodecyl)phenyl)nonane,
1,2-bis(4-(1-(4-aminophenyl)tridecyl)phenyl)nonane,
1,2-bis(4-(1-(4-aminophenyl)ethyl)phenyl)decane,
1,2-bis(4-(1-(4-aminophenyl)propyl)phenyl)decane,
1,2-bis(4-(1-(4-aminophenyl)butyl)phenyl)decane,
1,2-bis(4-(1-(4-aminophenyl)pentyl)phenyl)decane,
1,2-bis(4-(1-(4-aminophenyl)hexyl)phenyl)decane,
1,2-bis(4-(1-(4-aminophenyl)heptyl)phenyl)decane,
1,2-bis(4-(1-(4-aminophenyl)nonyl)phenyl)decane,
1,2-bis(4-(1-(4-aminophenyl)decyl)phenyl)decane,
1,2-bis(4-(1-(4-aminophenyl)undecyl)phenyl)decane,
1,2-bis(4-(1-(4-aminophenyl)dodecyl)phenyl)decane,
1,2-bis(4-(1-(4-aminophenyl)tridecyl)phenyl)decane,
1,2-bis(4-(1-(4-aminophenyl)ethyl)phenyl)undecane,
1,2-bis(4-(1-(4-aminophenyl)propyl)phenyl)undecane,
1,2-bis(4-(1-(4-aminophenyl)butyl)phenyl)undecane,
1,2-bis(4-(1-(4-aminophenyl)pentyl)phenyl)undecane,
1,2-bis(4-(1-(4-aminophenyl)hexyl)phenyl)undecane,
1,2-bis(4-(1-(4-aminophenyl)heptyl)phenyl)undecane,
1,2-bis(4-(1-(4-aminophenyl)nonyl)phenyl)undecane,
1,2-bis(4-(1-(4-aminophenyl)decyl)phenyl)undecane,
1,2-bis(4-(1-(4-aminophenyl)undecyl)phenyl)undecane,
1,2-bis(4-(1-(4-aminophenyl)dodecyl)phenyl)undecane,
1,2-bis(4-(1-(4-aminophenyl)tridecyl)phenyl)undecane,
1,2-bis(4-(1-(4-aminophenyl)ethyl)phenyl)dodecane,
1,2-bis(4-(1-(4-aminophenyl)propyl)phenyl)dodecane,
1,2-bis(4-(1-(4-aminophenyl)butyl)phenyl)dodecane,
1,2-bis(4-(1-(4-aminophenyl)pentyl)phenyl)dodecane,
1,2-bis(4-(1-(4-aminophenyl)hexyl)phenyl)dodecane,
1,2-bis(4-(1-(4-aminophenyl)heptyl)phenyl)dodecane,
1,2-bis(4-(1-(4-aminophenyl)nonyl)phenyl)dodecane,
1,2-bis(4-(1-(4-aminophenyl)decyl)phenyl)dodecane,
1,2-bis(4-(1-(4-aminophenyl)undecyl)phenyl)dodecane,
1,2-bis(4-(1-(4-aminophenyl)dodecyl)phenyl)dodecane,
1,2-bis(4-(1-(4-aminophenyl)tridecyl)phenyl)dodecane,
1,1-bis(4-(1-(4-aminophenyl)ethyl)benzyl)ethane,
1,1-bis(4-(1-(4-aminophenyl)propyl)benzyl)ethane,
1,1-bis(4-(1-(4-aminophenyl)butyl)benzyl)ethane,
1,1-bis(4-(1-(4-aminophenyl)pentyl)benzyl)ethane,
1,1-bis(4-(1-(4-aminophenyl)hexyl)benzyl)ethane,
1,1-bis(4-(1-(4-aminophenyl)heptyl)benzyl)ethane,
1,1-bis(4-(1-(4-aminophenyl)nonyl)benzyl)ethane,
1,1-bis(4-(1-(4-aminophenyl)decyl)benzyl)ethane,
1,1-bis(4-(1-(4-aminophenyl)undecyl)benzyl)ethane,
1,1-bis(4-(1-(4-aminophenyl)dodecyl)benzyl)ethane,
1,1-bis(4-(1-(4-aminophenyl)tridecyl)benzyl)ethane,
1,1-bis(4-(1-(4-aminophenyl)ethyl)benzyl)propane,
1,1-bis(4-(1-(4-aminophenyl)propyl)benzyl)propane,
1,1-bis(4-(1-(4-aminophenyl)butyl)benzyl)propane,
1,1-bis(4-(1-(4-aminophenyl)pentyl)benzyl)propane,
1,1-bis(4-(1-(4-aminophenyl)hexyl)benzyl)propane,
1,1-bis(4-(1-(4-aminophenyl)heptyl)benzyl)propane,
1,1-bis(4-(1-(4-aminophenyl)nonyl)benzyl)propane,
1,1-bis(4-(1-(4-aminophenyl)decyl)benzyl)propane,
1,1-bis(4-(1-(4-aminophenyl)undecyl)benzyl)propane,
1,1-bis(4-(1-(4-aminophenyl)dodecyl)benzyl)propane,
1,1-bis(4-(1-(4-aminophenyl)tridecyl)benzyl)propane,
1,1-bis(4-(1-(4-aminophenyl)ethyl)benzyl)butane,
1,1-bis(4-(1-(4-aminophenyl)propyl)benzyl)butane,
1,1-bis(4-(1-(4-aminophenyl)butyl)benzyl)butane,
1,1-bis(4-(1-(4-aminophenyl)butyl)benzyl)butane,
1,1-bis(4-(1-(4-aminophenyl)pentyl)benzyl)butane,
1,1-bis(4-(1-(4-aminophenyl)hexyl)benzyl)butane,
1,1-bis(4-(1-(4-aminophenyl)heptyl)benzyl)butane,
1,1-bis(4-(1-(4-aminophenyl)nonyl)benzyl)butane,
1,1-bis(4-(1-(4-aminophenyl)decyl)benzyl)butane,
1,1-bis(4-(1-(4-aminophenyl)undecyl)benzyl)butane,
1,1-bis(4-(1-(4-aminophenyl)dodecyl)benzyl)butane,
1,1-bis(4-(1-(4-aminophenyl)tridecyl)benzyl)butane,
1,1-bis(4-(1-(4-aminophenyl)ethyl)benzyl)pentane,
1,1-bis(4-(1-(4-aminophenyl)propyl)benzyl)pentane,
1,1-bis(4-(1-(4-aminophenyl)butyl)benzyl)pentane,
1,1-bis(4-(1-(4-aminophenyl)pentyl)benzyl)pentane,
1,1-bis(4-(1-(4-aminophenyl)hexyl)benzyl)pentane,
1,1-bis(4-(1-(4-aminophenyl)heptyl)benzyl)pentane,
1,1-bis(4-(1-(4-aminophenyl)nonyl)benzyl)pentane,
1,1-bis(4-(1-(4-aminophenyl)decyl)benzyl)pentane,
1,1-bis(4-(1-(4-aminophenyl)undecyl)benzyl)pentane,
1,1-bis(4-(1-(4-aminophenyl)dodecyl)benzyl)pentane,
1,1-bis(4-(1-(4-aminophenyl)tridecyl)benzyl)pentane,
1,1-bis(4-(1-(4-aminophenyl)ethyl)benzyl)hexane,
1,1-bis(4-(1-(4-aminophenyl)propyl)benzyl)hexane,
1,1-bis(4-(1-(4-aminophenyl)butyl)benzyl)hexane,
1,1-bis(4-(1-(4-aminophenyl)pentyl)benzyl)hexane,
1,1-bis(4-(1-(4-aminophenyl)hexyl)benzyl)hexane,
1,1-bis(4-(1-(4-aminophenyl)heptyl)benzyl)hexane,
1,1-bis(4-(1-(4-aminophenyl)nonyl)benzyl)hexane,
1,1-bis(4-(1-(4-aminophenyl)decyl)benzyl)hexane,
1,1-bis(4-(1-(4-aminophenyl)undecyl)benzyl)hexane,
1,1-bis(4-(1-(4-aminophenyl)dodecyl)benzyl)hexane,
1,1-bis(4-(1-(4-aminophenyl)tridecyl)benzyl)hexane,
1,1-bis(4-(1-(4-aminophenyl)ethyl)benzyl)heptane,
1,1-bis(4-(1-(4-aminophenyl)propyl)benzyl)heptane,
1,1-bis(4-(1-(4-aminophenyl)butyl)benzyl)heptane,
1,1-bis(4-(1-(4-aminophenyl)pentyl)benzyl)heptane,
1,1-bis(4-(1-(4-aminophenyl)hexyl)benzyl)heptane,
1,1-bis(4-(1-(4-aminophenyl)heptyl)benzyl)heptane,
1,1-bis(4-(1-(4-aminophenyl)nonyl)benzyl)heptane,
1,1-bis(4-(1-(4-aminophenyl)decyl)benzyl)heptane,
1,1-bis(4-(1-(4-aminophenyl)undecyl)benzyl)heptane,
1,1-bis(4-(1-(4-aminophenyl)dodecyl)benzyl)heptane,
1,1-bis(4-(1-(4-aminophenyl)tridecyl)benzyl)heptane,
1,1-bis(4-(1-(4-aminophenyl)ethyl)benzyl)octane,
1,1-bis(4-(1-(4-aminophenyl)propyl)benzyl)octane,
1,1-bis(4-(1-(4-aminophenyl)butyl)benzyl)octane,
1,1-bis(4-(1-(4-aminophenyl)pentyl)benzyl)octane,
1,1-bis(4-(1-(4-aminophenyl)hexyl)benzyl)octane
1,1-bis(4-(1-(4-aminophenyl)heptyl)benzyl)octane,
1,1-bis(4-(1-(4-aminophenyl)nonyl)benzyl)octane,
1,1-bis(4-(1-(4-aminophenyl)decyl)benzyl)octane,
1,1-bis(4-(1-(4-aminophenyl)undecyl)benzyl)octane,
1,1-bis(4-(1-(4-aminophenyl)dodecyl)benzyl)octane, 1,1-bis(4-(1-(4-aminophenyl)tridecyl)benzyl)octane,
1,1-bis(4-(1-(4-aminophenyl)ethyl)benzyl)nonane,
1,1-bis(4-(1-(4-aminophenyl)propyl)benzyl)nonane,
1,1-bis(4-(1-(4-aminophenyl)butyl)benzyl)nonane,
1,1-bis(4-(1-(4-aminophenyl)pentyl)benzyl)nonane,
1,1-bis(4-(1-(4-aminophenyl)hexyl)benzyl)nonane,
1,1-bis(4-(1-(4-aminophenyl)heptyl)benzyl)nonane,
1,1-bis(4-(1-(4-aminophenyl)nonyl)benzyl)nonane,
1,1-bis(4-(1-(4-aminophenyl)decyl)benzyl)nonane,
1,1-bis(4-(1-(4-aminophenyl)undecyl)benzyl)nonane,
1,1-bis(4-(1-(4-aminophenyl)dodecyl)benzyl)nonane,
1,1-bis(4-(1-(4-aminophenyl)tridecyl)benzyl)nonane,
1,1-bis(4-(1-(4-aminophenyl)ethyl)benzyl)decane,
1,1-bis(4-(1-(4-aminophenyl)propyl)benzyl)decane,
1,1-bis(4-(1-(4-aminophenyl)butyl)benzyl)decane,
1,1-bis(4-(1-(4-aminophenyl)pentyl)benzyl)decane,
1,1-bis(4-(1-(4-aminophenyl)hexyl)benzyl)decane,
1,1-bis(4-(1-(4-aminophenyl)heptyl)benzyl)decane,
1,1-bis(4-(1-(4-aminophenyl)nonyl)benzyl)decane,
1,1-bis(4-(1-(4-aminophenyl)decyl)benzyl)decane,
1,1-bis(4-(1-(4-aminophenyl)undecyl)benzyl)decane,
1,1-bis(4-(1-(4-aminophenyl)dodecyl)benzyl)decane,
1,1-bis(4-(1-(4-aminophenyl)tridecyl)benzyl)decane,
1,1-bis(4-(1-(4-aminophenyl)ethyl)benzyl)undecane,
1,1-bis(4-(1-(4-aminophenyl)propyl)benzyl)undecane,
1,1-bis(4-(1-(4-aminophenyl)butyl)benzyl)undecane,
1,1-bis(4-(1-(4-aminophenyl)pentyl)benzyl)undecane,
1,1-bis(4-(1-(4-aminophenyl)hexyl)benzyl)undecane,
1,1-bis(4-(1-(4-aminophenyl)heptyl)benzyl)undecane,
1,1-bis(4-(1-(4-aminophenyl)nonyl)benzyl)undecane,
1,1-bis(4-(1-(4-aminophenyl)decyl)benzyl)undecane,
1,1-bis(4-(1-(4-aminophenyl)undecyl)benzyl)undecane,
1,1-bis(4-(1-(4-aminophenyl)dodecyl)benzyl)undecane,
1,1-bis(4-(1-(4-aminophenyl)tridecyl)benzyl)undecane,
1,1-bis(4-(1-(4-aminophenyl)ethyl)benzyl)dodecane,
1,1-bis(4-(1-(4-aminophenyl)propyl)benzyl)dodecane,
1,1-bis(4-(1-(4-aminophenyl)butyl)benzyl)dodecane,
1,1-bis(4-(1-(4-aminophenyl)pentyl)benzyl)dodecane,
1,1-bis(4-(1-(4-aminophenyl)hexyl)benzyl)dodecane,
1,1-bis(4-(1-(4-aminophenyl)heptyl)benzyl)dodecane,
1,1-bis(4-(1-(4-aminophenyl)nonyl)benzyl)dodecane,
1,1-bis(4-(1-(4-aminophenyl)decyl)benzyl)dodecane,
1,1-bis(4-(1-(4-aminophenyl)undecyl)benzyl)dodecane,
1,1-bis(4-(1-(4-aminophenyl)dodecyl)benzyl)dodecane,
1,1-bis(4-(1-(4-aminophenyl)tridecyl)benzyl)dodecane,
1,1-bis(4-(1-(4-aminophenyl)ethyl)phenyl)cyclohexane,
1,1-bis(4-(1-(4-aminophenyl)propyl)phenyl)cyclohexane,
1,1-bis(4-(1-(4-aminophenyl)butyl)phenyl)cyclohexane,
1,1-bis(4-(1-(4-aminophenyl)pentyl)phenyl)cyclohexane,
1,1-bis(4-(1-(4-aminophenyl)hexyl)phenyl)cyclohexane,
1,1-bis(4-(1-(4-aminophenyl)heptyl)phenyl)cyclohexane,
1,1-bis(4-(1-(4-aminophenyl)nonyl)phenyl)cyclohexane,
1,1-bis(4-(1-(4-aminophenyl)decyl)phenyl)cyclohexane,
1,1-bis(4-(1-(4-aminophenyl)undecyl)phenyl)cyclohexane,
1,1-bis(4-(1-(4-aminophenyl)dodecyl)phenyl)cyclohexane,
1,1-bis(4-(1-(4-aminophenyl)tridecyl)phenyl)cyclohexane,
1,1-bis(4-(1-(4-aminophenyl)ethyl)phenyl)-4-methylcyclohexane,
1,1-bis(4-(1-(4-aminophenyl)propyl)phenyl)-4-methylcyclohexane,
1,1-bis(4-(1-(4-aminophenyl)butyl)phenyl)-4-methylcyclohexane,
1,1-bis(4-(1-(4-aminophenyl)pentyl)phenyl)-4-methylcyclohexane,
1,1-bis(4-(1-(4-aminophenyl)hexyl)phenyl)-4-methylcyclohexane,
1,1-bis(4-(1-(4-aminophenyl)heptyl)phenyl)-4-methylcyclohexane,
1,1-bis(4-(1-(4-aminophenyl)nonyl)phenyl)-4-methylcyclohexane,
1,1-bis(4-(1-(4-aminophenyl)decyl)phenyl)-4-methylcyclohexane,
1,1-bis(4-(1-(4-aminophenyl)undecyl)phenyl)-4-methylcyclohexane,
1,1-bis(4-(1-(4-aminophenyl)dodecyl)phenyl)-4-methylcyclohexane,
1,1-bis(4-(1-(4-aminophenyl)tridecyl)phenyl)-4-methylcyclohexane,
1,1-bis(4-(1-(4-aminophenyl)ethyl)phenyl)-4-ethylcyclohexane,
1,1-bis(4-(1-(4-aminophenyl)propyl)phenyl)-4-ethylcyclohexane,
1,1-bis(4-(1-(4-aminophenyl)butyl)phenyl)-4-ethylcyclohexane,
1,1-bis(4-(1-(4-aminophenyl)pentyl)phenyl)-4-ethylcyclohexane,
1,1-bis(4-(1-(4-aminophenyl)hexyl)phenyl)-4-ethylcyclohexane,
1,1-bis(4-(1-(4-aminophenyl)heptyl)phenyl)-4-ethylcyclohexane,
1,1-bis(4-(1-(4-aminophenyl)nonyl)phenyl)-4-ethylcyclohexane,
1,1-bis(4-(1-(4-aminophenyl)decyl)phenyl)-4-ethylcyclohexane,
1,1-bis(4-(1-(4-aminophenyl)undecyl)phenyl)-4-ethylcyclohexane,
1,1-bis(4-(1-(4-aminophenyl)dodecyl)phenyl)-4-ethylcyclohexane,
1,1-bis(4-(1-(4-aminophenyl)tridecyl)phenyl)-4-ethylcyclohexane,
1,1-bis(4-(1-(4-aminophenyl)ethyl)phenyl)-4-propylcyclohexane,
1,1-bis(4-(1-(4-aminophenyl)propyl)phenyl)-4-propylcyclohexane,
1,1-bis(4-(1-(4-aminophenyl)butyl)phenyl)-4-propylcyclohexane,
1,1-bis(4-(1-(4-aminophenyl)pentyl)phenyl)-4-propylcyclohexane,
1,1-bis(4-(1-(4-aminophenyl)hexyl)phenyl)-4-propylcyclohexane,
1,1-bis(4-(1-(4-aminophenyl)heptyl)phenyl)-4-propylcyclohexane,
1,1-bis(4-(1-(4-aminophenyl)nonyl)phenyl)-4-propylcyclohexane,
1,1-bis(4-(1-(4-aminophenyl)decyl)phenyl)-4-propylcyclohexane,
1,1-bis(4-(1-(4-aminophenyl)undecyl)phenyl)-4-propylcyclohexane,
1,1-bis(4-(1-(4-aminophenyl)dodecyl)phenyl)-4-propylcyclohexane,
1,1-bis(4-(1-(4-aminophenyl)tridecyl)phenyl)-4-propylcyclohexane,
1,1-bis(4-(1-(4-aminophenyl)ethyl)phenyl)-4-butylcyclohexane,
1,1-bis(4-(1-(4-aminophenyl)propyl)phenyl)-4-butylcyclohexane,
1,1-bis(4-(1-(4-aminophenyl)butyl)phenyl)-4-butylcyclohexane,
1,1-bis(4-(1-(4-aminophenyl)pentyl)phenyl)-4-butylcyclohexane,
1,1-bis(4-(1-(4-aminophenyl)hexyl)phenyl)-4-butylcyclohexane,
1,1-bis(4-(1-(4-aminophenyl)heptyl)phenyl)-4-butylcyclohexane,
1,1-bis(4-(1-(4-aminophenyl)nonyl)phenyl)-4-butylcyclohexane, 1,1-bis(4-(1-(4-aminophenyl)decyl)phenyl)-4-butylcyclohexane,
1,1-bis(4-(1-(4-aminophenyl)undecyl)phenyl)-4-butylcyclohexane,
1,1-bis(4-(1-(4-aminophenyl)dodecyl)phenyl)-4-butylcyclohexane,
1,1-bis(4-(1-(4-aminophenyl)tridecyl)phenyl)-4-butylcyclohexane,
1,1-bis(4-(1-(4-aminophenyl)ethyl)phenyl)-4-pentylcyclohexane,
1,1-bis(4-(1-(4-aminophenyl)propyl)phenyl)-4-pentylcyclohexane,
1,1-bis(4-(1-(4-aminophenyl)butyl)phenyl)-4-pentylcyclohexane,
1,1-bis(4-(1-(4-aminophenyl)pentyl)phenyl)-4-pentylcyclohexane,
1,1-bis(4-(1-(4-aminophenyl)hexyl)phenyl)-4-pentylcyclohexane,
1,1-bis(4-(1-(4-aminophenyl)heptyl)phenyl)-4-pentylcyclohexane,
1,1-bis(4-(1-(4-aminophenyl)nonyl)phenyl)-4-pentylcyclohexane,
1,1-bis(4-(1-(4-aminophenyl)decyl)phenyl)-4-pentylcyclohexane,
1,1-bis(4-(1-(4-aminophenyl)undecyl)phenyl)-4-pentylcyclohexane,
1,1-bis(4-(1-(4-aminophenyl)dodecyl)phenyl)-4-pentylcyclohexane,
1,1-bis(4-(1-(4-aminophenyl)tridecyl)phenyl)-4-pentylcyclohexane,
1,1-bis(4-(1-(4-aminophenyl)ethyl)phenyl)-4-hexylcyclohexane,
1,1-bis(4-(1-(4-aminophenyl)propyl)phenyl)-4-hexylcyclohexane,
1,1-bis(4-(1-(4-aminophenyl)butyl)phenyl)-4-hexylcyclohexane,
1,1-bis(4-(1-(4-aminophenyl)pentyl)phenyl)-4-hexylcyclohexane,
1,1-bis(4-(1-(4-aminophenyl)hexyl)phenyl)-4-hexylcyclohexane,
1,1-bis(4-(1-(4-aminophenyl)heptyl)phenyl)-4-hexylcyclohexane,
1,1-bis(4-(1-(4-aminophenyl)nonyl)phenyl)-4-hexylcyclohexane,
1,1-bis(4-(1-(4-aminophenyl)decyl)phenyl)-4-hexylcyclohexane,
1,1-bis(4-(1-(4-aminophenyl)undecyl)phenyl)-4-hexylcyclohexane,
1,1-bis(4-(1-(4-aminophenyl)dodecyl)phenyl)-4-hexylcyclohexane,
1,1-bis(4-(1-(4-aminophenyl)tridecyl)phenyl)-4-hexylcyclohexane,
1,1-bis(4-(1-(4-aminophenyl)ethyl)phenyl)-4-heptylcyclohexane,
1,1-bis(4-(1-(4-aminophenyl)propyl)phenyl)-4-heptylcyclohexane,
1,1-bis(4-(1-(4-aminophenyl)butyl)phenyl)-4-heptylcyclohexane,
1,1-bis(4-(1-(4-aminophenyl)pentyl)phenyl)-4-heptylcyclohexane,
1,1-bis(4-(1-(4-aminophenyl)hexyl)phenyl)-4-heptylcyclohexane,
1,1-bis(4-(1-(4-aminophenyl)heptyl)phenyl)-4-heptylcyclohexane,
1,1-bis(4-(1-(4-aminophenyl)nonyl)phenyl)-4-heptylcyclohexane,
1,1-bis(4-(1-(4-aminophenyl)decyl)phenyl)-4-heptylcyclohexane,
1,1-bis(4-(1-(4-aminophenyl)undecyl)phenyl)-4-heptylcyclohexane,
1,1-bis(4-(1-(4-aminophenyl)dodecyl)phenyl)-4-heptylcyclohexane,
1,1-bis(4-(1-(4-aminophenyl)tridecyl)phenyl)-4-heptylcyclohexane,
1,1-bis(4-(1-(4-aminophenyl)ethyl)phenyl)-4-octylcyclohexane,
1,1-bis(4-(1-(4-aminophenyl)propyl)phenyl)-4-octylcyclohexane,
1,1-bis(4-(1-(4-aminophenyl)butyl)phenyl)-4-octylcyclohexane,
1,1-bis(4-(1-(4-aminophenyl)pentyl)phenyl)-4-octylcyclohexane,
1,1-bis(4-(1-(4-aminophenyl)hexyl)phenyl)-4-octylcyclohexane,
1,1-bis(4-(1-(4-aminophenyl)heptyl)phenyl)-4-octylcyclohexane,
1,1-bis(4-(1-(4-aminophenyl)nonyl)phenyl)-4-octylcyclohexane,
1,1-bis(4-(1-(4-aminophenyl)decyl)phenyl)-4-octylcyclohexane,
1,1-bis(4-(1-(4-aminophenyl)undecyl)phenyl)-4-octylcyclohexane,
1,1-bis(4-(1-(4-aminophenyl)dodecyl)phenyl)-4-octylcyclohexane,
1,1-bis(4-(1-(4-aminophenyl)tridecyl)phenyl)-4-octylcyclohexane,
1,1-bis(4-(1-(4-aminophenyl)ethyl)phenyl)-4-nonylcyclohexane,
1,1-bis(4-(1-(4-aminophenyl)propyl)phenyl)-4-nonylcyclohexane,
1,1-bis(4-(1-(4-aminophenyl)butyl)phenyl)-4-nonylcyclohexane,
1,1-bis(4-(1-(4-aminophenyl)pentyl)phenyl)-4-nonylcyclohexane,
1,1-bis(4-(1-(4-aminophenyl)hexyl)phenyl)-4-nonylcyclohexane,
1,1-bis(4-(1-(4-aminophenyl)heptyl)phenyl)-4-nonylcyclohexane,
1,1-bis(4-(1-(4-aminophenyl)nonyl)phenyl)-4-nonylcyclohexane,
1,1-bis(4-(1-(4-aminophenyl)decyl)phenyl)-4-nonylcyclohexane,
1,1-bis(4-(1-(4-aminophenyl)undecyl)phenyl)-4-nonylcyclohexane,
1,1-bis(4-(1-(4-aminophenyl)dodecyl)phenyl)-4-nonylcyclohexane,
1,1-bis(4-(1-(4-aminophenyl)tridecyl)phenyl)-4-nonylcyclohexane,
1,1-bis(4-(1-(4-aminophenyl)ethyl)phenyl)-4-decylcyclohexane,
1,1-bis(4-(1-(4-aminophenyl)propyl)phenyl)-4-decylcyclohexane,
1,1-bis(4-(1-(4-aminophenyl)butyl)phenyl)-4-decylcyclohexane,
1,1-bis(4-(1-(4-aminophenyl)pentyl)phenyl)-4-decylcyclohexane,
1,1-bis(4-(1-(4-aminophenyl)hexyl)phenyl)-4-decylcyclohexane,
1,1-bis(4-(1-(4-aminophenyl)heptyl)phenyl)-4-decylcyclohexane,
1,1-bis(4-(1-(4-aminophenyl)nonyl)phenyl)-4-decylcyclohexane,
1,1-bis(4-(1-(4-aminophenyl)decyl)phenyl)-4-decylcyclohexane,
1,1-bis(4-(1-(4-aminophenyl)undecyl)phenyl)-4-decylcyclohexane, 1,1-bis(4-(1-(4-aminophenyl)dodecyl)phenyl)-4-decylcyclohexane,
1,1-bis(4-(1-(4-aminophenyl)tridecyl)phenyl)-4-decylcyclohexane,
1,1-bis(4-(1-(4-aminophenyl)ethyl)phenyl)-4-undecylcyclohexane,
1,1-bis(4-(1-(4-aminophenyl)propyl)phenyl)-4-undecylcyclohexane,
1,1-bis(4-(1-(4-aminophenyl)butyl)phenyl)-4-undecylcyclohexane,
1,1-bis(4-(1-(4-aminophenyl)pentyl)phenyl)-4-undecylcyclohexane,
1,1-bis(4-(1-(4-aminophenyl)hexyl)phenyl)-4-undecylcyclohexane,
1,1-bis(4-(1-(4-aminophenyl)heptyl)phenyl)-4-undecylcyclohexane,
1,1-bis(4-(1-(4-aminophenyl)nonyl)phenyl)-4-undecylcyclohexane,
1,1-bis(4-(1-(4-aminophenyl)decyl)phenyl)-4-undecylcyclohexane,
1,1-bis(4-(1-(4-aminophenyl)undecyl)phenyl)-4-undecylcyclohexane,
1,1-bis(4-(1-(4-aminophenyl)dodecyl)phenyl)-4-undecylcyclohexane,
1,1-bis(4-(1-(4-aminophenyl)tridecyl)phenyl)-4-undecylcyclohexane,
1,1-bis(4-(1-(4-aminophenyl)ethyl)phenyl)-4-dodecylcyclohexane,
1,1-bis(4-(1-(4-aminophenyl)propyl)phenyl)-4-dodecylcyclohexane,
1,1-bis(4-(1-(4-aminophenyl)butyl)phenyl)-4-dodecylcyclohexane,
1,1-bis(4-(1-(4-aminophenyl)pentyl)phenyl)-4-dodecylcyclohexane,
1,1-bis(4-(1-(4-aminophenyl)hexyl)phenyl)-4-dodecylcyclohexane,
1,1-bis(4-(1-(4-aminophenyl)heptyl)phenyl)-4-dodecylcyclohexane,
1,1-bis(4-(1-(4-aminophenyl)nonyl)phenyl)-4-dodecylcyclohexane,
1,1-bis(4-(1-(4-aminophenyl)decyl)phenyl)-4-dodecylcyclohexane,
1,1-bis(4-(1-(4-aminophenyl)undecyl)phenyl)-4-dodecylcyclohexane,
1,1-bis(4-(1-(4-aminophenyl)dodecyl)phenyl)-4-dodecylcyclohexane,
1,1-bis(4-(1-(4-aminophenyl)tridecyl)phenyl)-4-dodecylcyclohexane,
1,1-bis(4-(1-(2-methyl-4-aminophenyl)ethyl)phenyl)cyclohexane,
1,1-bis(4-(1-(2-methyl-4-aminophenyl)propyl)phenyl)cyclohexane,
1,1-bis(4-(1-(2-methyl-4-aminophenyl)butyl)phenyl)cyclohexane,
1,1-bis(4-(1-(2-methyl-4-aminophenyl)pentyl)phenyl)cyclohexane,
1,1-bis(4-(1-(2-methyl-4-aminophenyl)hexyl)phenyl)cyclohexane,
1,1-bis(4-(1-(2-methyl-4-aminophenyl)heptyl)phenyl)cyclohexane,
1,1-bis(4-(1-(2-methyl-4-aminophenyl)nonyl)phenyl)cyclohexane,
1,1-bis(4-(1-(2-methyl-4-aminophenyl)decyl)phenyl)cyclohexane,
1,1-bis(4-(1-(2-methyl-4-aminophenyl)undecyl)phenyl)cyclohexane,
1,1-bis(4-(1-(2-methyl-4-aminophenyl)dodecyl)phenyl)cyclohexane,
1,1-bis(4-(1-(2-methyl-4-aminophenyl)tridecyl)phenyl)cyclohexane,
1,1-bis(4-(1-(2-methyl-4-aminophenyl)ethyl)phenyl)-4-methylcyclohexane,
1,1-bis(4-(1-(2-methyl-4-aminophenyl)propyl)phenyl)-4-methylcyclohexane,
1,1-bis(4-(1-(2-methyl-4-aminophenyl)butyl)phenyl)-4-methylcyclohexane,
1,1-bis(4-(1-(2-methyl-4-aminophenyl)pentyl)phenyl)-4-methylcyclohexane,
1,1-bis(4-(1-(2-methyl-4-aminophenyl)hexyl)phenyl)-4-methylcyclohexane,
1,1-bis(4-(1-(2-methyl-4-aminophenyl)heptyl)phenyl)-4-methylcyclohexane,
1,1-bis(4-(1-(2-methyl-4-aminophenyl)nonyl)phenyl)-4-methylcyclohexane,
1,1-bis(4-(1-(2-methyl-4-aminophenyl)decyl)phenyl)-4-methylcyclohexane,
1,1-bis(4-(1-(2-methyl-4-aminophenyl)undecyl)phenyl)-4-methylcyclohexane,
1,1-bis(4-(1-(2-methyl-4-aminophenyl)dodecyl)phenyl)-4-methylcyclohexane,
1,1-bis(4-(1-(2-methyl-4-aminophenyl)tridecyl)phenyl)-4-methylcyclohexane,
1,1-bis(4-(1-(2-methyl-4-aminophenyl)ethyl)phenyl)-4-ethylcyclohexane,
1,1-bis(4-(1-(2-methyl-4-aminophenyl)propyl)phenyl)-4-ethylcyclohexane,
1,1-bis(4-(1-(2-methyl-4-aminophenyl)butyl)phenyl)-4-ethylcyclohexane,
1,1-bis(4-(1-(2-methyl-4-aminophenyl)pentyl)phenyl)-4-ethylcyclohexane,
1,1-bis(4-(1-(2-methyl-4-aminophenyl)hexyl)phenyl)-4-ethylcyclohexane,
1,1-bis(4-(1-(2-methyl-4-aminophenyl)heptyl)phenyl)-4-ethylcyclohexane,
1,1-bis(4-(1-(2-methyl-4-aminophenyl)nonyl)phenyl)-4-ethylcyclohexane,
1,1-bis(4-(1-(2-methyl-4-aminophenyl)decyl)phenyl)-4-ethylcyclohexane,
1,1-bis(4-(1-(3-methyl-4-aminophenyl)undecyl)phenyl)-4-ethylcyclohexane,
1,1-bis(4-(1-(2-methyl-4-aminophenyl)dodecyl)phenyl)-4-ethylcyclohexane,
1,1-bis(4-(1-(2-methyl-4-aminophenyl)tridecyl)phenyl)-4-ethylcyclohexane,
1,1-bis(4-(1-(2-methyl-4-aminophenyl)ethyl)phenyl)-4-propylcyclohexane,
1,1-bis(4-(1-(2-methyl-4-aminophenyl)propyl)phenyl)-4-propylcyclohexane,
1,1-bis(4-(1-(2-methyl-4-aminophenyl)butyl)phenyl)-4-propylcyclohexane,
1,1-bis(4-(1-(2-methyl-4-aminophenyl)pentyl)phenyl)-4-propylcyclohexane,
1,1-bis(4-(1-(2-methyl-4-aminophenyl)hexyl)phenyl)-4-propylcyclohexane,
1,1-bis(4-(1-(2-methyl-4-aminophenyl)heptyl)phenyl)-4-propylcyclohexane,
1,1-bis(4-(1-(2-methyl-4-aminophenyl)nonyl)phenyl)-4-propylcyclohexane,
1,1-bis(4-(1-(2-methyl-4-aminophenyl)decyl)phenyl)-4-propylcyclohexane,
1,1-bis(4-(1-(2-methyl-4-aminophenyl)undecyl)phenyl)-4-propylcyclohexane,
1,1-bis(4-(1-(2-methyl-4-aminophenyl)dodecyl)phenyl)-4-propylcyclohexane,
1,1-bis(4-(1-(2-methyl-4-aminophenyl)tridecyl)phenyl)-4-propylcyclohexane, 1,1-bis(4-(1-(2-methyl-4-aminophenyl)ethyl)phenyl)-4-butylcyclohexane,
1,1-bis(4-(1-(2-methyl-4-aminophenyl)propyl)phenyl)-4-butylcyclohexane,
1,1-bis(4-(1-(2-methyl-4-aminophenyl)butyl)phenyl)-4-butylcyclohexane,
1,1-bis(4-(1-(2-methyl-4-aminophenyl)pentyl)phenyl)-4-butylcyclohexane,
1,1-bis(4-(1-(2-methyl-4-aminophenyl)hexyl)phenyl)-4-butylcyclohexane,
1,1-bis(4-(1-(2-methyl-4-aminophenyl)heptyl)phenyl)-4-butylcyclohexane,
1,1-bis(4-(1-(2-methyl-4-aminophenyl)nonyl)phenyl)-4-butylcyclohexane,
1,1-bis(4-(1-(2-methyl-4-aminophenyl)decyl)phenyl)-4-butylcyclohexane,
1,1-bis(4-(1-(2-methyl-4-aminophenyl)undecyl)phenyl)-4-butylcyclohexane,
1,1-bis(4-(1-(2-methyl-4-aminophenyl)dodecyl)phenyl)-4-butylcyclohexane,
1,1-bis(4-(1-(2-methyl-4-aminophenyl)tridecyl)phenyl)-4-butylcyclohexane,
1,1-bis(4-(1-(2-methyl-4-aminophenyl)ethyl)phenyl)-4-pentylcyclohexane,
1,1-bis(4-(1-(2-methyl-4-aminophenyl)propyl)phenyl)-4-pentylcyclohexane,
1,1-bis(4-(1-(2-methyl-4-aminophenyl)butyl)phenyl)-4-pentylcyclohexane,
1,1-bis(4-(1-(2-methyl-4-aminophenyl)pentyl)phenyl)-4-pentylcyclohexane,
1,1-bis(4-(1-(2-methyl-4-aminophenyl)hexyl)phenyl)-4-pentylcyclohexane,
1,1-bis(4-(1-(2-methyl-4-aminophenyl)heptyl)phenyl)-4-pentylcyclohexane,
1,1-bis(4-(1-(2-methyl-4-aminophenyl)nonyl)phenyl)-4-pentylcyclohexane,
1,1-bis(4-(1-(2-methyl-4-aminophenyl)decyl)phenyl)-4-pentylcyclohexane,
1,1-bis(4-(1-(l-methyl-4-aminophenyl)undecyl)phenyl)-4-pentylcyclohexane,
1,1-bis(4-(1-(2-methyl-4-aminophenyl)dodecyl)phenyl)-4-pentylcyclohexane,
1,1-bis(4-(1-(2-methyl-4-aminophenyl)tridecyl)phenyl)-4-pentylcyclohexane,
1,1-bis(4-(1-(2-methyl-4-aminophenyl)ethyl)phenyl)-4-hexylcyclohexane,
1,1-bis(4-(1-(2-methyl-4-aminophenyl)propyl)phenyl)-4-hexylcyclohexane,
1,1-bis(4-(1-(2-methyl-4-aminophenyl)butyl)phenyl)-4-hexylcyclohexane,
1,1-bis(4-(1-(2-methyl-4-aminophenyl)pentyl)phenyl)-4-hexylcyclohexane,
1,1-bis(4-(1-(2-methyl-4-aminophenyl)hexyl)phenyl)-4-hexylcyclohexane,
1,1-bis(4-(1-(2-methyl-4-aminophenyl)heptyl)phenyl)-4-hexylcyclohexane,
1,1-bis(4-(1-(2-methyl-4-aminophenyl)nonyl)phenyl)-4-hexylcyclohexane,
1,1-bis(4-(1-(2-methyl-4-aminophenyl)decyl)phenyl)-4-hexylcyclohexane,
1,1-bis(4-(1-(2-methyl-4-aminophenyl)undecyl)phenyl)-4-hexylcyclohexane,
1,1-bis(4-(1-(2-methyl-4-aminophenyl)dodecyl)phenyl)-4-hexylcyclohexane,
1,1-bis(4-(1-(2-methyl-4-aminophenyl)tridecyl)phenyl)-4-hexylcyclohexane,
1,1-bis(4-(1-(2-methyl-4-aminophenyl)ethyl)phenyl)-4-heptylcyclohexane,
1,1-bis(4-(1-(2-methyl-4-aminophenyl)propyl)phenyl)-4-heptylcyclohexane,
1,1-bis(4-(1-(2-methyl-4-aminophenyl)butyl)phenyl)-4-heptylcyclohexane,
1,1-bis(4-(1-(2-methyl-4-aminophenyl)pentyl)phenyl)-4-heptylcyclohexane,
1,1-bis(4-(1-(2-methyl-4-aminophenyl)hexyl)phenyl)-4-heptylcyclohexane,
1,1-bis(4-(1-(2-methyl-4-aminophenyl)heptyl)phenyl)-4-heptylcyclohexane,
1,1-bis(4-(1-(2-methyl-4-aminophenyl)nonyl)phenyl)-4-heptylcyclohexane,
1,1-bis(4-(1-(2-methyl-4-aminophenyl)decyl)phenyl)-4-heptylcyclohexane,
1,1-bis(4-(1-(2-methyl-4-aminophenyl)undecyl)phenyl)-4-heptylcyclohexane,
1,1-bis(4-(1-(2-methyl-4-aminophenyl)dodecyl)phenyl)-4-heptylcyclohexane,
1,1-bis(4-(1-(2-methyl-4-aminophenyl)tridecyl)phenyl)-4-heptylcyclohexane,
1,1-bis(4-(1-(2-methyl-4-aminophenyl)ethyl)phenyl)-4-octylcyclohexane,
1,1-bis(4-(1-(2-methyl-4-aminophenyl)propyl)phenyl)-4-octylcyclohexane,
1,1-bis(4-(1-(2-methyl-4-aminophenyl)butyl)phenyl)-4-octylcyclohexane,
1,1-bis(4-(1-(2-methyl-4-aminophenyl)pentyl)phenyl)-4-octylcyclohexane,
1,1-bis(4-(1-(2-methyl-4-aminophenyl)hexyl)phenyl)-4-octylcyclohexane,
1,1-bis(4-(1-(2-methyl-4-aminophenyl)heptyl)phenyl)-4-octylcyclohexane,
1,1-bis(4-(1-(2-methyl-4-aminophenyl)nonyl)phenyl)-4-octylcyclohexane,
1,1-bis(4-(1-(2-methyl-4-aminophenyl)decyl)phenyl)-4-octylcyclohexane,
1,1-bis(4-(1-(2-methyl-4-aminophenyl)undecyl)phenyl)-4-octylcyclohexane,
1,1-bis(4-(1-(2-methyl-4-aminophenyl)dodecyl)phenyl)-4-octylcyclohexane,
1,1-bis(4-(1-(2-methyl-4-aminophenyl)tridecyl)phenyl)-4-octylcyclohexane,
1,1-bis(4-(1-(2-methyl-4-aminophenyl)ethyl)phenyl)-4-nonylcyclohexane,
1,1-bis(4-(1-(2-methyl-4-aminophenyl)propyl)phenyl)-4-nonylcyclohexane,
1,1-bis(4-(1-(2-methyl-4-aminophenyl)butyl)phenyl)-4-nonylcyclohexane,
1,1-bis(4-(1-(2-methyl-4-aminophenyl)pentyl)phenyl)-4-nonylcyclohexane,
1,1-bis(4-(1-(2-methyl-4-aminophenyl)hexyl)phenyl)-4-nonylcyclohexane,
1,1-bis(4-(1-(2-methyl-4-aminophenyl)heptyl)phenyl)-4-nonylcyclohexane,
1,1-bis(4-(1-(2-methyl-4-aminophenyl)nonyl)phenyl)-4-nonylcyclohexane,
1,1-bis(4-(1-(2-methyl-4-aminophenyl)decyl)phenyl)-4-nonylcyclohexane,
1,1-bis(4-(1-(2-methyl-4-aminophenyl)undecyl)phenyl)-4-nonylcyclohexane,
1,1-bis(4-(1-(2-methyl-4-aminophenyl)dodecyl)phenyl)-4-nonylcyclohexane,
1,1-bis(4-(1-(2-methyl-4-aminophenyl)tridecyl)phenyl)-4-nonylcyclohexane,
1,1-bis(4-(1-(2-methyl-4-aminophenyl)ethyl)phenyl)-4-decylcyclohexane,
1,1-bis(4-(1-(2-methyl-4-aminophenyl)propyl)phenyl)-4-decylcyclohexane, 1,1-bis(4-(1-(2-methyl-4-aminophenyl)butyl)phenyl)-4-decylcyclohexane,
1,1-bis(4-(1-(2-methyl-4-aminophenyl)pentyl)phenyl)-4-decylcyclohexane,
1,1-bis(4-(1-(2-methyl-4-aminophenyl)hexyl)phenyl)-4-decylcyclohexane,
1,1-bis(4-(1-(2-methyl-4-aminophenyl)heptyl)phenyl)-4-decylcyclohexane,
1,1-bis(4-(1-(2-methyl-4-aminophenyl)nonyl)phenyl)-4-decylcyclohexane,
1,1-bis(4-(1-(2-methyl-4-aminophenyl)decyl)phenyl)-4-decylcyclohexane,
1,1-bis(4-(1-(2-methyl-4-aminophenyl)undecyl)phenyl)-4-decylcyclohexane,
1,1-bis(4-(1-(2-methyl-4-aminophenyl)dodecyl)phenyl)-4-decylcyclohexane,
1,1-bis(4-(1-(2-methyl-4-aminophenyl)tridecyl)phenyl)-4-decylcyclohexane,
1,1-bis(4-(1-(2-methyl-4-aminophenyl)ethyl)phenyl)-4-undecylcyclohexane,
1,1-bis(4-(1-(2-methyl-4-aminophenyl)propyl)phenyl)-4-undecylcyclohexane,
1,1-bis(4-(1-(2-methyl-4-aminophenyl)butyl)phenyl)-4-undecylcyclohexane,
1,1-bis(4-(1-(2-methyl-4-aminophenyl)pentyl)phenyl)-4-undecylcyclohexane,
1,1-bis(4-(1-(2-methyl-4-aminophenyl)hexyl)phenyl)-4-undecylcyclohexane,
1,1-bis(4-(1-(2-methyl-4-aminophenyl)heptyl)phenyl)-4-undecylcyclohexane,
1,1-bis(4-(1-(2-methyl-4-aminophenyl)nonyl)phenyl)-4-undecylcyclohexane,
1,1-bis(4-(1-(2-methyl-4-aminophenyl)decyl)phenyl)-4-undecylcyclohexane,
1,1-bis(4-(1-(2-methyl-4-aminophenyl)undecyl)phenyl)-4-undecylcyclohexane,
1,1-bis(4-(1-(2-methyl-4-aminophenyl)dodecyl)phenyl)-4-undecylcyclohexane,
1,1-bis(4-(1-(2-methyl-4-aminophenyl)tridecyl)phenyl)-4-undecylcyclohexane,
1,1-bis(4-(1-(2-methyl-4-aminophenyl)ethyl)phenyl)-4-dodecylcyclohexane,
1,1-bis(4-(1-(2-methyl-4-aminophenyl)propyl)phenyl)-4-dodecylcyclohexane,
1,1-bis(4-(1-(2-methyl-4-aminophenyl)butyl)phenyl)-4-dodecylcyclohexane,
1,1-bis(4-(1-(2-methyl-4-aminophenyl)pentyl)phenyl)-4-dodecylcyclohexane,
1,1-bis(4-(1-(2-methyl-4-aminophenyl)hexyl)phenyl)-4-dodecylcyclohexane,
1,1-bis(4-(1-(2-methyl-4-aminophenyl)heptyl)phenyl)-4-dodecylcyclohexane,
1,1-bis(4-(1-(2-methyl-4-aminophenyl)nonyl)phenyl)-4-dodecylcyclohexane,
1,1-bis(4-(1-(2-methyl-4-aminophenyl)decyl)phenyl)-4-dodecylcyclohexane,
1,1-bis(4-(1-(2-methyl-4-aminophenyl)undecyl)phenyl)-4-dodecylcyclohexane,
1,1-bis(4-(1-(2-methyl-4-aminophenyl)dodecyl)phenyl)-4-dodecylcyclohexane,
1,1-bis(4-(1-(2-methyl-4-aminophenyl)tridecyl)phenyl)-4-dodecylcyclohexane,
1,4-bis(4-(1-(4-aminophenyl)ethyl)benzyl)benzene,
1,4-bis(4-(1-(4-aminophenyl)propyl)benzyl)benzene,
1,4-bis(4-(1-(4-aminophenyl)butyl)benzyl)benzene,
1,4-bis(4-(1-(4-aminophenyl)pentyl)benzyl)benzene,
1,4-bis(4-(1-(4-aminophenyl)hexyl)benzyl)benzene,
1,4-bis(4-(1-(4-aminophenyl)heptyl)benzyl)benzene,
1,4-bis(4-(1-(4-aminophenyl)nonyl)benzyl)benzene,
1,4-bis(4-(1-(4-aminophenyl)decyl)benzyl)benzene,
1,4-bis(4-(1-(4-aminophenyl)undecyl)benzyl)benzene,
1,4-bis(4-(1-(4-aminophenyl)dodecyl)benzyl)benzene,
1,4-bis(4-(1-(4-aminophenyl)tridecyl)benzyl)benzene, etc.

Amongst them, preferred compounds are mentioned as follows:
1,4-bis(4-(4-aminophenylmethyl)phenylmethyl)benzene,
1,4-bis(2-methyl-4-(4-aminophenylmethyl)phenylmethyl)benzene,
1,4-bis(3-methyl-4-(4-aminophenylmethyl)phenylmethyl)benzene,
1,4-bis(4-(4-aminophenylmethyl)phenylmethyl)-2-methylbenzene,
1-(4-(4-aminophenylmethyl)phenylmethyl)-4-(2-methyl-4-(4-aminophenylmethyl)phenylmethyl)benzene,
1-(4-(4-aminophenylmethyl)phenylmethyl)-4-(3-methyl-4-(4-aminophenylmethyl)phenylmethyl)benzene,
1-(4-(4-aminophenylmethyl)phenylmethyl)-4-(2-methyl-4-(4-aminophenylmethyl)phenylmethyl)-2-methylbenzene,
1-(4-(4-aminophenylmethyl)phenylmethyl)-4-(3-methyl-4-(4-aminophenylmethyl)phenylmethyl)-2-methylbenzene,
1,1-bis(4-(4-(4-aminophenylmethyl)phenylmethyl)phenyl)methane,
1,1-bis(4-(2-methyl-4-(4-aminophenylmethyl)phenylmethyl)phenyl)methane,
1,1-bis(4-(3-methyl-4-(4-aminophenylmethyl)phenylmethyl)phenyl)methane,
1,1-bis(2-methyl-4-(4-(4-aminophenylmethyl)phenylmethyl)phenyl)methane,
1,1-bis(3-methyl-4-(4-(4-aminophenylmethyl)phenylmethyl)phenyl)methane,
1-(4-(4-(4-aminophenylmethyl)phenylmethyl)phenyl)-1-(2-methyl-4-(4-(4-aminophenylmethyl)phenylmethyl)phenyl)methane,
1-(4-(4-(4-aminophenylmethyl)phenylmethyl)phenyl)-1-(3-methyl-4-(4-(4-aminophenylmethyl)phenylmethyl)phenyl)methane,
1-(4-(4-(4-aminophenylmethyl)phenylmethyl)phenyl)-1-(4-(2-methyl-4-(4-aminophenylmethyl)phenylmethyl)phenyl)methane,
1-(4-(4-(4-aminophenylmethyl)phenylmethyl)phenyl)-1-(4-(3-methyl-4-(4-aminophenylmethyl)phenylmethyl)phenyl)methane,
1,2-bis(4-(4-aminobenzyl)phenyl)ethane,
1,3-bis(4-(4-aminobenzyl)phenyl)propane,
1,4-bis(4-(4-aminobenzyl)phenyl)butane,
1,5-bis(4-(4-aminobenzyl)phenyl)pentane,
1,6-bis(4-(4-aminobenzyl)phenyl)hexane,
1,7-bis(4-(4-aminobenzyl)phenyl)heptane,
1,8-bis(4-(4-aminobenzyl)phenyl)octane,
1,9-bis(4-(4-aminobenzyl)phenyl)nonane,
1,10-bis(4-(4-aminobenzyl)phenyl)decane,
1,11-bis(4-(4-aminobenzyl)phenyl)undecane,
1,12-bis(4-(4-aminobenzyl)phenyl)dodecane,
1,13-bis(4-(4-aminobenzyl)phenyl)tridecane,
1,14-bis(4-(4-aminobenzyl)phenyl)tetradecane,
1,15-bis(4-(4-aminobenzyl)phenyl)pentadecane,
1,16-bis(4-(4-aminobenzyl)phenyl)hexadecane,
1,17-bis(4-(4-aminobenzyl)phenyl)heptadecane,
1,18-bis(4-(4-aminobenzyl)phenyl)octadecane,
1,19-bis(4-(4-aminobenzyl)phenyl)nonadecane,
1,20-bis(4-(4-aminobenzyl)phenyl)icosane,
1,3-bis(4-(4-aminobenzyl)phenyl)-2-methylpropane,
1,3-bis(4-(4-aminobenzyl)phenyl)-2-ethylpropane,
1,3-bis(4-(4-aminobenzyl)phenyl)-2-propylpropane, 1,3-bis(4-(4-aminobenzyl)phenyl)-2-butylpropane,
1,3-bis(4-(4-aminobenzyl)phenyl)-2-pentylpropane,
1,3-bis(4-(4-aminobenzyl)phenyl)-2-hexylpropane,
1,3-bis(4-(4-aminobenzyl)phenyl)-2-heptylpropane,
1,3-bis(4-(4-aminobenzyl)phenyl)-2-octylpropane,
1,3-bis(4-(4-aminobenzyl)phenyl)-2-nonylpropane,
1,3-bis(4-(4-aminobenzyl)phenyl)-2-decylpropane,
1,3-bis(4-(4-aminobenzyl)phenyl)-2-undecylpropane,
1,3-bis(4-(4-aminobenzyl)phenyl)-2-dodecylpropane,
1,1-bis(4-(4-aminobenzyl)phenyl)ethane,
1,1-bis(4-(4-aminobenzyl)phenyl)propane,
1,1-bis(4-(4-aminobenzyl)phenyl)butane,
1,1-bis(4-(4-aminobenzyl)phenyl)pentane,
1,1-bis(4-(4-aminobenzyl)phenyl)hexane,
1,1-bis(4-(4-aminobenzyl)phenyl)heptane,
1,1-bis(4-(4-aminobenzyl)phenyl)octane,
1,1-bis(4-(4-aminobenzyl)phenyl)nonane,
1,1-bis(4-(4-aminobenzyl)phenyl)decane,
1,1-bis(4-(4-aminobenzyl)phenyl)undecane,
1,1-bis(4-(4-aminobenzyl)phenyl)dodecane,
bis(4-(1-(4-aminophenyl)ethyl)phenyl)methane,
bis(4-(1-(4-aminophenyl)propyl)phenyl)methane,
bis(4-(1-(4-aminophenyl)butyl)phenyl)methane,
bis(4-(1-(4-aminophenyl)pentyl)phenyl)methane,
bis(4-(1-(4-aminophenyl)hexyl)phenyl)methane,
bis(4-(1-(4-aminophenyl)heptyl)phenyl)methane,
bis(4-(1-(4-aminophenyl)nonyl)phenyl)methane,
bis(4-(1-(4-aminophenyl)decyl)phenyl)methane,
bis(4-(1-(4-aminophenyl)undecyl)phenyl)methane,
bis(4-(1-(4-aminophenyl)dodecyl)phenyl)methane,
bis(4-(1-(4-aminophenyl)tridecyl)phenyl)methane,
1,1-bis(4-(1-(4-aminophenyl)ethyl)phenyl)cyclohexane,
1,1-bis(4-(1-(4-aminophenyl)propyl)phenyl)cyclohexane,
1,1-bis(4-(1-(4-aminophenyl)butyl)phenyl)cyclohexane,
1,1-bis(4-(1-(4-aminophenyl)pentyl)phenyl)cyclohexane,
1,1-bis(4-(1-(4-aminophenyl)hexyl)phenyl)cyclohexane,
1,1-bis(4-(1-(4-aminophenyl)heptyl)phenyl)cyclohexane,
1,1-bis(4-(1-(4-aminophenyl)nonyl)phenyl)cyclohexane,
1,1-bis(4-(1-(4-aminophenyl)decyl)phenyl)cyclohexane,
1,1-bis(4-(1-(4-aminophenyl)undecyl)phenyl)cyclohexane,
1,1-bis(4-(1-(4-aminophenyl)dodecyl)phenyl)cyclohexane,
1,1-bis(4-(1-(4-aminophenyl)tridecyl)phenyl)cyclohexane,
1,1-bis(4-(1-(4-aminophenyl)ethyl)phenyl)-4-butylcyclohexane,
1,1-bis(4-(1-(4-aminophenyl)propyl)phenyl)-4-butylcyclohexane,
1,1-bis(4-(1-(4-aminophenyl)butyl)phenyl)-4-butylcyclohexane,
1,1-bis(4-(1-(4-aminophenyl)pentyl)phenyl)-4-butylcyclohexane,
1,1-bis(4-(1-(4-aminophenyl)hexyl)phenyl)-4-butylcyclohexane,
1,1-bis(4-(1-(4-aminophenyl)heptyl)phenyl)-4-butylcyclohexane,
1,1-bis(4-(1-(4-aminophenyl)nonyl)phenyl)-4-butylcyclohexane,
1,1-bis(4-(1-(4-aminophenyl)decyl)phenyl)-4-butylcyclohexane,
1,1-bis(4-(1-(4-aminophenyl)undecyl)phenyl)-4-butylcyclohexane,
1,1-bis(4-(1-(4-aminophenyl)dodecyl)phenyl)-4-butylcyclohexane,
1,1-bis(4-(1-(4-aminophenyl)tridecyl)phenyl)-4-butylcyclohexane, etc.

Amongst them, particularly preferred compounds are mentioned as follows:
1,4-bis(4-(4-aminophenylmethyl)phenylmethyl)benzene,
1,1-bis(4-(4-(4-aminophenylmethyl)phenylmethyl)phenyl)methane,
1,2-bis(4-(4-aminobenzyl)phenyl)ethane,
1,3-bis(4-(4-aminobenzyl)phenyl)propane,
1,4-bis(4-(4-aminobenzyl)phenyl)butane,
1,5-bis(4-(4-aminobenzyl)phenyl)pentane,
1,6-bis(4-(4-aminobenzyl)phenyl)hexane,
1,7-bis(4-(4-aminobenzyl)phenyl)heptane,
1,8-bis(4-(4-aminobenzyl)phenyl)octane,
1,9-bis(4-(4-aminobenzyl)phenyl)nonane,
1,10-bis(4-(4-aminobenzyl)phenyl)decane,
1,3-bis(4-(4-aminobenzyl)phenyl)-2-methylpropane,
1,3-bis(4-(4-aminobenzyl)phenyl)-2-ethylpropane,
1,3-bis(4-(4-aminobenzyl)phenyl)-2-propylpropane,
1,3-bis(4-(4-aminobenzyl)phenyl)-2-butylpropane,
1,3-bis(4-(4-aminobenzyl)phenyl)-2-pentylpropane,
1,3-bis(4-(4-aminobenzyl)phenyl)-2-hexylpropane,
1,3-bis(4-(4-aminobenzyl)phenyl)-2-heptylpropane,
1,3-bis(4-(4-aminobenzyl)phenyl)-2-octylpropane,
1,3-bis(4-(4-aminobenzyl)phenyl)-2-nonylpropane,
1,3-bis(4-(4-aminobenzyl)phenyl)-2-decylpropane,
1,1-bis(4-(4-aminobenzyl)phenyl)ethane,
1,1-bis(4-(4-aminobenzyl)phenyl)propane,
1,1-bis(4-(4-aminobenzyl)phenyl)butane,
1,1-bis(4-(4-aminobenzyl)phenyl)pentane,
1,1-bis(4-(4-aminobenzyl)phenyl)hexane,
1,1-bis(4-(4-aminobenzyl)phenyl)heptane,
1,1-bis(4-(4-aminobenzyl)phenyl)octane,
1,1-bis(4-(4-aminobenzyl)phenyl)nonane,
1,1-bis(4-(4-aminobenzyl)phenyl)decane,
bis(4-(1-(4-aminophenyl)ethyl)phenyl)methane,
bis(4-(1-(4-aminophenyl)propyl)phenyl)methane,
bis(4-(1-(4-aminophenyl)butyl)phenyl)methane,
bis(4-(1-(4-aminophenyl)pentyl)phenyl)methane,
bis(4-(1-(4-aminophenyl)hexyl)phenyl)methane,
bis(4-(1-(4-aminophenyl)heptyl)phenyl)methane,
1,1-bis(4-(1-(4-aminophenyl)ethyl)phenyl)cyclohexane,
1,1-bis(4-(1-(4-aminophenyl)propyl)phenyl)cyclohexane,
1,1-bis(4-(1-(4-aminophenyl)butyl)phenyl)cyclohexane,
1,1-bis(4-(1-(4-aminophenyl)pentyl)phenyl)cyclohexane,
1,1-bis(4-(1-(4-aminophenyl)hexyl)phenyl)cyclohexane,
1,1-bis(4-(1-(4-aminophenyl)heptyl)phenyl)cyclohexane,
1,1-bis(4-(1-(4-aminophenyl)ethyl)phenyl)-4-butylcyclohexane,
1,1-bis(4-(1-(4-aminophenyl)propyl)phenyl)-4-butylcyclohexane,
1,1-bis(4-(1-(4-aminophenyl)butyl)phenyl)-4-butylcyclohexane,
1,1-bis(4-(1-(4-aminophenyl)pentyl)phenyl)-4-butylcyclohexane,
1,1-bis(4-(1-(4-aminophenyl)hexyl)phenyl)-4-butylcyclohexane,
1,1-bis(4-(1-(4-aminophenyl)heptyl)phenyl)-4-butylcyclohexane.

The preparation of the diamino compounds according to the invention will be explained more concretely as follows.

Diphenylmethane and its derivatives to be used in the invention are expressed by formula (5), and they can be commercially available or synthesized easily by known methods. There may be mentioned the following compounds as concrete examples: diphenylmethane, 2-methyl diphenylmethane, 2-ethyl diphenylmethane, 2-propyl diphenylmethane, 2-butyl diphenylmethane, 2-pentyl diphenylmethane, 2-hexyl diphenylmethane, 2-heptyl diphenylmethane, 2-octyl diphenylmethane, 3-methyl diphenylmethane, 3-ethyl diphenylmethane, 3-propyl diphenylmethane, 3-butyl diphenylmethane, 3-pentyl diphenylmethane, 3-hexyl diphenylmethane, 3-heptyl diphenylmethane, 3-octyl diphenylmethane, 2,2'-dimethyl diphenylmethane, 2,2'-diethyl diphenylmethane, 2,2'-dipropyl diphenylmethane, 2,2'-dibutyl diphenylmethane, 2,2'-dipentyl diphenylmethane, 2,2'-dihexyl diphenylmethane, 2,2'-diheptyl diphenylmethane, 2,2'-dioctyl diphenylmethane, 2,3'-dimethyl diphenylmethane, 2,3'-diethyl diphenylmethane, 2,3'-dipropyl diphenylmethane, 2,3'-dibutyl diphenylmethane, 2,3'-dipentyl diphenylmethane, 2,3'-dihexyl diphenylmethane, 2,3'-diheptyl diphenylmethane, 2,3'-dioctyl diphenylmethane, 3,3'-dimethyl diphenylmethane, 3,3'-diethyl diphenylmethane, 3,3'-dipropyl diphenylmethane, 3,3'-dibutyl diphenylmethane, 3,3'-dipentyl diphenylmethane, 3,3'-dihexyl diphenylmethane, 3,3'-diheptyl diphenylmethane, 3,3'-dioctyl diphenylmethane, 2,3-dimethyl diphenylmethane, 2,3-diethyl diphenylmethane, 2,3-dipropyl diphenylmethane, 2,3-dibutyl diphenylmethane, 2,3-dipentyl diphenylmethane, 2,3-dihexyl diphenylmethane, 2,3-diheptyl diphenylmethane, 2,3-dioctyl diphenylmethane, 2,5-dimethyl diphenylmethane, 2,5-diethyl diphenylmethane, 2,5-dipropyl diphenylmethane, 2,5-dibutyl diphenylmethane, 2,5-dipentyl diphenylmethane, 2,5-dihexyl diphenylmethane, 2,5-diheptyl diphenylmethane, 2,5-dioctyl diphenylmethane, 2,6-dimethyl diphenylmethane, 2,6-diethyl diphenylmethane, 2,6-dipropyl diphenylmethane, 2,6-dibutyl diphenylmethane, 2,6-dipentyl diphenylmethane, 2,6-dihexyl diphenylmethane, 2,6-diheptyl diphenylmethane, 2,6-dioctyl diphenylmethane, 3,5-dimethyl diphenylmethane, 3,5-diethyl diphenylmethane, 3,5-dipropyl diphenylmethane, 3,5-dibutyl diphenylmethane, 3,5-dipentyl diphenylmethane, 3,5-dihexyl diphenylmethane, 3,5-diheptyl diphenylmethane, 3,5-dioctyl diphenylmethane, 2-methyl-2'-ethyl diphenylmethane, 2-methyl-2'-propyl diphenylmethane, 2-methyl-2'-butyl diphenylmethane, 2-methyl-2-pentyl diphenylmethane, 2-methyl-2'-hexyl diphenylmethane, 2-methyl-2'-heptyl diphenylmethane, 2-methyl-2'-octyl diphenylmethane, 2-methyl-3'-ethyl diphenylmethane, 2-methyl-3'-propyl diphenylmethane, 2-methyl-3'-butyl diphenylmethane, 2-methyl-3'-pentyl diphenylmethane, 2-methyl-3'-hexyl diphenylmethane, 2-methyl-3'-heptyl diphenylmethane, 2-methyl-3'-octyl diphenylmethane, 3-methyl-2'-ethyl diphenylmethane, 3-methyl-2'-propyl diphenylmethane, 3-methyl-2'-butyl diphenylmethane, 3-methyl-2'-pentyl diphenylmethane, 3-methyl-2'-hexyl diphenylmethane, 3-methyl-2'-heptyl diphenylmethane, 3-methyl-2'-octyl diphenylmethane, 3-methyl-3'-ethyl diphenylmethane, 3-methyl-3'-propyl diphenylmethane, 3-methyl-3'-butyl diphenylmethane, 3-methyl-3'-pentyl diphenylmethane, 3-methyl-3'-hexyl diphenylmethane, 3-methyl-3'-heptyl diphenylmethane, 3-methyl-3'-octyl diphenylmethane, 2,2',3-trimethyl diphenylmethane, 2,2',5-trimethyl diphenylmethane, 2,2',6-trimethyl diphenylmethane, 2,3,3'-trimethyl diphenylmethane, 2,3',5-trimethyl diphenylmethane, 2,3',6-trimethyl diphenylmethane, 2,2',6,6'-tetramethyl diphenylmethane, 2,2',5,6'-tetramethyl diphenylmethane, and 2,2',5,5'-tetramethyl diphenylmethane.

Benzoyl halides or their derivatives to be used in the invention are expressed by formula (6), and they can be commercially available or synthesized easily by known methods. There may be mentioned the following compounds as concrete examples: benzoyl chloride, benzoyl bromide, 2-methyl benzoyl chloride, 2-methyl benzoyl bromide, 2-ethyl benzoyl chloride, 2-ethyl benzoyl bromide, 2-propyl benzoyl chloride, 2-propyl benzoyl bromide, 2-butyl benzoyl chloride, 2-butyl benzoyl bromide, 2-pentyl benzoyl chloride, 2-pentyl benzoyl bromide, 2-hexyl benzoyl chloride, 2-hexyl benzoyl bromide, 2-heptyl benzoyl chloride, 2-heptyl benzoyl bromide, 2-octyl benzoyl chloride, 2-octyl benzoyl bromide, 3-methyl benzoyl chloride, 3-methyl benzoyl bromide, 3-ethyl benzoyl chloride, 3-ethyl benzoyl bromide, 3-propyl benzoyl chloride, 3-propyl benzoyl bromide, 3-butyl, benzoyl chloride, 3-butyl benzoyl bromide, 3-pentyl benzoyl chloride, 3-pentyl benzoyl bromide, 3-hexyl benzoyl chloride, 3-hexyl benzoyl bromide, 3-heptyl benzoyl chloride, 3-heptyl benzoyl bromide, 3-octyl benzoyl chloride, 3-octyl benzoyl bromide, 2,3-dimethyl benzoyl chloride, 2,3-dimethyl benzoyl bromide, 2,5-dimethyl benzoyl chloride, 2,5-dimethyl benzoyl bromide, 2,6-dimethyl benzoyl chloride, 2,6-dimethyl benzoyl bromide, 2-methyl-3-ethyl benzoyl chloride, 2-methyl-3-ethyl benzoyl bromide, 2-methyl-3-propyl benzoyl chloride, 2-methyl-3-propyl benzoyl bromide, 2-methyl-3-butyl benzoyl chloride, 2-methyl-3-butyl benzoyl bromide, 2-methyl-3-pentyl benzoyl chloride, 2-methyl-3-pentyl benzoyl bromide, 2-methyl-3-hexyl benzoyl chloride, 2-methyl-3-hexyl benzoyl bromide, 2-methyl-3-heptyl benzoyl chloride, 2-methyl-3-heptyl benzoyl bromide, 2-methyl-3-octyl benzoyl chloride, 2-methyl-3-octyl benzoyl bromide, 2-methyl-6-ethyl benzoyl chloride, 2-methyl-6-ethyl benzoyl bromide, 2-methyl-6-propyl benzoyl chloride, 2-methyl-6-propyl benzoyl bromide, 2-methyl-6-butyl benzoyl chloride, 2-methyl-6-butyl benzoyl bromide, 2-methyl-6-pentyl benzoyl chloride, 2-methyl-6-pentyl benzoyl bromide, 2-methyl-6-hexyl benzoyl chloride, 2-methyl-6-hexyl benzoyl bromide, 2-methyl-6-heptyl benzoyl chloride, 2-methyl-6-heptyl benzoyl bromide, 2-methyl-6-octyl benzoyl chloride, 2-methyl-6-octyl benzoyl bromide, 2,3,5-trimethyl benzoyl chloride, 2,3,5-trimethyl benzoyl bromide, 2,3,5,6-tetramethyl benzoyl chloride, and 2,3,5,6-tetramethyl benzoyl bromide.

For the reaction of diphenylmethane or its derivatives and benzoyl halide or its derivative, a catalyst is generally used. As the catalyst, there may be mentioned $AlCl_3$, $SbCl_5$, $FeCl_3$, $TeCl_2$, $SnCl_4$, $TiCl_4$, $BiCl_3$, $ZnCl_2$, etc., $AlCl_3$ and $FeCl_3$ being preferable from view points of reactivity, safety and economy.

Furthermore, a solvent such as carbon disulfide, dichloromethane, chloroform, dichloroethane, nitrobenzene etc. is generally used for the reaction.

The reaction is carried out by mixing the catalyst and benzoyl halide or its derivative with stirring and then adding dropwise diphenylmethane or its derivative (if required, dissolved in the solvent) to be reacted.

After the end of reaction, the mixed reaction solution is poured on ice in order to decompose an adduct of a product and the catalyst, removed off the solvent etc. by a water washing, a distillation or a steam distillation etc. and purified. Furthermore, carbonyl groups can be reduced by a Clemensen reduction, a Wolf-Kishner reduction, a catalytic hydrogen reduction with palladium carbon etc. or by use of lithium aluminum hydride-aluminum chloride etc., to obtain the bis(benzyl)phenyl methane derivatives. These compounds belong to one type of the compounds expressed by the formula (3).

Furthermore, the compounds expressed by the formula (3), dibenzylbenzene or its derivatives, are expressed by the formula (7), and they can be commercially available or synthesized easily by known methods. There may be mentioned the following compounds as concrete examples:

1,4-bis(phenylmethyl)benzene,
1-phenylmethyl-4-(1-(2-methylphenyl)methyl)benzene,
1-phenylmethyl-4-(1-(2-ethylphenyl)methyl)benzene,
1-phenylmethyl-4-(1-(2-propylphenyl)methyl)benzene,
1-phenylmethyl-4-(1-(2-butylphenyl)methyl)benzene,
1-phenylmethyl-4-(1-(2-pentylphenyl)methyl)benzene,
1-phenylmethyl-4-(1-(2-hexylphenyl)methyl)benzene,
1-phenylmethyl-4-(1-(2-heptylphenyl)methyl)benzene,
1-phenylmethyl-4-(1-(2-octylphenyl)methyl)benzene,
1-phenylmethyl-4-(1-(3-methylphenyl)methyl)benzene,
1-phenylmethyl-4-(1-(3-ethylphenyl)methyl)benzene,
1-phenylmethyl-4-(1-(3-propylphenyl)methyl)benzene,
1-phenylmethyl-4-(1-(3-butylphenyl)methyl)benzene,
1-phenylmethyl-4-(1-(3-pentylphenyl)methyl)benzene,
1-phenylmethyl-4-(1-(3-hexylphenyl)methyl)benzene,
1-phenylmethyl-4-(1-(3-heptylphenyl)methyl)benzene,
1-phenylmethyl-4-(1-(3-octylphenyl)methyl)benzene,
1-phenylmethyl-2-methyl-4-(1-(2-methylphenyl)methyl)benzene,
1-phenylmethyl-2-ethyl-4-(1-(2-methylphenyl)methyl)benzene,
1-phenylmethyl-2-propyl-4-(1-(2-methylphenyl)methyl)benzene,
1-phenylmethyl-2-butyl-4-(1-(2-methylphenyl)methyl)benzene,
1-phenylmethyl-2-pentyl-4-(1-(2-methylphenyl)methyl)benzene,
1-phenylmethyl-2-hexyl-4-(1-(2-methylphenyl)methyl)benzene,
1-phenylmethyl-2-heptyl-4-(1-(2-methylphenyl)methyl)benzene,
1-phenylmethyl-2-octyl-4-(1-(2-methylphenyl)methyl)benzene,
1-phenylmethyl-2-methyl-4-(1-(3-methylphenyl)methyl)benzene,
1-phenylmethyl-2-ethyl-4-(1-(3-methylphenyl)methyl)benzene,
1-phenylmethyl-2-propyl-4-(1-(3-methylphenyl)methyl)benzene,
1-phenylmethyl-2-butyl-4-(1-(3-methylphenyl)methyl)benzene,
1-phenylmethyl-2-pentyl-4-(1-(3-methylphenyl)methylbenzene,
1-phenylmethyl-2-hexyl-4-(1-(3-methylphenyl)methyl)benzene,
1-phenylmethyl-2-heptyl-4-(1-(3-methylphenyl)methyl)benzene,
1-phenylmethyl-2-octyl-4-(1-(3-methylphenyl)methyl)benzene,
1,4-bis(1-(2-methylphenyl)methyl)benzene,
1,4-bis(1-(2-ethylphenyl)methyl)benzene,
1,4-bis(1-(2-propylphenyl)methyl)benzene,
1,4-bis(1-(2-butylphenyl)methyl)benzene,
1,4-bis(1-(2-pentylphenyl)methyl)benzene,
1,4-bis(1-(2-hexylphenyl)methyl)benzene,
1,4-bis(1-(2-heptylphenyl)methyl)benzene,
1,4-bis(1-(2-octylphenyl)methyl)benzene,
1,4-bis(1-(3-methylphenyl)methyl)benzene,
1,4-bis(1-(3-ethylphenyl)methyl)benzene,
1,4-bis(1-(3-propylphenyl)methyl)benzene,
1,4-bis(1-(3-butylphenyl)methyl)benzene,
1,4-bis(1-(3-pentylphenyl)methyl)benzene,
1,4-bis(1-(3-hexylphenyl)methyl)benzene,
1,4-bis(1-(3-heptylphenyl)methyl)benzene,
1,4-bis(1-(3-octylphenyl)methyl)benzene,
1,4-bis(1-(2-methylphenyl)methyl)-2-methylbenzene,
1,4-bis(1-(2-methylphenyl)methyl)-2-ethylbenzene,
1,4-bis(1-(2-methylphenyl)methyl)-2-propylbenzene,
1,4-bis(1-(2-methylphenyl)methyl)-2-butylbenzene,
1,4-bis(1-(2-methylphenyl)methyl)-2-pentylbenzene,
1,4-bis(1-(2-methylphenyl)methyl)-2-hexylbenzene,
1,4-bis(1-(2-methylphenyl)methyl)-2-heptylbenzene,
1,4-bis(1-(2-methylphenyl)methyl)-2-octylbenzene,
1,4-bis(1-(3-methylphenyl)methyl)-2-methylbenzene,
1,4-bis(1-(3-methylphenyl)methyl)-2-ethylbenzene,
1,4-bis(1-(3-methylphenyl)methyl)-2-propylbenzene,
1,4-bis(1-(3-methylphenyl)methyl)-2-butylbenzene,
1,4-bis(1-(3-methylphenyl)methyl)-2-pentylbenzene,
1,4-bis(1-(3-methylphenyl)methyl)-2-hexylbenzene,
1,4-bis(1-(3-methylphenyl)methyl)-2-heptylbenzene,
1,4-bis(1-(3-methylphenyl)methyl)-2-octylbenzene,
1-(2-methylphenyl)methyl-4-(2-ethylphenyl)methylbenzene,
1-(2-methylphenyl)methyl-4-(2-propylphenyl)methylbenzene,
1-(2-methylphenyl)methyl-4-(2-butylphenyl)methylbenzene,
1-(2-methylphenyl)methyl-4-(2-pentylphenyl)methylbenzene,
1-(2-methylphenyl)methyl-4-(2-hexylphenyl)methylbenzene,
1-(2-methylphenyl)methyl-4-(2-heptylphenyl)methylbenzene,
1-(2-methylphenyl)methyl-4-(2-octylphenyl)methylbenzene,
1-(3-methylphenyl)methyl-4-(2-ethylphenyl)methylbenzene,
1-(3-methylphenyl)methyl-4-(2-propylphenyl)methylbenzene,
1-(3-methylphenyl)methyl-4-(2-butylphenyl)methylbenzene,
1-(3-methylphenyl)methyl-4-(2-pentylphenyl)methylbenzene,
1-(3-methylphenyl)methyl-4-(2-hexylphenyl)methylbenzene,
1-(3-methylphenyl)methyl-4-(2-heptylphenyl)methylbenzene,
1-(3-methylphenyl)methyl-4-(2-octylphenyl)methylbenzene,
1,4-bis(phenylmethyl)-2-methylbenzene,
1,4-bis(phenylmethyl)-2-ethylbenzene,
1,4-bis(phenylmethyl)-2-propylbenzene,
1,4-bis(phenylmethyl)-2-butylbenzene,
1,4-bis(phenylmethyl)-2-pentylbenzene,
1,4-bis(phenylmethyl)-2-hexylbenzene,
1,4-bis(phenylmethyl)-2-heptylbenzene,
1,4-bis(phenylmethyl)-2-octylbenzene,
1,4-bis(phenylmethyl)-2,3-dimethylbenzene,
1,4-bis(phenylmethyl)-2,5-dimethylbenzene, and
1,4-bis(phenylmethyl)-2,6-dimethylbenzene.

As concrete examples of the compounds expressed by the formula (7) or the formula (8), the other aromatic compounds expressed by the formula (3), the followings are mentioned and they can be commercially available or synthesized easily by known methods:

1,2-diphenylethane,
1,3-diphenylpropane,
1,4-diphenylbutane,
1,5-diphenylpentane,
1,6-diphenylhexane,
1,7-diphenylheptane,
1,8-diphenyloctane, 1,9-diphenylnonane,
1,10-diphenyldecane,
1,11-diphenylundecane,
1,12-diphenyldodecane,
1,13-diphenyltridecane,
1,14-diphenyltetradecane,
1,15-diphenylpentadecane,
1,16-diphenylhexadecane,
1,17-diphenylheptadecane,
1,18-diphenyloctadecane,
1,19-diphenylnonadecane,
1,20-diphenylicosane,
1,2-bis(2-methylphenyl)ethane,
1,3-bis(2-methylphenyl)propane,
1,4-bis(2-methylphenyl)butane,
1,5-bis(2-methylphenyl)pentane,
1,6-bis(2-methylphenyl)hexane,
1,7-bis(2-methylphenyl)heptane,
1,8-bis(2-methylphenyl)octane,
1,9-bis(2-methylphenyl)nonane,
1,10-bis(2-methylphenyl)decane,
1,11-bis(2-methylphenyl)undecane,
1,12-bis(2-methylphenyl)dodecane,
1,13-bis(2-methylphenyl)tridecane,
1,14-bis(2-methylphenyl)tetradecane,
1,15-bis(2-methylphenyl)pentadecane,
1,16-bis(2-methylphenyl)hexadecane,
1,17-bis(2-methylphenyl)heptadecane,
1,18-bis(2-methylphenyl)octadecane,
1,19-bis(2-methylphenyl)nonadecane,
1,20-bis(2-methylphenyl)icosane,
1,2-bis(3-methylphenyl)ethane,
1,3-bis(3-methylphenyl)propane,
1,4-bis(3-methylphenyl)butane,
1,5-bis(3-methylphenyl)pentane,
1,6-bis(3-methylphenyl)hexane,
1,7-bis(3-methylphenyl)heptane,
1,8-bis(3-methylphenyl)octane,
1,9-bis(3-methylphenyl)nonane,
1,10-bis(3-methylphenyl)decane,
11-bis(3-methylphenyl)undecane,
12-bis(3-methylphenyl)dodecane,
1,13-bis(3-methylphenyl)tridecane,
1,14-bis(3-methylphenyl)tetradecane,
1,15-bis(3-methylphenyl)pentadecane,
1,16-bis(3-methylphenyl)hexadecane,
1,17-bis(3-methylphenyl)heptadecane,
1,18-bis(3-methylphenyl)octadecane,
1,19-bis(3-methylphenyl)nonadecane,
1,20-bis(3-methylphenyl)icosane,
1,2-bis(2,6-dimethylphenyl)ethane,
1,3-bis(2,6-dimethylphenyl)propane,
1,4-bis(2,6-dimethylphenyl)butane,
1,5-bis(2,6-dimethylphenyl)pentane,
1,6-bis(2,6-dimethylphenyl)hexane,
1,7-bis(2,6-dimethylphenyl)heptane,
1,8-bis(2,6-dimethylphenyl)octane,
1,9-bis(2,6-dimethylphenyl)nonane,
1,10-bis(2,6-dimethylphenyl)decane,
1,11-bis(2,6-dimethylphenyl)undecane,
1,12-bis(2,6-dimethylphenyl)dodecane,
1,13-bis(2,6-dimethylphenyl)tridecane,
1,14-bis(2,6-dimethylphenyl)tetradecane,
1,15-bis(2,6-dimethylphenyl)pentadecane,
1,16-bis(2,6-dimethylphenyl)hexadecane,
1,17-bis(2,6-dimethylphenyl)heptadecane,
1,18-bis(2,6-dimethylphenyl)octadecane,
1,19-bis(2,6-dimethylphenyl)nonadecane,
1,20-bis(2,6-dimethylphenyl)icosane,
1,2-bis(3,5-dimethylphenyl)ethane,
1,3-bis(3,5-dimethylphenyl)propane,
1,4-bis(3,5-dimethylphenyl)butane,
1,5-bis(3,5-dimethylphenyl)pentane,
1,6-bis(3,5-dimethylphenyl)hexane,
1,7-bis(3,5-dimethylphenyl)heptane,
1,8-bis(3,5-dimethylphenyl)octane,
1,9-bis(3,5-dimethylphenyl)nonane,
1,10-bis(3,5-dimethylphenyl)decane,
1,11-bis(3,5-dimethylphenyl)undecane,
1,12-bis(3,5-dimethylphenyl)dodecane,
1,13-bis(3,5-dimethylphenyl)tridecane,
1,14-bis(3,5-dimethylphenyl)tetradecane,
1,15-bis(3,5-dimethylphenyl)pentadecane,
1,16-bis(3,5-dimethylphenyl)hexadecane,
1,17-bis(3,5-dimethylphenyl)heptadecane,
1,18-bis(3,5-dimethylphenyl)octadecane,
1,19-bis(3,5-dimethylphenyl)nonadecane,
1,20-bis(3,5-dimethylphenyl)icosane,
1,1-diphenylmethane,
1,1-diphenylethane,
1,1-diphenylpropane,
1,1-diphenylbutane,
1,1-diphenylpentane,
1,1-diphenylhexane,
1,1-diphenylheptane,
1,1-diphenyloctane,
1,1-diphenylnonane,
1,1-diphenyldecane,
1,1-diphenylundecane,
1,1-diphenyldodecane,
1,3-diphenyl-2-methylpropane,
1-phenyl-2-(phenylmethyl)butane,
1-phenyl-2-(phenylmethyl)pentane,
1-phenyl-2-(phenylmethyl)hexane,
1-phenyl-2-(phenylmethyl)heptane,
1-phenyl-2-(phenylmethyl)octane,
1-phenyl-2-(phenylmethyl)nonane,
1-phenyl-2-(phenylmethyl)decane,
1-phenyl-2-(phenylmethyl)undecane,
1-phenyl-2-(phenylmethyl)dodecane,
1-phenyl-2-(phenylmethyl)tridecane,
1-phenyl-2-(phenylmethyl)tetradecane,
1,5-diphenyl-3-methylpentane, 1,5-diphenyl-3-ethylpentane,
1-phenyl-3-(2-phenylethyl)hexane,
1-phenyl-3-(2-phenylethyl)heptane,
1-phenyl-3-(2-phenylethyl)octane,
1-phenyl-3-(2-phenylethyl)nonane,
1-phenyl-3-(2-phenylethyl)decane,
1-phenyl-3-(2-phenylethyl)undecane,
1-phenyl-3-(2-phenylethyl)dodecane,
1-phenyl-3-(2-phenylethyl)tridecane,
1-phenyl-3-(2-phenylethyl)tetradecane,
1-phenyl-3-(2-phenylethyl)pentadecane,
2,2-diphenylpropane,
2,2-diphenylbutane,
2,2-diphenylpentane,
2,2-diphenylhexane,
2,2-diphenylheptane,
2,2-diphenyloctane,
2,2-diphenylnonane,
2,2-diphenyldecane,
2,2-diphenylundecane,
2,2-diphenyldodecane, 2,2-diphenyltridecane,
2,2-diphenyltetradecane,
1,1-diphenyltridecane,
1,2-diphenylpropane,
1,2-diphenylbutane,
1,2-diphenylpentane,
1,2-diphenylhexane,
1,2-diphenylheptane,
1,2-diphenyloctane,
1,2-diphenylnonane,
1,2-diphenyldecane,
1,2-diphenylundecane,
1,2-diphenyldodecane, 1,2-diphenyltridecane,
1,2-diphenyltetradecane,
1,1-dibenzylethane,
1,1-dibenzylpropane,
1,1-dibenzylbutane,
1,1-dibenzylpentane,
1,1-dibenzylhexane,
1,1-dibenzylheptane,
1,1-dibenzyloctane,
1,1-dibenzylnonane,
1,1-dibenzyldecane,
1,1-dibenzylundecane,
1,1-dibenzyldodecane,
1,1-dibenzylcyclohexane,
1,1-diphenyl-4-methylcyclohexane,
1,1-diphenyl-4-ethylcyclohexane,
1,1-diphenyl-4-propylcyclohexane,
1,1-diphenyl-4-butylcyclohexane,
1,1-diphenyl-4-pentylcyclohexane,
1,1-diphenyl-4-hexylcyclohexane,
1,1-diphenyl-4-heptylcyclohexane,
1,1-diphenyl-4-octylcyclohexane,
1,1-diphenyl-4-nonylcyclohexane,
1,1-diphenyl-4-decylcyclohexane,
1,1-diphenyl-4-undecylcyclohexane,
1,1-diphenyl-4-dodecylcyclohexane,
biphenyl,
2-methylbiphenyl,
2,2'-dimethylbiphenyl,
p-terphenyl,
m-terphenyl,
o-terphenyl,
1,4-dibenzylbenzene,
1,1-bis(4-benzylphenyl)methane.

Paranitrobenzoyl halide derivatives to be used in the invention are expressed by the formula (4), and they can be commercially available or synthesized easily by known methods. There may be mentioned the following compounds as concrete examples: paranitrobenzoyl chloride, paranitrobenzoyl bromide, 2-methyl-4-nitrobenzoyl chloride, 2-ethyl-4-nitrobenzoyl chloride, 2-propyl-4-nitrobenzoyl chloride, 2-butyl-4-nitrobenzoyl chloride, 2-pentyl-4-nitrobenzoyl chloride, 2-hexyl-4-nitrobenzoyl chloride, 2-heptyl-4-nitrobenzoyl chloride, 2-octyl-4-nitrobenzoyl chloride, 3-methyl-4-nitrobenzoyl chloride, 3-ethyl-4-nitrobenzoyl chloride, 3-propyl-4-nitrobenzoyl chloride, 3-butyl-4-nitrobenzoyl chloride, 3-pentyl-4-nitrobenzoyl chloride, 3-hexyl-4-nitrobenzoyl chloride, 3-heptyl-4-nitrobenzoyl chloride, 3-octyl-4-nitrobenzoyl chloride, 2,3-dimethyl-4-nitrobenzoyl chloride, 2,5-dimethyl-4-nitrobenzoyl chloride, 2,6-dimethyl-4-nitrobenzoyl chloride, 3,5-dimethyl-4-nitrobenzoyl chloride, 2,3,5-trimethyl-4-nitrobenzoyl chloride, 2,3,5,6-tetramethyl-4-nitrobenzoyl chloride,
2-methyl-4-nitrobenzoyl bromide, 2-ethyl-4-nitrobenzoyl bromide, 2-propyl-4-nitrobenzoyl bromide, 2-butyl-4-nitrobenzoyl bromide, 2-pentyl-4-nitrobenzoyl bromide, 2-hexyl-4-nitrobenzoyl bromide, 2-heptyl-4-nitrobenzoyl bromide, 2-octyl-4-nitrobenzoyl bromide, 3-methyl-4-nitrobenzoyl bromide, 3-ethyl-4-nitrobenzoyl bromide, 3-propyl-4-nitrobenzoyl bromide, 3-butyl-4-nitrobenzoyl bromide, 3-pentyl-4-nitrobenzoyl bromide, 3-hexyl-4-nitrobenzoyl bromide, 3-heptyl-4-nitrobenzoyl bromide, 3-octyl-4-nitrobenzoyl bromide, 2,3-dimethyl-4-nitrobenzoyl bromide, 2,5-dimethyl-4-nitrobenzoyl bromide, 2,6-dimethyl-4-nitrobenzoyl bromide, 3,5-dimethyl-4-nitrobenzoyl bromide, 2,3,5-trimethyl-4-nitrobenzoyl bromide, 2,3,5,6-tetramethyl-4-nitrobenzoyl bromide.

For the reaction of the aromatic compound expressed by the formula (3) and paranitrobenzoyl halide derivative expressed by the formula (4), a catalyst is generally used. As the catalyst, there may be mentioned $AlCl_3$, $SbCl_5$, $FeCl_3$, $TeCl_2$, $SnCl_4$, $TiCl_4$, $BiCl_3$, $ZnCl_2$, etc., $AlCl_3$ and $FeCl_3$ being preferable from view points of reactivity, safety and economy.

Furthermore, a solvent such as carbon disulfide, dichloromethane, chloroform, dichloroethane and nitrobenzene is generally used for the reaction.

The reaction is carried out by mixing the catalyst and the paranitrobenzoyl halide derivative with stirring and then adding dropwise the diphenyl alkane derivative (if required, dissolved in the solvent) to be reacted.

After the end of the reaction, the mixed reaction solution is poured on ice in order to decompose an adduct of a product and the catalyst, then removed off the solvent etc. by a water washing, a distillation or a steam distillation etc. and purified, to obtain the bis(4-nitrobenzoyl)phenyl)alkane derivative.

Reduction of carbonyl groups can be carried out by reacting with trialkyl silane, for example, triethyl silane in the presence of catalyst such as trifluoromethanesulfonic acid, titanium tetrachloride, boron trifluoride or its complexes. The temperature during reduction is preferably at from 0° C. to 100° C. For the reaction, a solvent may be used, halogenated hydrocarbons such as dichloromethane, chloroform, and dichloroethane being preferable.

Furthermore, alkylation of carbonyl groups can be carried out by reacting with a phosphorus compound such as an alkyl phosphonium salt to produce a phosphorus ylid, then reacting the ylid with the above-mentioned bis(4-(4-nitrobenzoyl)phenyl)alkane derivative and then reducing the double bond formed.

As the phosphorus compound, there may be mentioned methyltriphenylphosphonium chloride, methyltriphenylphosphonium bromide, ethyltriphenylphosphonium chloride, ethyltriphenylphosphonium bromide, propyltriphenylphosphonium chloride, propyltriphenylphosphonium bromide, isopropyltriphenylphosphonium chloride, isopropyltriphenylphosphonium bromide, butyltriphenylphosphonium chloride, butyltriphenylphosphonium bromide, isobutyltriphenylphosphonium chloride, isobutyltriphenylphosphonium bromide, pentyltriphenylphosphonium chloride, pentyltriphenylphosphonium bromide, cyclopentyltriphenylphosphonium chloride, cyclopentyltriphenylphosphonium bromide, hexyltriphenylphosphonium chloride, hexyltriphenylphosphonium bromide, cyclohexyltriphenylphosphonium chloride, cyclohexyltriphenylphosphonium bromide, heptyltriphenylphosphonium chloride, heptyltriphenylphosphonium bromide, 2-ethylhexyltriphenylphosphonium chloride, 2-ethylhexyltriphenylphosphonium bromide, octyltriphenylphosphonium chloride, octyltriphenylphosphonium bromide, nonyltriphenylphosphonium chloride, nonyltriphenylphosphonium bromide, decyltriphenylphosphonium chloride, decyltriphenylphosphonium bromide, undecyltriphenylphosphonium chloride, undecyltriphenylphosphonium bromide, dodecyltriphenylphosphonium chloride, and dodecyltriphenylphosphonium bromide.

As the base, there may be used sodium hydroxide, sodium carbonate, sodium methoxide, sodium ethoxide, potassium-t-butoxide, triethylamine, pyridine, 1,5-diazabicyclo[4,3,0]nonene-5, n-butyl lithium, phenyl lithium, sodium amide and sodium hydride etc.

The reaction is carried out by stirring the phosphorus compound in a solvent such as methanol, ethanol, dichloromethane, dichloroethane, chloroform, ether, tetrahydrofuran, dimethyl formamide, benzene, ammonia, dimethyl sulfoxide, nitromethane, ethylene glycol dimethyl ether or diethylene glycol dimethyl ether to be dissolved or suspended and then reacting with the base to produce the ylid, then adding dropwise the above-mentioned bis(4-(4-nitrobenzoyl)phenyl) alkane derivative (if required, dissolved in the solvent) to be reacted. The temperature thereof depends on the reactivity and stability of the ylid, $-78°$ C. to $150°$ C. being preferable.

After the end of reaction, purification is carried out by a water washing, an extraction, and a silica gel column treatment etc.

Reductions of double bonds and nitro groups are carried out by a hydrogen reduction in a solvent such as toluene, xylene, methanol, ethanol, ethylene glycol monoethyl ether, ethylene glycol monobutyl ether, ethyl acetate, tetrahydrofuran, or acetic acid, with a catalyst such as platinum-carbon, platinum oxide, Raney nickel, palladium-carbon, and if required with addition of an acid such as acetic acid, hydrochloric acid, phosphoric acid, oxalic acid, and trifluoroacetic acid, under a normal pressure or an increased pressure, at from $0°$ to $150°$ C.

Alternatively, reductions of carbonyl groups and nitro groups may be carried out by a hydrogen reduction in a solvent such as toluene, xylene, methanol, ethanol, ethylene glycol monoethyl ether, ethylene glycol monobutyl ether, ethyl acetate, tetrahydrofuran, and acetic acid, with a catalyst such as platinum-carbon, platinum oxide, Raney nickel, palladium-carbon, and if required with addition of an acid such as acetic acid, hydrochloric acid, phosphoric acid, oxalic acid, and trifluoroacetic acid, under an increased pressure, at from $80°$ to $150°$ C.

By selecting appropriately substituents $R^{11}, R^{12}, R^{13}, R^{14}, R^{21}, R^{22}, R^{23}, R^{24}, R^{31}, R^{32}, R^{33}, R^{34}$ and D in the above-mentioned formula (3) and formula (4) as well as an alkyl group in the above-mentioned phosphorus compound, the objective diamino compounds can be prepared.

Owing to an unique chemical structure of the diamino compound according to the invention, a liquid crystal element with use of a polyimide aligning film obtained from the said compound has such characteristics that it has a less image sticking, and can maintain a high voltage holding ratio from at a lower temperature to a high temperature, particularly at a relatively high temperature such as from $60°$ to $90°$ C., and also it does not produce any Vth unevenness at a high temperature and under a high humid atmosphere around a panel.

In addition to the use as polyimide resins for liquid crystal aligning films, the diamino compounds according to the invention can be used in various polyimide coating agents or polyimide resin moldings, films and fibers, by utilizing such characteristics thereof that they are relatively weak polar diamino compounds. Furthermore, they can be used as raw materials for polyamide resins, polyamideimide resins and polyurea resins, or used as hardeners for epoxy resins.

Effect of the Invention

The novel diamino compounds and the process for their preparation are proposed according to the invention.

The polyimide compounds obtained by using the said diamino compounds as raw materials have a superior effect as liquid crystal aligning films. For example, the liquid crystal display element with use of the said liquid crystal aligning film has high qualities, that is, it has a less image sticking and can maintain a high voltage holding ratio from at a lower temperature to a high temperature, and also it does not produce any Vth unevenness at a high temperature and under a high humid atmosphere around a panel. The said facts are thinkable to be produced, since the raw material, the diamino compound, has no polar group such as —O— or —$SO_2$—, and has a large molecular weight so that a proportion of an imide bonding with a relatively large polarity is decreased. Although the diamino compounds according to the invention with such characteristics are designed for intermediate raw materials of the liquid crystal aligning films as a main object, they can be used to make and modify another high molecular weight compounds such as polyimide and polyamide, and also used for another objects such as epoxy crosslinking agents etc, as well as they can be expected to produce novel characteristics for high molecular weight compounds.

The compounds according to the invention are illustrated in more detail by the following Examples, and products obtained by using the compounds, that is, the liquid crystal aligning films of polyimide resins are shown in Application examples, but the invention is not limited by these examples.

Figure 1:
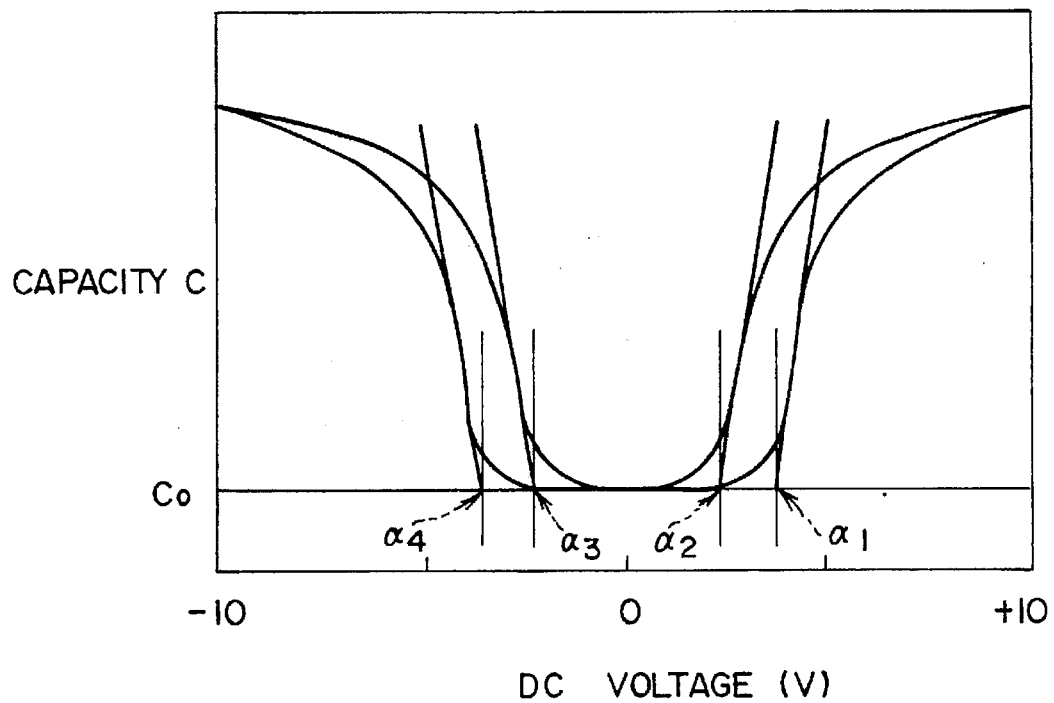
FIG. 1 is a drawing to show C-V hysteresis curves.

In Application Examples and Comparative Application Examples, a degree of an image sticking was determined with the use of a C-V curve method. The C-V curve method is to apply an alternate current of from 25 mV to 1 kHz on a liquid crystal cell, pile up a triangle wave of a direct current with a frequency of 0.0036 Hz (hereinbelow, referred to a DC voltage), sweep the DC voltage in a range between $-10$ V and $10$ V, and then record a capacity C changed. When the DC voltage is swept to a positive side ($0 \rightarrow 10$ V), the capacity becomes high. Then when it is swept to a negative side ($10 \rightarrow 0$ V), the capacity becomes low. When swept to the negative side from 0 ($0 \rightarrow -10$ V), the capacity becomes high again, and when swept to the positive side ($-10 \rightarrow 0$ V) it becomes low again. By repeating the said operation for several cycles, the wave form shown in FIG. 1 can be obtained. When a deviation of an electric charge on a surface of the liquid crystal aligning film is produced and the deviation becomes stabilized, hysteresis curves shown in FIG. 1 can be pictured at the both positive and negative sides. Based on FIG. 1, tangent lines are drawn against each C-V curves and a straight line denoting a capacity (CO) at the DC voltage of 0 is also drawn. Then, each cross points ($\alpha 1$–$\alpha 4$) are obtained, and the voltage difference between 2 points at $|\alpha 1-\alpha 2|$ in the positive side and $|\alpha 3-\alpha 4|$ in the negative side, and thereafter an average voltage difference, i.e. $(|\alpha 1-\alpha 2|+|\alpha 3-\alpha 4|)/2$, is calculated and the obtained value is regarded as a residual electric charge. The residual electric charge can be used as a parameter to show a deviation of the electric charge and its stabilization degree, if the thickness of the liquid crystal cell and the thickness of the aligning film are identical. That is, image sticking can be alleviated by using an aligning film with a less residual electric charge.

The voltage holding ratio was determined by a circuit shown in FIG. 2. The determination method was carried out by applying a rectangular wave (Vs) with a gate pulse width of 69 μs, a frequency of 30 Hz and a wave height of ±4.5 V on a source and reading a drain (VD) changed. For example, if a positive rectangular wave is applied on the source, a drain (VD) denotes a positive value till a negative rectangular wave being applied next. In the case of the holding ratio being 100%, VD shown in FIG. 3 has a rectangular orbit expressed by a dotted line, but VD generally becomes a full line orbit and approaches gradually to 0. Then, an orbit area determined (the area surrounded by V=0 and the orbit), that is the obliqued line area, is calculated, which being carried out for 4 times, and then an average value is obtained. The area obtained in the case of no voltage decrease is regarded as 100%, and a relative value of the determined area is expressed as a voltage holding ratio (%).

Observation of a Vth unevenness

The liquid crystal element is kept in a tank at such a high temperature and a humidity that 60° C. and 90% for 200 hours, thereafter lighted from all directions and observed for a Vth unevenness around a panel.

EXAMPLE 1

In a 2-liter four-necked flask equipped with a stirring device, a thermometer, a condenser and a nitrogen substituting device, 177.4 g of aluminum chloride and 300 milliliters of nitrobenzene were mixed and then 99.54 g of paranitrobenzoyl chloride was introduced with ice cooling to be dissolved. Then, a solution of 46.10 g of 1,4-bis (phenylmethyl)benzene in 100 milliliters of nitrobenzene was added dropwise for 30 minutes. 30 minutes after the end of the dropwise adding, an ice bath was removed and stirring was carried out at room temperature for 40 hours. After the end of the reaction was confirmed by a liquid chromatography, the reaction solution was poured on 1.5 liters of ice, and then extracted with 1.0 liter of chloroform. The solution was filtered through a Celite, washed with a 6N-HCl aqueous solution, an aqueous solution of sodium hydrogencarbonate, brine and water, removed off chloroform by a rotary evaporator, and thereafter removed off nitrobenzene by a steam distillation. By dissolving the solution in chloroform, purifying it with a silica gel column, and recrystallizing it from ethyl acetate, 35.72 g of 1,4-bis (4-(4-nitrobenzoyl)phenylmethyl)benzene was obtained as crystals.

In a 3-liter four-necked flask equipped with a stirring device, a thermometer, a condenser and a nitrogen substituting device, 34.39 g of 1,4-bis(4-(4-nitrobenzoyl) phenylmethyl) benzene was dissolved in 1000 milliliters of dichloromethane, and a solution of 37.8 g of titanium tetrachloride in 50 milliliters of dichloromethane was added dropwise for 1 hour with ice cooling. Subsequently, a solution of 41.46 g of triethylsilane in 50 milliliters of dichloromethane was added for 1 hour. 30 minutes after the end of the dropwise addition, stirring was carried out for 7 hours with ice cooling. After the end of the reaction was confirmed by a liquid chromatography, the reaction solution was neutralized with an aqueous solution of sodium carbonate and then washed with water. After removing off dichloromethane by a rotary evaporator, the solution was dissolved in chloroform, treated with an alumina column, and removed off the solvent from the solute. By recrystallizing the concentrate from an ethyl acetate solvent, 26.48 g of 1,4-bis(4-(4-nitrophenylmethyl)phenylmethyl)benzene was obtained as crystals.

In a 1-liter three-necked flask equipped with a stirring device and a nitrogen substituting device, 25.00 g of 1,4-bis(4-(4-nitrophenylmethyl)phenylmethyl)benzene was dissolved in 400 milliliters of tetrahydrofuran, 2.5 g of a Pd-C catalyst (a 5% product, containing 55.9% of water) was added and contacted with hydrogen gas while cooled with water at a normal pressure and then stirred. By recrystallizing the concentrate from a tetrahydrofuran solvent, 21.13 g of a diamino compound according to the invention, that is, 1,4-bis(4-(4-aminophenylmethyl)phenylmethyl)benzene was obtained. Melting point was from 177.9° to 179.7° C.

A proton nuclear magnetic resonance spectrum (1H-NMR) of the compound is shown in FIG. 4, and an infrared absorption spectrum is shown in FIG. 5, respectively.

EXAMPLE 2

In a 5-liter four-necked flask equipped with a stirring device, a thermometer, a condenser and a nitrogen substituting device, 317.0 g of aluminum chloride and 1.5 liters of nitrobenzene were mixed and then 209.0 g of benzoyl chloride was introduced with ice cooling to be dissolved, and then a solution of 100.0 g of diphenylmethane in 100 milliliters of nitrobenzene was added dropwise for 30 minutes. 30 minutes after the end of the dropwise adding, the temperature was increased to 70° C. by removing an ice bath, and stirring was carried out with maintaining the temperature for 5 hours. After the end of the reaction was confirmed by a gas chromatography, the reaction solution was poured on 1.0 liter of ice, and then extracted with 2.5 liters of chloroform. Thereafter, the solution was washed with a 6N-HCl aqueous solution, an aqueous solution of sodium hydrogencarbonate, brine and water, removed off chloroform and nitrobenzene by a rotary evaporator, and then 150.7 g of 1,1-bis(4-benzoylphenyl)methane was obtained as crystals after recrystallizing from ethyl acetate.

In a 5-liter four-necked flask equipped with a stirring device, a thermometer, a condenser and a nitrogen substituting device, 54.4 g of lithium aluminum hydride and 382.6 g of aluminum chloride were introduced slowly in 2.0 liters of tetrahydrofuran to make a mixed solution, to which 150 g of 1,1-bis(4-benzoylphenyl)methane was added at room temperature and then heated for 1 hour at 60° C. and then stirred for 4 hours with maintaining the temperature. After the end of the reaction was confirmed by a liquid chromatography, the reaction solution was cooled to room temperature and 600 milliliters of ethyl acetate was added dropwise for 30 minutes with stirring, then 500 milliliters of water was added dropwise for 30 minutes with stirring. Thereafter, the reaction solution was washed with a 6N-HCl aqueous solution, an aqueous solution of sodium hydrogencarbonate, brine and water, removed off chloroform and nitrobenzene by a rotary evaporator, and then subjected to a column purification with a mixed solvent of 2:1 toluene and heptane, removed off the solvent and then recrystallized from ethyl acetate, to obtain 115 g of 1,1-bis (4-(1-phenylmethyl)phenyl)methane as crystals.

In a 5-liter four-necked flask equipped with a stirring device, a thermometer, a condenser and a nitrogen substituting device, 382.6 g of aluminum chloride and 1.25 liters of nitrobenzene were mixed and then 115 g of 1,1-bis(4-(1-phenylmethyl)phenyl)methane was added at room temperature and stirred for 10 hours with maintaining a temperature at from 20° to 23° C. After the end of the reaction was confirmed by a liquid chromatography, the reaction solution was poured in 1.0 liter of ice water and then extracted with 2.0 liters of chloroform. Thereafter, the solution was washed with a 6N-HCl aqueous solution of 50° to 55° C., a warm aqueous solution of sodium hydrogencarbonate, warm brine and warm water, removed off chloroform and nitrobenzene by a rotary evaporator, then subjected to a column purification by dissolving in chloroform, and recrystallized from chloroform, to obtain 17.7 g of 1,1-bis(4-(4-(4-nitrobenzoyl)phenylmethyl)phenyl)methane as crystals.

In a 1-liter four-necked flask equipped with a stirring device, a thermometer, a condenser and a nitrogen substituting device, 17.7 g of 1,1-bis(4-(4-(4-nitrobenzoyl)phenylmethyl) phenyl)methane was dissolved in 150 milliliters of dichloromethane, 14.5 g of triethylsilane and 20.7 g of boron trifluoride ethyl ether complex were added, and they were stirred for 20 hours at reflux of dichloroethane. After the end of the reaction was confirmed by a liquid chromatography, the reaction solution was cooled to room temperature, poured in 100 milliliters of ice water, and then 150 milliliters of chloroform was added for extraction. Thereafter, the solution was washed with a 6N-HCl aqueous solution of from 50° to 55° C., an aqueous solution of sodium hydrogencarbonate, brine and water, removed off chloroform and dichloroethane by a rotary evaporator, and then recrystallized from a chloroform solvent, to obtain 16.4 g of 1,1-bis(4-(4-(4-nitrophenylmethyl)phenylmethyl)phenyl)methane as crystals.

In a 1-liter three-necked flask equipped with a stirring device and a nitrogen substituting device, 16.4 g of 1,1-bis(4-(4-(4-nitrophenylmethyl)phenylmethyl)phenyl)methane was dissolved in 500 milliliters of tetrahydrofuran, 1.7 g of a Pd-C catalyst (a 5% product, containing 54.8% of water) was added and contacted with hydrogen gas while cooled with water at a normal pressure and then stirred. After absorption of hydrogen was stopped, the catalyst was filtered off and the objective product adhered to a residual layer of the catalyst was washed with chloroform thoroughly and then the filtrate was concentrated. By recrystallizing the concentrate from a chloroform solvent, 11.0 g of a diamino compound according to the invention, that is, 1,1-bis(4-(4-(4-aminophenylmethyl)phenylmethyl)phenyl)methane was obtained as crystals. Melting point was from 192.0° to 193.0° C.

A proton nuclear magnetic resonance spectrum (1H-NMR) of the compound is shown in FIG. 6, and an infrared absorption spectrum is shown in FIG. 7, respectively.

EXAMPLE 3

In a 1-liter three-necked flask equipped with a stirring device, a thermometer and a nitrogen substituting device, 66.7 g of aluminum chloride and 200 milliliters of 1,2-dichloroethane were mixed and then 44.5 g of paranitrobenzoyl chloride was introduced with ice cooling to be dissolved. Then, a solution of 18.3 g of dibenzyl in 50 milliliters of 1,2-dichloroethane was added dropwise for 5 minutes. After the end of the dropwise adding, the solution was stirred for 6 hours with warming to room temperature. After the end of the reaction was confirmed by a liquid chromatography, the reaction solution was poured in 500 milliliters of ice water, and then extracted with 500 milliliters of chloroform. The solution was washed with a 6N-HCl aqueous solution, an aqueous solution of sodium hydrogencarbonate, brine and water, and then the solution was dried with magnesium sulfate. The solution was removed off chloroform by a rotary evaporator, and then filtered when crystals were deposited sufficiently. A filtered substance was washed subsequently with water, ethanol and toluene and then dried under a decreased pressure in a desiccator, to obtain 35.8 g of 1,2-bis(4-(4-nitrobenzoyl)phenyl)ethane as crystals.

In a 1-liter three-necked flask equipped with a stirring device, a thermometer and a nitrogen substituting device, 32.6 g of 1,2-bis(4-(4-nitrobenzoyl)phenyl)ethane and 200 milliliters of dichloromethane were introduced. 42.0 g of trifluoromethane sulfonic acid was added dropwise for 15 minutes. Subsequently, a solution of 40.7 g of triethylsilane in 50 milliliters of dichloromethane was added dropwise for 1 hour. After the end of the dropwise addition, stirring was carried out for 18 hours with warming to room temperature. After the end of the reaction was confirmed by a liquid chromatography, the reaction solution was neutralized with an aqueous solution of sodium carbonate and washed with water. After removing dichloromethane by a rotary evaporator, 27.6 g of 1,2-bis(4-(4-nitrobenzyl)phenyl)ethane was obtained as crystals by recrystallizing from a toluene solvent.

In a 1-liter three-necked flask equipped with a stirring device and a nitrogen substituting device, 2.5 g of a Pd-C catalyst (a 5% product, containing 55.9% of water) and a solution of 25.1 g of 1,2-bis(4-(4-nitrobenzyl)phenyl)ethane in 400 milliliters of tetrahydrofuran were introduced and contacted with hydrogen gas at a normal pressure with stirring. After hydrogen absorption was stopped, the catalyst was filtered off and the solution was concentrated. Crystals were dissolved in chloroform, subjected to a column chromatography treatment with active alumina and silica gel, and thereafter the solution was reconcentrated to give a concentrate, which was then recrystallized from a toluene solvent, to obtain 13.7 g of 1,2-bis(4-(4-aminobenzyl)phenyl)ethane. Melting point was from 138.8° to 140.4° C.

A proton nuclear magnetic resonance spectrum (1H-NMR) of the compound is shown in FIG. 8, and an infrared absorption spectrum is shown in FIG. 9, respectively.

EXAMPLE 4

In a 2-liter three-necked flask equipped with a stirring device, a thermometer and a nitrogen substituting device, 700 milliliters of benzene was introduced and 177.0 g of aluminum chloride was added with ice cooling. Then, a solution of 101.6 g of adipoyl chloride in 300 milliliters of benzene was added dropwise for 35 minutes. After stirring for one day and one night with warming back to the room temperature, the solution was poured in 3 liters of ice water containing dilute hydrochloric acid, and extracted with 2.5 liters of toluene. Thereafter, the solution was washed with a 0.5N aqueous solution of sodium hydroxide and water, and then dried with anhydrous magnesium sulfate. After removing off the solvent by a rotary evaporator, 128.4 g of 1,6-diphenylhexane-1,6-dione was obtained as crystals by recrystallizing the obtained crystals from ethyl acetate.

In a 2-liter three-necked flask equipped with a stirring device and a nitrogen substituting device, 5 g of a Pd-C catalyst (a 5% product, containing 55.9% of water) and a solution of 100.9 g of 1,6-diphenylhexane-1,6-dione in 400 milliliters of tetrahydrofuran and 400 milliliters of denatured ethanol as well as 5 milliliters of 6N-hydrochloric acid were introduced, stirred at a normal pressure and contacted with hydrogen gas. After absorption of hydrogen was stopped, the catalyst was filtered off and the solution was concentrated. The concentrate was dissolved in ethyl acetate, washed with a dilute aqueous solution of sodium hydrogencarbonate and water, and thereafter dried with anhydrous sodium sulfate. After removing off the solvent by a rotary evaporator, a distillation under a decreased pressure was carried out, to obtain 85.3 g of 1,6-diphenylhexane as colorless liquid.

In a 1-liter three-necked flask equipped with a stirring device, a thermometer and a nitrogen substituting device, 33.3 g of aluminum chloride and 200 milliliters of 1,2- dichloroethane were mixed and then 40.8 g of paranitrobenzoyl chloride was introduced with ice cooling to be dissolved. Then, a solution of 23.6 g of 1,6-diphenylhexane in 50 milliliters of 1,2-dichloroethane was added dropwise for 30 minutes. After the end of the dropwise adding, the solution was stirred for 3 hours with warming back to the room temperature. After the end of reaction was confirmed by a liquid chromatography, the reaction solution was poured in 500 milliliters of ice water, and then extracted with 1.8 liters of chloroform. The solution was washed with an aqueous solution of sodium hydrogencarbonate and water, and then dried with magnesium sulfate. Chloroform was removed off by a rotary evaporator, and then 56.0 g of 1,6-bis(4-(4-nitrobenzoyl)phenyl)hexane was obtained as crystals by recrystallizing from a mixed solvent of chloroform and ethyl acetate.

In a 1-liter three-necked flask equipped with a stirring device, a thermometer and a nitrogen substituting device, 40.0 g of 1,6-bis(4-(.4-nitrobenzoyl)phenyl)hexane, 200 milliliters of dichloroethane and 52.9 g of boron trifluoride diethyl ether complex were introduced and heated at reflux. 39.0 g of triethylsilane was added dropwise for 35 minutes with maintaining the temperature. After the end of the reaction was confirmed by a liquid chromatography, the reaction solution was poured in water and extracted with ethyl acetate. After the solution was washed with an aqueous solution of sodium hydrogencarbonate and water, it was dried with anhydrous sodium sulfate. After removing off the solvent by a rotary evaporator, 35.3 g of 1,6-bis(4-(4-nitrobenzyl)phenyl)hexane was obtained as crystals by recrystallizing from an ethyl acetate solvent.

In a 1-liter three-necked flask equipped with a stirring device and a nitrogen substituting device, 3.5 g of a Pd-C catalyst (a 5% product, containing 55.9% of water) and a solution of 35.0 g of 1,6-bis(4-(4-nitrobenzyl)phenyl)hexane in 200 milliliters of tetrahydrofuran were introduced, and contacted with hydrogen gas at a normal pressure with stirring. After hydrogen absorption was stopped, the catalyst was filtered off and the solution was concentrated. Crystals were dissolved in chloroform, subjected to a column chromatography treatment with active alumina and silica gel, and thereafter the solution was reconcentrated to give a concentrate, which was then recrystallized from a mixed solvent of toluene and denatured ethanol, to obtain 26.1 g of 1,6-bis(4-(4-aminobenzyl)phenyl)hexane. Melting point was from 111.4° to 112.2° C.

A proton nuclear magnetic resonance spectrum (1H-NMR) of the compound is shown in FIG. 10, and an infrared absorption spectrum is shown in FIG. 11, respectively.

EXAMPLE 5

In a 200-milliliter three-necked flask equipped with a stirring device, a thermometer and a nitrogen substituting device, 25.5 g of hexyltriphenylphosphonium bromide and 100 milliliters of tetrahydrofuran were introduced and a nitrogen atmosphere was realized, and then 6.7 g of potassium tert-butoxide was added with ice cooling. After stirring for 70 minutes, a solution of 9.1 g of benzophenon in 30 milliliters of tetrahydrofuran was added dropwise. After stirring for 3 hours and 20 minutes, the solution was poured in ice water containing dilute hydrochloric acid, and extracted with toluene. The solution was washed with an aqueous solution of sodium hydrogencarbonate and water, and thereafter dried with anhydrous sodium sulfate. After removing off the solvent by a rotary evaporator, dissolving the residue in a small amount of toluene, carrying out a separating operation by a column chromatography with silica gel and removing off the solvent by a rotary evaporator, 12.4 g of 1,1-diphenyl-1-heptene was obtained as colorless liquid.

In a 100-milliliter three-necked flask equipped with a stirring device and a nitrogen substituting device, 1.2 g of a Pd-C catalyst (a 5% product, containing 55.9% of water) and a solution of 12.4 g of 1,1-diphenyl-1-heptene in 50 milliliters of tetrahydrofuran were introduced, and contacted with hydrogen gas at a normal pressure with stirring. After hydrogen absorption was stopped, the catalyst was filtered off and the solution was concentrated. Thereafter, by carrying out a distillation under a decreased pressure, 9.8 g of 1,1-diphenyl heptane was obtained as colorless liquid.

In a 200-milliliter three-necked flask equipped with a stirring device, a thermometer and a nitrogen substituting device, 17.4 g of iron chloride, 16.7 g of paranitrobenzoyl chloride and 40 milliliters of 1,2-dichloroethane were introduced. Then, a solution of 9.0 g of 1,1-diphenyl heptane in 10 milliliters of 1,2-dichloroethane was added dropwise for 15 minutes with an ice bath. Thereafter, the solution was stirred for 3 hours and 40 minutes with heating to a reflux temperature. After the end of the reaction was confirmed by a liquid chromatography, the solution was poured in ice water containing dilute hydrochloric acid, and then extracted with chloroform. The solution was washed with hydrochloric acid, an aqueous solution of sodium hydroxide and water, and then dried with anhydrous sodium sulfate. After removing off the solvent by a rotary evaporator, the solution was dissolved in chloroform and subjected to a separating operation by a column chromatography with silica gel, to obtain 14.4 g of 1,1-bis(4-(4-nitrobenzoyl)phenyl)heptane as red oil.

In a 1-liter three-necked flask equipped with a stirring device, a thermometer and a nitrogen substituting device, 14.4 g of 1,1-bis(4-(4-nitrobenzoyl)phenyl)heptane, 60 milliliters of 1,2-dichloroethane and 19.4 g of boron trifluoride diethyl ether complex were introduced and heated at reflux. 14.4 g of triethylsilane was added dropwise for 15 minutes with maintaining the temperature. After the end of the reaction was confirmed by a liquid chromatography, the reaction solution was poured in water and extracted with chloroform. The solution was washed with an aqueous solution of sodium hydrogencarbonate and water, and then dried with anhydrous sodium sulfate. After removing off the solvent by a rotary evaporator, the solution was dissolved in toluene and subjected to a separating operation by a column chromatography with silica gel. After removing off the solvent again, 14.08 g of 1,1-bis(4-(4-nitrobenzyl)phenyl) heptane was obtained as red oil.

In a 1-liter three-necked flask having a fit equipped with a stirring device and a nitrogen substituting device, 2 g of a Pd-C catalyst (a 5% product, containing 55.9% of water) and a solution of 14.08 g of 1,1-bis(4-(4-nitrobenzyl)phenyl) heptane in 100 milliliters of tetrahydrofuran were introduced, and contacted with hydrogen gas at a normal pressure with stirring. After hydrogen absorption was stopped, the catalyst was filtered off and the solution was concentrated. Residue was dissolved in a mixed solvent of toluene and denatured ethanol, and subjected to a separating operation by a column chromatography with silica gel. By removing off the solvent again, 9.2 g of a diamino compound according to the invention, 1,1-bis(4-(4-aminobenzyl)phenyl)heptane, was obtained as red oil.

A proton nuclear magnetic resonance spectrum (1H-NMR) of the compound is shown in FIG. 12, and an infrared absorption spectrum is shown in FIG. 13, respectively.

EXAMPLE 6

In a 2-liter three-necked flask equipped with a stirring device, a thermometer and a nitrogen substituting device, 13.2 g of magnesium and 300 milliliters of tetrahydrofuran were introduced and stirred violently. Then, a solution of 83.2 g of benzene bromide in 100 milliliters of tetrahydrofuran was added dropwise for 40 minutes. At that time, cooling was carried out with an ice bath if required. After the dropwise addition was ended, stirring was carried out at room temperature for 1 hour, and thereafter 108.2 g of α-n-hexyl cinnamaldehyde was added dropwise. After stirring for one day and one night, the solution was poured in ice water containing dilute hydrochloric acid, and extracted with 1 liter of ethyl acetate. After the solution was washed with an aqueous solution of sodium hydrogencarbonate and water, it was dried with anhydrous magnesium sulfate. After removing the solvent off by a rotary evaporator, 169.6 g of 1,3-diphenyl-2-n-hexyl-2-propen-1-ol was obtained.

In a 2-liter three-necked flask equipped with a stirring device and a nitrogen substituting device, 169.6 g of 1,3-diphenyl-2-n-hexyl-2-propen-1-ol, 0.4 milliliters of trifluoroacetic acid and 17 g of a Pd-C catalyst (a 5% product, containing 55.9% of water) were introduced, and stirred at 50° C. and contacted with hydrogen gas. After stirring for 30 hours, the catalyst was filtered off, water was added, and an extraction was carried out with n-heptane. After washing with sodium hydrogencarbonate and water, the solution was dried with anhydrous sodium sulfate. After removing off the solvent by a rotary evaporator and dissolving the residue in a small amount of n-heptane, a separating operation was carried out by a column chromatography with silica gel. By removing off the solvent again and carrying out a distillation under a decreased pressure, to obtain 98.9 g of 1,3-diphenyl-2-n-hexyl propane as colorless liquid.

In a 1-liter three-necked flask equipped with a stirring device, a thermometer and a nitrogen substituting device, 33.3 g of aluminum chloride, 150 milliliters of 1,2-dichloroethane and 40.8 g of paranitrobenzoyl chloride were introduced to be dissolved. Then, a solution of 28.0 g of 1,6-diphenyl-2-n-hexyl propane in 50 milliliters of 1,2-dichloroethane was added dropwise for 30 minutes. After the end of the dropwise adding, the solution was stirred for 3 hours and 30 minutes with warming back to room temperature. After the end of the reaction was confirmed by a liquid chromatography, the reaction solution was poured in ice water containing dilute hydrochloric acid, and then extracted with 401 milliliters of chloroform. The solution was washed with an aqueous solution of sodium hydroxide and water, and then dried with magnesium sulfate. By removing off the solvent by a rotary evaporator and recrystallizing from a mixed solvent of ethyl acetate and denatured ethanol, 48.6 g of 1,3-bis(4-(4-nitrobenzoyl)phenyl)-2-n-hexyl propane was obtained as crystals.

In a 1-liter three-necked flask equipped with a stirring device, a thermometer and a nitrogen substituting device, 40.5 g of 1,3-bis(4-(4-nitrobenzoyl)phenyl)-2-n-hexyl propane, 100 milliliters of 1,2-dichloroethane and 49.7 g of boron trifluoride diethyl ether complex were introduced and heated at reflux. 36.2 g of triethylsilane was added dropwise for 20 minutes with maintaining the temperature. After the end of the reaction was confirmed by a liquid chromatography, the reaction solution was poured in water and extracted with chloroform. After washing with an aqueous solution of sodium hydrogencarbonate and water, the solution was dried with anhydrous sodium sulfate. After removing off the solvent by a rotary evaporator, the residue was dissolved in toluene, and a separating operation was carried out by a column chromatography with silica gel. After removing off the solvent again, 40.9 g of 1,3-bis(4-(4-nitrobenzyl)phenyl)-2-n-hexyl propane was obtained as yellow oil.

In a 1-liter three-necked flask having a fit equipped with a stirring device and a nitrogen substituting device, 40.9 g of 1,3-bis(4-(4-nitrobenzyl)phenyl)-2-n-hexyl propane, 5 g of a Pd-C catalyst (a 5% product, containing 55.9% of water) and 300 milliliters of tetrahydrofuran were introduced, and contacted with hydrogen gas at a normal pressure with stirring. After hydrogen absorption was stopped, the catalyst was filtered off and the solution was concentrated. Residues were dissolved in chloroform, and then subjected to a separating operation by a column chromatography with silica gel. By removing off the solvent again, 35.3 g of 1,3-bis(4-(4-aminobenzyl)phenyl)-2-n-hexyl propane was obtained as yellow oil.

A proton nuclear magnetic resonance spectrum (1H-NMR) of the compound is shown in FIG. 14, and an infrared absorption spectrum is shown in FIG. 15, respectively.

EXAMPLE 7

In a 10-liters three-necked flask equipped with a stirring device, a thermometer and a nitrogen substituting device, 1300 g (9.75 mole) of aluminum chloride and 4.2 liters of 1,2-dichloroethane were mixed, and 1323 g (7.13 mole) of paranitrobenzoyl chloride was introduced with ice cooling to be dissolved. After warming the reaction solution to 47° C., a solution of 500 g (2.97 mole) of diphenylmethane in 500 milliliters of 1,2-dichloroethane was added dropwise for 3 hours and 30 minutes. After the dropwise addition was ended, the solution was stirred at 50° C. for 4 hours. After the end of the reaction was confirmed by a liquid chromatography, the reaction solution was poured in 7 liters of ice water, and then extracted with 7 liters of chloroform. The solution was washed with a 6N-HCl aqueous solution, an aqueous solution of sodium hydrogencarbonate, brine and water, and then dried with magnesium sulfate. After removing off chloroform by a rotary evaporator, filtration was carried out when crystals being deposited sufficiently. Filtered substances were treated with a silica gel column and recrystallized from chloroform/ethyl acetate, to obtain 867 g of 1,1-bis(4-(4-nitrobenzoyl)phenyl)methane as crystals.

In a three-necked flask equipped with a stirring device, a thermometer and a nitrogen substituting device, 61.6 g (0.154 mole) of butyltriphenylphosphonium bromide and 200 milliliters of tetrahydrofuran were introduced under $N_2$ sealing, and the reaction solution was cooled to 3° C. with an ice bath and thereafter stirred for 1 hour. Then, 17.4 g (0.155 mole) of potassium-t-butoxide was added gradually. At that time, the reaction solution became yellow instantaneously with a slight exothermic reaction. Thereafter, the reaction solution was stirred for 45 minutes with maintaining it at 3° to 5° C.

Then, a solution of 30.0 g (0.064 mole) of 1,1-bis(4-(4-nitrobenzoyl)phenyl)methane in 1 liter of tetrahydrofuran was added dropwise for 1 hour, and stirred for 8 hours with maintaining at 3° to 5° C. At that time, hue was changed to dark purple. After the end of the reaction was confirmed by a liquid chromatography, the solution was poured in 400 milliliters of ice water, and extracted with 800 milliliters of chloroform after adding 400 milliliters of a 4N-HCl aqueous solution. Thereafter, the solution was washed with a 6N-HCl aqueous solution, an aqueous solution of sodium hydrogencarbonate, brine and water, and then removed off chloroform by a rotary evaporator. The residue was dissolved in toluene and treated with a silica gel (800 g) column, to obtain 17.1 g of 1,1-bis(4-(1-(4-nitrophenyl)butylidene)phenyl)methane as highly viscous oil.

17.1 g of the obtained product was dissolved in 200 milliliters of tetrahydrofuran, and 2.0 g of a 5% palladium carbon catalyst (containing 54.8% of water) and then contacted with hydrogen gas under a normal pressure and at room temperature with stirring. After hydrogen absorption was stopped, the catalyst was filtered off, and the residual solution was concentrated and treated with a silica gel column, to obtain 10.5 g of 1,1-bis(4-(1-(4-aminophenyl)butyl)phenyl)methane. The compound was liquid with high viscosity at a normal temperature.

Proton nuclear magnetic resonance spectra (1H-NMR, solvent; CDCl$_3$, TMS standard) of the compound were 6.54–7.16 ppm (m, 16H), 3.63–3.85 ppm (m, 4H), 3.51 ppm (s, 4H), and 0.77–2.01 ppm (m, 18H).

And, an infrared absorption spectrum is shown in FIG. 14.

EXAMPLE 8

In a 10-liters three-necked flask equipped with a stirring device, a thermometer and a nitrogen substituting device, 703 g (4.33 mole) of iron chloride and 1.7 liters of 1,2-dichloroethane were mixed, and 732 g (3.94 mole) of paranitrobenzoyl chloride was introduced with ice cooling to be dissolved. After warming the reaction solution to 80° C., a solution of 395 g (1.67 mole) of diphenylcyclohexane in 630 milliliters of 1,2-dichloroethane was added dropwise for 3 hours and 40 minutes. After the dropwise addition was ended, the solution was stirred gently at reflux for 6 hours. After the end of the reaction was confirmed by a liquid chromatography, the reaction solution was poured in 2 liters of ice, 1 liter of a 4N-HCl aqueous solution was added and then extracted with 1.5 liters of chloroform. The solution was washed with a 6N-HCl aqueous solution, an aqueous solution of sodium hydrogencarbonate, brine and water, and then dried with magnesium sulfate. After removing off chloroform by a rotary evaporator, 700 milliliters of ethyl acetate was added still hot and cooled to deposit crystals. Deposited crystals were filtered off and the filtrate was treated with a silica gel column and purified by recrystallization from chloroform/ethyl acetate, to obtain 485 g of 1,1-bis(4-(4-nitrobenzoyl)phenyl)cyclohexane as crystals.

In a three-necked flask equipped with a stirring device, a thermometer and a nitrogen substituting device, 54.0 g (0.158 mole) of methyltriphenylphosphonium bromide and 750 milliliters of tetrahydrofuran were introduced under N$_2$ sealing, and a slurry containing solid was heated at 50° C. to 55° C. for 1 hour by a mantle heater. Thereafter, a bath was set at −5° C. to cool the reaction solution to 3° C., and thereafter 17.0 g (0.151 mole) of potassium-t-butoxide was added. At that time, the reaction solution became yellow instantaneously with a slight exothermic reaction.

After cooling the reaction solution to 2° C. by cooling the bath temperature to −10° C., 30.0 g (0.056 mole) of 1,1-bis(4-(4-nitrobenzoyl)phenyl)cyclohexane was added gradually. Hue was changed to dark purple and simultaneously an exothermic reaction was occurred to increase the temperature of the reaction solution to 5° C. The reaction solution was stirred for 4 hours with maintaining it at 3° to 5° C. After the end of the reaction was confirmed by a liquid chromatography, the solution was poured in 750 milliliters of ice water, and then extracted with 250 milliliters of chloroform added. Thereafter, the solution was washed with a 6N-HCl aqueous solution, an aqueous solution of sodium hydrogencarbonate, brine and water, and then removed off chloroform by a rotary evaporator, to obtain 59.3 g of highly viscous liquid.

59.3 g of the obtained product was dissolved in an equal amount of chloroform, treated by a silica gel (250 g) column with a chloroform solvent to remove off the solvent, then dissolved in toluene again, treated by a silica gel (100 g) column, and then a fraction with purity of 97.3% was concentrated, to obtain 5.0 g of 1,1-bis(4-(1-(4-nitrophenyl)vinylidene)phenyl)cyclohexane as highly viscous liquid. 5.0 g of the obtained product was dissolved in 15 milliliters of tetrahydrofuran, 0.5 g of a 5% palladium-carbon catalyst (containing 54.8% of water) and contacted with hydrogen gas with stirring under a normal pressure and at room temperature. After absorption of hydrogen was stopped, the solvent was filtered off and the filtrate was concentrated, to obtain 3.0 g of 1,1-bis(4-(1-(4-aminophenyl)ethyl)phenyl)cyclohexane. The compound was liquid having high viscosity at a normal temperature.

Proton nuclear magnetic resonance spectra (1H-NMR, solvent; CDCl$_3$, TMS standard) of the compound were 6.55–7.21 ppm (m, 16H), 3.96 ppm (q, 2H), 3.53 ppm (s, 4H), and 1.26–2.36 ppm (m, 16H).

And, an infrared absorption spectrum is shown in FIG. 17.

EXAMPLE 9

In a 10-liters three-necked flask equipped with a stirring device, a thermometer and a nitrogen substituting device, 629 g (3.88 mole) of iron chloride and 1.7 liters of 1,2-dichloroethane were mixed, and 595 g (3.21 mole) of paranitrobenzoyl chloride was introduced with ice cooling to be dissolved. After warming the reaction solution to 80° C., a solution of 391 g (1.34 mole) of 1,1-diphenyl-4-butylcyclohexane in 630 milliliters of 1,2-dichloroethane was added dropwise for 3 hours and 30 minutes. After the dropwise addition was ended, the solution was stirred gently at reflux for 6 hours. After the end of the reaction was confirmed by a liquid chromatography, the reaction solution was poured on 2 liters of ice, and 1 liter of a 4N-HCl aqueous solution was added and then extracted with 1.5 liters of chloroform. The solution was washed with a 6N-HCl aqueous solution, an aqueous solution of sodium hydrogencarbonate, brine and water, and dried with magnesium sulfate. After removing off chloroform by a rotary evaporator, treating with a silica gel column and purifying by recrystallization from ethyl acetate, 435 g of 1,1-bis(4-(4-nitrobenzoyl)phenyl)-4-butylcyclohexane was obtained as crystals.

In a three-necked flask equipped with a stirring device, a thermometer and a nitrogen substituting device, 49.2 g (0.138 mole) of methyltriphenylphosphonium bromide and 750 milliliters of tetrahydrofuran were introduced under N$_2$ sealing, and a slurry containing solid was heated at 50° to 55° C. for 1 hour by a mantle heater. Thereafter, a bath was set at −5° C. and after cooling the reaction solution to 3° C., 14.3 g (0.128 mole) of potassium-t-butoxide was added. At that time, the reaction solution was changed instantaneously to yellow with a slight exothermic reaction. Thereafter the reaction solution was stirred for 45 minutes with maintaining at 4° to 5° C.

After cooling the reaction solution to 2° C. by cooling the bath temperature to −10° C., 30.2 g (0.051 mole) of 1,1-bis (4-(4-nitrobenzoyl)phenyl)-4-butylcyclohexane was added gradually. Hue was changed to dark purple, and simultaneously an exothermic reaction was occurred to increase the temperature of the reaction solution to 5° C. The reaction solution was stirred for 4 hours with maintaining at 3° to 5° C. After the end of the reaction was confirmed by a liquid chromatography, the solution was poured in 750 milliliters of ice water, and then extracted with 250 milliliters of chloroform added. Thereafter, the solution was washed with a 6N-HCl aqueous solution, an aqueous solution of sodium hydrogencarbonate, brine and water, and then removed off chloroform by a rotary evaporator, to obtain 85.9 g of highly viscous liquid. 85.9 g of the obtained product was dissolved in an equal amount of toluene and treated with a silica gel (1 Kg) column, and the fraction with purity of 99.5% was concentrated, to obtain 29.6 g of 1,1-bis(4-(1-(4-nitrophenyl)vinylidene) phenyl)-4-butylcyclohexane as highly viscous liquid.

29.0 g of the obtained product was dissolved in 150 milliliters of tetrahydrofuran, and 3.0 g of a 5% palladium-carbon catalyst (containing 54.8% of water) was added, and then contacted with hydrogen gas under a normal pressure and at room temperature with stirring. After hydrogen absorption was stopped, the filtrate free from the catalyst was concentrated, to obtain 25.2 g of 1,1-bis(4-(1-(4-aminophenyl)ethyl)phenyl)-4-butylcyclohexane. The compound was liquid having high viscosity at a normal temperature.

Proton nuclear magnetic resonance spectra (1H-NMR, CDCl$_3$ solvent, TMS standard) of the compound were 6.53–7.18 ppm (m, 16H), 3.81–4.14 ppm (m, 2H), 3.15 ppm (s, 4H), and 0.85–2.66 ppm (m, 24H).

And, an infrared absorption spectrum is shown in FIG. 18.

Application Example 1

In a 200-milliliter four-necked flask equipped with a stirring device, a thermometer, a condenser and a nitrogen substituting device, 50 g of dehydrated and purified N-methyl-2-pyrrolidone and then 7.80 g of 1,4-bis(4-(4-aminophenylmethyl) phenylmethyl)benzene were introduced and stirred to be dissolved. The solution was cooled to 13° C. and 3.69 g of pyromellitic dianhydride was introduced at a time and stirred with cooling to be reacted. After 1 hour, 0.11 g of paraaminophenyltrimethoxysilane was added and stirred at 20° C. for 1 hour to be reacted.

Thereafter, by diluting the reaction solution with 54.4 g of N-methyl-2-pyrrolidone (NMP), a transparent solution of 10% by weight of polyamide acid was obtained. A viscosity of the solution at 25° C. was 1890 centipoises.

To the said solution, a 1:1 mixed solution of 2-butoxyethanol and NMP was added for diluting the polyamide acid to 3% by weight, and thereafter coated on a transparent glass substrate with an ITO electrode at one side by a rotation coating method (a spinner method). The rotation conditions were 5000 rpm and 15 seconds. After coating, it was dried at 100° C. for 10 minutes, the temperature was increased to 200° C. for 1 hour in an oven and then a heat treatment was carried out at 200° C. for 90 minutes, to obtain a polybenzylimide film with a film thickness of about 600 angstrom. The coated surfaces of two substrates with the said polybenzylimide film formed were treated by rubbing respectively to obtain a liquid crystal aligning film, from which a liquid crystal cell having a cell thickness of 6 microns was constituted with rubbing directions being parallel and facing each other, and then a liquid crystal FB01 for TFT made by Chisso Corp. was enclosed. After enclosing, the cell was subjected to an isotropic treatment at 120° C. for 30 minutes and then cooled gradually to room temperature, to obtain a liquid crystal element.

The residual electric charge of the said liquid crystal element was 0.06 V at 25° C., and the voltage holding ratios at 20° C., 60° C. and 90° C. were 98.0%, 97.6% and 95.3%, respectively.

Application Example 2

In accordance with the similar procedure of Application Example 1 except that 9.30 g of 1,1-bis(4-(4-(4-aminophenylmethyl)phenylmethyl)phenyl)methane was used in place of 7.80 g of 1,4-bis(4-(4-aminophenylmethyl) phenylmethyl)benzene, a polyamide acid was obtained. The compound was used according to Application Example 1, to obtain a liquid crystal element.

Application Example 3

In a 200-milliliter four-necked flask equipped with a stirring device, a thermometer, a condenser and a nitrogen substituting device, 50 g of dehydrated and purified N-methyl-2-pyrrolidone and then 7.80 g of 1,2-bis(4-(4-aminobenzyl)phenyl)ethane were introduced and stirred to be dissolved. The solution was cooled to 13° C. and 3.69 g of pyromellitic dianhydride was introduced at a time and stirred with cooling to be reacted. After 1 hour, 0.11 g of paraaminophenyl trimethoxysilane was added and stirred at 20° C. for 1 hour to be reacted.

Thereafter, by diluting the reaction solution with 54.4 g of N-methyl-2-pyrrolidone (NMP), a transparent solution containing 10% by weight of a polyamide acid was obtained. The viscosity of the solution at 25° C. was 1890 mP.s.

To the said solution, a 1:1 mixed solution of ethylene glycol monobutyl ether and NMP was added for diluting the polyamide acid to 3% by weight, and thereafter the solution was coated on a transparent glass substrate having an ITO electrode at one side by a rotational coating method (a spinner method). The rotational conditions were 5000 rpm and 15 seconds. After coating, the substrate was dried at 100° C. for 10 minutes, and thereafter a temperature increase to 200° C. for 1 hour in an oven and a heat treatment at 200° C. for 90 minutes were carried out, to obtain polyimide with a film thickness of 60 nm. The coated surfaces of two substrates having the formed polyimide film were subjected to a rubbing treatment respectively, to obtain a liquid crystal aligning film, from which a liquid crystal cell having a cell thickness of 6 microns was constituted with rubbing directions being parallel and facing each other, and then a liquid crystal FB01 for TFT made by Chisso Corp. was enclosed. After enclosing, the cell was subjected to an isotropic treatment at 120° C. for 30 minutes and then cooled gradually to room temperature, to obtain a liquid crystal element.

The residual electric charge of the said liquid crystal element was 0.06 V at 25° C., and the voltage holding ratios at 20° C., 60° C. and 90° C. were 98.2%, 97.5% and 95.1%, respectively.

Furthermore, there could not be seen any Vth unevenness around a panel.

Application Example 4

In a 200-milliliter four-necked flask equipped with a stirring device, a thermometer, a condenser and a nitrogen substituting device, 50 g of dehydrated and purified N-methyl-2-pyrrolidone and then 7.95 g of 1,6-bis(4-(4-aminobenzyl)phenyl) hexane were introduced and stirred to be dissolved. The solution was cooled to 15° C. and 3.93 g of pyromellitic dianhydride was introduced at a time and stirred with cooling to be reacted. After 1 hour, 0.12 g of paraaminophenyltrimethoxysilane was added and stirred at 20° C. for 1 hour to be reacted.

Thereafter, by diluting the reaction solution with 58.0 g of N-methyl-2-pyrrolidone (NMP), a transparent solution containing 10% by weight of a polyamide acid was obtained. The viscosity of the solution at 25° C. was 2263 mP.s.

To the said solution, a 1:1 mixed solution of ethylene glycol monobutyl ether and NMP was added for diluting the polyamide acid to 3% by weight, and thereafter the solution was coated on a transparent glass substrate having an ITO electrode at one side by a rotational coating method (a spinner method). The rotational conditions were 5000 rpm and 15 seconds. After coating, the substrate was dried at 100 for 10 minutes, and thereafter a temperature increase to 200 for 1 hour in an oven and a heat treatment at 200 for 90 minutes were carried out, to obtain polyimide with a film thickness of 60 nm. The coated surfaces of two substrates having the formed polyimide film were subjected to a rubbing treatment respectively, to obtain a liquid crystal aligning film, from which a liquid crystal cell having a cell thickness of 6 microns was constituted with rubbing directions being parallel and facing each other, and then a liquid crystal FB01 for TFT made by Chisso Corp. was enclosed. After enclosing, the cell was subjected to an isotropic treatment at 120 for 30 minutes and then cooled gradually to room temperature, to obtain a liquid crystal element.

The residual electric charge of the said liquid crystal element was 0.04 V at 25, and the voltage holding ratios at 20° C., 60° C. and 90° C. were 98.3%, 97.3% and 95.6%, respectively.

Furthermore, there could not be seen any Vth unevenness around a panel.

Application Example 5

In a 200-milliliter four-necked flask equipped with a stirring device, a thermometer, a condenser and a nitrogen substituting device, 50 g of dehydrated and purified N-methyl-2-pyrrolidone and then 8.03 g of 1,1-bis(4-(4-aminobenzyl)phenyl)heptane were introduced and stirred to be dissolved. The solution was cooled to 13 and 3.85 g of pyromellitic dianhydride was introduced at a time and stirred with cooling to be reacted. After 1 hour, 0.11 g of paraaminophenyltrimethoxy-silane was added and stirred at 20 for 1 hour to be reacted.

Thereafter, by diluting the reaction solution with 58.0 g of N-methyl-2-pyrrolidone (NMP), a transparent solution containing 10% by weight of a polyamide acid was obtained. The viscosity of the solution at 25 was 1610 mPs.

To the said solution, a 1:1 mixed solution of ethylene glycol monobutyl ether and NMP was added for diluting the polyamide acid to 3% by weight, and thereafter the solution was coated on a transparent glass substrate having an ITO electrode at one side by a rotational coating method (a spinner method). The rotational conditions were 5000 rpm and 15 seconds. After coating, the substrate was dried at 100 for 10 minutes, and thereafter a temperature increase to 200 for 1 hour in an oven and a heat treatment at 200 for 90 minutes were carried out, to obtain polyimide with a film thickness of 60 nm. The coated surfaces of two substrates having the formed polyimide film were subjected to a rubbing treatment respectively, to obtain a liquid crystal aligning film, from which a liquid crystal cell having a cell thickness of 6 microns was constituted with rubbing directions being parallel and facing each other, and then a liquid crystal FB01 for TFT made by Chisso Corp. was enclosed. After enclosing, the cell was subjected to an isotropic treatment at 120 for 30 minutes and then cooled gradually to room temperature, to obtain a liquid crystal element.

The residual electric charge of the said liquid crystal element was 0.10 V at 25, and the voltage holding ratios at 20° C., 60° C. and 90° C. were 98.0%, 97.1% and 94.8%, respectively.

Furthermore, there could not be seen any Vth unevenness around a panel.

Application Example 6

In a 200-milliliter four-necked flask equipped with a stirring device, a thermometer, a condenser and a nitrogen substituting device, 50 g of dehydrated and purified N-methyl-2-pyrrolidone and then 8.19 g of 1,3-bis(4-(4-aminobenzyl)phenyl)-2-n-hexylpropane were introduced and stirred to be dissolved. The solution was cooled to 10 and 3.70 g of pyromellitic dianhydride was introduced at a time and stirred with cooling to be reacted. After 1 hour, 0.11 g of paraaminophenyltrimethoxy-silane was added and stirred at 20 for 1 hour to be reacted.

Thereafter, by diluting the reaction solution with 58.0 g of N-methyl-2-pyrrolidone (NMP), a transparent solution containing 10% by weight of a polyamide acid was obtained. The viscosity of the solution at 25 was 1850 mPs.

To the said solution, a 1:1 mixed solution of ethylene glycol monobutyl ether and NMP was added for diluting the polyamide acid to 3% by weight, and thereafter the solution was coated on a transparent glass substrate having an ITO electrode at one side by a rotational coating method spinner method). The rotational conditions were 5000 rpm and 15 seconds. After coating, the substrate was dried at 100 for 10 minutes, and thereafter a temperature increase to 200 for 1 hour in an oven and a heat treatment at 200 for 90 minutes were carried out, to obtain polyimide with a film thickness of 60 nm. The coated surfaces of two substrates having the formed polyimide film were subjected to a rubbing treatment respectively, to obtain a liquid crystal aligning film, from which a liquid crystal cell having a cell thickness of 6 microns was constituted with rubbing directions being parallel and facing each other, and then a liquid crystal FB01 for TFT made by Chisso Corp. was enclosed. After enclosing, the cell was subjected to an isotropic treatment at 120 for 30 minutes and then cooled gradually to room temperature, to obtain a liquid crystal element.

The residual electric charge of the said liquid crystal element was 0.08 V at 25, and the voltage holding ratios at 20° C., 60° C. and 90° C. were 98.8%, 97.6% and 95.9%, respectively.

Furthermore, there could not be seen any Vth unevenness around a panel.

Application Example 7

In a 200-milliliter four-necked flask equipped with a stirring device, a thermometer, a condenser and a nitrogen substituting device, 50 g of dehydrated and purified N-methyl-2-pyrrolidone and then 8.16 g of 1,1-bis(4-(1-(4-aminophenyl)butyl)phenyl)-methane were introduced and stirred to be dissolved. The solution was cooled to 13 and 3.69 g of pyromellitic dianhydride was introduced at a time and stirred with cooling to be reacted. After 1 hour, 0.11 g of paraaminophenyltrimethoxy-silane was added and stirred at 20 for 1 hour to be reacted.

Thereafter, by diluting the reaction solution with 57.6 g of N-methyl-2-pyrrolidone, a transparent solution containing 10% by weight of a polyamide acid was obtained. The viscosity of the solution at 25 was 1820 mPs.

To the said solution, a 1:1 mixed solution of ethylene glycol monobutyl ether and N-methyl-2-pyrrolidone was added for diluting the polyamide acid to 3% by weight, and thereafter the solution was coated on a transparent glass substrate having an ITO electrode at one side by a rotational coating method (a spinner method). The rotational conditions were 5000 rpm and 15 seconds. After coating, the substrate was dried at 100 for 10 minutes, and thereafter a temperature increase to 200 for 1 hour in an oven and a heat treatment at 200 for 90 minutes were carried out, to obtain polyimide with a film thickness of 60 nm. The coated surfaces of two substrates having the formed polyimide film were subjected to a rubbing treatment respectively, to obtain a liquid crystal aligning film, from which a liquid crystal cell having a cell thickness of 6 microns was constituted with rubbing directions being parallel and facing each other, and then a liquid Crystal FB01 for TFT made by Chisso Corp. was enclosed. After enclosing, the cell was subjected to an isotropic treatment at 120 for 30 minutes and then cooled gradually to room temperature, to obtain a liquid crystal element.

The residual electric charge of the said liquid crystal element was 0.06 V at 25, and the voltage holding ratios at 20° C., 60° C. and 90° C. were 98.1%, 97.4% and 95.0%, respectively.

Furthermore, there could not be seen any Vth unevenness around a panel.

Application Example 8

In a 200-milliliter four-necked flask equipped with a stirring device, a thermometer, a condenser and a nitrogen substituting device, 50 g of dehydrated and purified N-methyl-2-pyrrolidone and then 7.90 g of 1,1-bis(4-(1-(4-aminophenyl)ethyl)phenyl)-cyclohexane were introduced and stirred to be dissolved. The solution was cooled to 13 and 3.69 g of pyromellitic dianhydride was introduced at a time and stirred with cooling to be reacted. After 1 hour, 0.11 g of paraaminophenyltrimethoxy-silane was added and stirred at 20 for 1 hour to be reacted.

Thereafter, by diluting the reaction solution with 55.3 g of N-methyl-2-pyrrolidone, a transparent solution of 10% by weight of polyamide acid was obtained. The viscosity of the solution at 25 was 1970 mPs.

To the said solution, a 1:1 mixed solution of ethylene glycol monobutyl ether and N-methyl-2-pyrrolidone was added for diluting the polyamide acid to 3% by weight, and thereafter the solution was coated on a transparent glass substrate having an ITO electrode at one side by a rotational coating method (a spinner method). The rotational conditions were 5000 rpm and 15 seconds. After coating, the substrate was dried at 100 for 10 minutes, and thereafter a temperature increase to 200 for 1 hour in an oven and a heat treatment at 200 for 90 minutes were carried out, to obtain polyimide with a film thickness of 60 nm. The coated surfaces of two substrates having the formed polyimide film were subjected to a rubbing treatment respectively, to obtain a liquid crystal aligning film, from which a liquid crystal cell having a cell thickness of 6 microns was constituted with rubbing directions being parallel and facing each other, and then a liquid crystal FB01 for TFT made by Chisso Corp. was enclosed. After enclosing, the cell was subjected to an isotropic treatment at 120 for 30 minutes and then cooled gradually to room temperature, to obtain a liquid crystal element.

The residual electric charge of the said liquid crystal element was 0.05 V at 25, and the voltage holding ratios at 20° C., 60° C. and 90° C. were 98.7%, 97.6% and 95.6%, respectively.

Furthermore, there could not be seen any Vth unevenness around a panel.

Application Example 9

In a 200-milliliter four-necked flask equipped with a stirring device, a thermometer, a condenser and a nitrogen substituting device, 50 g of dehydrated and purified N-methyl-2-pyrrolidone and then 7.90 g of 1,1-bis(4-(1-(4-aminophenyl)ethyl)phenyl)-4-butylcyclohexane were introduced and stirred to be dissolved. The solution was cooled to 13 and 3.69 of pyromellitic dianhydride was introduced at a time and stirred with cooling to be reacted. After 1 hour, 0.11 g of paraaminophenyl trimethoxysilane was added and stirred at 20 for 1 hour to be reacted.

Thereafter, by diluting the reaction solution with 63.7 g of N-methyl-2-pyrrolidone (NMP), a transparent solution containing 10% by weight of polyamide acid was obtained. The viscosity of the solution at 25 was 1920 mPs.

To the said solution, a 1:1 mixed solution of ethylene glycol monobutyl ether and NMP was added for diluting the polyamide acid to 3% by weight, and thereafter the solution was coated on a transparent glass substrate having an ITO electrode at one side by a rotational coating method (a spinner method). The rotational conditions were 5000 rpm and 15 seconds. After coating, the substrate was dried at 100 for 10 minutes, end thereafter a temperature increase to 200 for 1 hour in an oven and a heat treatment at 200 for 90 minutes were carried out, to obtain polyimide with a film thickness of 60 nm. The coated surfaces of two substrates having the formed polyimide film were subjected to a rubbing treatment respectively, to obtain a liquid crystal aligning film, from which a liquid crystal cell having a cell thickness of 6 microns was constituted with rubbing directions being parallel and facing each other, and then a liquid crystal FB01 for TFT made by Chisso Corp. was enclosed. After enclosing, the cell was subjected to an isotropic treatment at 120 for 30 minutes and then cooled gradually to room temperature, to obtain a liquid crystal element.

The residual electric charge of the said liquid crystal element was 0.05 V at 25, and the voltage holding ratios at 20° C., 60° C. and 90° C. were 98.6%, 97.7% and 95.7%, respectively.

Furthermore, there could not be seen any Vth unevenness around a panel.

Comparative Application Example 1

In accordance with a similar procedure in Application Example 1 except that 7.40 g of 2,2-bis(4-(4-aminophenoxy) phenyl)propane was used in place of 7.80 g of 1,4-bis(4-(4-amonophenylmethyl) phenylmethyl)benzene, a polyamide acid was obtained. The compound was used according to Application Example 1, to obtain a liquid crystal element.

The residual electric charge of the said liquid crystal element was 0.20 V at 25, and the voltage holding ratios at 20° C., 60° C. and 90° C. were 90.0%, 82.3% and 65.6%, respectively.

Comparative Application Example 2

In accordance with a similar procedure in Application Example 1 except that 3.33 g of 4,4-diaminodiphenyl ether was used in place of 7.80 g of 1,4-bis(4-(4-amonophenylmethyl)phenylmethyl)-benzene, a polyamide acid was obtained. The compound was used according to Application Example 1, to obtain a liquid crystal element.

The residual electric charge of the said liquid crystal element was 0.26 V at 25, and the voltage holding ratios at 20° C., 60° C. and 90° C. were 89.0%, 80.1% and 58.4%, respectively.

What we claim is:

1. Diamino compounds represented by formula (1):

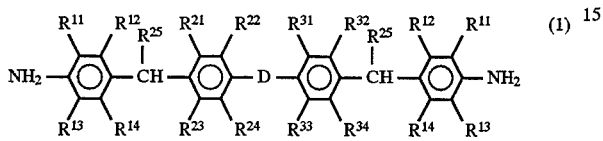

wherein, (a) when $R^{25}$ being a hydrogen atom and D being

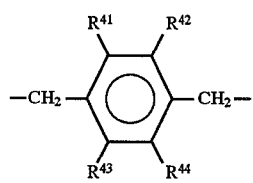

all of $R^{11}$, $R^{12}$, $R^{13}$ and $R^{14}$ denote a hydrogen atom, and $R^{21}$, $R^{22}$, $R^{23}$, $R^{24}$, $R^{31}$, $R^{32}$, $R^{33}$, $R^{34}$, $R^{41}$, $R^{42}$, $R^{43}$ and $R^{44}$ denote independently each other a hydrogen atom or an alkyl group with 1 to 8 carbon atoms, (b) when $R^{25}$ being a hydrogen atom and D being

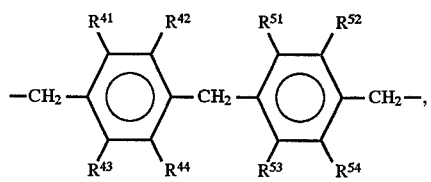

all of $R^{11}$, $R^{12}$, $R^{13}$ and $R^{14}$ denote a hydrogen atom, and $R^{21}$ and $R^{32}$, $R^{22}$ and $R^{31}$, $R^{23}$ and $R^{34}$, as well as $R^{24}$ and $R^{33}$ are respectively the same atoms or groups and denote independently each other hydrogen atoms or straight-chain or branched alkyl groups with 1 to 8 carbon atoms, and $R^{41}$, $R^{42}$, $R^{43}$, $R^{44}$, $R^{51}$, $R^{52}$, $R^{53}$ and $R^{54}$ denote independently each other a hydrogen atom or an alkyl group with 1 to 8 carbon atoms, (c) when $R^{25}$ being a hydrogen atom and D being a divalent straight-chain or branched hydrocarbon alkyl group with 2 to 30 carbon atoms, $R^{11}$, $R^{12}$, $R^{13}$ and $R^{14}$ denote independently a hydrogen atom or a straight-chain or branched alkyl group with 1 to 8 carbon atoms, and $R^{21}$ and $R^{32}$, and $R^{22\ and\ R31}$, $R^{23}$ and $R^{34}$ as well as $R^{24}$ and $R^{33}$ are respectively the same atoms or groups and denote independently each other hydrogen atoms or straight-chain or branched alkyl groups with 1 to 8 carbon atoms, (d) when $R^{25}$ being a straight-chain or branched alkyl group with 1 to 12 carbon atoms, D denotes a direct bond, an aliphatic group with 1 to 30 carbon atoms, an aromatic group with 6 to 30 carbon atoms, or a hydrocarbon group with 7 to 30 carbon atoms having both an aliphatic group and an aromatic group, $R^{11}$, $R^{12}$, $R^{13}$ and $R^{14}$ denote independently a hydrogen atom or a straight-chain or branched alkyl group with 1 to 8 carbon atoms, and $R^{21}$ and $R^{32}$, $R^{22}$ and $R^{31}$, $R^{23}$ and $R^{34}$ as well as $R^{24}$ and $R^{33}$ are respectively the same atoms or groups and denote independently each other hydrogen atoms or straight-chain or branched alkyl groups with 1 to 8 carbon atoms with the proviso that when D is —C(CH$_3$)$_2$—$R^{25}$ is not —CH$_3$.

2. The diamino compounds according to claim 1, in which all of $R^{11}$, $R^{12}$, $R^{13}$, $R^{14}$, $R^{21}$, $R^{22}$, $R^{23}$, $R^{24}$, $R^{25}$, $R^{31}$, $R^{32}$, $R^{33}$ and $R^{34}$ denote a hydrogen atom and D denotes

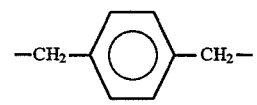

in the general formula (1).

3. The diamino compounds according to claim 1, in which all of $R^{11}$, $R^{12}$, $R^{13}$, $R^{14}$, $R^{21}$, $R^{22}$, $R^{23}$, $R^{24}$, $R^{25}$, $R^{31}$, $R^{32}$, $R^{33}$ and $R^{34}$ denote a hydrogen atom and D denotes

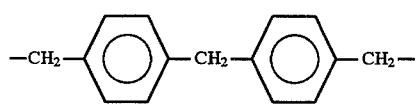

in the general formula (1).

4. The diamino compounds according to claim 1, in which $R^{25}$ denotes a hydrogen atom, D denotes a group expressed by the following formula (2), $R^{11}$, $R^{12}$, $R^{13}$ and $R^{14}$ denote independently a hydrogen atom or a straight-chain or branched alkyl group with 1 to 8 carbon atoms, $R^{21}$ and $R^{32}$, $R^{22}$ and $R^{31}$, $R^{23}$ and $R^{34}$, as well as $R^{24}$ and $R^{33}$ are respectively the same atoms or groups and denote independently each other hydrogen atoms or straight-chain or branched alkyl groups with 1 to 8 carbon atoms in the general formula (1):

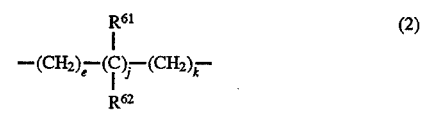

wherein, $R^{61}$ denotes a hydrogen atom or a straight-chain or branched alkyl group with 1 to 12 carbon atoms, $R^{62}$ denotes a straight-chain or branched alkyl group with 1 to 12 carbon atoms, e and k denote independently each other 0 to 10, j denotes 0 to 20, and when j being 0, the sum of e and k is 2 or more than 2, and when j being 1 or more than 1, the sum of e and k is 0 or more than 0 in the general formula (2).

5. Diamino compounds according to claim 1, in which $R^{25}$ denotes a straight-chain or branched alkyl group with 1 to 12 carbon atoms, D denotes any group expressed by the following formulae, $R^{11}$, $R^{12}$, $R^{13}$ and $R^{14}$ denote independently a hydrogen atom or a straight-chain or branched alkyl group with 1 to 8 carbon atoms, $R^{21}$ and $R^{32}$, $R^{22}$ and $R^{31}$, $R^{23}$ and $R^{34}$, as well as $R^{24}$ and $R^{33}$ are respectively the same atoms or groups and denote independently each other hydrogen atoms or straight-chain or branched alkyl groups with 1 to 8 carbon atoms in the general formula (1):

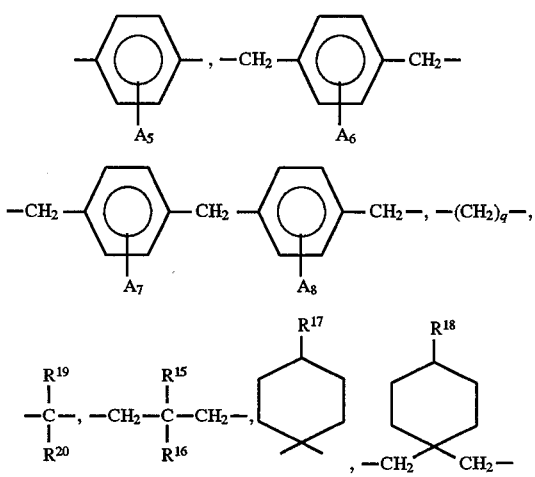

wherein, $A_5$, $A_6$, $A_7$ and $A_8$ denote independently each other a hydrogen atom or a straight-chain or branched alkyl group with 1 to 8 carbon atoms, q denotes an integer of zero to 30, $R^{15}$, $R^{16}$, $R^{19}$ and $R^{20}$ denote independently each other a hydrogen atom or a straight-chain or branched alkyl group with 1 to 20 carbon atoms, and $R^{17}$ and $R^{18}$ denote independently each other a hydrogen atom or a straight-chain or branched alkyl group with 1 to 8 carbon atoms with the proviso that when D is —C(CH$_3$)$_2$—, $R^{25}$ is not —CH$_3$.

6. The diamino compounds according to claim 1, in which all of $R^{11}$, $R^{12}$, $R^{13}$, $R^{14}$, $R^{21}$, $R^{22}$, $R^{23}$, $R^{24}$, $R^{25}$, $R^{31}$, $R^{32}$, $R^{33}$, $R^{34}$, denote a hydrogen atom and D denotes a group expressed by the general formula (2) in general formula (1); wherein, $R^{61}$ denotes a hydrogen atom or a straight-chain or branched alkyl group with 1 to 12 carbon atoms, $R^{62}$ denotes a straight-chain or branched alkyl group with 1 to 12 carbon atoms, e and k denote independently each other 0 to 10, j denotes 0 to 20, and when j being 0, the sum of e and k is 2 or more than 2, and when j is being 1 or more than 1, the sum of e and k is 0 or more than 0 in the general formula (2).

7. The diamino compounds according to claim 1, in which all of $R^{11}$, $R^{12}$, $R^{13}$, $R^{14}$, $R^{21}$, $R^{22}$, $R^{23}$, $R^{24}$, $R^{25}$, $R^{31}$, $R^{32}$, $R^{33}$, $R^{34}$, denotes a hydrogen atom and D denotes a group expressed by the general formula (2) in the general formula (1), as well as j is 0 and the sum of e and k is from 2 to 20 in the general formula (2); wherein, $R^{61}$ denotes a hydrogen atom or a straight-chain or branched alkyl group with 1 to 12 carbon atoms, $R^{62}$ denotes a straight-chain or branched alkyl group with 1 to 12 carbon atoms, e and k denote independently each other 0 to 10, j denotes 0 to 20, and when j being 0, the sum of e and k is 2 or more than 2, and when j is being 1 or more than 1, the sum of e and k is 0 or more than 0 the general formula (2).

8. The diamino compounds according to claim 1, in which all of $R^{11}$, $R^{12}$, $R^{13}$, $R^{14}$, $R^{21}$, $R^{22}$, $R^{23}$, $R^{24}$, $R^{25}$, $R^{31}$, $R^{32}$, $R^{33}$, $R^{34}$, denote a hydrogen atom and D denotes a group expressed by the general formula (2)

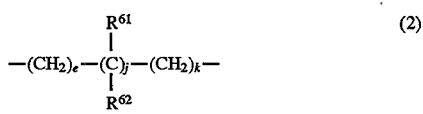

in the general formula (1), as well as $R^{61}$ denotes a hydrogen atom, $R^{62}$ denotes a straight-chain alkyl group with 1 to 10 carbon atoms, and all of e, j and k are 1 in the general formula (2).

9. The diamino compounds according to claim 1, in which all of $R^{11}$, $R^{12}$, $R^{13}$, $R^{14}$, $R^{21}$, $R^{22}$, $R^{23}$, $R^{24}$, $R^{25}$, $R^{31}$, $R^{32}$, $R^{33}$, $R^{34}$, denote a hydrogen atom and D denotes a group expressed by the general formula (2)

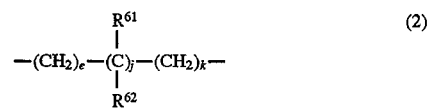

in the general formula (1), as well as $R^{61}$ denotes a hydrogen atom, $R^{62}$ denotes a straight-chain alkyl group with 1 to 9 carbon atoms, and e and k are both 0 and j is 0 to 20 in the general formula (2).

10. The diamino compounds according to claim 5, in which all of $R^{11}$, $R^{12}$, $R^{13}$, $R^{14}$, $R^{21}$, $R^{22}$, $R^{23}$, $R^{24}$, $R^{31}$, $R^{32}$, $R^{33}$ and $R^{34}$ denote a hydrogen atom in the general formula (1).

11. The diamino compounds according to claim 1, which are bis-(4-(1-(4-aminophenyl)alkyl)phenyl)methanes and in which $R^{25}$ denotes a straight-chain alkyl group with 1 to 6 carbon atoms.

12. The diamino compounds according to claim 1, which are bis-(4-(1-(4-aminophenyl) alkyl)phenyl)cyclohexanes and in which $R^{25}$ denotes a straight-chain alkyl group with 1 to 6 carbon atoms.

13. The diamino compounds according to claim 1, which are, bis-(4-(1-(4-aminophenyl)alkyl)phenyl)4-butylcyclohexane and in which $R^{25}$ denotes a straight-chain alkyl group with 1 to 6 carbon atoms.

14. A method for preparing a diamino compound expressed by the following general formula (1), characterized in that an aromatic compound expressed by the following formula (3) is reacted with a paranitrobenzoyl halide derivative expressed by the following general formula (4) and thereafter carbonyl groups are reduced or alkylated and nitro groups are reduced:

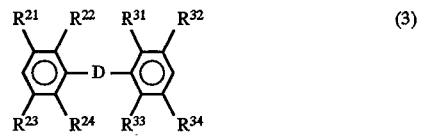

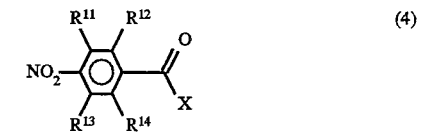

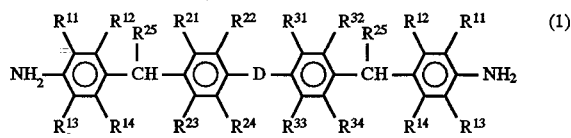

wherein, (a) when $R^{25}$ being a hydrogen atom and D being

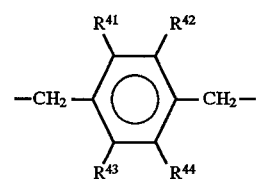

all of $R^{11}$, $R^{12}$, $R^{13}$ and $R^{14}$ denotes a hydrogen atom, and $R^{21}$, $R^{22}$, $R^{23}$, $R^{24}$, $R^{31}$, $R^{32}$, $R^{33}$, $R^{34}$, $R^{41}$, $R^{42}$, $R^{43}$ and $R^{44}$ denote independently each other a hydrogen atom or an alkyl group with 1 to 8 carbon atoms, (b) when $R^{25}$ being a hydrogen atom and D being

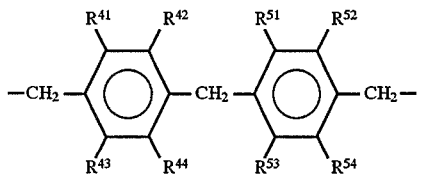

all of $R^{11}$, $R^{12}$, $R^{13}$ and $R^{14}$ denote a hydrogen atom, and $R^{21}$ and $R^{32}$, $R^{22}$ and $R^{31}$, $R^{23}$ and $R^{34}$, as well as $R^{24}$ and $R^{33}$ are respectively the same atoms or groups and denote independently each other hydrogen atoms or straight-chain or branched alkyl groups with 1 to 8 carbon atoms, and $R^{41}$, $R^{42}$, $R^{43}$, $R^{44}$, $R^{51}$, $R^{52}$, $R^{53}$ and $R^{54}$ denote independently each other a hydrogen atom or an alkyl group with 1 to 8 carbon atoms, (c) when $R^{25}$ being a hydrogen atom and D being a divalent straight-chain or branched hydrocarbon group with 2 to 30 carbon atoms, $R^{11}$, $R^{12}$, $R^{13}$ and $R^{14}$ denote independently a hydrogen atom or a straight-chain or branched alkyl group with 1 to 8 carbon atoms, and $R^{21}$ and $R^{32}$, $R^{22}$ and $R^{31}$, $R^{23}$ and $R^{34}$ as well as $R^{24}$ and $R^{33}$ are respectively the same atoms or groups and denote independently each other hydrogen atoms or straight-chain or branched alkyl groups with 1 to 8 carbon atoms, (d) when $R^{25}$ being a straight-chain or branched alkyl group with 1 to 12 carbon atoms, D denotes a direct bond, an aliphatic group with 1 to 30 carbon atoms, an aromatic group with 6 to 30 carbon atoms, or a hydrocarbon group with 7 to 30 carbon atoms having both an aliphatic group and an aromatic group, $R^{11}$, $R^{12}$, $R^{13}$ and $R^{14}$ denote independently a hydrogen atom or a straight-chain or branched alkyl group with 1 to 8 carbon atoms, $R^{21}$ and $R^{32}$, $R^{22}$ and $R^{31}$, $R^{23}$ and $R^{34}$ as well as $R^{24}$ and $R^{33}$ are respectively the same atoms or groups and denote independently each other hydrogen atoms or straight-chain or branched alkyl groups with 1 to 8 carbon atoms, and X denotes a chlorine atom or a bromine atom, in the general formula (4).

15. A method for preparing a diamino compound according to claim 14, characterized in that a diphenyl methane derivative expressed by the following formula (5) is reacted with a benzoyl halide derivative expressed by the following general formula (6) and thereafter a carbonyl group is reduced to synthesize an aromatic compound expressed by the formula (3), which is subsequently reacted with paranitrobenzoyl halide expressed by the general formula (4) and thereafter carbonyl groups and nitro groups are reduced:

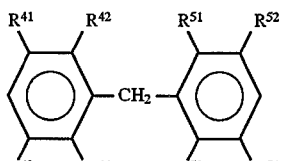 (5)

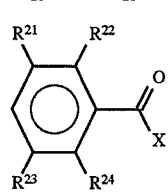 (6)

wherein,

D denotes

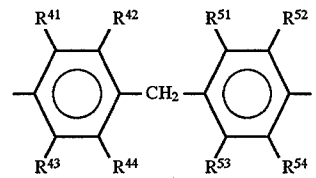

in the general formula (3), and all of $R^{11}$, $R^{12}$, $R^{13}$ and $R^{14}$ denote a hydrogen atom, and $R^{21}$, $R^{22}$, $R^{23}$, $R^{24}$, $R^{31}$, $R^{32}$, $R^{33}$, $R^{34}$, $R^{41}$, $R^{42}$, $R^{43}$, $R^{44}$, $R^{51}$, $R^{52}$, $R^{53}$ and $R^{54}$ denote independently each other a hydrogen atom or an alkyl group with 1 to 8 carbon atoms, X denotes a chlorine atom or a bromine atom in the general formula (4) and (6).

16. A method for preparing a diamino compound according to claim 14, characterized in that a dibenzyl benzene derivative expressed by the following formula (7) is reacted with paranitrobenzoyl halide expressed by the general formula (4) and thereafter carbonyl groups and nitro groups are reduced:

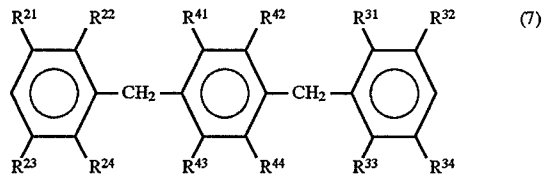 (7)

wherein, $R^{21}$, $R^{22}$, $R^{23}$, $R^{23}$, $R^{31}$, $R^{32}$, $R^{33}$, $R^{34}$, $R^{41}$, $R^{42}$, $R^{43}$ and $R^{44}$ denote independently each other a hydrogen atom or an alkyl group with 1 to 8 carbon atoms in the general formula (7).

17. A method for preparing a diamino compound according to claim 14, characterized in that a diphenyl alkane derivative expressed by the following formula (8) is reacted with a paranitrobenzoyl halide derivative expressed by the general formula (4) and thereafter carbonyl groups and nitro groups are reduced:

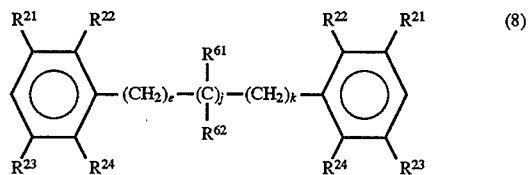 (8)

wherein, $R^{61}$ denotes a hydrogen atom or a straight-chain or branched alkyl group with 1 to 12 carbon atoms, $R^{62}$ denotes a straight-chain or branched alkyl group with 1 to 12 carbon atoms, e and k denote independently each other 0 to 10, j denotes 0 to 20, and when j being 0, the sum of e and k are 2 or more than 2, and when j being 1 or more than 1, the sum of e and k is 0 or more than 0, as well as $R^{21}$, $R^{22}$, $R^{23}$, and $R^{24}$ denote independently each other a hydrogen atom or an alkyl group with 1 to 8 carbon atoms in the general formula (8).

18. A method for preparing a diamino compound expressed by the general formula (10), characterized in that a compound expressed by the following formula (9) is reacted with a paranitrobenzoyl halide derivative expressed by the general formula (4)

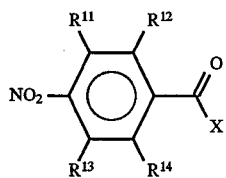 (4)

and thereafter carbonyl groups are alkylated and nitro groups are reduced:

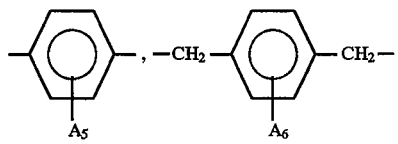 (9)

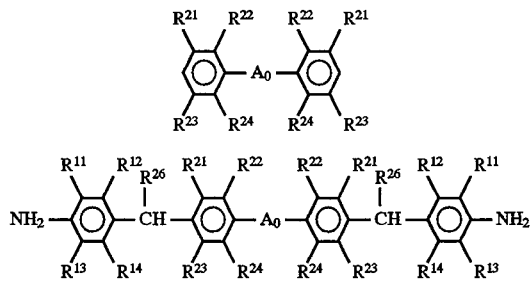 (10)

wherein, $A_0$ denotes any of the following groups in the general formula (9) and (10):

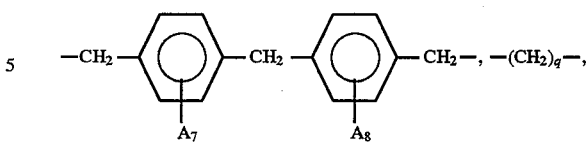

wherein, $A_5$, $A_6$, $A_7$ and $A_8$ denote independently each other a hydrogen atom or a straight-chain or branched alkyl group with 1 to 8 carbon atoms, q denotes an integer of zero to 30, $R^{15}$, $R^{16}$, $R^{19}$, and $R^{20}$ denote independently each other a hydrogen atom or a straight-chain or branched alkyl group with 1 to 20 carbon atoms, $R^{11}$, $R^{12}$, $R^{13}$, $R^{14}$, $R^{17}$, $R^{18}$, $R^{21}$, $R^{22}$, $R^{23}$, and $R^{24}$ denote independently each other a hydrogen atom or an alkyl group with 1 to 8 carbon atoms, and $R^{26}$ denotes a straight-chain or branched alkyl group with 1 to 12 carbon atoms.

* * * * *